US012576234B2

(12) United States Patent
Gillerman et al.

(10) Patent No.: US 12,576,234 B2
(45) Date of Patent: Mar. 17, 2026

(54) SYSTEMS AND METHODS FOR GENERATING NITRIC OXIDE

(71) Applicant: Third Pole, Inc., Waltham, MA (US)

(72) Inventors: Ian J. Gillerman, Somerville, MA (US); Gregory W. Hall, Belmont, MA (US); Wolfgang Scholz, Beverly, MA (US); David G. Zapol, San Francisco, CA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 18/494,217

(22) Filed: Oct. 25, 2023

(65) Prior Publication Data

US 2024/0325672 A1      Oct. 3, 2024

Related U.S. Application Data

(63) Continuation of application No. 17/855,592, filed on Jun. 30, 2022, now Pat. No. 11,833,309, which is a (Continued)

(51) Int. Cl.
*A61M 16/12*        (2006.01)
*A61K 33/00*        (2006.01)
(Continued)

(52) U.S. Cl.
CPC .............. *A61M 16/12* (2013.01); *A61K 33/00* (2013.01); *A61M 16/0057* (2013.01);
(Continued)

(58) Field of Classification Search
CPC .............. A61M 16/0057; A61M 16/04; A61M 16/0666; A61M 16/12; A61M 16/0093;
(Continued)

(56) References Cited

U.S. PATENT DOCUMENTS

| | | | |
|---|---|---|---|
| 709,867 | A | 9/1902 | Bradley et al. |
| 2,485,478 | A | 10/1949 | Cotton |

(Continued)

FOREIGN PATENT DOCUMENTS

| | | |
|---|---|---|
| CA | 2413834 | 6/2004 |
| CN | 1099997 | 3/1995 |

(Continued)

OTHER PUBLICATIONS

Beanland et al., "PreInsertion Resistors in High Voltage Capicitor Bank Switching", prepared for Western Protective Relay Conference, Oct. 19-21, 2004, Spokane, WA.

(Continued)

*Primary Examiner* — Valerie L Woodward
(74) *Attorney, Agent, or Firm* — Greenberg Traurig, LLP; David J. Dykeman; Jaime Burke

(57) ABSTRACT

Systems and methods for nitric oxide generation are provided. In an embodiment, an NO generation system can include a controller and disposable cartridge that can provide nitric oxide to two different treatments simultaneously. The disposable cartridge has multiple purposes including preparing incoming gases for exposure to the NO generation process, scrubbing exhaust gases for unwanted materials, characterizing the patient inspiratory flow, and removing moisture from sample gases collected. Plasma generation can be done within the cartridge or within the controller. The system has the capability of calibrating NO and $NO_2$ gas analysis sensors without the use of a calibration gas.

20 Claims, 151 Drawing Sheets

Related U.S. Application Data continuation of application No. 17/197,911, filed on Mar. 10, 2021, now Pat. No. 11,376,390, which is a continuation of application No. 16/909,722, filed on Jun. 23, 2020, now Pat. No. 10,946,163, which is a continuation of application No. 16/697,498, filed on Nov. 27, 2019, now Pat. No. 10,695,523, which is a continuation of application No. 16/388,464, filed on Apr. 18, 2019, now Pat. No. 10,532,176, which is a continuation of application No. 15/907,241, filed on Feb. 27, 2018, now Pat. No. 10,286,176.

(60) Provisional application No. 62/614,492, filed on Jan. 7, 2018, provisional application No. 62/574,173, filed on Oct. 18, 2017, provisional application No. 62/553,572, filed on Sep. 1, 2017, provisional application No. 62/509,394, filed on May 22, 2017, provisional application No. 62/463,943, filed on Feb. 27, 2017, provisional application No. 62/463,956, filed on Feb. 27, 2017.

(51) Int. Cl.

| | |
|---|---|
| *A61M 16/00* | (2006.01) |
| *A61M 16/04* | (2006.01) |
| *A61M 16/06* | (2006.01) |
| *A61M 16/10* | (2006.01) |
| *A61M 16/20* | (2006.01) |
| *C01B 21/32* | (2006.01) |

(52) U.S. Cl.
CPC ...... *A61M 16/0093* (2014.02); *A61M 16/022* (2017.08); *A61M 16/024* (2017.08); *A61M 16/04* (2013.01); *A61M 16/0666* (2013.01); *A61M 16/101* (2014.02); *A61M 16/107* (2014.02); *A61M 16/202* (2014.02); *C01B 21/32* (2013.01); *A61M 2202/0275* (2013.01); *A61M 2202/0283* (2013.01); *A61M 2205/05* (2013.01); *A61M 2205/054* (2013.01); *A61M 2205/125* (2013.01); *A61M 2205/3584* (2013.01); *A61M 2205/502* (2013.01); *A61M 2205/80* (2013.01); *A61M 2205/8206* (2013.01); *A61M 2209/088* (2013.01)

(58) Field of Classification Search
CPC .............. A61M 16/101; A61M 16/107; A61M 16/202; A61M 16/024; A61M 16/022; C01B 21/24–32
See application file for complete search history.

(56) References Cited

U.S. PATENT DOCUMENTS

| | | |
|---|---|---|
| 2,485,481 A | 10/1949 | Cotton |
| 2,525,938 A | 10/1950 | Peck |
| 2,684,448 A | 7/1954 | Nilles |
| 3,047,370 A | 7/1962 | Aviges et al. |
| 3,225,309 A | 12/1965 | Phelps |
| 3,805,590 A | 4/1974 | Ringwall et al. |
| 4,287,040 A | 9/1981 | Alamaro |
| 4,500,563 A | 2/1985 | Ellenberger et al. |
| 4,505,795 A | 3/1985 | Alamaro |
| 4,680,694 A | 7/1987 | Huynh et al. |
| 4,695,358 A | 9/1987 | Mizuno et al. |
| 4,705,670 A | 11/1987 | O'Hare |
| 4,816,229 A | 3/1989 | JeRnsen et al. |
| 4,877,589 A | 10/1989 | Conrad |
| 5,285,372 A | 2/1994 | Huynh et al. |
| 5,378,436 A | 1/1995 | Endoh et al. |
| 5,396,882 A | 3/1995 | Zapol |
| 5,413,097 A | 5/1995 | Birenheide et al. |
| 5,471,977 A | 12/1995 | Olsson et al. |
| 5,485,827 A | 1/1996 | Zapol et al. |
| 5,531,218 A | 7/1996 | Krebs |
| 5,546,935 A | 8/1996 | Champeau |
| 5,558,083 A | 9/1996 | Bathe et al. |
| 5,573,733 A | 11/1996 | Salama |
| 5,674,381 A | 10/1997 | Dekker |
| 5,692,495 A | 12/1997 | Sheu |
| 5,732,693 A | 3/1998 | Bathe et al. |
| 5,749,937 A | 5/1998 | Detering et al. |
| 5,752,504 A | 5/1998 | Bathe |
| 5,827,420 A | 10/1998 | Shirazi et al. |
| 5,839,433 A | 11/1998 | Higenbottam |
| 5,845,633 A | 12/1998 | Psaros |
| 5,918,596 A | 7/1999 | Heinonen |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,186,140 B1 | 2/2001 | Hoague |
| 6,186,142 B1 | 2/2001 | Schmidt et al. |
| 6,197,091 B1 | 3/2001 | Ji et al. |
| 6,224,653 B1 | 5/2001 | Shvedchikov et al. |
| 6,250,302 B1 | 6/2001 | Rantala |
| 6,290,683 B1 | 9/2001 | Erez et al. |
| 6,296,827 B1 | 10/2001 | Castor et al. |
| 6,365,868 B1 | 4/2002 | Borowy et al. |
| 6,432,077 B1 | 8/2002 | Stenzler |
| 6,532,956 B2 | 3/2003 | Hill |
| 6,536,429 B1 | 3/2003 | Pavlov et al. |
| 6,581,599 B1 | 6/2003 | Stenzler |
| 6,612,306 B1* | 9/2003 | Mault .................. A61B 5/6838 |
| | | 128/200.22 |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,984,256 B2 | 1/2006 | Lamprecht et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,299,785 B1 | 11/2007 | Lee |
| 7,312,584 B2 | 12/2007 | Tamita et al. |
| 7,335,181 B2 | 2/2008 | Miller et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,520,866 B2 | 4/2009 | Stenzler et al. |
| 7,523,752 B2 | 4/2009 | Montgomery et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,597,731 B2 | 10/2009 | Palmerton et al. |
| 7,618,594 B2 | 11/2009 | Rounbehler et al. |
| 7,744,812 B2 | 6/2010 | Witherspoon et al. |
| 7,861,516 B2 | 1/2011 | Allanson et al. |
| 7,861,717 B1 | 1/2011 | Krebs |
| 7,914,743 B2 | 3/2011 | Fine et al. |
| 7,947,227 B2 | 5/2011 | Fine et al. |
| 7,955,294 B2 | 6/2011 | Stenzler et al. |
| 8,030,849 B2 | 10/2011 | Suslov |
| 8,043,252 B2 | 10/2011 | Miller et al. |
| 8,057,742 B2 | 11/2011 | Rounbehler et al. |
| 8,066,904 B2 | 11/2011 | Fine et al. |
| 8,079,998 B2 | 12/2011 | Hole et al. |
| 8,083,997 B2 | 12/2011 | Rounbehler et al. |
| 8,091,549 B2 | 1/2012 | Montgomery et al. |
| 8,151,791 B2 | 4/2012 | Arlow et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,267,884 B1 | 9/2012 | Hicks |

(56) References Cited

U.S. PATENT DOCUMENTS

| | | | |
|---|---|---|---|
| 8,268,252 B2 | 9/2012 | Fuller et al. |
| 8,277,399 B2 | 10/2012 | Hamilton et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,328,998 B2 | 12/2012 | Wada et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |
| D688,352 S | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,887,721 B2 | 11/2014 | Zapol et al. |
| 8,893,717 B2 | 11/2014 | Montgomery et al. |
| 8,944,049 B2 | 2/2015 | Fine et al. |
| 9,035,045 B2 | 5/2015 | Chu et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,260,399 B2 | 2/2016 | Ruan et al. |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,993 B2 | 8/2016 | Bathe et al. |
| 9,408,994 B2 | 8/2016 | Fine et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,562,113 B2 | 2/2017 | Ruan et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,188,822 B2 | 1/2019 | Flanagan et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,750,606 B1 | 8/2020 | Liu et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 11,478,601 B2 | 10/2022 | Hall et al. |
| 11,479,464 B2 | 10/2022 | Hall et al. |
| 11,524,134 B2 | 12/2022 | Zapol et al. |
| 11,554,240 B2 | 1/2023 | Hall et al. |
| 11,660,416 B2 | 5/2023 | Goldstein et al. |
| 11,691,879 B2 | 7/2023 | Kondiboyina et al. |
| 11,754,538 B1 | 9/2023 | Fine |
| 11,827,989 B2 | 11/2023 | Silkoff et al. |
| 11,833,309 B2 | 12/2023 | Gillerman et al. |
| 11,877,378 B2 | 1/2024 | Wu et al. |
| 11,911,566 B2 | 2/2024 | Zapol et al. |
| 11,975,139 B2 | 5/2024 | Miles et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0074493 A1* | 4/2004 | Seakins ............... A61M 16/161 |
| | | 128/203.16 |
| 2004/0149282 A1 | 8/2004 | Hickle |
| 2004/0168686 A1 | 9/2004 | Krebs |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian et al. |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |

(56) References Cited

U.S. PATENT DOCUMENTS

| | | |
|---|---|---|
| 2008/0078382 A1 | 4/2008 | LeMahieu et al. |
| 2008/0119754 A1* | 5/2008 | Hietala .............. A61M 16/085 |
| | | 600/532 |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0076325 A1 | 3/2010 | Cho et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1* | 5/2014 | Fine ...................... A61M 16/12 |
| | | 422/198 |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0155684 A1 | 6/2014 | Ehrenreich |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0075522 A1 | 3/2015 | Acker et al. |
| 2015/0090261 A1 | 4/2015 | Crosbie |
| 2015/0101600 A1* | 4/2015 | Miller .............. A61M 16/1095 |
| 2015/0101604 A1 | 4/2015 | Crosbie |
| 2015/0174158 A1 | 6/2015 | Av-Gay et al. |
| 2015/0190565 A1 | 7/2015 | Ohdaira et al. |
| 2015/0238248 A1 | 8/2015 | Thompson et al. |
| 2015/0272988 A1 | 10/2015 | Av-Gay et al. |
| 2015/0273176 A1* | 10/2015 | Acker .............. A61M 16/0003 |
| | | 128/202.22 |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0045685 A1 | 2/2016 | Hyde et al. |
| 2016/0106946 A1 | 4/2016 | Gellman et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0193336 A1 | 7/2016 | Nelson et al. |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0310693 A1 | 10/2016 | Bathe et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0095634 A1 | 4/2017 | Miller et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0071467 A1 | 3/2018 | Fine et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0228836 A1 | 8/2018 | Nelson et al. |
| 2018/0243527 A1 | 8/2018 | Zapol et al. |
| 2018/0243528 A1 | 8/2018 | Zapol et al. |
| 2018/0264032 A1 | 9/2018 | Jaffri et al. |
| 2018/0280920 A1 | 10/2018 | Zapol et al. |
| 2018/0296790 A1 | 10/2018 | Zapol et al. |
| 2018/0304038 A1 | 10/2018 | Jafri et al. |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0083699 A1 | 3/2019 | Spohn et al. |
| 2019/0092639 A1 | 3/2019 | Fine et al. |
| 2019/0127223 A1 | 5/2019 | Montgomery et al. |
| 2019/0134574 A1 | 5/2019 | Tsuchiya et al. |
| 2019/0135633 A1 | 5/2019 | Montgomery et al. |
| 2019/0143068 A1 | 5/2019 | Rounbehler et al. |
| 2019/0184116 A1 | 6/2019 | Acker et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0030553 A1 | 1/2020 | Keip et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0188319 A1 | 6/2020 | Quinn et al. |
| 2020/0197318 A1 | 6/2020 | Widgerow et al. |
| 2020/0254199 A1 | 8/2020 | Bassin |
| 2020/0282375 A1 | 9/2020 | Fine et al. |
| 2020/0308032 A1 | 10/2020 | Domrese et al. |
| 2020/0360647 A1 | 11/2020 | Quinn et al. |
| 2020/0360649 A1 | 11/2020 | Hall et al. |
| 2020/0360690 A1 | 11/2020 | Evans et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |
| 2021/0214222 A1 | 7/2021 | Kondiboyia et al. |
| 2021/0220586 A1 | 7/2021 | Shah et al. |
| 2021/0268221 A1 | 9/2021 | Gillerman et al. |
| 2021/0330957 A1 | 10/2021 | Potenziano et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0080147 A1 | 3/2022 | Shah et al. |
| 2022/0096535 A1 | 3/2022 | Shah et al. |
| 2022/0135406 A1 | 5/2022 | Apollonio et al. |
| 2022/0162070 A1 | 5/2022 | Silkoff et al. |
| 2022/0193623 A1 | 6/2022 | Nakao |
| 2022/0211967 A1 | 7/2022 | Hall et al. |
| 2022/0296845 A1 | 9/2022 | Jackson et al. |

(56) References Cited

U.S. PATENT DOCUMENTS

| | | |
|---|---|---|
| 2022/0298653 A1 | 9/2022 | Silkoff et al. |
| 2022/0339391 A1 | 10/2022 | Gillerman et al. |
| 2023/0001119 A1 | 1/2023 | Richardson et al. |
| 2023/0053201 A1 | 2/2023 | Miles et al. |
| 2023/0058407 A1 | 2/2023 | Hall |
| 2023/0098706 A1 | 3/2023 | Miles et al. |
| 2023/0112963 A1 | 4/2023 | Yuen et al. |
| 2023/0149556 A1 | 5/2023 | Hall et al. |
| 2023/0158064 A1 | 5/2023 | Shah |
| 2023/0158260 A1 | 5/2023 | Shah et al. |
| 2023/0158261 A1 | 5/2023 | Trias et al. |
| 2023/0201497 A1 | 6/2023 | Dekker |
| 2023/0263986 A1 | 8/2023 | Hall et al. |
| 2023/0330359 A1 | 10/2023 | Scholz et al. |
| 2024/0067523 A1 | 2/2024 | Hall et al. |
| 2024/0076185 A1 | 3/2024 | Hall et al. |
| 2024/0076186 A1 | 3/2024 | Kondiboyina et al. |
| 2024/0209521 A1 | 6/2024 | Silkoff et al. |
| 2024/0253990 A1 | 8/2024 | Apollonio et al. |
| 2024/0325672 A1 | 10/2024 | Gillerman et al. |
| 2025/0128946 A1 | 4/2025 | Silkoff et al. |

FOREIGN PATENT DOCUMENTS

| | | |
|---|---|---|
| CN | 1730115 | 2/2006 |
| CN | 201037113 | 3/2008 |
| CN | 100404083 | 7/2008 |
| CN | 101036482 | 12/2010 |
| CN | 110662339 A | 1/2020 |
| CN | 110872714 | 3/2020 |
| DE | 101 51 270 | 10/2006 |
| EP | 621051 | 10/1994 |
| EP | 0763500 | 3/1997 |
| EP | 0878208 | 11/1998 |
| EP | 1036758 | 9/2000 |
| EP | 2151554 | 2/2010 |
| EP | 1854494 | 6/2012 |
| EP | 2565157 | 10/2017 |
| EP | 3372267 | 12/2018 |
| JP | H04132560 | 5/1992 |
| JP | 2000102616 | 4/2000 |
| JP | 2003339872 | 12/2003 |
| JP | 2003339872 A | 12/2003 |
| JP | 2004065636 | 3/2004 |
| JP | 2006273677 | 10/2006 |
| KR | 100841741 | 6/2008 |
| KR | 20100087977 | 8/2010 |
| RU | 2199167 | 2/2003 |
| WO | WO199507610 | 3/1995 |
| WO | WO2004032719 | 4/2004 |
| WO | WO2005094138 | 10/2005 |
| WO | WO2005110441 | 11/2005 |
| WO | WO2008/019102 | 2/2008 |
| WO | WO2008/112143 | 9/2008 |
| WO | WO2008116991 | 10/2008 |
| WO | WO2009018837 | 2/2009 |
| WO | WO2010021944 | 2/2010 |
| WO | WO2011/002606 | 1/2011 |
| WO | WO2012014805 | 2/2012 |
| WO | WO2012/034089 | 3/2012 |
| WO | WO2012/094008 | 7/2012 |
| WO | WO2012/155213 | 11/2012 |
| WO | WO2013/052548 | 4/2013 |
| WO | WO2013/070712 | 5/2013 |
| WO | WO2013/181179 | 12/2013 |
| WO | WO2014/085719 | 6/2014 |
| WO | 2014144184 A2 | 9/2014 |
| WO | WO2014/143842 | 9/2014 |
| WO | WO2014/144151 | 9/2014 |
| WO | WO2015/049783 | 4/2015 |
| WO | WO2015/066278 | 5/2015 |
| WO | WO2015/127085 | 8/2015 |
| WO | 2015168517 A1 | 11/2015 |
| WO | 2015172160 A1 | 11/2015 |
| WO | WO2016/064863 | 4/2016 |
| WO | WO-2016064863 A1 * | 4/2016 | ........ A61M 16/0003 |
| WO | WO2018/157172 | 8/2018 |
| WO | WO2018/157175 | 8/2018 |
| WO | WO2019/046413 | 3/2019 |
| WO | WO2019/046415 | 3/2019 |
| WO | WO2019/133776 | 7/2019 |
| WO | WO2019/133777 | 7/2019 |
| WO | WO2019/222640 | 11/2019 |
| WO | WO2020/033768 | 2/2020 |
| WO | WO2020/115473 | 6/2020 |
| WO | WO2020/142658 | 7/2020 |
| WO | WO2020/148155 | 7/2020 |
| WO | WO2020/150195 | 7/2020 |
| WO | WO2020/232414 | 11/2020 |
| WO | WO2020/232419 | 11/2020 |
| WO | WO2021/087382 | 5/2021 |
| WO | WO2021/142472 | 7/2021 |
| WO | WO2021/154833 | 8/2021 |
| WO | WO2021/245667 | 12/2021 |
| WO | WO2021/258025 | 12/2021 |
| WO | WO2022/123567 | 6/2022 |
| WO | WO2022/123574 | 6/2022 |
| WO | WO2022/123580 | 6/2022 |
| WO | WO2022/192757 | 9/2022 |
| WO | WO2023018992 | 2/2023 |
| WO | WO2023049873 | 3/2023 |
| WO | WO2023092103 | 5/2023 |
| WO | 2023201363 A1 | 10/2023 |
| WO | WO2023201363 | 10/2023 |

OTHER PUBLICATIONS

DiBlasi et al., "Evidence-Based Clinical Practice Guideline: Inhaled Nitric Oxide for Neonates With Acute Hypoxic Respiratory Failure", Respiratory Care (2010), vol. 55, No. 12, pp. 1717-1745.

Edwards et al., "Current Modes of Conventional Ventilation in Intensive Care", BJA CEPD Reviews, vol. 2, No. 2, pp. 41-44, Apr. 1, 2002.

Ehrenwerth et al., Anesthesia Equipment, Principles and Applications, Chapter 6, Anesthesia Ventilators, pp. 140-171, Mosby Publishing, 1993.

Engstrom Ventilator Technical Reference Manual.

Ikaria, INOmax DSIR® Operation Manual (2012).

Kirmse et al., "Delivery of Inhaled Nitric Oxide Using the Ohmeda INOvent Delivery System", Chest (1998), vol. 113, Issue 6, pp. 1650-1657.

Maeda et al., "Generation Mechanism of Micro-Bubbles in a Pressurized Dissolution Method", Experimental Thermal and Fluid Science, vol. 60, pp. 201-207, Jan. 1, 2015.

Malik, "Nitric Oxide Production by High Voltage Electrical Discharges for Medical Uses: A Review" Plasma Chem Plasma Process, (2016), vol. 36, pp. 737-766.

Montgomery et al., "Inhaled Nitric Oxide Delivery and Monitoring", Journal of Clinical Monitoring and Computing (1999), vol. 15, pp. 325-335.

Shoobert et al., "Iridium Electrodes Increase Spark Plug Life", Platinum Metals Rev., 1962, vol. 6, No. 3, pp. 92-94.

Ventilator/Respirator Hardware and Software Design Specification, Rev. 0, Nov. 2011, Freescale Semiconductor, Inc.

Young et al., "Delivery and monitoring of inhaled nitric oxide", Intensive Care Med. (1996), vol. 22, pp. 77-86.

Arjunan Thesis—Plasma Produced Reactive Oxygen and Nitrogen Species in Angiogenesis—May 2011—Krishna Priya Arjunan.

Arora et al., Nitric Oxide Regulation of Bacterial Biofilms, Biochemistry, vol. 54, pp. 3717-3728, May 21, 2015.

Barraud et al., Involvement of Nitric Oxide n Biofilm Dispersal of Pseudomonas Aeruginosa, Journal of Bacteriology, vol. 188, No. 21, pp. 7344-7353, Nov. 2006.

Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.

Bentur et al., Pilot Study to Test Inhaled Nitric Oxide in Cystic Fibrosis Patients with Refractory *Mycobacterium abscessus* Lung Infection, Journal of Cystic Fibrosis, vol. 19, pp. 225-231, May 23, 2019.

(56)                    References Cited

OTHER PUBLICATIONS

Birkeland, K., "On the Oxidation of Atmospheric Nitrogen in Electric Arcs", A Paper read before the Faraday Society on Monday, Jul. 2, 1906, Published on Jan. 1, 1906.

Bogdonovski et al., Anti-Mycobacterial Activity of High-Dose Nitric Oxide Against *Mycobacterium abscessus* In Vitro, National Institutes of Health Poster, Jul. 8, 2018.

Charles, et al., "SiO2 Deposition from Oxygen/Silane Pulsed Helicon Diffusion Plasmas" Applied Physics Letters, vol. 67, No. 1, pp. 40-42, Jul. 3, 1995.

Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.

Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.

Donohoe et al., "Production of O3, NO, and N2O in a Pulsed Discharge at 1 Atm", Ind. Eng. Chem., Fundam., vol. 16, No. 2, pp. 208-215, May 1977.

Encyclopaedia Britannica, "Soda Lime" published Nov. 12, 2018, https://www.britannica.com/science/soda-lime.

Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.

Fowler, "Exercise Intolerance in Pulmonary Arterial Hypertension", Pulmonary Medicine, vol. 2012, Article ID 39204, 11 pages, (2012).

Habib, Bassam Hanna, "A Simple Model of Spark Gap Discharge Phase", Eng. & Tech. Journal, vol. 31, Part (A), No. 9, pp. 1692-1704, 2013.

Hanning et al., "Pulse Oximetry: A Practical Review", British Medical Journal, vol. 311, pp. 367-370, Aug. 5, 1995.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).

Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.

Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.

Hu, Hui et al., "Study on Production of Nitric Monoxide for Respiratory Distress by Pulsed Discharge", Proceedings of the CSEE, vol. 23, No. 2, Jan. 2005.

Hu, Hui et al., "Study on Pulsed Arc Discharge Conditions on Production of Nitric Oxide for Medical Application", High Voltage Apparatus, Issue 3, Mar. 2005.

Hu et al., "Study on Production of Inhaled Nitric Oxide for Medical Applications by Pulsed Discharge" IEEE Transactions on Plasma Science, vol. 35, No. 3, pp. 619-625, Jun. 2007.

Hu, Hui et al., "The Effect of Flow Distribution on the Concentration of NO Produced by Pulsed Arc Discharge", Plasma Science and Technology, vol. 9, No. 6, pp. 766-769, Dec. 2007.

Hu, Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).

Intersurgical Complete Respiratory Systems, Carbon Dioxide Absorbents Catalogue, www.intersurgical.com/distributors, Issue 5, Oct. 17, 2021.

Johns Hopkins University—"American Chemical Journal vol. XXXV"—No. 4, Reports Chapter, pp. 358-368, Apr. 1906.

Keshav, Saurabh. "Using Plasmas for High-speed Flow Control and Combustion Control" Diss. The Ohio State University, 2008.

Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.

Kuo, Spencer P. "Air Plasma for Medical Applications" J. Biomedical Science and Engineering, vol. 5, pp. 481-495, Sep. 2012.

Li, Z. et al., "Development of Miniature Pulsed Power Generator," 2005 IEEE Pulsed Power Conference, Monterey, CA, pp. 1053-1056, Jul. 2005.

Li et al., Production of Medically Useful Nitric Monoxide Using AC Arc Discharge, Nitric Oxide, vol. 73, pp. 89-95, Feb. 28, 2018.

Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.

Lovich et al., "Generation of Purified Nitric Oxide from Liquid N204 for the Treatment of Pulmonary Hypertension in Hypoxemic Swine", Nitric Oxide vol. 37, pp. 66-77, Feb. 15, 2014.

Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.

McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.

Miller et al., Gaseous Nitric Oxide Bactericidal Activity Retained During Intermittent High-Dose Short Duration Exposure, Nitric Oxide, vol. 20, Issue 1, pp. 16-23, Feb. 2009.

Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.

Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.

Miller et al., A Phase I Clinical Study of Inhaled Nitric Oxide in Healthy Adults, Journal of Cystic Fibrosis, vol. 11, pp. 324-331, Apr. 18, 2012.

Mok et al. "Application of Positive Pulsed Corona Discharge to Removal of SO2 and NOx," Proceedings, ICESP VII, Sep. 20-25, 1998, Kyongiu, Korea.

Namihira et al., Production of Nitric Monoxide Using Pulsed Discharges for a Medical Application, IEEE Transactions on Plasma Science, vol. 28, No. 1, pp. 109-114, Feb. 2000.

Namihara et al., "Production of NO Using Pulsed Arc Discharges and Its Medical Applications", Journal of Plasma and Fusion Research, vol. 79, No. 1 pp. 35-38, Jun. 25, 2002.

Namihira et al., "Production of Nitric Monoxide in Dry Air Using Pulsed Discharge," Digest of Technical Papers. 12th IEEE International Pulsed Power Conference. (Cat. No. 99CH36358), Monterey, CA, pp. 1313-1316 vol. 2, Aug. 6, 2002.

Namihira et al., Production of Nitric Oxide Using a Pulsed Arc Discharge, IEEE Transactions on Plasma Science, vol. 30, No. 5, pp. 1993-1998, Oct. 2002.

Namihira et al., "Temperature and Nitric Oxide Generation in a Pulsed Arc Discharge Plasma" Plasma Science and Technology, vol. 9, No. 6, pp. 747-751, Dec. 2007.

Navarro-Gonzalez et al., "The Physical Mechanism of Nitric Oxide Formation in Simulated Lightning" Geophysical Research Letters, vol. 28, No. 20, pp. 3867-3870, Oct. 15, 2001.

Olivier et al., Treatment of Refractory *Mycobacterium abscessus* Lung Infection with Inhaled Intermittent Nitric Oxide, Poster, Jul. 8, 2018.

Overzet, et al. "Why and How to Pulse a Plasma"—slide show presentation, Oct. 1997.

Patil et al., Plasma Assisted Nitrogen Oxide Production from Air, AiChE Journal, vol. 64, Issue 2, pp. 526-537, Aug. 14, 2017.

Pawlat et al., Evaluation of Oxidative Species in Gaseous, Plasma Chemistry and Plasma Processing, vol. 39, pp. 627-642, Mar. 28, 2019.

(56) References Cited

OTHER PUBLICATIONS

Pontiga, F., et al., "Nitrogen Oxides Generation Induced by Negative Corona Discharge in N2+02 Mixtures," 2006 IEEE Conference on Electrical Insulation and Dielectric Phenomena, Kansas City, MO, pp. 264-267, Oct. 2006.

Sakai, et al., "A Compact Nitric Oxide Supply for Medical Application," 2007 16th IEEE International Pulsed Power Conference, Albuquerque, NM, pp. 752-755, Oct. 14, 2008.

Sakai et al., "Nitric Oxide Generator Based on Pulsed Arc Discharge" Acta Physica Polonica A, vol. 115, No. 6, pp. 1104-1106, Jun. 2009.

Schilz, "Treatment of Pulmonary Hypertension Related to Disorders of Hypoxia" Advances in Pulmonary Hypertension, vol. 4, No. 2, pp. 14-22, May 2005.

Takaki, et al., "Resistance of Pulsed Arc Discharge in Air and SF/sub 6", Pulsed Power Plasma Science, vol. 2, pp. 1758-1761, Jun. 2001.

Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.

Tsukahara et al., "Gas-Phase Oxidation of Nitric Oxide: Chemical Kinetics and Rate Constant," Nitric Oxide: Biology and Chemistry, vol. 3, No. 3, pp. 191-198, Jun. 1999.

Wang et al., Gliding Arc Plasma for CO2 Conversion, Chemical Engineering Journal, vol. 330, pp. 11-25, 2017.

Yaacoby-Bianu et al., Compassionate Nitric Oxide Adjuvant Treatment of Persistent Mycobacterium Infection in Cystic Fibrosis Patients, The Pediatric Infectious Disease Journal, vol. 37, No. 4, Apr. 2018.

Yu, et al., "Detection and Removal of Impurities in Nitric Oxide Generated from Air by Pulsed Electrical Discharge", Nitric Oxide, vol. 60, pp. 16-23, Nov. 30, 2016.

Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.

* cited by examiner

Air Pump 96

High Voltage PCB 98

Upper Manifold & PCB 100

Proportional Valve 102

DC Power Entry 104

HV Transformer 106

AC Power Entry 108

Air Reservoir 110

Flow Director Valve 112

Lower Manifold 94

Gas Sensor Pack 92

Carrying Handle 80

Touchscreen Interface 82

High Voltage Faraday Cage 84

Main Control Board 86

Cooling Fan(s) 88

Water Trap Level PCB 90

510

Burst

Discharge Pulse

Plasma AC Current

Side View

Cross-Section

Packaged
Assembly

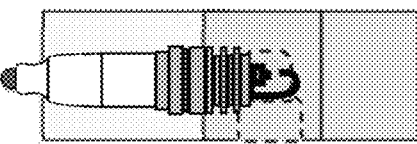
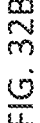
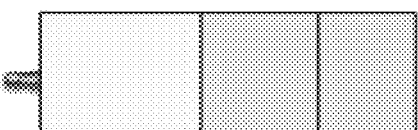
FIG. 32B
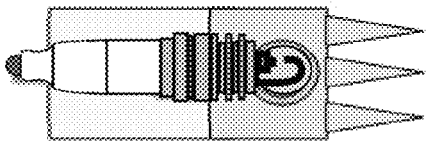
FIG. 32A
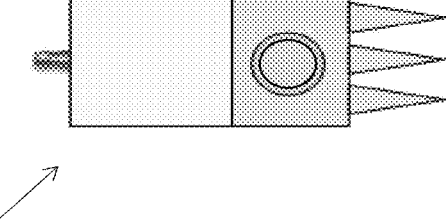
540

610

620

Spacer

630

640

560

Electrode
662

664

Insulative
frame 666

Cooling Fin
669

Sputtering
Surface
668

690

Threaded Connector

Ceramic Insulator
698

Shell

Center Electrode

Ground Electrode
696

694

Gap
702

O-ring
700

Ground Electrode Pad
692

960  Scavenger Cartridge

962  Vent Cartridge

Sensor Pack

970

984 U-Channel

986 Custom Bagging component supports dP flow sensing.

982 Flow Sensor(s) that cover Neo thru Adult

972 Vent Flow In

974 Vent Flow Out

976 NO Injected through Sample Line Adapter

978 Bag Flow In

980 Bag Flow Out

1000

Vent NO Circuit 1 1002

Vent NO Circuit 2 1004

Vent NO Circuit 1006

Bag

Pre-Spark Scavenger 1008

Box Air Inlet + Filter 1010

1012 Extruded or molded Scavenger Tubes

1014 End Cap

1016 Air Inlet Grille

- Waveform generator was used to match vent activity with valve operation.

Spark rate was held constant. Flow rate was varied.

1160
Pump

1162
Pump

1166
Variable
Orifice

1164
Fixed Orifice

1168
Electrode Assembly
& Plasma Chamber

1224

1228

1230

1226

Nasal prongs

One or more solid-walled lumens for O2 delivery

End view of prongs.
Red is NO lumen

1270

Perforated Air Lumen

Red line is separate
NO line that
delivers all the way
into nasal prongs

NO Generation
Device Controller

1300

Barbs Lower

Female in

Barbs Higher

Possible cartridge location

Possible cartridge location

Ambulatory Configuration with O2 source

Device design that measures O2 pressure to detect respirations and synchronize gas delivery Ambulatory Configuration with O2 source Device measures flow of O2 and scales
NO delivery accordingly
FS = Flow sensor
P = Pressure sensor for detecting
inspirations Ambulatory Configuration with O2 source Device measures flow of O2 and scales
NO delivery accordingly
FS = Flow sensor
P = Pressure sensor for detecting inspirations Sample gas flow in Water trap
1596

Sample gas pump
1598

Flow restriction to make sample gas flow consistent
1600

Nafion tubing to control humidity
1602

$O_2$, NO, $NO_2$, or $CO_2$ sensors
1592

1590

1594

1610

1616 Sensors

1615 Manifold

Self-test gas inlet

1618 Gas outlet

Pump located 1620 under manifold

Electrical connections to primary equipment

1614 Sample gas inlet from water trap

Location of water trap 1612

Location of capacitive sensors for water trap

Circuit board for A2D, I2C communication, pump power, water trap sensors

1730

Flow Sensor
NO Out

Filter

1734

Scavenger

Air inlet 1732

1736

Triple-lumen

P1

P2

NO + air output

Combined Scavenger and Ambient Air Filter

Filtered Ambient
Air Out

1744
NO + air out

Ambient Air in
1748

1742
NO + NO2 + Air in

Partition
1748

1740

1760

Flow Sensor

NO Out

Flow Sensor
Electrical Connection     1762

Combined NO2 scavenger and
NO output fitting     1764

Ambient Air inlet

SYSTEMS AND METHODS FOR GENERATING NITRIC OXIDE

RELATED APPLICATIONS

This application is a continuation patent application of U.S. application Ser. No. 17/855,592, filed Jun. 30, 2022, which is a continuation patent application of U.S. application Ser. No. 17/197,911, filed Mar. 10, 2021, now U.S. Pat. No. 11,376,390, which is a continuation patent application of U.S. application Ser. No. 16/909,722, filed Jun. 23, 2020, now U.S. Pat. No. 10,946,163, which is a continuation patent application of U.S. application Ser. No. 16/697,498, filed Nov. 27, 2019, now U.S. Pat. No. 10,695,523, which is a continuation patent application of U.S. application Ser. No. 16/388,464, filed Apr. 18, 2019, now U.S. Pat. No. 10,532, 176, which is a continuation patent application of U.S. application Ser. No. 15/907,241, filed Feb. 27, 2018, now U.S. Pat. No. 10,286,176, which claims the benefit of and priority to U.S. Provisional Application No. 62/463,943 filed Feb. 27, 2017, U.S. Provisional Application No. 62/463,956 filed Feb. 27, 2017, U.S. Provisional Application No. 62/509,394 filed May 22, 2017, U.S. Provisional Application No. 62/553,572 filed Sep. 1, 2017, U.S. Provisional Application No. 62/574,173 filed Oct. 18, 2017, and U.S. Provisional Application No. 62/614,492 filed Jan. 7, 2018, and the contents of each of these applications are hereby incorporated herein by reference in their entireties.

FEDERALLY SPONSORED RESEARCH OR DEVELOPMENT

This invention was made with government support under Grant No. R44 HL134429, awarded by the National Institutes of Health (NIH). The government has certain rights in the invention.

FIELD

The present disclosure relates to systems and methods for generating nitric oxide for use with a ventilation device.

BACKGROUND

Nitric oxide has found to be useful in a number of ways for treatment of disease, particularly cardiac and respiratory ailments. Previous systems for producing NO and delivering the NO gas to a patient have a number of disadvantages. For example, tank-based systems required large tanks of NO gas at a high concentration and pressure. When treatment using this system is paused, NO in the circuit stalls and converts into $NO_2$, requiring the user to purge the manual ventilation circuit before resuming manual ventilation. Synthesizing NO from $NO_2$ or $N_2O_4$ requires the handling of toxic chemicals. Prior electric generation systems involve generating plasma in the main flow of air to be delivered to patients, or pumped through a delivery tube.

Calibration of current systems can also be difficult, as a user is required to connect high pressure gas canisters containing calibration gas to the system. Calibration gases typically include NO, $NO_2$, and $O_2$. For one concentration and one gas at a time, gas is flowed through the sensor chamber to provide a known input. This manual calibration can take roughly 15 minutes or more of trained personnel time. When tank-based systems flow, they release high-concentration (approximately 800 ppm) NO into the ventilation system. When treatment with a tank-based system is paused, NO in the manual circuit (Ambu-bag or equivalent) stalls and converts into NO, requiring the user to purge the manual ventilation device circuit before resuming manual ventilation.

SUMMARY

The present disclosure is directed to systems, methods and devices for nitric oxide generation for use with various ventilation devices. In some embodiments, a nitric oxide generation system comprises one or more plasma chambers each including one or more electrodes configured to generate a product gas containing nitric oxide using a flow of a reactant gas through the one or more plasma chambers. A controller is configured to regulate the amount of nitric oxide generated in the product gas by the one or more electrodes in the one or more plasma chambers using one or more parameters as input to a control algorithm, and at least one of the one or more parameters being related to the flow rate of the reactant gas into the one or more plasma chambers. A reactant gas source is configured to provide instantaneous high-pressure reactant gas to the one or more plasma chambers. A flow controller is positioned between the reactant gas source and the one or more plasma chambers and configured to provide a controlled continuous variable flow of the reactant gas from the reactant gas source based on a measurement associated with a medical gas into which the product gas flows. One or more scavenger paths configured to remove $NO_2$ from the product gas generated by the one or more plasma chambers. The concentration of NO in the combined product gas and medical gas is a target value.

In some embodiments, the measurement associated with the medical gas is the flow rate of the medial gas such that the air flow of the reactant gas through the one or more plasma chambers is proportional to the flow rate of the medical gas.

In some embodiments, the reactant gas source is in the form of a reservoir. In some embodiments, the reactant gas source is in the form of a pump. In some embodiments, the flow controller is selected from the group consisting of one or more proportional valves, one or more digital valves, and a combination of at least one proportional valve and at least one digital valves. In some embodiments, the system also includes one or more filters positioned to receive NO-enriched air from the one or more scavenger paths and configured to filter the NO-enriched air. In some embodiments, the system also includes a digital signal processor that generates a continuous, customizable control AC waveform as an input to a high voltage circuit. The digital signal processor is configured to control the shape of the AC waveform by controlling its frequency and duty cycle.

In some embodiments, a nitric oxide generation system comprises one or more plasma chambers each including one or more electrodes configured to generate a product gas containing nitric oxide using a flow of a reactant gas through the one or more plasma chambers. A controller is configured to regulate the amount of nitric oxide generated in the product gas by the one or more electrodes in the one or more plasma chambers using one or more parameters as input to a control algorithm, and at least one of the one or more parameters being related to the flow rate of the reactant gas into the one or more plasma chambers. A reactant gas source is configured to provide instantaneous high pressure reactant gas to the one or more plasma chambers. A flow controller is positioned between the reactant gas source and the one or more plasma chambers and configured to provide a controlled continuous variable flow of the reactant gas from the reactant gas source based on a measurement associated with a medical gas into which the product gas flows. The concentration of NO in the combined product gas and medical gas is a target value.

In some embodiments, the system also includes one or more scavenger paths configured to remove $NO_2$ from the product gas generated by the one or more plasma chambers. In some embodiments, the reactant gas source is in the form of a reservoir. In some embodiments, the reactant gas source is in the form of a pump.

In some embodiments, a nitric oxide generation system comprises one or more plasma chambers each including one or more electrodes configured to generate a product gas containing nitric oxide using a flow of a reactant gas through the one or more plasma chambers. A controller is configured to control the amount of nitric oxide generated in the product gas by the one or more electrodes in the one or more plasma chambers based on a control algorithm with one or more input parameters by varying at least one or more of the flow rate of the reactant gas into the one or more plasma chambers and a plasma power in the one or more plasma chambers. A reactant gas source is configured to provide instantaneous high pressure reactant gas to the one or more plasma chambers. A flow controller is positioned between the reactant gas source and the one or more plasma chambers and configured to provide a controlled continuous variable flow of the reactant gas from the reactant gas source based on a measurement associated with a medical gas into which the product gas flows. The concentration of NO in the combined product gas and medical gas is a target value.

In some embodiments, the control algorithm input parameters are selected from the group consisting of concomitant treatment parameters, patient parameters, ambient environment parameters, device parameters, and NO treatment parameters. In some embodiments, the concomitant treatment parameters include flow, pressure, gas temperature, gas humidity information relating to one or more device being used in conjunction with the NO generation system. In some embodiments, the patient parameters include inspiratory flow, $SpO_2$, breath detection, tidal volume, minute volume, or expiratory $NO_2$. In some embodiments, the ambient environment parameters include ambient temperature, ambient pressure, ambient humidity, ambient NO, or ambient $NO_2$. In some embodiments, the device parameters include plasma chamber pressure, plasma chamber flow, plasma chamber temperature, plasma chamber humidity, electrode temperature, electrode type, or electrode gap. In some embodiments, the NO treatment parameters include target NO concentration, indicated NO concentration, or indicated $NO_2$ concentration.

In some embodiments, the system also includes one or more scavenger paths configured to remove $NO_2$ from the product gas generated by the one or more plasma chambers. In some embodiments, the reactant gas source is in the form of a reservoir.

A method for generating NO in a product gas is also provided, and includes generating a product gas using one or more plasma chambers each including one or more electrodes containing nitric oxide using a flow of a reactant gas through the one or more plasma chambers, and regulating the amount of NO generated in the product gas using a controller in conjunction with the one or more electrodes in the one or more plasma chambers by using one or more parameters as input to a control algorithm. At least one of the one or more parameters is related to the flow rate of the reactant gas into the one or more plasma chambers. The method also includes providing instantaneous high pressure reactant gas to the one or more plasma chambers from a reactant gas source. The method also includes providing a controlled continuous variable flow of the reactant gas from the reactant gas source based on a measurement associated with a medical gas into which the product gas flows using a flow controller that is positioned between the reactant gas source and the one or more plasma chambers. One or more scavenger paths removes $NO_2$ from the product gas generated by the one or more plasma chambers. The concentration of NO in the combined product gas and medical gas is a target value.

In some embodiments, a system for generating nitric oxide is provided that comprises a cartridge configured to produce nitric oxide to be delivered through a respiratory gas delivery device. The cartridge includes an inlet for receiving reactant gas, one or more plasma chambers configured to produce nitric oxide from the reactant gas, and an outlet for delivering the nitric oxide to the respiratory gas delivery device. A controller is configured to receive feedback from the cartridge to allow the controller to regulate the production of nitric oxide by the cartridge by adjusting the flow rate of the plasma chamber gas and a duration or intensity of plasma activity in the plasma chamber. In some embodiments, the cartridge does not include a plasma chamber.

In some embodiments, the cartridge can also include one or more scavengers coupled between the one or more plasma chambers and the outlet, and the one or more scavengers (scrubbers) can be configured to remove $NO_2$ from the generated nitric oxide. The one or more scavengers can be the same length, or different lengths. Different lengths can be desirable when the purpose of each scavenger differs. Differing applications can include neonate ventilation, adult ventilation, face mask treatment and manual respiration with a bag. In some embodiments, the cartridge is a calibration cartridge that directs known amounts of NO and $NO_2$ output to one or more sensors. In an embodiment, the reactant gas is atmospheric air.

In some embodiments, the controller can also include one or more sensors configured to sense the nitric oxide concentration in the cartridge and/or patient inspiratory circuit such that the nitric oxide production can be adjusted based on feedback from the one or more sensors. In an embodiment, the controller is configured to control the duty cycle of plasma activity in a first plasma chamber at a first duty cycle to allow for the delivery of nitric oxide and to control the duty cycle of plasma activity in a second plasma chamber at a second duty cycle. The second duty cycle is less than the first duty cycle such that the plasma activity in the second plasma chamber is used to check the viability of the second plasma chamber as a backup plasma chamber to the first plasma chamber. In some embodiments, a first plasma chamber and a second plasma chamber are used in an alternating fashion to even the wear on both while still retaining a viable back-up.

In some embodiments, the one or more plasma chambers allow for simultaneous delivery of nitric oxide to one or more ventilation devices. The one or more ventilation devices can include an automatic ventilation device and a manual ventilation device. In an embodiment, the one or more plasma chambers allows for redundancy to allow for continuous nitric oxide delivery in the event of a fault in one of the one or more plasma chambers. In some embodiments, both plasma chambers are used in unison to deliver a maximum dose of NO. In some embodiments, one plasma chamber is used to deliver NO to a patient while the other plasma chamber delivers NO to a sensor bank to confirm functionality.

In some embodiments, a system for generating nitric oxide is provided that comprises a cartridge configured to deliver nitric oxide to be delivered through a respiratory gas delivery device. The cartridge includes an inlet for receiving reactant gas and an outlet for delivering the nitric oxide to the respiratory gas delivery device. A controller includes one or more plasma chambers configured to produce nitric oxide from the reactant gas. The controller is configured to receive control input from the cartridge to allow the controller to regulate the production of nitric oxide by adjusting the flow rate of the plasma chamber gas and a duration of plasma activity in the plasma chamber. In an embodiment, the control input is in the form of a flow measurement of inspiratory gases in the cartridge. In another embodiment, the control input is in the form of a pressure measurement of inspiratory gases in the cartridge.

In some embodiments, the cartridge is a self-test (calibration) cartridge that is configured to direct flow from the plasma chamber to system gas analysis sensors in the controller. In some embodiments, the cartridge is a scavenger cartridge that includes one or more scavengers configured to remove $NO_2$ from the generated nitric oxide. The one or more scavengers can be oriented in a vertical plane with a two-dimensional switchback or maze configuration. This approach provides a benefit in that product gases plunge down into pockets of scavenger material, ensuring that all gas comes into contact with scavenger material.

In some embodiments, the controller is configured to communicate with the cartridge such that the controller can access information relating to the cartridge, the information being an expiration date of the cartridge or cartridge type or unique ID. The controller can utilize the information from the cartridge related to cartridge type to control NO production.

In some embodiments, an NO generation system can vary the flow rate of air through the plasma chamber. In an embodiment, an NO generation system can use an air pump to pull $NO_2$-contaminated air away from the patient to clean the lines. In some embodiments, an NO generation system uses oxygen concentrator membrane technology to increase the $O_2$ content of gas in the plasma chamber thereby increasing the NO production efficiency. In some embodiments, an NO generation system can use oxygen concentrator technology to reduce $O_2$ concentration in the NO-containing post-plasma gas stream to reduce the $NO_2$ formation rate. In some embodiments, an NO generation system has an inspiratory flow IN and an Inspiratory flow OUT connection, but does not generate NO within the inspiratory flow. In an embodiment, an NO generation system can support two or more independent NO treatments at once, for example a ventilator circuit and a manual ventilation device.

In some embodiments, an NO generation system continues NO generation despite any alarm. In some embodiments, an NO generation system includes a watchdog circuit that monitors plasma activity and can switch plasma activity from one plasma chamber to another plasma chamber.

In some embodiments, an NO generation system includes wireless communication capability that enables two controllers to communicate, for example, directly, in order to transfer treatment and system information from one controller to the other. In another embodiment, NO generation systems can communicate indirectly through the internet or a cloud network to transfer information.

In some embodiments, an NO generation system uses one or more of inspiratory air flow, inspiratory air pressure, inspiratory air humidity, ambient temperature, ambient pressure, plasma chamber pressure, and/or humidity as inputs into the plasma control algorithm. In an embodiment, an NO generation system uses pulse width modulation of a resonating circuit to vary NO production. In some embodiments, the NO generation system modulates air flow and a plasma parameter (for example, pulse duty cycle, pulse frequency, or, burst duty cycle, burst frequency, burst duration, and/or pulse power) to maintain a constant concentration of NO leaving the plasma chamber. In some embodiments, the NO generation system modulates air flow and a plasma parameter (pulse width, frequency, or power) to maintain a constant concentration of NO in the main airflow to a patient (ventilator air stream, for example).

In some embodiments, an NO generation system uses gas output of the plasma chamber to self-check that NO and $NO_2$ are being generated. In some embodiments, an NO generation system includes a self-test (calibration) cartridge that, when inserted, either enables or initiates a self-calibration process for NO and $NO_2$ sensors. In some embodiments, the calibration cartridge can shunt flow from the calibration cartridge to the gas sensors. In some embodiments, an NO generation system includes an integrated calibration pathway for self-calibration of sensors.

In some embodiments, an NO generation system has a mode that checks the expiration date (shelf life) of a cartridge prior to permitting clinical use, or can check whether or not a cartridge has been inserted into a system previously. In some embodiments, an NO generation system can enter a cartridge check mode upon start-up, when a cartridge is removed, and when the system wakes from a sleep mode.

In some embodiments, users want to be able to direct NO to more than one treatment at a time from the same system, for example: simultaneous manual and automatic ventilation. In order to support both modes simultaneously with different flow rates and NO concentrations, in some embodiments there is an NO generation system disposable cartridge with more than one scavenger path. A system that includes redundant scavenger paths allows the system to support a plurality of different treatment methods at different NO concentrations.

In an embodiment, an $NO_2$ scavenger comprised of particles of soda lime material. This material is brittle and can fracture during transit, thus a physical filter (not to be confused with the chemical scavenger) is required to remove scavenger particulate from the air stream. In an embodiment shown in FIG. 86, the scavenger path has multiple particle filters spaced along the flow path to capture soda lime particles. This design limits the amount of particles that can collect in any one filter.

When a disposable cartridge is packaged and shipped to the customer, there is a risk that vibrations during transit could make the scavenger material settle, generating gas pathways through the cartridge that do not require contact with scavenger material. In some embodiments, the gas can make contact with scavenger material after vibration and/or when the cartridge is tilted with respect to vertical. In some embodiments, the gas can flow through the scavenger material after vibrations from transit.

In an embodiment, a cartridge can have a reusable housing that enables a user to replace scavenger material only. In an embodiment, a cartridge can include one or more outlet valves to prevent back flow from the patient inspiratory flow into the cartridge.

In an embodiment, an NO generation system includes composite electrodes comprised of a low-cost material connected to a noble metal/alloy pad. In an embodiment, an NO generation system can be used that includes an array of electrode pairs that are used one at a time for the purposes of prolonging the mean time between services. In an embodiment, electrodes may be exhausted in series or may be used in a cyclic pattern to even wear and reduce temperatures.

There are various ways to control the NO production. In some embodiments, an NO generation system can be used that determines plasma parameters by using a look up table with one or more of the following inputs: target inhaled NO concentration, cartridge type, inspired air flow rate, inspired air temperature, inspired air humidity, inspired air pressure, ambient temperature, plasma chamber pressure, plasma chamber gas flow rate, ambient pressure, ambient humidity, air reservoir pressure, inspired $O_2$ measured, inspired $O_2$ limits, reactant gas $O_2$ level and measured NO values in the ventilator inspiratory line. In some embodiments, an NO production system can be used that pulls in ambient air, pumps said air through a plasma, scavenges and filters said air prior to merging it with a secondary flow of air to a patient. In an embodiment, an NO generation system can be used that uses pumps that block flow when off to prevent creating a leak in the patient inspiratory flow. In some embodiments, an NO generation system can be used that uses a valve to block flow when NO generation is off to prevent creating a leak in the patient inspiratory flow.

In an embodiment, an NO generation system pulls in ambient air, pumps said air through a plasma, scavenges and filters said air prior to merging it with a secondary flow of air to a patient. In one embodiment, NO-containing air is filters before and after the scavenger.

In an embodiment, an NO generation system can, upon completion of patient manual ventilation, turn off the plasma but continue running the gas pump for a set time or pump rotations to purge the manual ventilation device of one or more of NO and $NO_2$. In another embodiment, the system can suck out the line to clear the line away from the patient. The time and/or pump rotations are determined based on the volume of air required to be moved to clean out the ventilator circuit of NO. Thus, air can be pumped without NO generation and air can be pumped before stopping the pump whenever treatment is stopped or paused. In an embodiment, the pump can continue to run until one or more of NO and $NO_2$ levels indicated by respective sensors are at acceptable levels.

In an embodiment, an NO generation system is provided that generates a plasma within a patient inspiratory air stream. The device measures $O_2$ levels within the inspiratory air and varies plasma parameters accordingly to maintain a particular NO concentration profile within the inspired air. In an embodiment, an NO generation system with replaceable electrodes is provided that can be used for multiple patients.

In an embodiment, an NO generation system is provided with one or more removable cartridges containing one or more of the following features: a housing, an incoming plasma air filter, ventilator flow inlet, ventilator flow conduit, ventilator flow outlet, incoming air scavenger material, enclosure air filter, plasma chamber, electrode assembly(s), an air pump, ventilator flow measurement, a manual ventilation device flow inlet, a manual ventilation device flow outlet, manual ventilation circuit flow measurement, a manual/backup selector, a sample line connection, a water trap, a water trap drain, dual $NO_2$ scavenger paths, outlet check valves, outlet filters and a memory device.

In an embodiment, an NO generation system is provided that includes redundant plasma generation that periodically checks the viability of the back-up plasma generator. In an embodiment, an NO generation system is provided with an electrode assembly comprised of an electrode pair, a heat sink, and a gas passageway. The electrode assembly can have a gas passageway consisting of a blind hole (a single opening for gas introduction and removal). In somes embodiment, an electrode assembly is configured as a Faraday-cage assembly with adequate air flow to reduce the broad-band emissions generated by the HV electrode assembly.

In an embodiment, an NO generation system with disposable cartridge with water-trap of volume greater than 20 ml (for example, 60 ml) is provided. In an embodiment, a disposable water trap with syringe-actuated valve for drainage is provided.

Relating to NO production control, in some embodiments, reactant gas flow rate and spark frequency are controlled. In an embodiment, reactant gas flow rate and spark duty cycle are controlled. In an embodiment, air flow rate is varied linearly with respiratory flow rate variation with breath. In an embodiment, plasma pulse rate can be varied as well to maintain constant NO concentration throughout the respiratory cycle. In an embodiment, air pump speed is held constant and only plasma control parameters (B=spark groups per second, P=time between discharges, N=number of discharges per group, and H=pulse time) are varied to produce required NO concentrations based on patient inspiratory flow.

In an embodiment, an NO generation system includes a mode that inspects a cartridge for proper function (spark, patency) and expiration date prior to permitting treatment. In an embodiment, an NO generation system can enter a demonstration mode when a training cartridge is inserted.

In an embodiment, an NO generation system uses $NO_2$ measurements as a substitute for NO measurements in the event of an NO sensor failure based on a known relationship between NO and $NO_2$ production. For example, for a system that generates $NO_2$ concentrations at 10% of NO concentrations, the system can only measure $NO_2$ and infer that NO levels are approximately 10x greater or more. The term "or more" is used because it takes time for inspiratory gases to travel from the sample collection location to the gas sensors. During that transit time, NO can oxidize to $NO_2$, making the indicated $NO_2$ reading higher than the level of $NO_2$ at the sample collection location.

When the NO delivery system is delivering NO to a ventilator circuit or other pulsatile air flow, the flow of air through the plasma chamber can vary. Often, the plasma chamber flow is controlled to vary in proportion to the ventilator circuit flow. Some ventilator circuit flows have zero bias flow, i.e. the flow in the circuit is zero between the end of one inspiratory period and the beginning of the subsequent inspiratory period. In this situation, a proportional NO flow would have zero flow during exhalation. Even if the plasma activity is stopped during periods of zero or very low ventilator flow, latent NO in and downstream from the plasma chamber will convert to $NO_2$ between patient breaths. In this scenario, it is beneficial to maintain a trivial amount of flow through the plasma chamber to flush remaining NO out of the system into the ventilator stream. The low flow may be generated by running a pump at a low speed, having a bleed hole in a valve before the plasma chamber so that it is never completely obstructs flow, having a side stream air path that is always open in parallel to a flow controller, having a flow proportional valve that never closes to zero opening, or other means. Without one or more of these mitigations to flush latent NO from the plasma chamber, $NO_2$ concentration may increase in the main air stream when ventilator flow, and NO delivery resume.

In an embodiment, the electrodes are located in a controller of the device rather than in a disposable cartridge. This allows the plastic of the cartridge to be positioned at a distance from the heat of the electrodes, a reduced cost of the cartridge, and increased distances from the user high voltage. It can also improve electro-magnetic interference (EMI) shielding, allow for the ability to self-calibrate the device using the controller without a calibration cartridge, and can eliminate a high voltage connection to the disposable cartridge.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 32A and FIG. 32B illustrate an exemplary embodiment of an electrode assembly with a blind hole for gas flow;

FIG. 132 is an exemplary removable combination NO module and Gas Analysis module;

FIG. 133 is an exemplary embodiment of a patient monitor coupled to an NO generation module;

FIG. 134 is an exemplary embodiment of a patient monitor coupled to an NO generation module;

FIG. 135 is an exemplary embodiment of a patient monitor and NO generation module for use in a catheterization laboratory.

FIG. 136 is an exemplary embodiment of an electric NO generation tank replacement device;

FIG. 137 is an exemplary embodiment of internal components of the device of FIG. 136;

FIG. 138 is an exemplary embodiment of an electric NO generation tank replacement device with a pressurized gas source;

FIG. 139 is an exemplary embodiment of an electric NO generation tank replacement device with a remote output;

FIGS. 140A and 140B illustrate multiple views of an exemplary embodiment of a combined scavenger and air filter;

FIG. 141 is an exemplary embodiment of an electric NO generation tank replacement device with a single lumen output;

FIG. 142 is an exemplary embodiment of an electric NO generation tank replacement device with a remote flow sensor;

FIG. 143 depicts an embodiment of a hardware architecture of an NO generation and delivery system with redundancy; and FIG. 144 is an embodiment of a Generate and Delivery NO (GDN) board.

Figure 1:
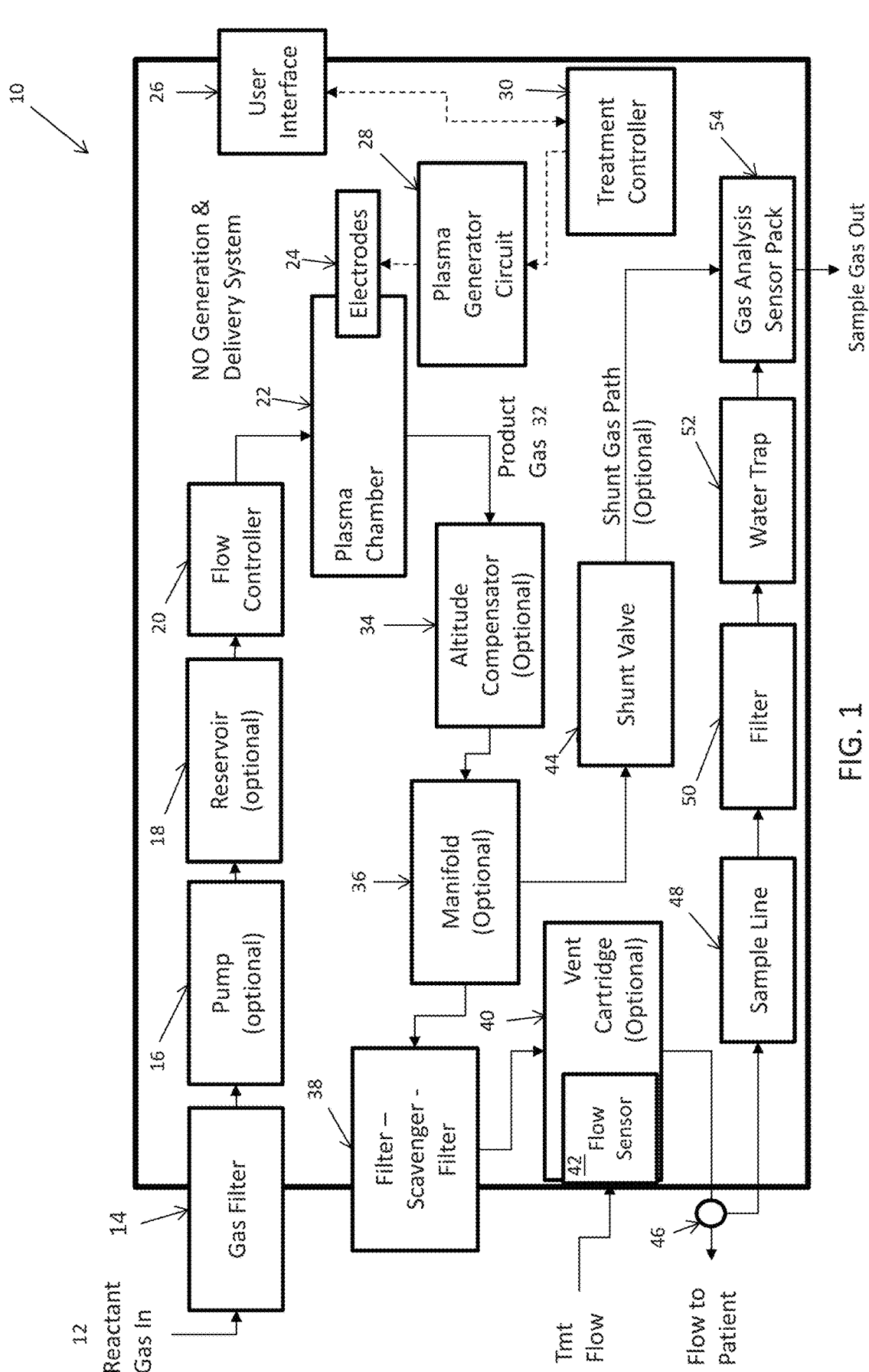
FIG. 1 is an exemplary embodiment of a system for generating an NO-enriched product gas.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure related to systems and methods of nitric oxide (NO) delivery for use in various applications, for example, in a hospital setting. An NO generation and/or delivery system can take many forms, including but not limited to a device configured to work with an existing medical device that utilizes a product gas, a stand-alone (ambulatory) device, a module that can be integrated with an existing medical device, one or more types of cartridges that can perform various functions of the NO system, and an electronic NO tank. The NO generation system uses a reactant gas, including but not limited to ambient air, to produce a product gas that is enriched with NO.

FIG. 1 illustrates an exemplary embodiment of an NO generation system 10 that includes components for reactant gas intake 12 and delivery to a plasma chamber 22. The plasma chamber 22 includes one or more electrodes 24 therein that are configured to produce, with the use of a high voltage circuit 28, a product gas 32 containing a desired amount of NO from the reactant gas. The system includes a controller 30 in electrical communication with the high voltage circuit 28 and the electrodes 24 that is configured to control the concentration of NO in the product gas 32 using one or more control parameters relating to conditions within the system and/or conditions relating to a separate device for delivering the product gas to a patient and/or conditions relating to the patient receiving the product gas. The controller 30 is also in communication with a user interface 26 that allows a user to interact with the system, view information about the system and NO production, and control parameters related to NO production.

The density of ambient air varies significantly with altitude. To support consistent operation at high altitudes or with changing ambient pressure, the pneumatic pathway can include one or more adjustable members (such as a needle valve, array of digital valves or proportional valve) whose purpose is to impose a flow restriction to raise the upstream pressure and density.

In some embodiments, the NO system pneumatic path includes a pump pushing air through a manifold 36. The manifold is configured with three-way valves and proportional orifices. The high voltage control circuit 28 controls the flow of the pump, the power in the plasma and the direction of the gas flow post-electrical discharge. By configuring valves, the high voltage control circuit can direct gas to the manual respiration pathway, the ventilator pathway or the gas sensor chamber for direct measurement of NO, $NO_2$ and $O_2$ levels in the product gas.

The output from the NO generation system in the form of the product gas 32 enriched with the NO produced in the plasma chamber 24 can either be directed to a respiratory or other device for delivery to a patient, or can be directed to a plurality of components provided for self-test or calibration of the NO generation system. In some embodiments, the system collects gases to sample in two ways: 1) gases are collected from a patient inspiratory circuit near the patient and pass through a sample line 48, a filter 50, and a water trap 52, or 2) gases are shunted directly from the pneumatic circuit as they exit plasma chamber. In another embodiment, product gases are shunted with a shunt valve 44 to the gas sensors after being scrubbed but before dilution into a patient airstream. In another embodiment, product gases are collected from an inspiratory air stream near the device and/or within the device post-dilution. Within the gas analysis portion of the device, the product gas passes through one or more sensors to measure concentrations, pressure, and flow rate of various gasses therein.

Figure 2:
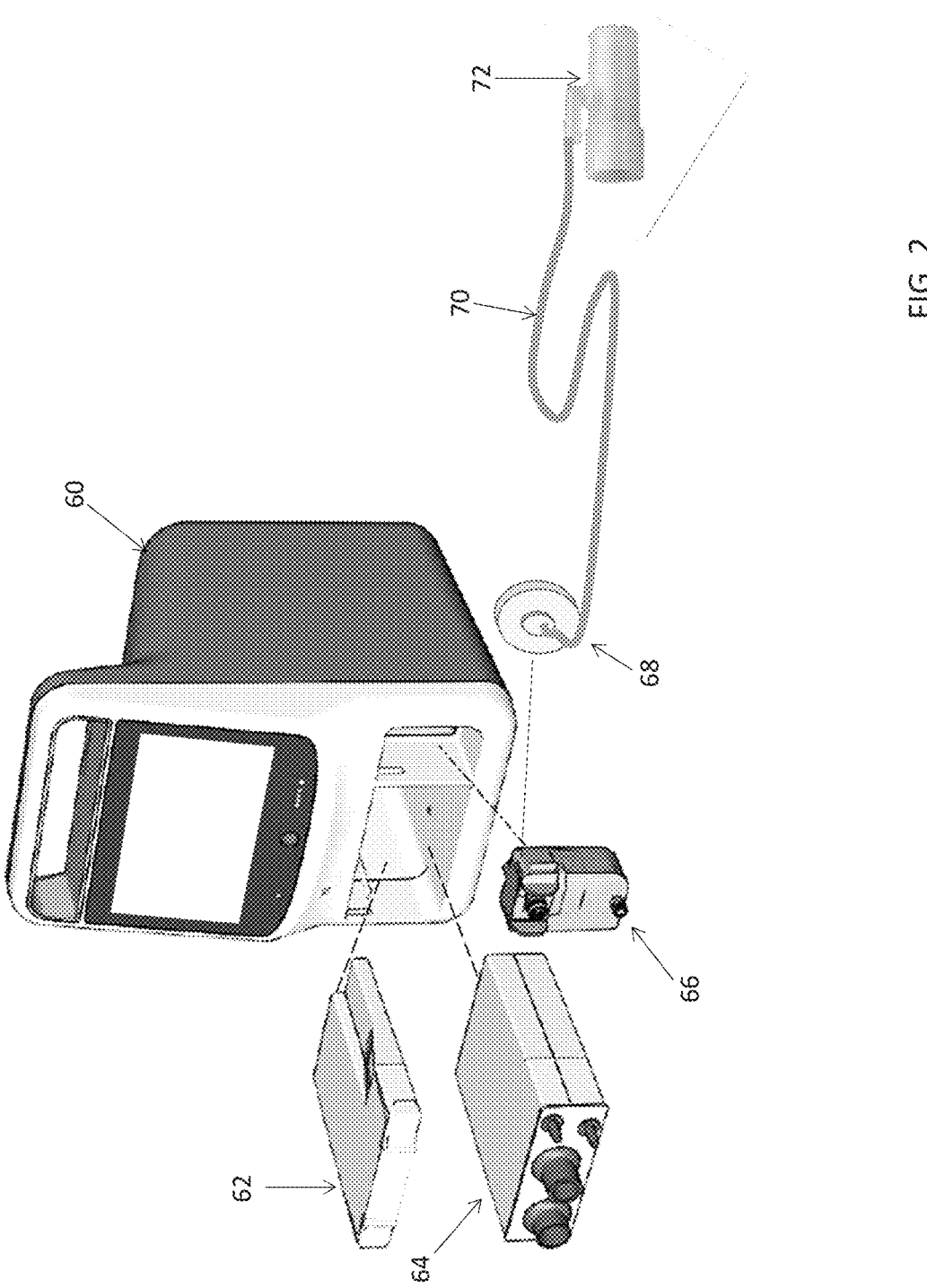
FIG. 2 is an exemplary embodiment of an NO generation system.
Figure 3:
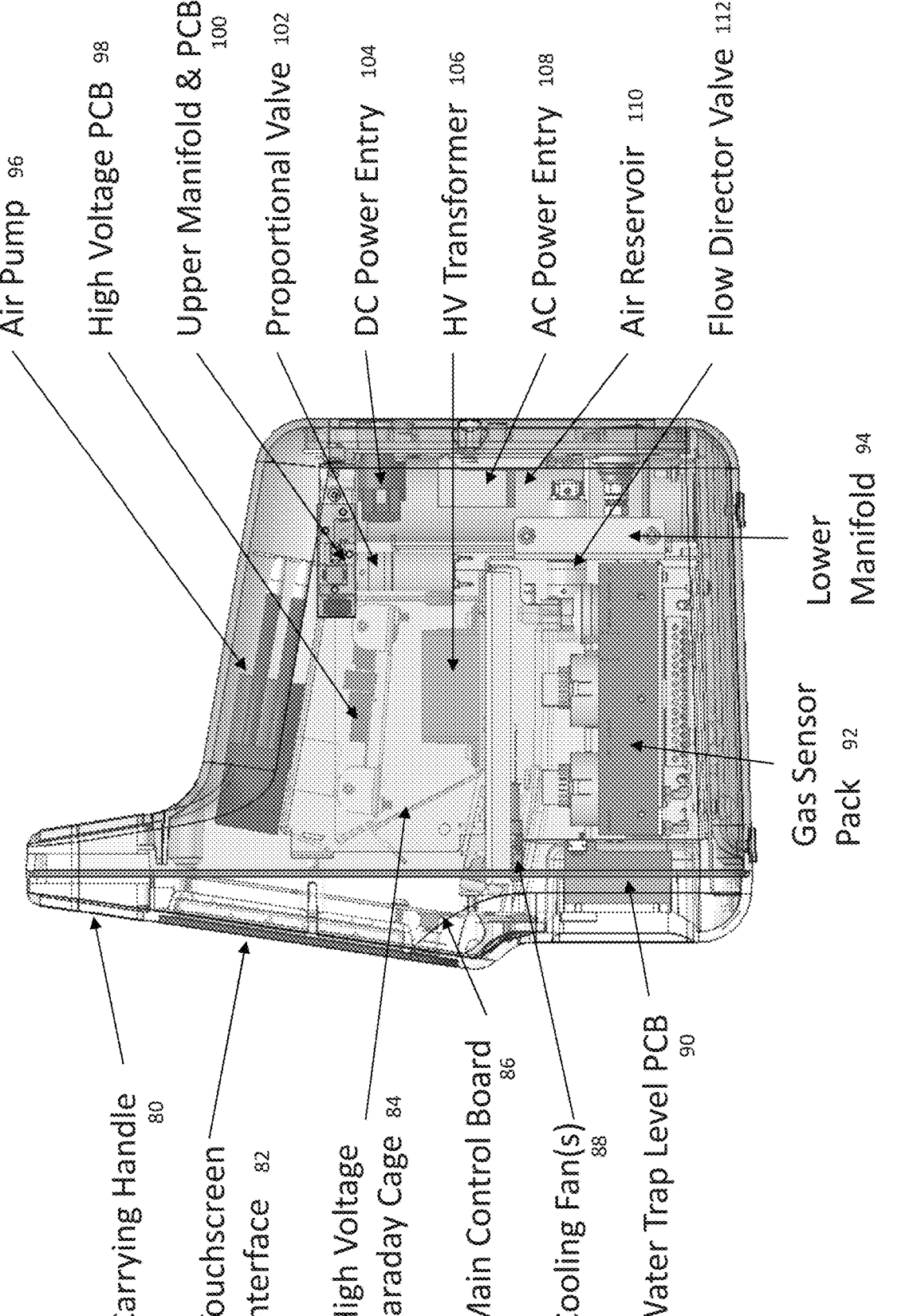
FIG. 3 is an exemplary embodiment of an NO generation system.

Another exemplary embodiment of an NO generation system 60 is shown in FIG. 2, which includes a scavenger cartridge 62, a ventilator cartridge 64, a water trap 66, a disc filter 68, a sample line 70, and a T fitting 72. Another exemplary embodiment of an NO generation system is shown in FIG. 3, which includes a carrying handle 80, an interface 82, a high voltage cage 84, a control board 86, one or more cooling fans 88, and a water trap PCB 90. The system also includes an air pump 96, a high voltage PCB 98, an upper manifold 100, a proportional valve 102, a DC power entry 104, an HV transformer 106, an AC power entry 108, a reservoir 110, and a flow director valve 112.

Delivery Types

Mechanical Ventilation

Nitric oxide in a product gas that is produced by an NO generation system can be delivered in a plurality of ways, for example, using mechanical techniques, such as inline (FIG. 4A), sidestream (FIG. 4B), and mainstream (FIG. 4C) gas delivery. Within FIG. 4A, FIG. 4B, and FIG. 4C, an NO generation device is coupled to a ventilator 122 to introduce NO-containing gas to a ventilator circuit. Inline delivery involves generating a plasma within the main flow of gas to the patient (depicted as a green box within the inspiratory airstream). Sidestream delivery 130 involves generating plasma in a small flow of gas, pumping that NO-containing gas through a tube to a fitting on the main flow of gas to the patient, as illustrated in FIG. 5A. Mainstream delivery 140 is similar to sidestream production without the tube between a plasma source and main flow of gas, as illustrated in FIG. 5B. For inline production and delivery of the NO, the nitric oxide is generated within the main gas flow of an inspiratory limb of a ventilator circuit, or an inhaler. Complexities arise, however, in this configuration because varying levels of oxygen in the inspired gas affect oxygen-nitrogen ratios, directly affecting the amount of nitric oxide generated for a given duration and intensity of plasma. In a case where a patient receives 100% oxygen, no NO could be formed due to the lack of nitrogen. Furthermore, the scavenger materials that clean $NO_2$ from the NO flow also remove $CO_2$. Scavenging the main flow of air requires a larger scavenger that can absorb $CO_2$ from the entire patient air flow in addition to $NO_2$. Another complexity with inline generation is that most configurations require opening of the ventilator circuit to replace scavenger material.

In some embodiments, an electric nitric oxide generation system can generate the plasma using atmospheric air as the reactant gas, where the oxygen composition is approximately 21% of the atmospheric air by volume. Two delivery schemes can be considered when generating nitric oxide from room air: sidestream (or off-line) and mainstream. In some embodiments of sidestream production, the plasma is generated within a controller and then pumped via a tube to the inspiratory limb of a ventilator circuit or other point of use. In some embodiments of mainstream production, the inspiratory limb flow may be routed either partially or in its entirety through the controller, thereby eliminating the need for a tube between controller and inspiratory limb.

Both sidestream and mainstream nitric oxide production within a controller can have advantages over producing nitric oxide within the inspiratory limb of a ventilator circuit. For example, production within a controller eliminates the need for a high voltage connector and cable from controller to plasma chamber, thereby eliminating the potential for a user to come into contact with the high voltage electricity required to generate a plasma. Electromagnetic emissions can be reduced owing to the lack of high voltage electrical cable that may emit electromagnetic interference during plasma generation. Generating plasma in atmospheric air can prolong electrode life because the oxygen concentration is lower than that which can be found in the inspiratory limb of a ventilator, where oxygen levels can reach up to 100%. The acoustic noise generated from continuous and/or intermittent plasma generation can be controlled better when the plasma is generated within an enclosure, as provided by the controller and/or disposable components. An oxygen sensor is not required in a system that generates plasma in atmospheric air. NO production levels vary with oxygen level, so an algorithm would be required to generate specific amounts of NO in the absence of control feedback. Less scavenger material is required for a given scavenger service life in systems that scavenge the sidestream NO-containing gas flow before it is blended with the inspiratory gas flow because the scavenger does not scavenge the entire gas flow to the patient.

Figures 4A, 4B, 4C:
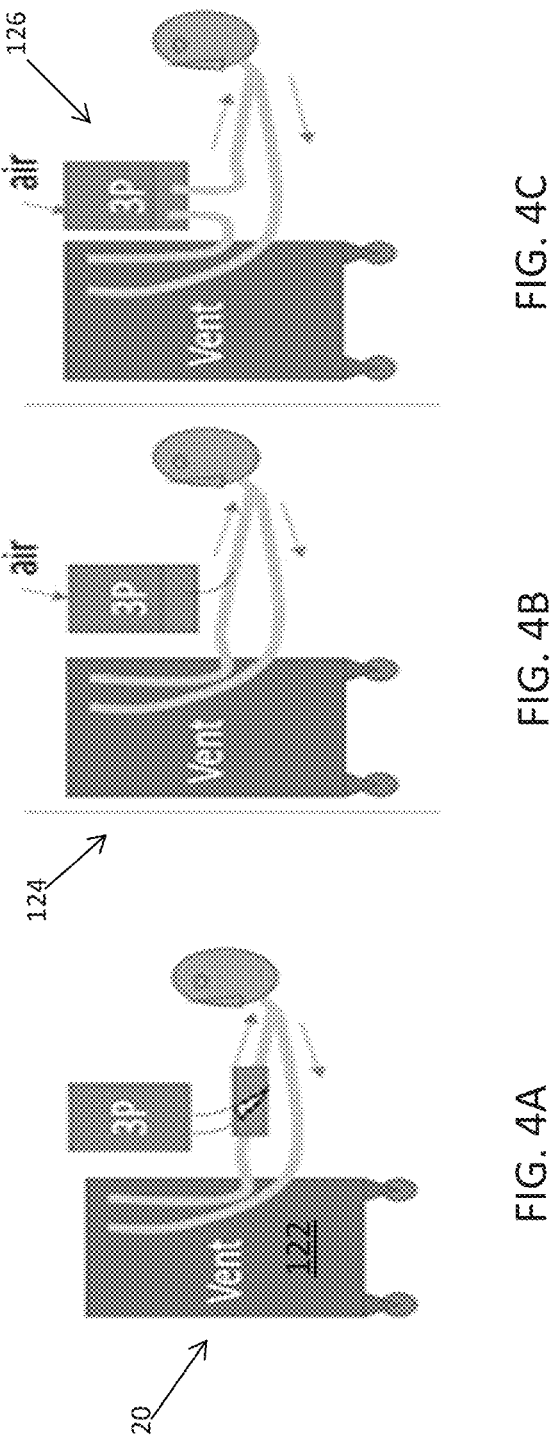
FIG. 4A is an exemplary embodiment of an inline nitric oxide generation system.
FIG. 4B is an exemplary embodiment of a sidestream nitric oxide generation system.
FIG. 4C is an exemplary embodiment of a mainstream nitric oxide generation system.
Figure 5B:
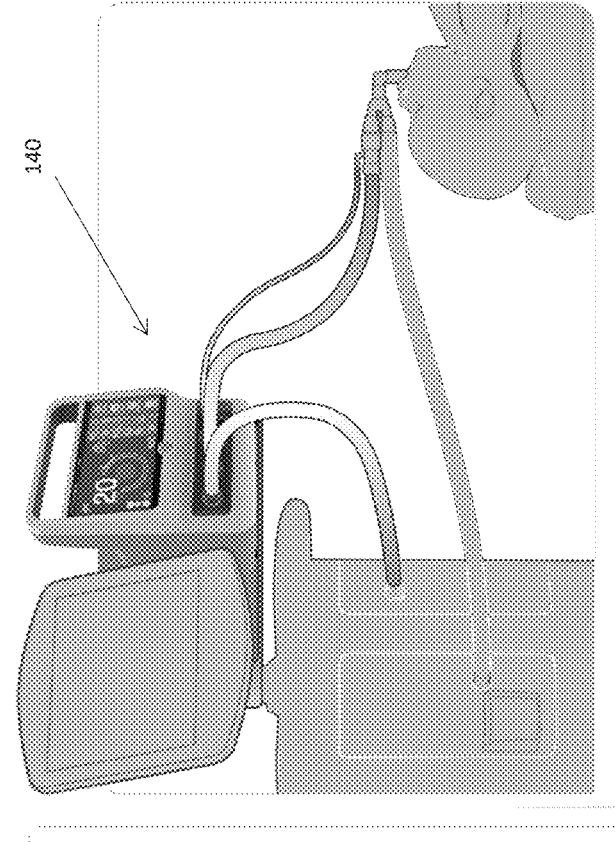
FIG. 5B is an exemplary embodiment of a mainstream nitric oxide generation system.
Figure 5A:
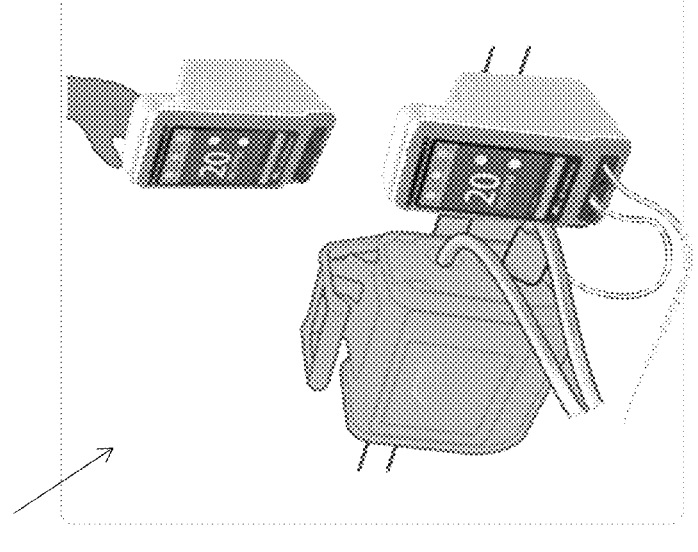
FIG. 5A is an exemplary embodiment of an inline nitric oxide generation system.

FIG. 4A, FIG. 4B, and FIG. 4C illustrate various configurations of nitric oxide generation systems for a ventilator or anesthesia circuit. FIG. 4A depicts an embodiment of an inline view 120, FIG. 4B depicts an embodiment of a sidestream view 124, and FIG. 4C depicts an embodiment of a mainstream view 126. In some sidestream embodiments, a scavenger/scrubber is located just prior to the point of injection of NO into the inspiratory flow, only scrubbing gases from the NO generation device. In some sidestream embodiments, a scavenger/scrubber is located downstream from the NO injection site, scrubbing the entire inspiratory flow.

The system can also be configured to enable the delivery of nitric oxide in either a sidestream or a mainstream mode. In some embodiments, a controller has two or more cartridge slots that can receive either a sidestream or a mainstream cartridge. The controller can generate plasma in the cartridges simultaneously, thereby supporting multiple treatments at once in any combination of mainstream and sidestream operations. In some embodiments, the controller can have a single cartridge slot and the cartridge can be used in either a sidestream or a mainstream mode.

Switching between sidestream and mainstream modes can be achieved in a variety of ways. In some embodiments, a selector switch/valve can manually reroute gas between a mainstream path and a sidestream path, or between two mainstream paths. In some embodiments, it can be achieved using software, such that a user can interact with the system, for example, with one or more buttons or a touchscreen of a user interface, such that the software can control an electromechanical apparatus to reroute flow of gas. In some embodiments, it can be achieved manually with a selector switch and software detection of switch position. Once software detects the change in switch position, it can alter air pump speed, air flow rate or plasma generation parameters to provide the desired nitric oxide concentration to the new destination. In some embodiments, gases can be rerouted passively to the sidestream application when the sidestream tubing is connected to the controller or cartridge. In some embodiments, gas can be switched between the sidestream and mainstream paths automatically based on a measured parameter from the environment, patient, or another source.

Figure 6:
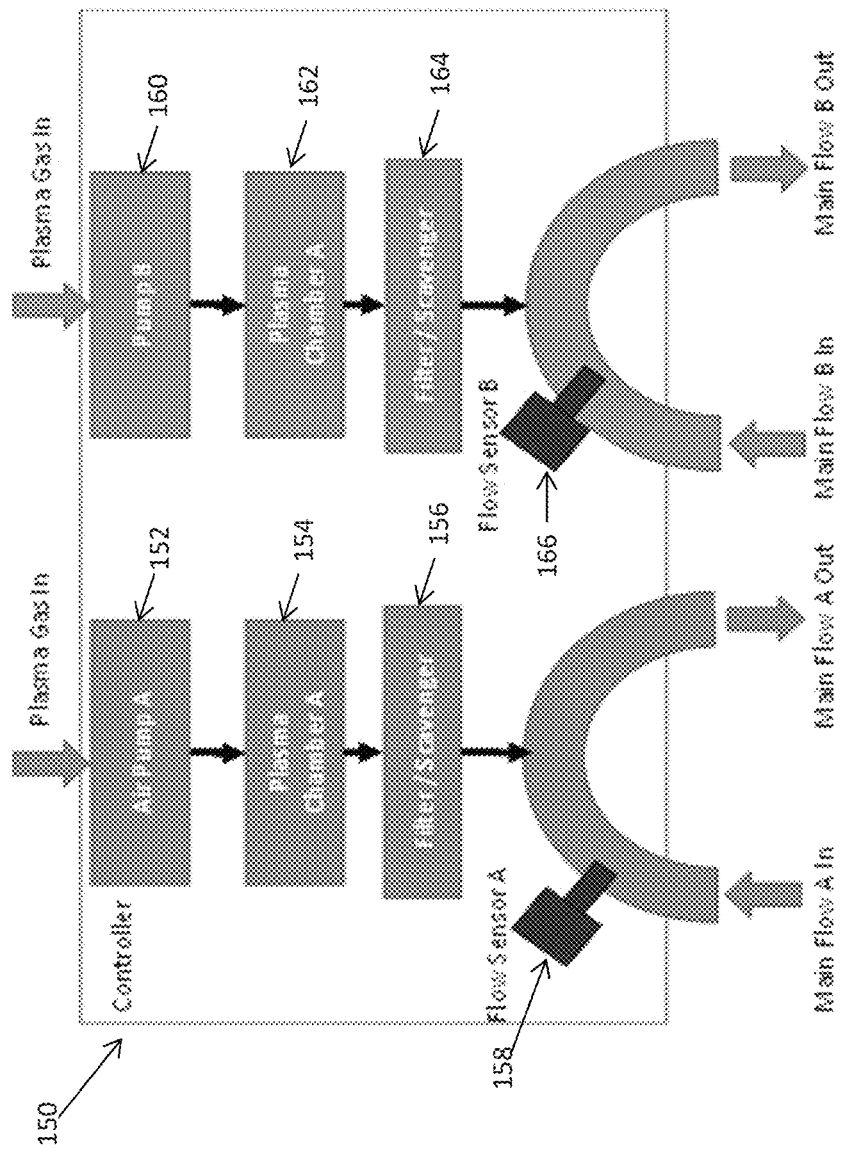
FIG. 6 is an exemplary embodiment of a controller of a nitric oxide generation system that includes more than one flow circuit.

In some embodiments, the controller can have more than one fully redundant flow circuits, each with a main flow input gas connection, a main flow output gas connection, main flow measurement, and a plasma generator with independent gas source. The redundant flow circuits allow the controller to support more than one mainstream function simultaneously. For example, the controller can support a mainstream ventilation circuit and a mainstream respiratory manual ventilation device circuit. When support of more than one separate NO application is not required, the additional circuit(s) can serve as a back-up to the first circuit. Engagement of the second circuit can occur based manual input (a lever position for example) or automatically (for example using a solenoid valve). It is common to have a filter/scavenger as part of the system which could be located between the plasma and ventilator flow gases or in-series with the ventilator gas flow. Referring to FIG. 6, a controller 150 is illustrated with two independent flow circuits to support ventilator and manual ventilation function simultaneously. Each flow circuit includes an air pump 152, 160, a plasma chamber 154, 162, and a filter/scavenger 156, 164 that couples to a main flow line having a flow sensor 158, 166.

In some embodiments, the controller receives flow from an external gas source, measures that flow and supplements that flow with plasma-generated NO at a rate consistent with the user-requested nitric oxide concentration. The gas source can be a ventilator, a compressed gas cylinder, a wall gas outlet, gas blender or other type of gas source that is configured to provide reactant gas to the system.

Figure 7:
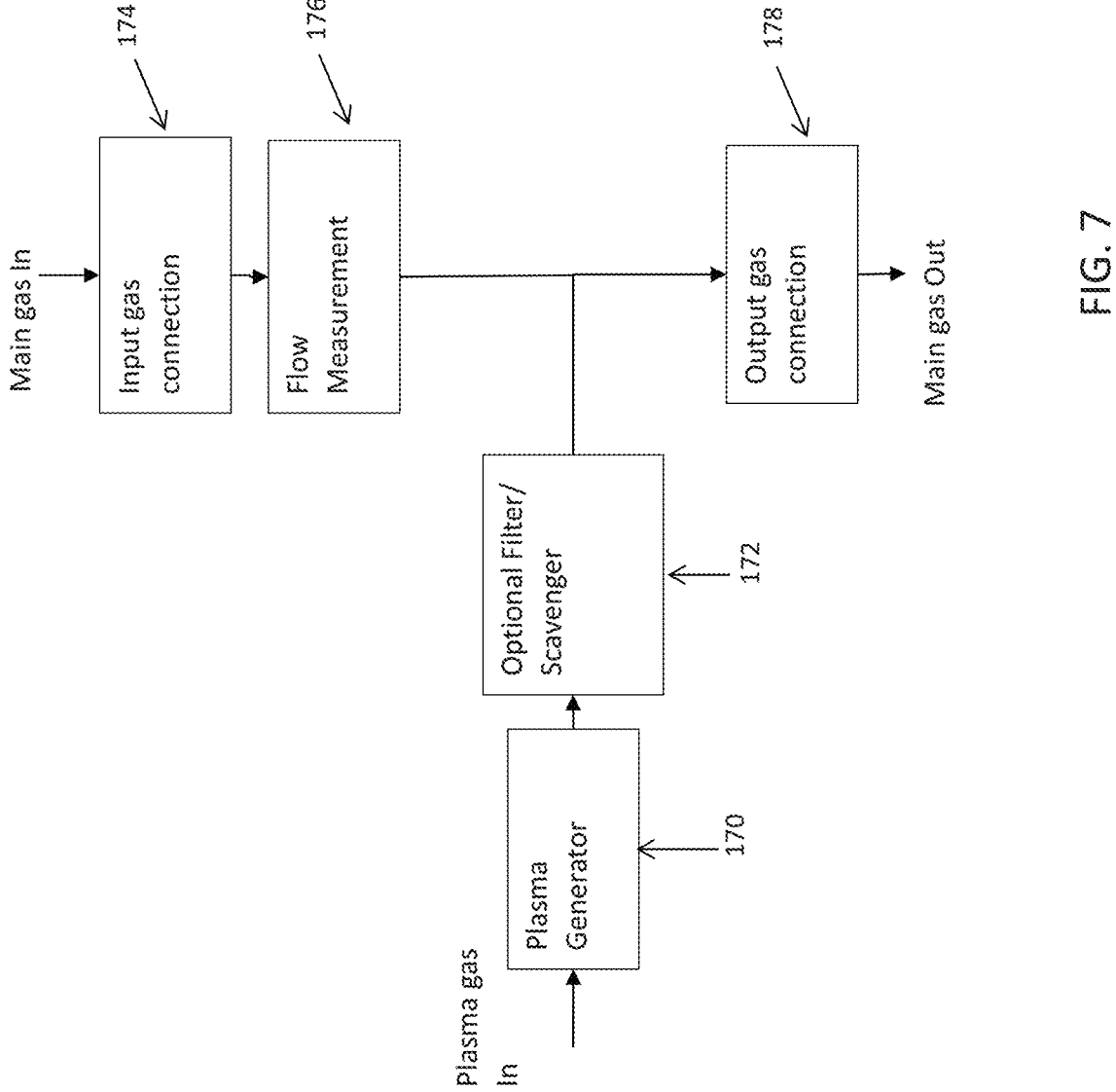
FIG. 7 is a flowchart of an embodiment of plasma generation that sources ambient air separate from a main gas stream.

FIG. 7 depicts an embodiment of a system that sources ambient air as the reactant gas for plasma generation that is separate from the main gas stream. The system of FIG. 7 includes a plasma generator 170 that intakes ambient air or gas. The output of the plasma generator 170 flows through an optional filter/scavenger 172. The system also includes an input gas connection 174 that takes in the main gas. The output of the input gas connection 174 flows to a flow measurement device 176. The output of the filter/scavenger 172 or the flow measurement device 176 can flow through an output gas connection 178 and out of a main gas outlet.

Figure 8:
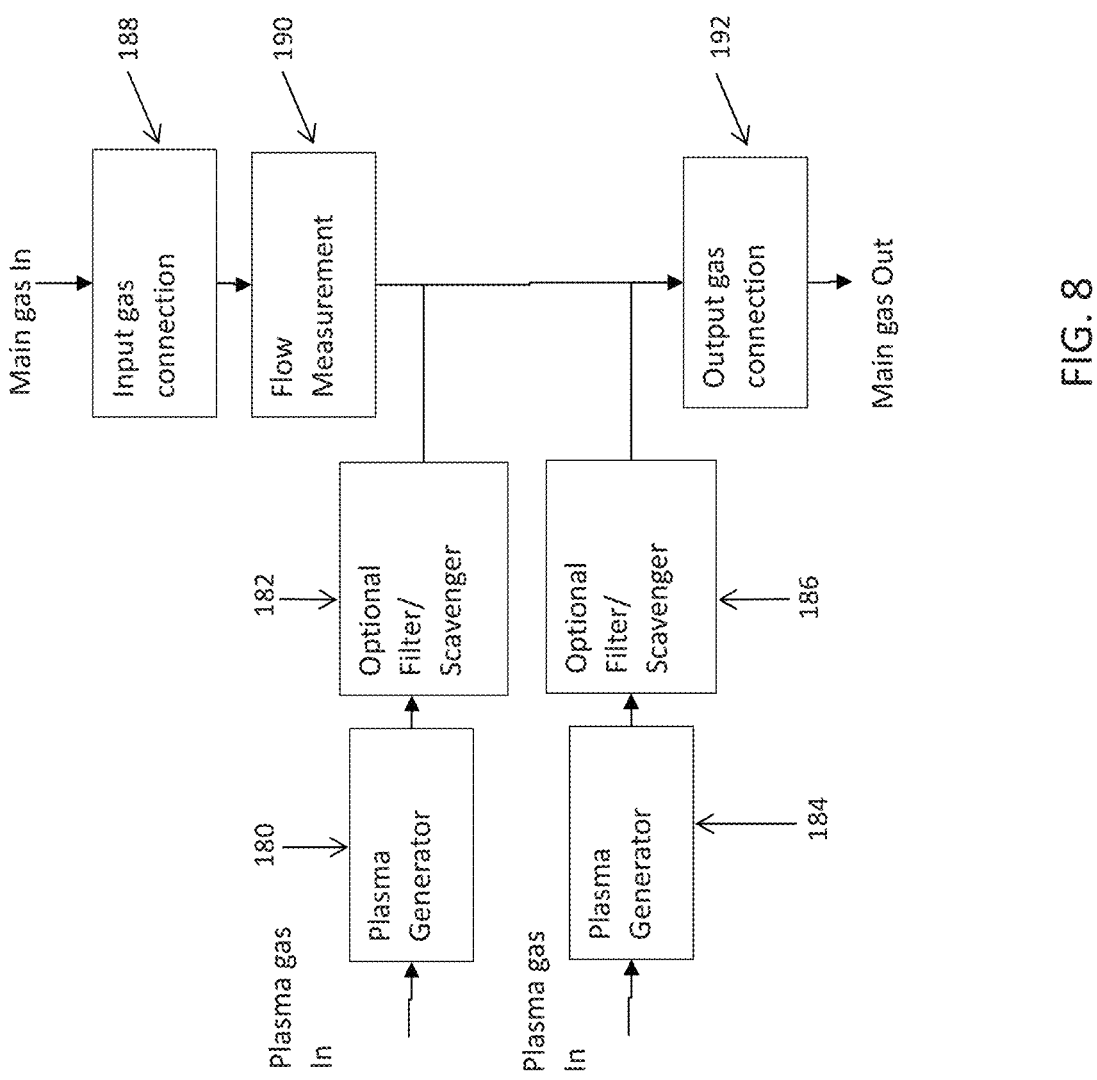
FIG. 8 is a flowchart of an embodiment of plasma generation with redundant plasma generators and scavengers.

FIG. 8 depicts an embodiment of a system with one or more redundant plasma generators and scavenger for safety. The system of FIG. 8 includes first and second plasma generators 180, 184 that are coupled to first and second optional filter/scavengers 182, 186. It should be noted that a filter/scavenger can have filters before the scavenger, after the scavenger, both before and after the scavenger, or have multiple filters distributed along the scavenger flow path. The system also includes an input gas connection 188 that takes in the main gas. The output of the input gas connection 188 flows to a flow measurement device 190. The output of the second filter/scavenger 186 or the flow measurement device 190 can flow through an output gas connection 192 and out of a main gas outlet.

Figure 9:
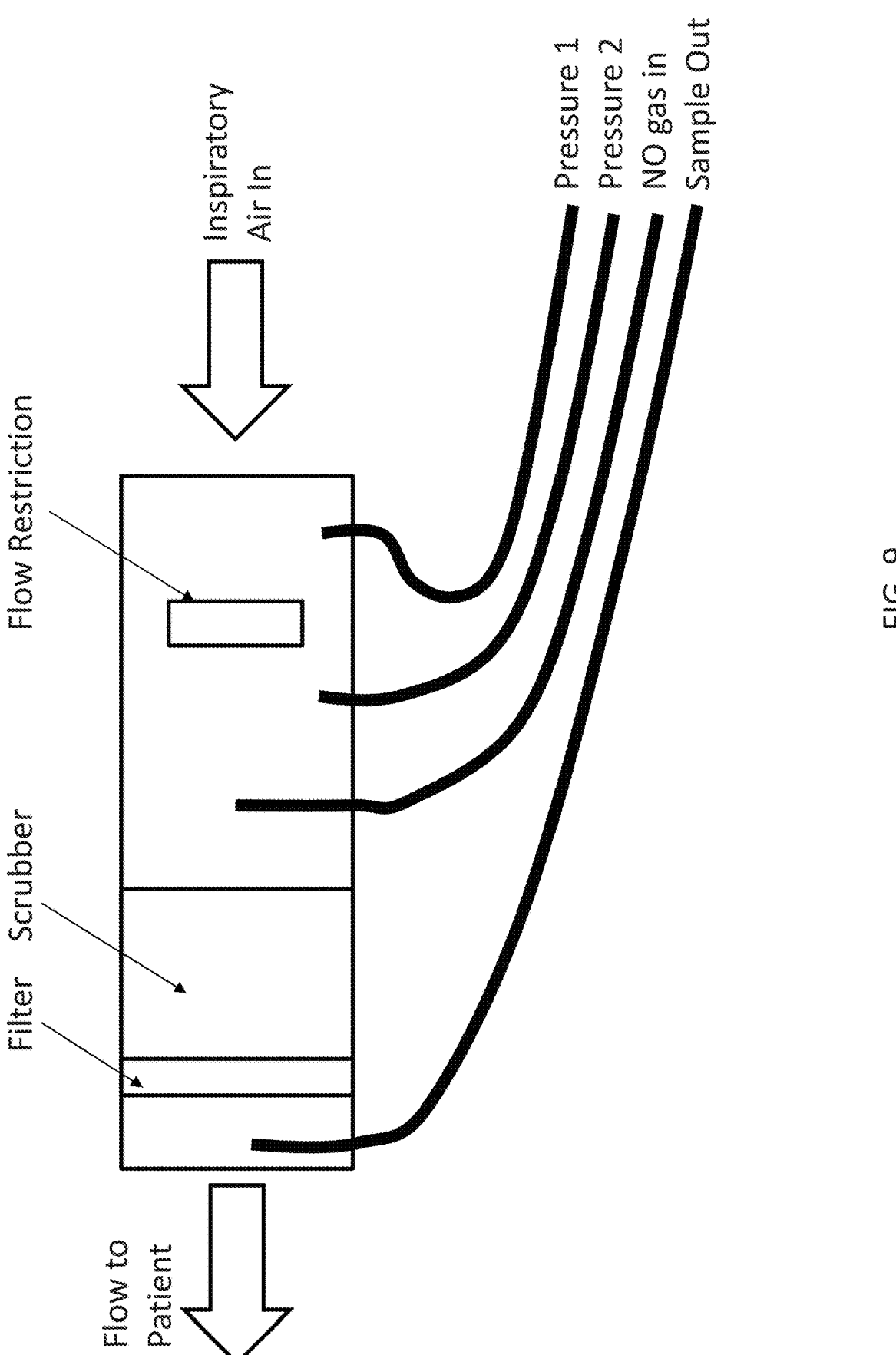
FIG. 9 is an embodiment of a sample line.

In some embodiments, the sample line connects to a "T"-fitting that is inserted into an inspiratory flow path. In one embodiment, the "T"-fitting is also used to measure gas flow within the inspiratory limb. Gas flow may be measured using one or more lumens for a differential pressure method. Flow can be measured based on the entire flow or within a side-stream of the inspiratory flow. In one embodiment, a flow sensor resides within the "T"-fitting. In one embodiment, NO containing gas is introduced to the inspiratory flow within the sample line "T"-fitting (FIG. 9). In one embodiment, a scavenger/scrubber and/or filter are included as a component in the "T"-fitting (FIG. 9). In one embodiment, a "T"-fitting scavenger/scrubber is used in addition to a scavenger/scrubber located within the controller/cartridges associated with NO production.

Figure 10:
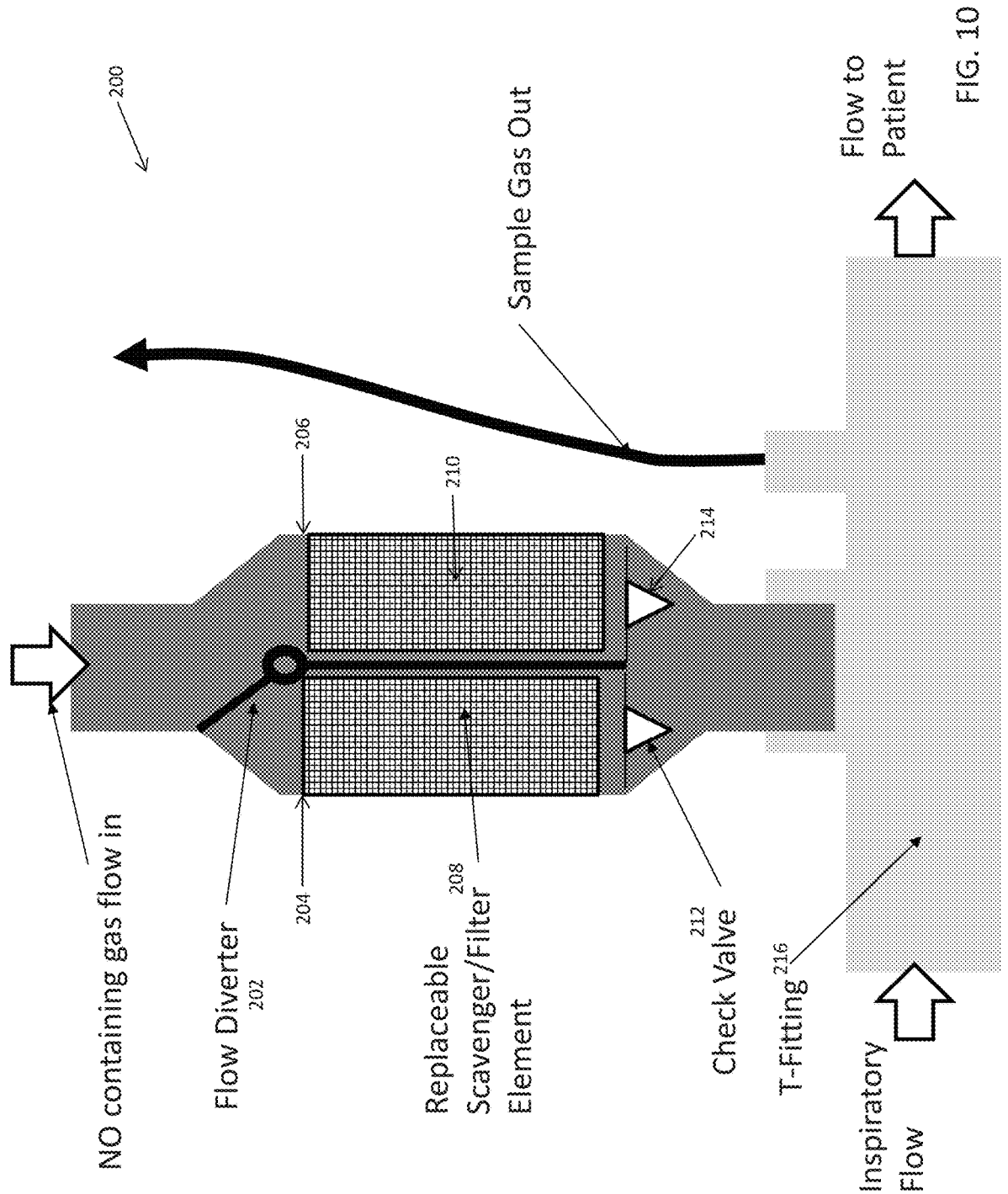
FIG. 10 is an embodiment of an injection end of a sample line.

FIG. 10 depicts one embodiment of the injection end of sidestream delivery line 200 with two parallel flow paths 204, 206 with a means, such as a flow diverter 202, to select which flow path is active. Each flow path can contain a scavenger cartridge 208, 210 that is removably connected. NO product gases from the NO generation device travel through one flow path until the scavenger is exhausted, then the product gas flow is redirected to the other flow path and scavenger. A scavenger cartridge can be replaced in one path while the other path is scrubbing the product gas flow. Check valves 212, 214 at the end of each of the parallel paths prevent reverse flow into the unused chamber. A similar dual-path design could be made within the "T"-fitting 216, itself, so that patient inspiratory air flows through one or two scavenger paths.

A similar dual-path design could also be utilized in a mainstream embodiment so that inspiratory gas delivery is not interrupted when a scavenger cartridge requires replacement. In an embodiment, an NO generation system is provided that uses a high voltage (HV) trigger circuit or waveform generator that can continue treatment in the event of control software crash and/or user interface crash. In an embodiment, an NO generation system is provided that filters, scavenges, and charcoal-filters incoming gas to remove impurities and increase NO partial pressure in the exhaust gases. In an embodiment, an NO generation system is provided with redundant HV trigger circuits and air pumps, electrode assemblies, batteries, and filter scavengers.

Manual Ventilation

A manual ventilation device (for example, a respiratory bag) can also include an NO generation feature. The NO-generating portion of the manual ventilation device can be an accessory to a manual ventilation device or integrated into a manual respiratory device. In some embodiments, the NO generation portion can include a control circuit, a HV circuit, electrode assembly, scavenger and filter at a minimum for constant NO production. In some embodiments, air flow and/or bag activity (pressure, deflection, strain) can be measured in order to match NO production with respiratory rate/volume. The control circuit can activate the HV circuit and related plasma generation based on, but not limited to, one of more of the following inputs: desired NO concentration indicated by the user, ambient temperature, ambient pressure, plasma chamber pressure, gas flow rate, and $O_2$ level in the gas. In some embodiments, the device generates a plasma in the gas that flows to and fills the respiratory bag. The device may be located in series before the gas supply for the bag or it may generate NO in a parallel path. In some embodiments, the device includes a pump that it uses to source atmospheric air for the plasma chamber. In some embodiments, the NO generation portion can be located between the manual ventilation bag and the patient and generates NO in the gas emitted from the bag. In an embodiment, the device can generate plasma for a set duration during each manual inspiration (for example, each squeeze of the bag) detected. When the bag of a manual ventilation device is filled with NO-containing gas, the device can include a scavenger after the bag since the time for a given $NO/NO_2$ molecule to leave the bag is not controlled. When atmospheric air is sourced for NO generation, the pump should prevent retrograde flow through it when off, or a valve should be used (for example, passive one way, or active) to ensure NO flow towards the patient and the air path does not present a leak to the system. In some embodiments, in which NO generation takes place in parallel to the bag with the same gas that fills the bag, a one-way valve can be used to prevent gases flowing backwards through the NO generator during patient exhalation.

Figure 11:
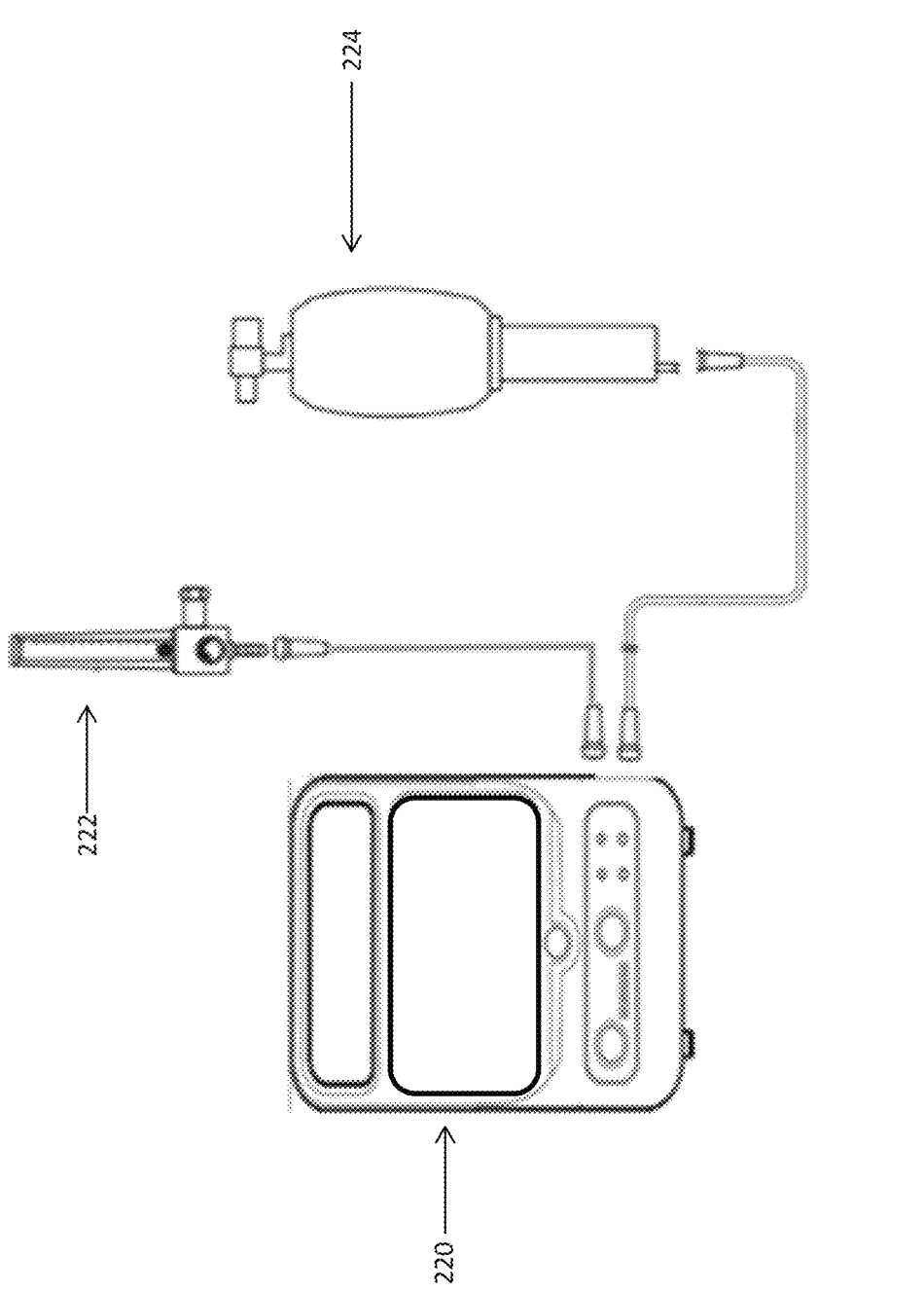
FIG. 11 is an exemplary embodiment of a mainstream NO generation system that can be used with a manual ventilation device.

FIG. 11 depicts an example of mainstream support of a manual ventilation device 224. A controller 220 receives gas from gas source 222, measures gas flow and supplements gas flow with prescribed level of NO as it passes to the manual ventilation device 224.

Figures 12A, 12B:
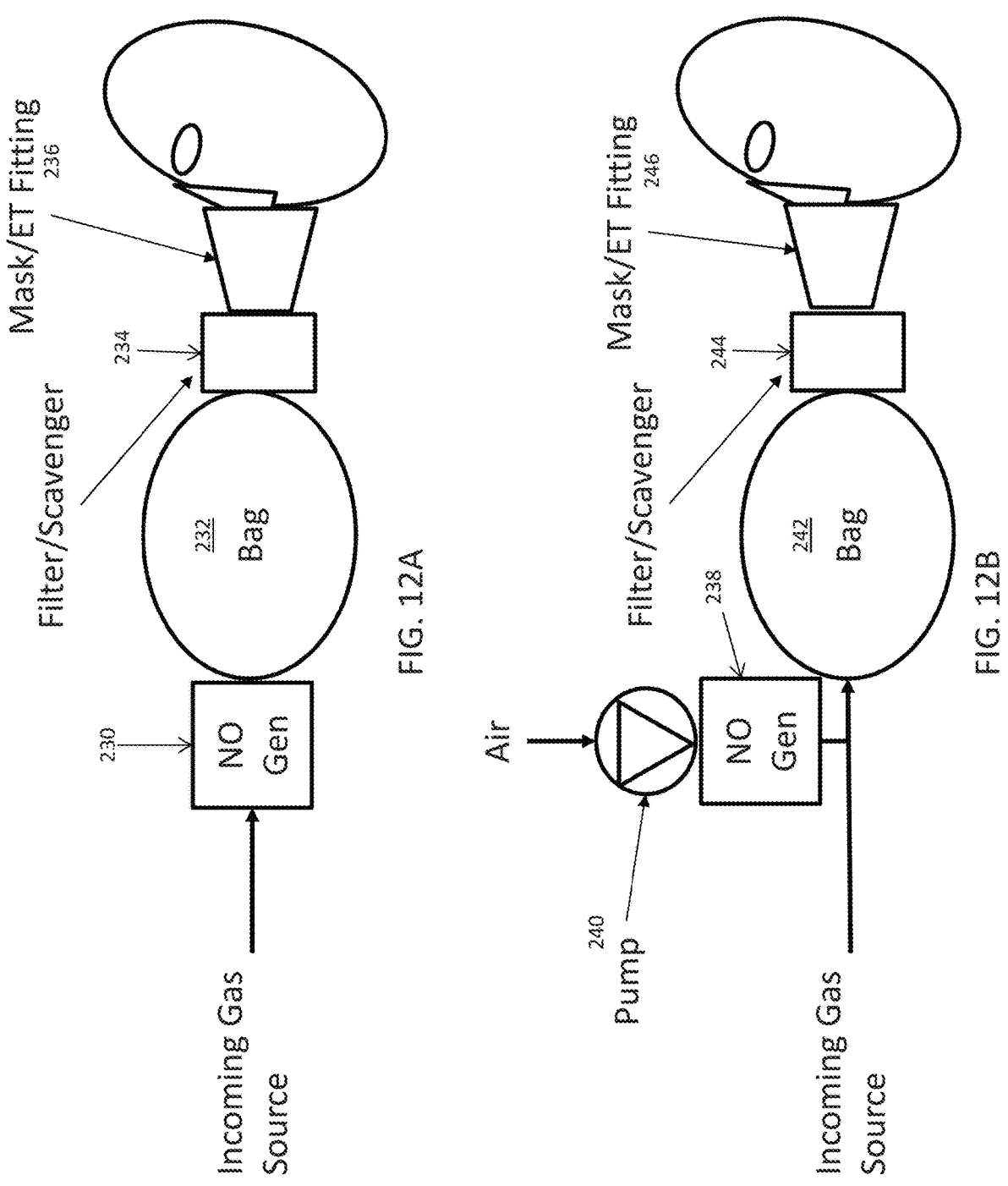
FIG. 12A and FIG. 12B are embodiments of manual ventilation devices for use with an NO generation device.

FIG. 12A shows an embodiment of an NO generator 230 in series with a manual bag 232. The air source can be any reactant gas, including atmospheric air or from a compressed gas source. Check valves before and after the bag can be used to direct flow towards the patient using a mask 236. A scavenger 234 is located after the bag because it is the last part of the airway before the patient and the residence time of NO in the bag is not controlled unless the bag is completely emptied with each breath.

FIG. 12B shows an embodiment of a system where NO is generated in atmospheric air and blended with another gas stream before entering the bag 242. A separate component (not shown) may be necessary to titrate the NO flow with other gas stream. Alternatively, the NO flow rate can be modulated with the speed of the pump 240 and plasma activity in the NO generator 238. Check valves (not shown) can be used to direct flow through the bag 242 and a scavenger 244 to the patient using a mask 246 and from the patient to atmosphere.

Figures 13A, 13B:
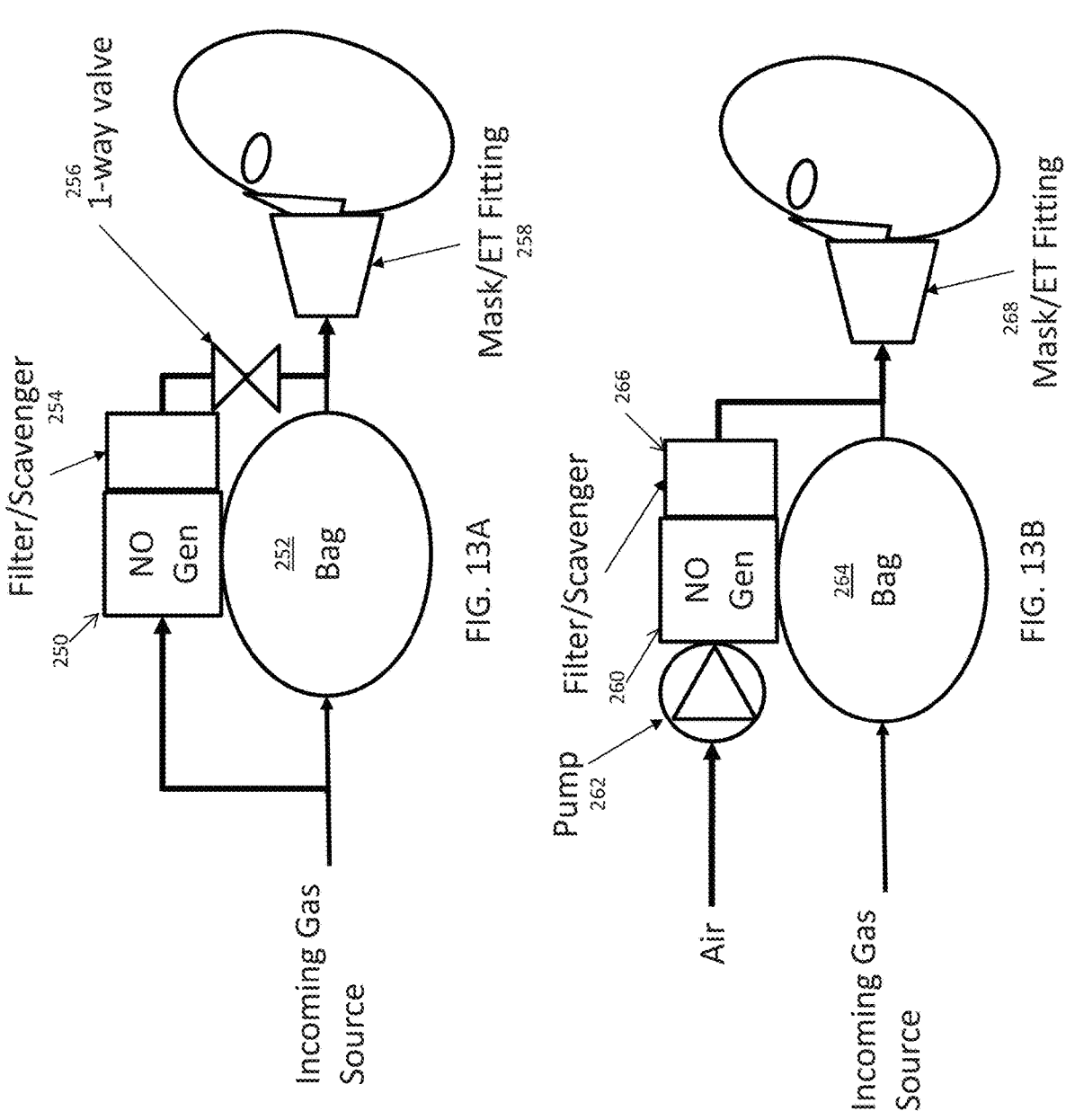
FIG. 13A and FIG. 13B are embodiments of manual ventilation devices for use with an NO generation device.

FIG. 13A shows an embodiment of an NO generator 250 that generates NO from the same high pressure gas source as the bag 252. The NO generator can bleed the product gas (NO-rich gas) into the patient airway at a constant rate or at a pulsatile rate. In some embodiments, a valve 256 opens to flow NO-rich gas into the inspiratory flow when a bag compression is sensed such that the product gas can flow to the patient using a mask 258. Bag compression can be sensed by pressure within the bag, bag strain, bag displacement, or exit flow from the bag.

FIG. 13B shows an embodiment of an NO generation system 260 that generates NO from atmospheric air and pumps NO-infused air into the inspiratory track between a manual bag 264 and the patient. In some embodiments, a pump 262 runs continuously. In some embodiments, the pump runs intermittently in unison with bag compressions. In some embodiments, a valve is located between the scavenger 266 and junction between NO flow and bag flow. The pump runs continuously, flowing air through the plasma chamber. The valve is closed during the expiratory phase so that the pressure in the NO-infused air increases. When bag compression is detected, the valve opens, releasing the pressurized NO gas into the airway. In some embodiments, an accumulator (not shown) is located between the NO generator and scavenger to provide additional volume of NO-laden gas for each breath.

Figure 14:
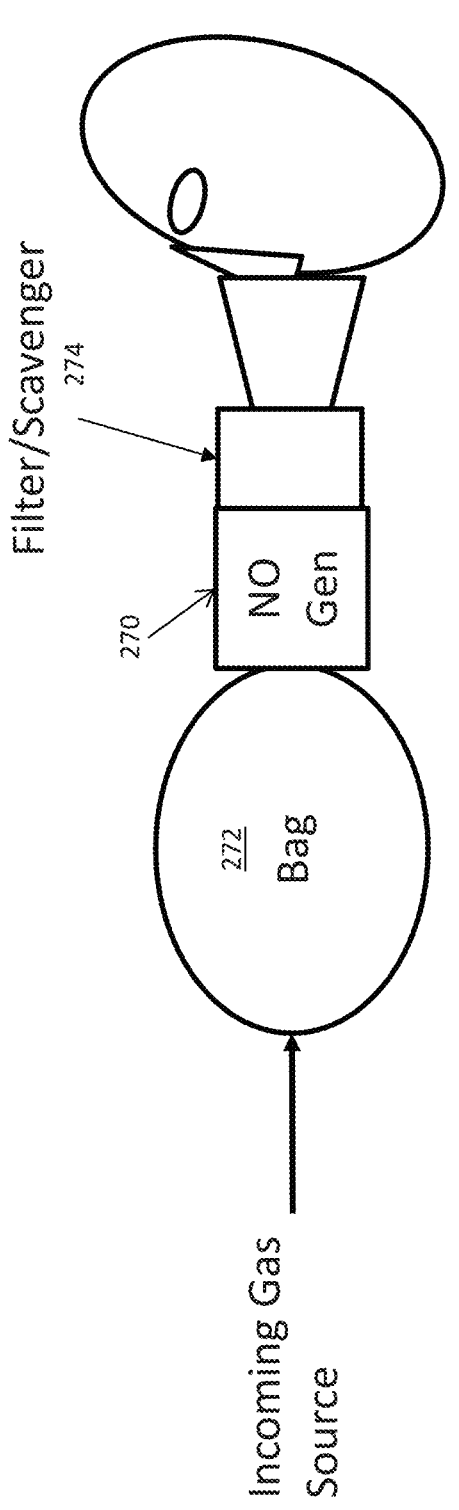
FIG. 14 is an embodiment of manual ventilation device for use with an NO generation device.

FIG. 14 shows an embodiment of an NO generating device 270 positioned between a manual respiratory bag 272 and the patient. The respiratory bag 272 receives incoming air from either a compressed gas source or the atmosphere. Gases that exit the respiratory bag flow through NO generation device, where they are supplemented with NO, and then through a scavenger 274.

The system can generate and deliver product gases in the absence of an external inspiratory flow. In some embodiments, a cap can be placed over the input for a bag connection and product gases flow out the output bag connection. Product gases are produced at the flow rate and concentration requested by the user. In some embodiments, the device dilutes incoming sample gases in a quantifiable way so that gas analysis sensors are not damaged by high concentration sample gases and concentrations are in the measurable range of the sensors.

Acute No Generation System

Figure 15:
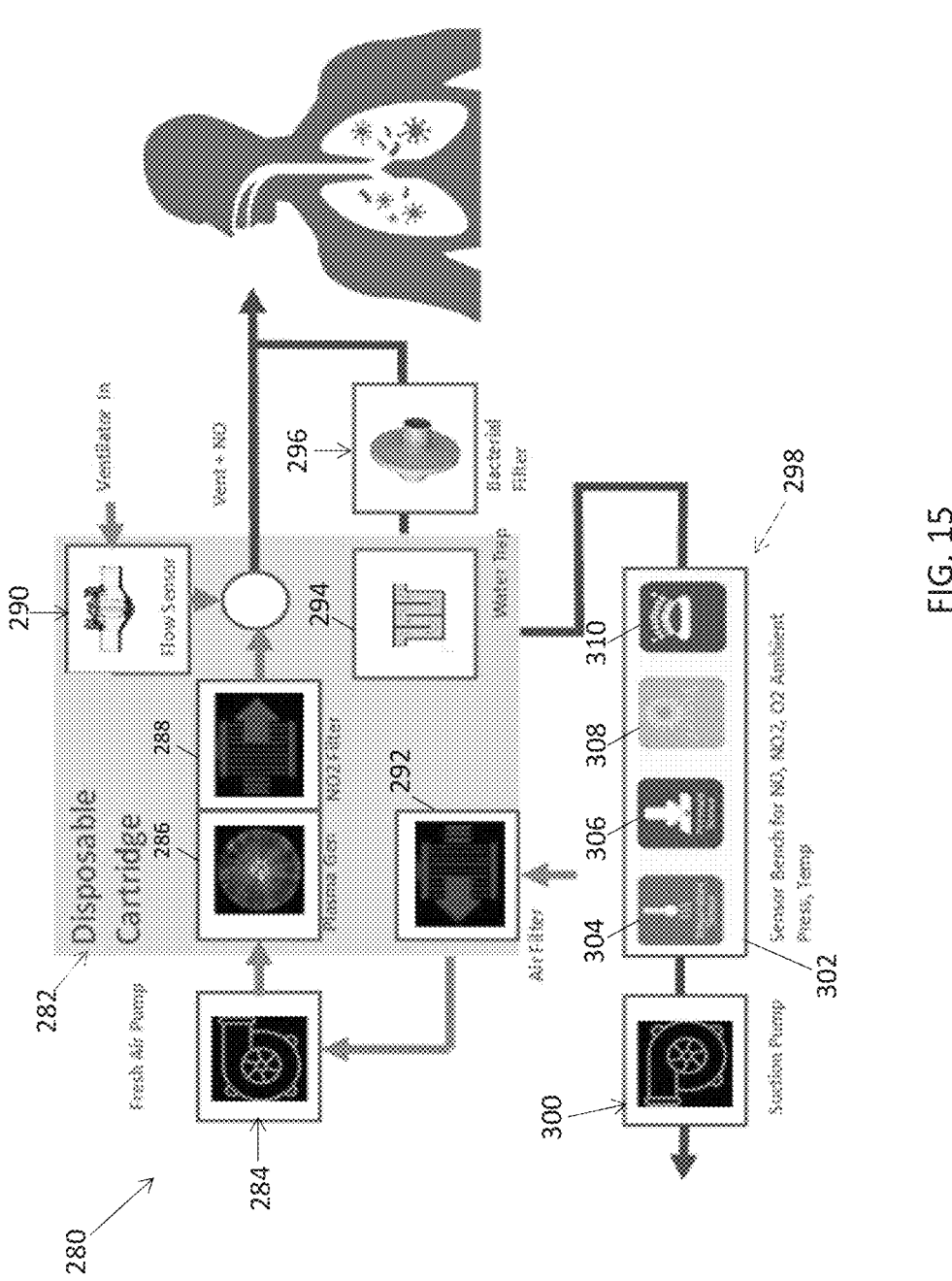
FIG. 15 is an exemplary embodiment of a NO generation system that includes a disposable cartridge and a controller.

FIG. 15 depicts a diagram shows an exemplary NO generation system 280. The destination for nitric oxide produced can be any type of ventilation device, including but not limited to a ventilator circuit, a nasal cannula, a manual ventilation device, a face mask, an anesthesia circuit, a CPAP machine, an ECMO machine, an oxygen concentrator, or any other circuit. In the illustrated embodiment, the NO generation system 280 includes an air pump 284 that pumps ambient air into the system 280 to be used as the reactant gas. The ambient air is pumped into the system, for example into a cartridge 282, and into a plasma generator 286 which generates NO using one more electrodes positioned therein. An $NO_2$ filter 288 is used to filter $NO_2$ out of the gas from the plasma generator 286. The filtered gas is then pumped out to a ventilation device to be delivered to a patient. The cartridge 282 includes additional features, including a flow sensor 290, an air filter 292, and a water trap 294. The system 280 also includes a controller 298 that has a suction pump 300 and one or more sensors 302. In the illustrated embodiment, the sensors include NO, $NO_2$, $O_2$, and sensor chamber pressure/flow.

The controller typically is a reusable device used for nitric oxide treatment. Some components of the controller can wear and require replacement schedules during the life of the system including the sensor pack, the electrode assembly (s), the pump(s), and the valve(s). On a more regular basis, the scavenger cartridge is replaced after a period of time, for example, days to weeks. The ventilator cartridge can also be replaceable in the event of a sensor failure or contamination.

The controller is designed so that no single fault will halt the production of nitric oxide. Instead of requiring user intervention when a single fault occurs, the system can provide continuous NO production while notifying the user of an issue. To accomplish this level of robustness, the controller can have one or more of redundant features. For example, the controller can include redundant batteries such that, in the event of a single battery fault, there is a back-up battery. The user also has the option of connecting AC power or DC power to the rear panel of the device. Redundant HV circuits can be used such that a second HV Circuit serves as a back-up to the ventilator circuit and can provide nitric oxide to a manual ventilation device circuit. Redundant air pumps can be used such that each high voltage circuit is supplied air from a dedicated air pump. Redundant electrode assemblies can be used such that each HV circuit drives a dedicated electrode assembly. Thus, if one electrode assembly fails or stops working, the system can automatically switch to using the other electrode assembly. Redundant sensors and actuators (valves, pumps) are also employed to prevent a single failure in the generation and delivery of NO.

Figure 16A:
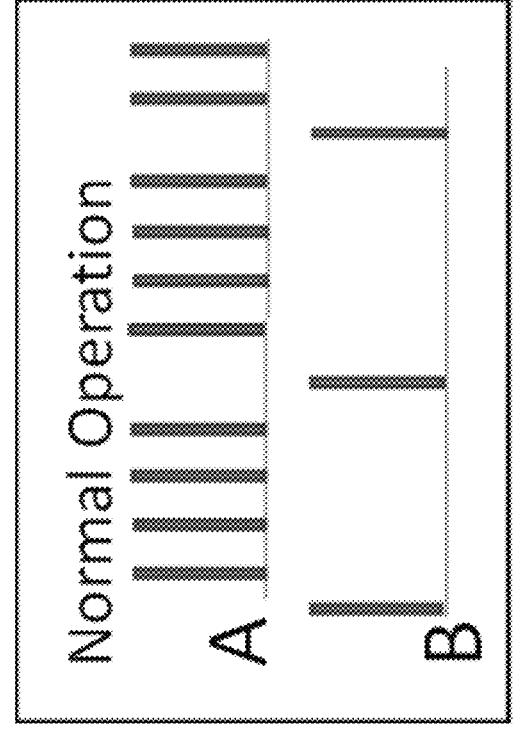
FIG. 16A and FIG. 16B illustrate exemplary plasma NO generating pulses for electrode assemblies in normal and failure states.
Figure 16B:
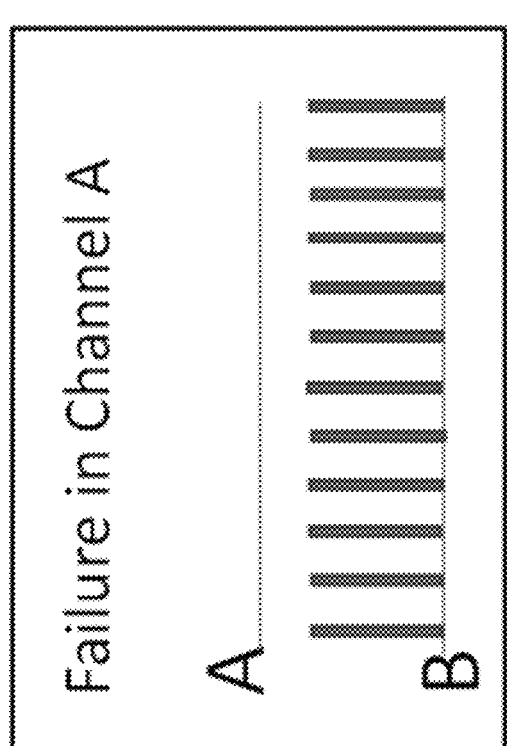

In some embodiments, the system periodically checks the back-up circuit to ensure that it is functional. FIG. 16A depicts how the system periodically checks Channel B. This check could be every 10th plasma pulse or a single check per day, for example. It will be understood that any measurement of time or plasma pulse can be used to perform a system check on the redundant components. FIG. 16B depicts a failure in Channel A. The system begins using Channel B for all nitric oxide production to replace Channel A. In some embodiments, the system can use both channels equally with the presumption that they will not both fail at the same time. In cases where both scavenger paths are being used for nitric oxide generation and one channel fails, the second channel is used to match the prior NO production or its maximum production limit, whichever is less. In some embodiments, the system can alternate at regular intervals between electrodes to improve electrode life. In some embodiments, the two channels are used simultaneously. This can have an advantage of increasing total NO production capacity of a system. Simultaneous use also decreases the temperatures and wear rate of each channel, reducing thermal degradation of components and electrode sputtering. Whenever the gas flow is changed from one channel to another, the previous flow channel is flushed with non-NO-containing gas to remove the NO-containing gases generated.

The system can also have more than one, for example, two independent scavenger paths to address the potential of scavenger path wear and/or obstruction. In cases of maximal nitric oxide generation, the system can utilize both HV circuits and scavenger paths simultaneously to double the nitric oxide output.

Figure 17A:
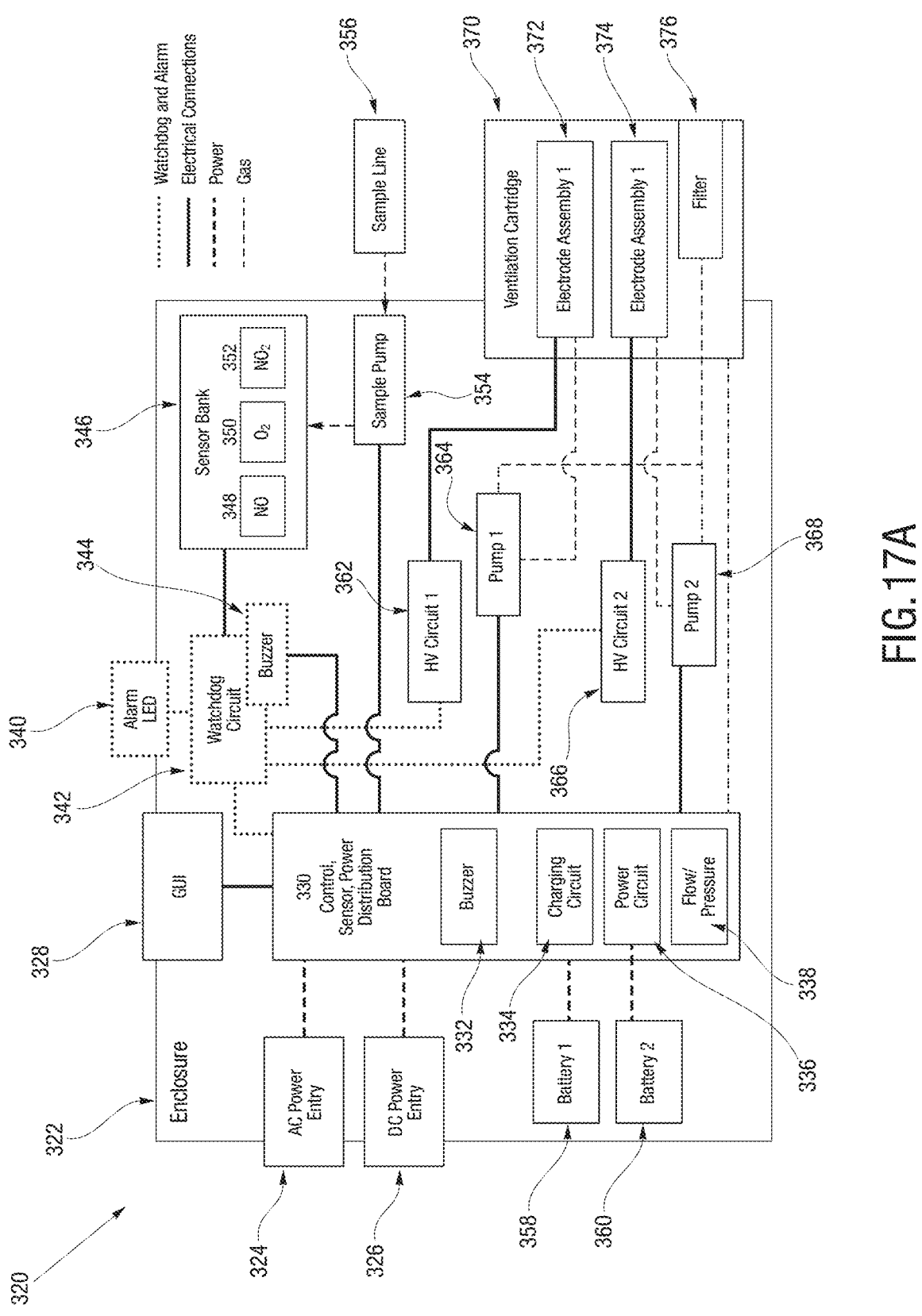
FIG. 17A is an embodiment of an NO generation system with one or more plasma chambers located within a cartridge.
Figure 17B:
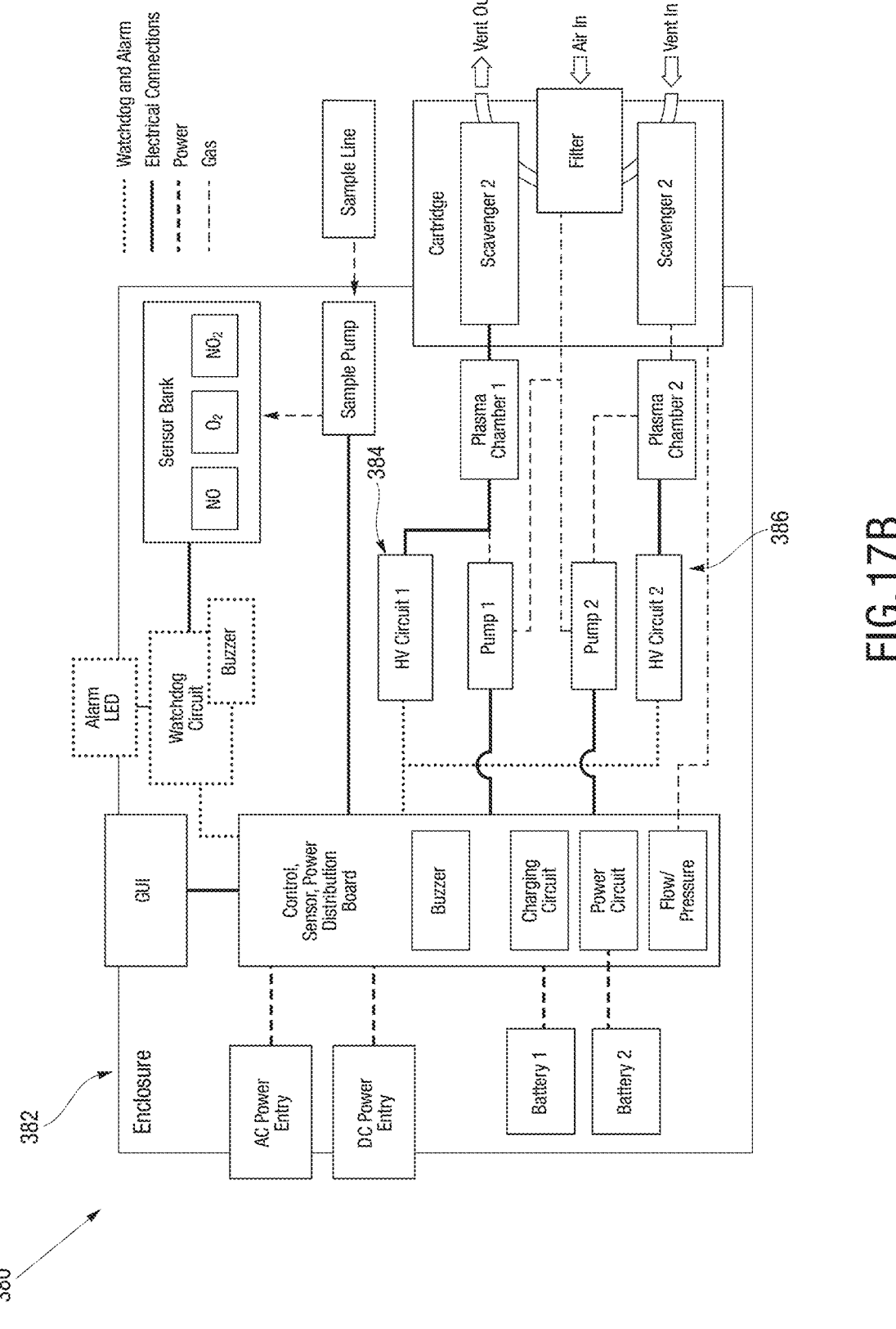
FIG. 17B is an embodiment of an NO generation system with one or more plasma chambers located within a controller.
Figure 18:
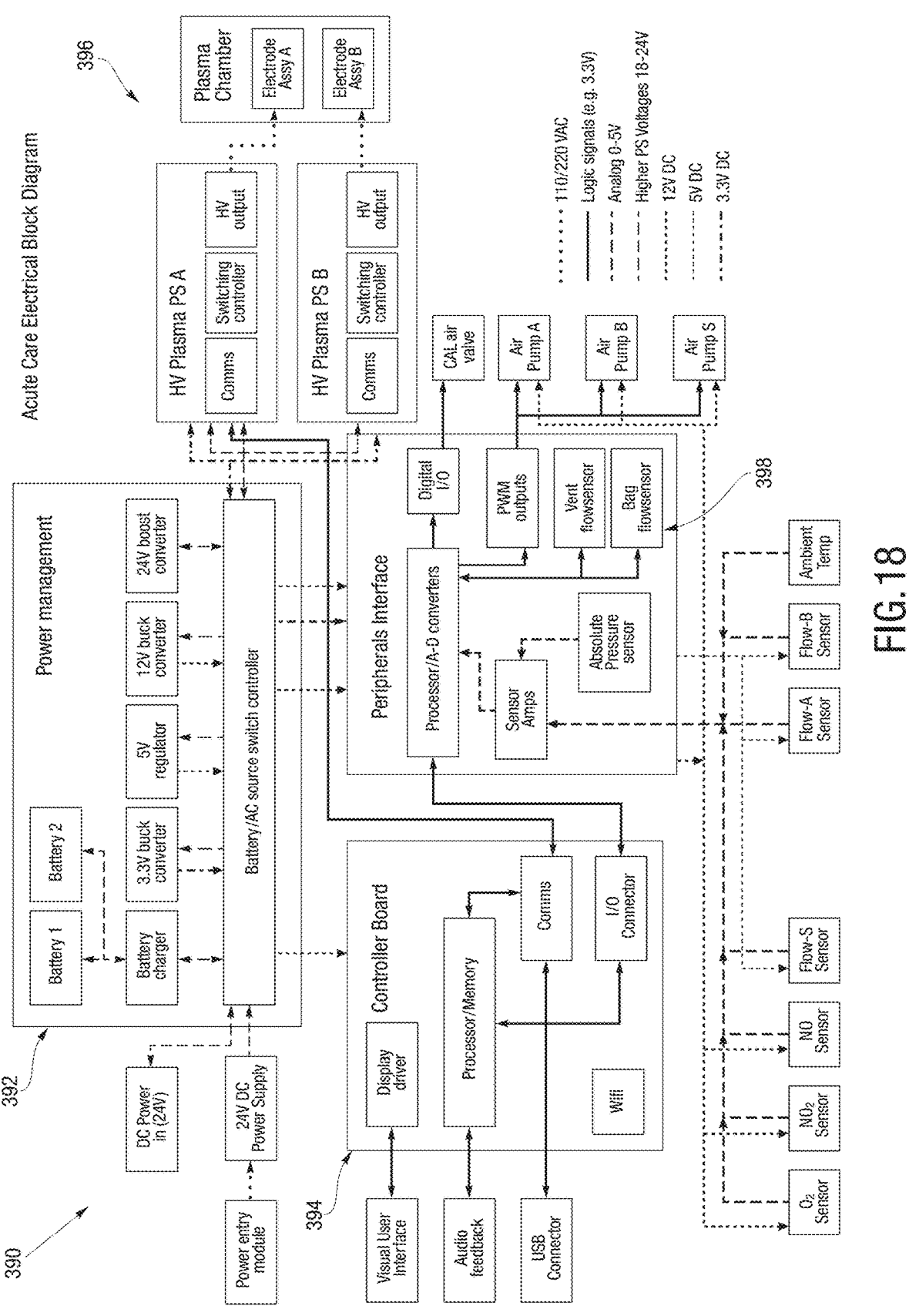
FIG. 18 illustrates an embodiment of a schematic of a controller of an NO generation system.
Figure 19:
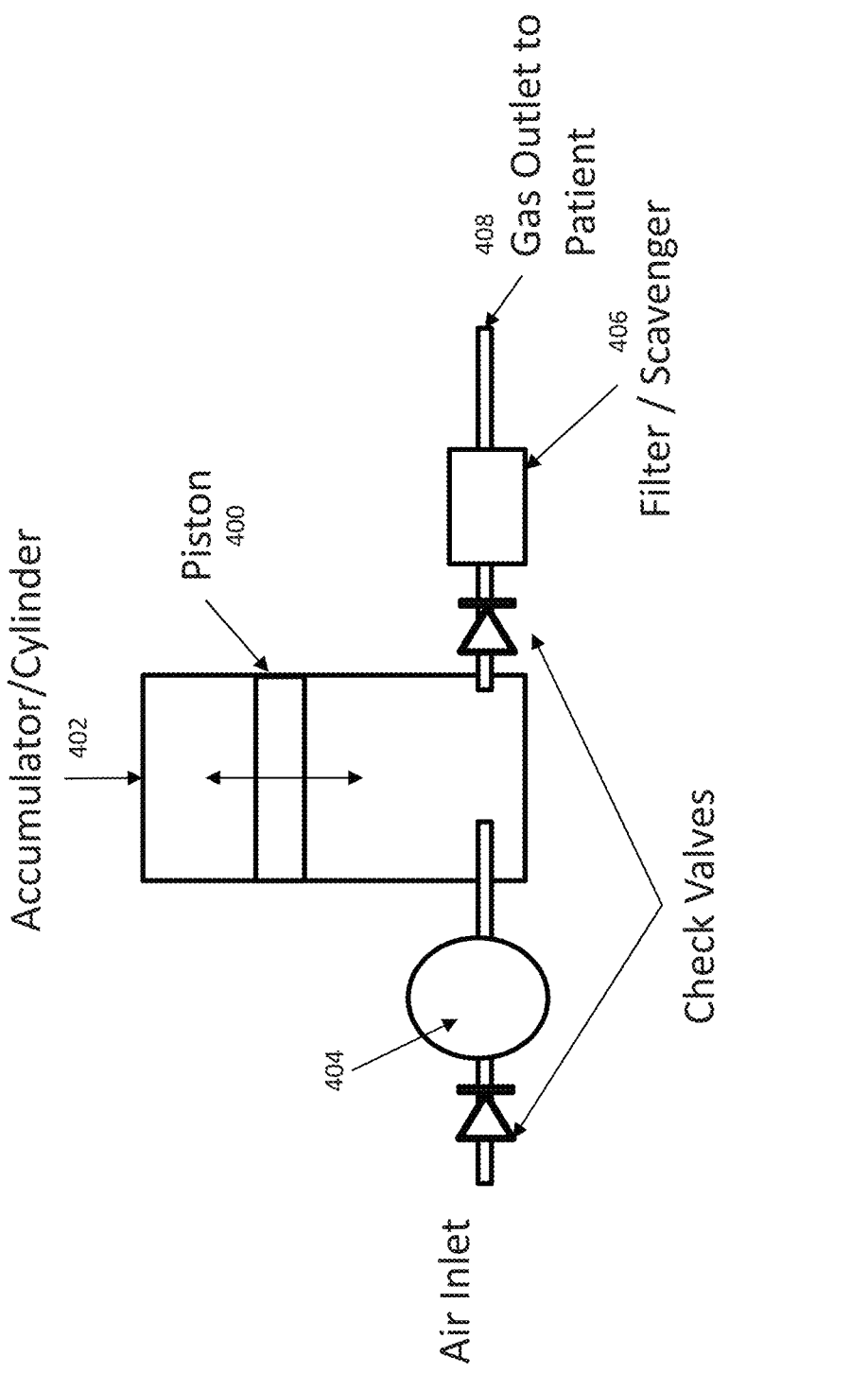
FIGS. 19, 20, 21, 22, 23, 24, and 25 are embodiments of mechanisms for creating a pulsatile air flow.
Figure 20:
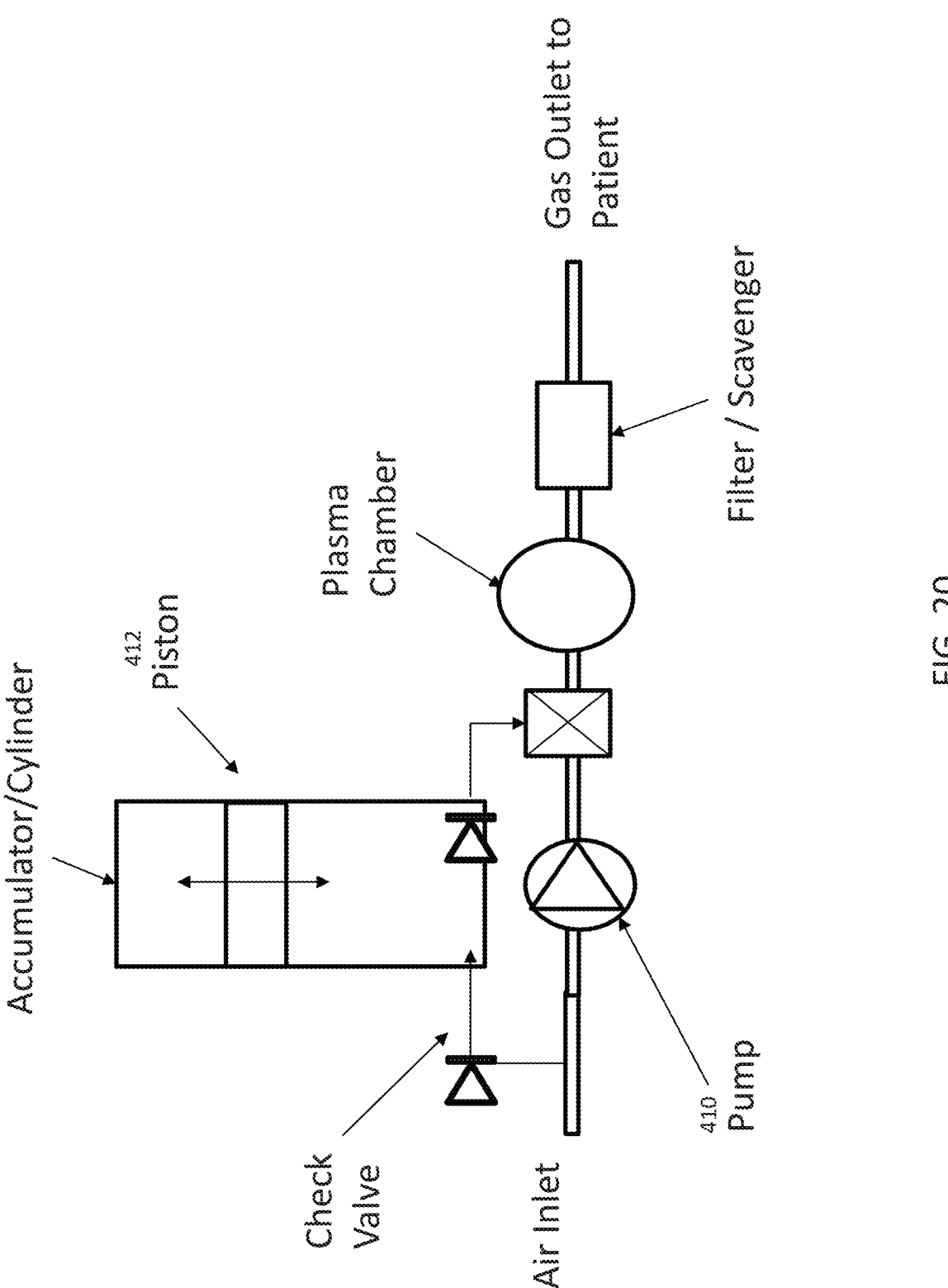

FIG. 17A depicts an embodiment in which the dual electrode assemblies (plasma chambers) are located within the disposable cartridge, as will be discussed in more detail below. $NO_2$ scrubbing features are not shown in the figure but can connect to the electrodes to scrub gases after they pass through the plasma generated at the electrodes. The cartridge 320 shown in FIG. 17A includes an enclosure 322 that houses a control board 330, a sensor bank 346, and dual electrode assemblies 372, 374 located within a ventilation cartridge 370 and in communication with high voltage circuits 362, 366. The control board 330 includes a buzzer 332, a charging circuit 334, a power circuit 336, and a flow/pressure circuit 338, with connections with batteries 358, 360 and AC and DC power 324, 326. The control board 330 is in communication with a user interface 328 and a watchdog circuit 342 having an alarm 340 and a buzzer 344. FIG. 17B depicts an embodiment of a cartridge 380 in which the dual electrode assemblies 384, 386 are located within the enclosure 382 of the cartridge 380. FIG. 18 depicts a schematic showing all the components of an embodiment of an NO device 390, including control board 394, a power management circuit 392, and electrode assemblies 396. A plasma chamber can be part of the controller or part of the cartridge, as will be discussed in more detail below.

Reactant Gas Intake and Flow Controllers

Various components can be used to take reactant gas into the NO generation system. In some embodiments, the reactant gas can pass through a gas filter, as shown in FIG. X. In some embodiments, the gas filter has a 0.22 micron pore size. The filter can be used to remove particulate from the ambient air prior to exposing the air to plasma. In some embodiments, the reactant gas filter is combined with the $NO_2$ scrubber cartridge to simplify use of the device by reducing use steps.

The pneumatic circuit which supplies the plasma chamber can have a precisely controlled flow because the reactant gas flow rate through the plasma chamber significantly affects NO generation. The pneumatic circuit can be constructed in many ways.

Pulsatile Air Flow Mechanisms

A variable flow can be used in some instances to provide NO to a pulsatile ventilator air flow, and various mechanisms can be used to achieve a pulsatile air flow. In some embodiments, a motor can be used that is concentric with the screw of a ball-screw. The motor can turn the ball-screw nut, which translates the screw and piston. This can be very compact and provide adjustable amount of stroke. In some embodiments, a diaphragm can be used and can be "tented" or flat to change the volume of the chamber to store NO prior to delivery to the ventilator circuit. The piston can be driven with a variety of mechanisms, including a pulley and return spring, rack & pinion, linear motor, motor with clutch, and pulley.

Various embodiments of techniques for achieving a pulsatile air flow, using pistons, diaphragms, and other mechanisms, are shown in FIGS. 19-25. Each of these embodiments can be controlled by an electronic control system using sensor inputs as required from the pneumatic system (chamber pressure, plasma chamber flow rate, reservoir/accumulator pressure, etc.) and from the patient (inspiratory flow rate, inspiratory pressure, etc.) to achieve the target NO dose delivery. In the embodiment depicted in FIG. 19, a piston 400 can draw in air through a plasma chamber 404 to fill an accumulator/cylinder 402. The piston 400 can push NO out through the filter/scavenger 406 to an outlet 408 to be synchronized with a patient's breathe. Stroke and speed can be varied based on the patient's lung volume and

US 12,576,234 B2

Figure 21:
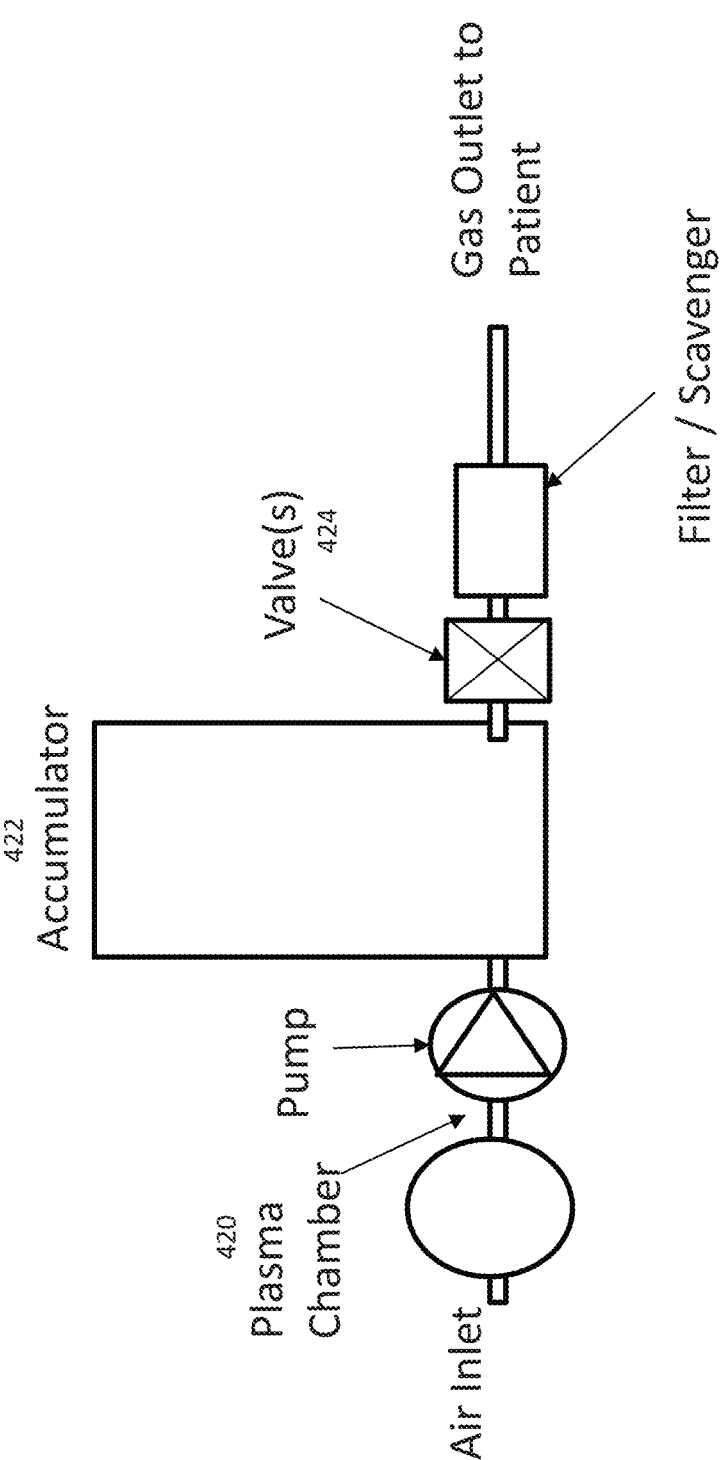
Figure 22:
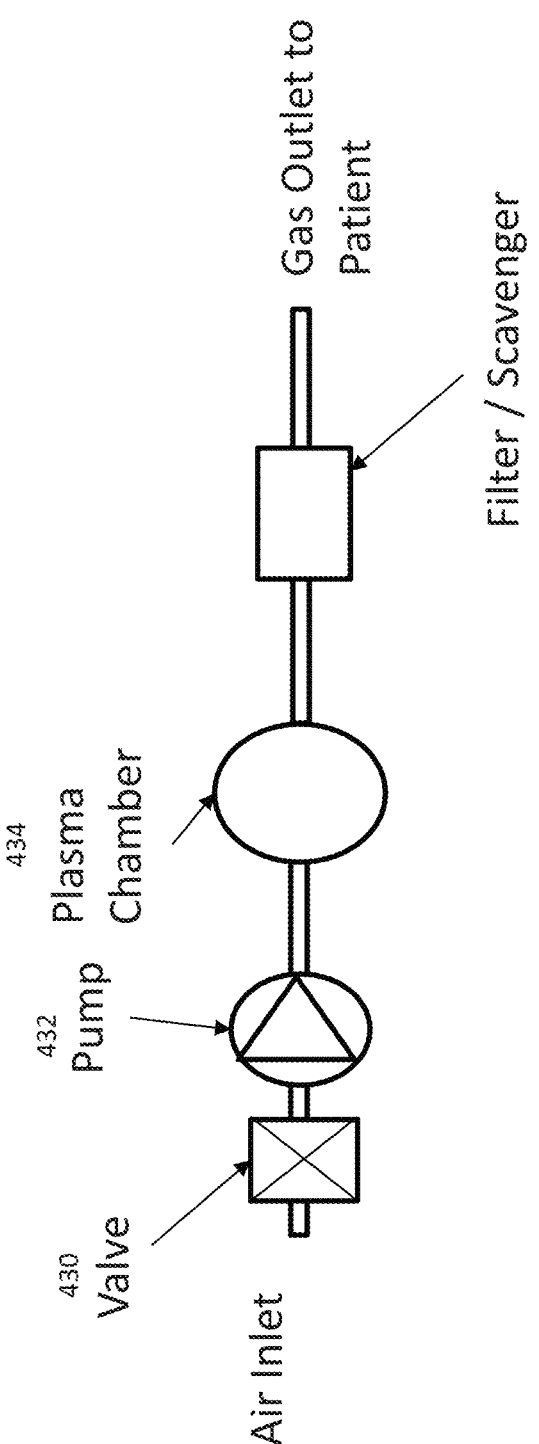
Figure 23:
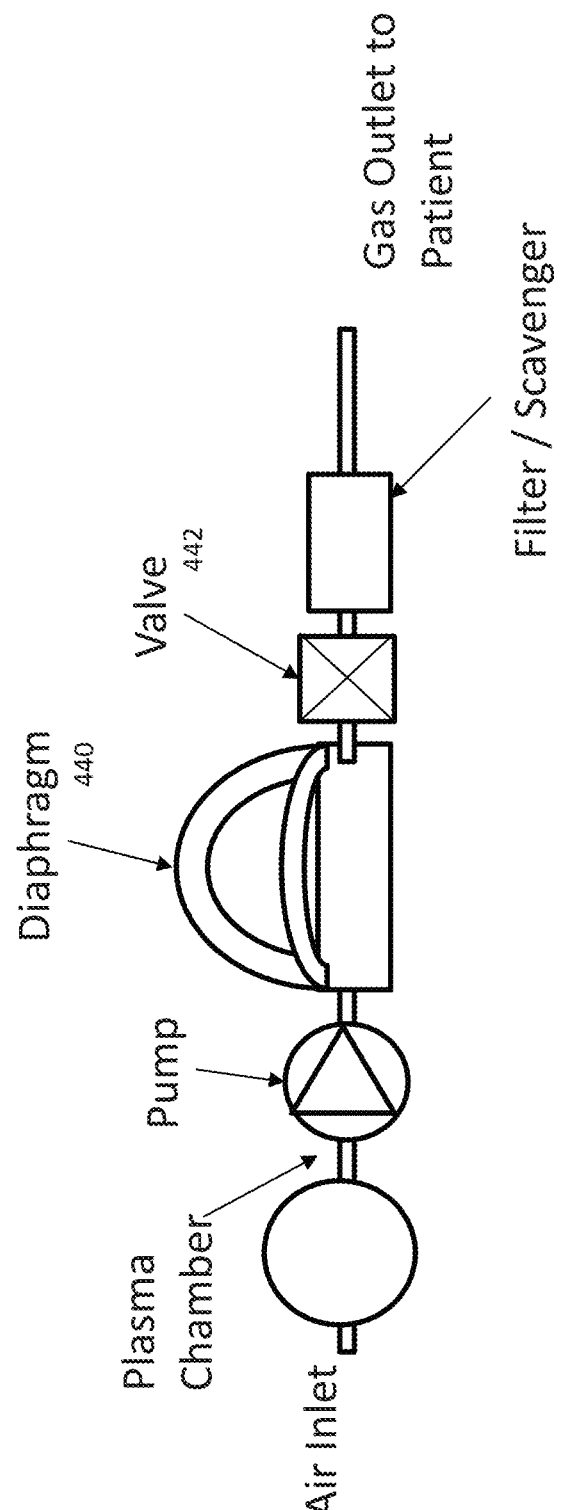
Figure 24:
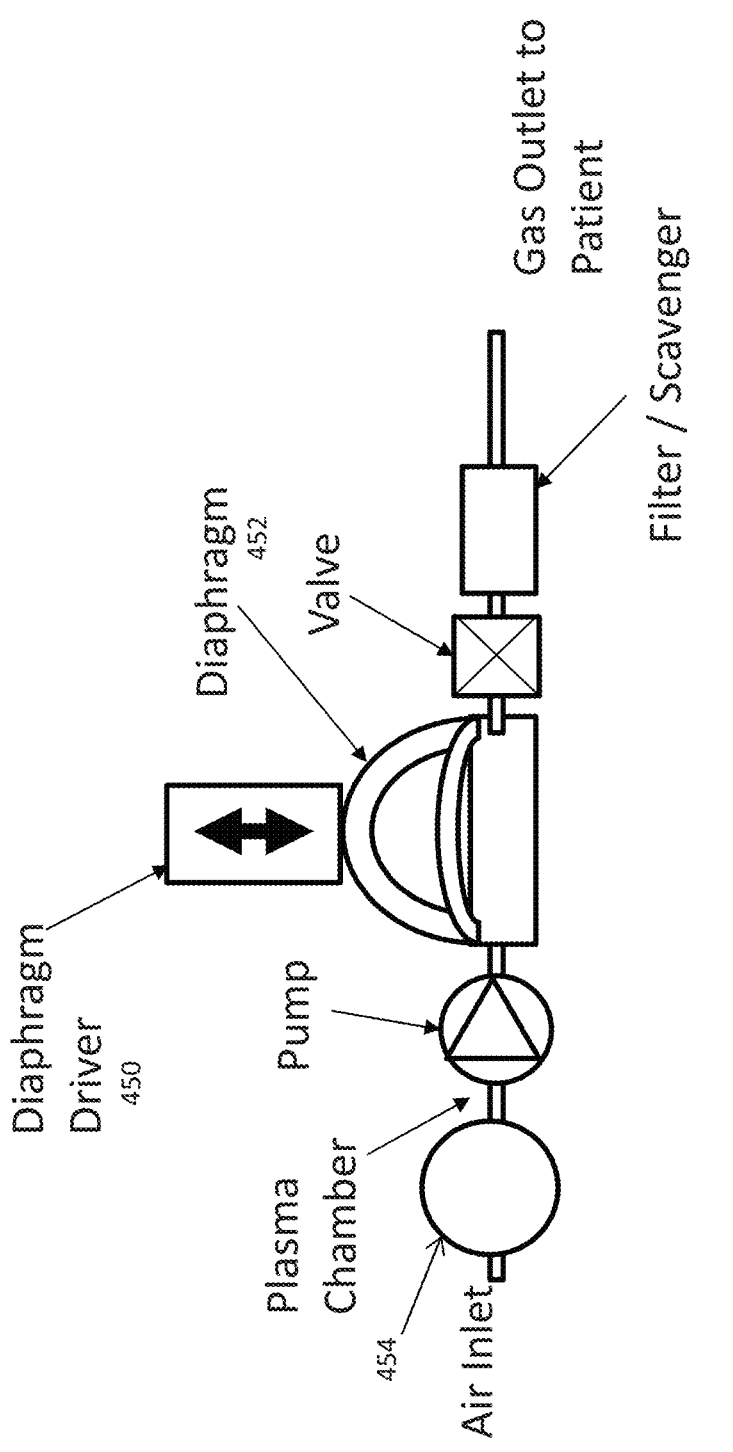
Figure 25:
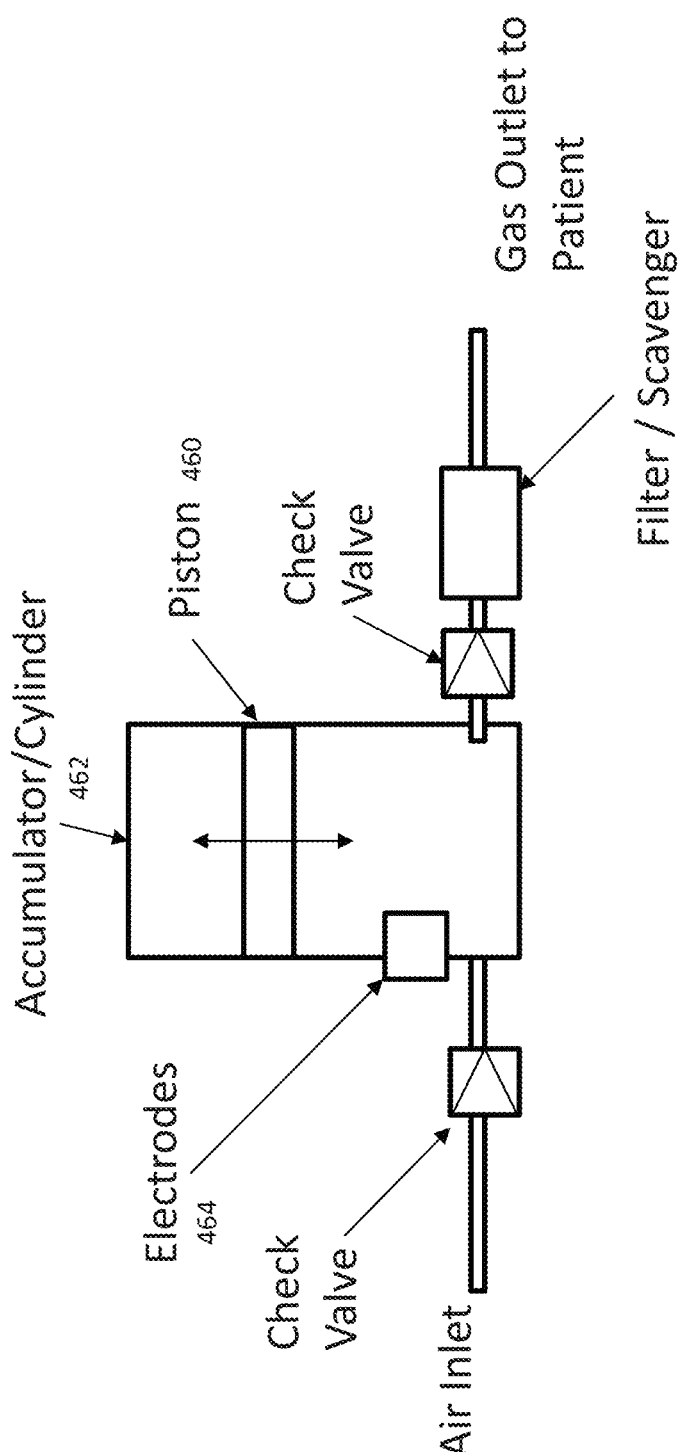

23 respiratory rate. In the embodiment depicted in FIG. 20, a pump 410 is used to deliver constant flow to a ventilator circuit to dose the bias flow while a piston pump 412 is used to provide boluses of air for additional NO generation during inhalation. In FIG. 21, the device can accumulate NO produced in the plasma chamber 420 in the accumulator 422 and releases it with patient inspiration using one or more valves 424, which can be, for example, a single proportional valve, or an array of valves with binary states (OPEN/CLOSED). In FIG. 22, one or more valves 430 are located before the pump 432 to modulate incoming air flow to the plasma chamber 434. Modulation can be done in a variety of means, including adjustable closure as with a proportional valve or pulse-width modulation of a digital valve. In some embodiments, the pump runs at constant speed while the valve is adjusted to variably starve the pump, thereby modulating flow rate and NO production. FIG. 23 depicts an alternative accumulator design that uses a diaphragm 440. The diaphragm 440 can be either an elastomeric or a rigid/stiff material. In some embodiments, a rolling diaphragm is used. A valve 442 downstream of the diaphragm 440 releases pressure from the diaphragm in a controlled manner as needed to dose inspiratory events. FIG. 24 depicts an accumulator/reservoir as a chamber with elastomeric or non-elastic diaphragm/balloon 452. A diaphragm driver 450 (solenoid, ball-screw, linear motor, rack and pinion, linear actuator, etc.) is used to displace the diaphragm 452 as needed to deliver boluses of gas to the patient. In the embodiment depicted, the plasma chamber 454 is the first element in the system, however, it can be located in other locations so long as its upstream of the filter/scavenger. The further downstream the plasma chamber is, the lower the exposure to NO and $NO_2$ for pneumatic system components. In some embodiments, NO can be generated as late as possible but before the scavenger so that the high concentration $NO/NO_2$ mixture exiting the plasma chamber has minimal time to oxidize and generate higher $NO_2$ levels. FIG. 25 depicts a system that utilizes a piston 460 to draw reactant gas into a chamber 462. Electrodes 464 within the chamber 462 are one or more times to generate NO. The piston 460 pushes the NO mixture out to a patient required by the therapy. In some embodiments, the piston pushes boluses of NO to the patient that coincide with patient inhalation. In some embodiments, the piston pushes out NO at a constant rate until the reservoir is empty. Then the piston refills the reservoir, NO is generated and NO delivery to the patient resumes. The piston can be driven by a many kinds of linear actuators as listed above.

The compressed gas chamber can include a variable restrictor on the exit. In some embodiments, the compressed gas chamber can be a volume within the manifold instead of an independent component of the system. In some embodiments, a pump supplies a pneumatic reservoir. In some embodiments, the pressure within the reservoir is sensed. In some embodiments, pneumatic reservoir pressure may be used as a signal to control pump speed. In some embodiments, flow from the reservoir is controlled by a proportional valve or one or more digital valves. In some embodiments, air pressure upstream and/or downstream of the flow control valve is sensed to improve the control or regulation of air flow. Pressure within the compressed gas chamber can be regulated by a closed-loop control using chamber pressure as input to control air pump activity. The variable restrictor can act like an analog valve instead of a digital valve ("digital" meaning discrete valve positions can be achieved, such as fully open, fully closed and half-closed). The variable restrictor can also include a digital valve that is PWM-controlled to vary air flow through the spark chamber. In some embodiments, one or more air flow sensors may be used to measure air flow downstream from the flow control valve, as part of an air flow control system.

In some embodiments, various flow paths can be included with independent pumps. In some embodiments, one pump can run to dose the bias flow with NO, and another pump can provide pulses of air to increase pressure to match the inspiratory activity. In some embodiments, a single flow path can provide both bias flow and inspiratory dosing in the event of a failure in another flow path. Lower dosing of the bias flow can be achieved by varying a valve position to slow air flow or generate intermittent air flow.

In some embodiments, a single pump can move air into a dual path flow circuit. A fixed orifice and pump rate are tuned for bias flow. The pump can maintain high pressure behind the fixed orifice. A variable orifice can open during patient inspiration to add additional flow. In some embodiments, the variable orifice diameter can be held constant for a given patient treatment and an in-line ON/OFF valve controls flow through the variable orifice. In some embodiments, a fixed orifice is not required because the ON/OFF valve can be intermittently opened and closed to vary flow.

In some embodiments, the pump can run continuously. A flow director can switch between the fixed orifice path (i.e., bias flow) and variable orifice path (i.e., inspiratory flow and bias flow). In some cases, an air reservoir can be filled by a smaller air pump that can run more continuously. The pump is used to maintain a constant pressure in the air reservoir. A pressurized reservoir delivering air through a proportional valve can be more responsive and provide more instantaneous flow than a pump that needs to accelerate to speed. In one embodiment, the air reservoir consists of a void built into the enclosure of the NO generator, rather than a separate component. This enables the reservoir to be a closed shape that takes up unused volume within the enclosure, thereby minimizing device size/volume. Combining the reservoir and enclosure also helps minimize the mass of the overall device.

Figures 26A, 26B, 26C:
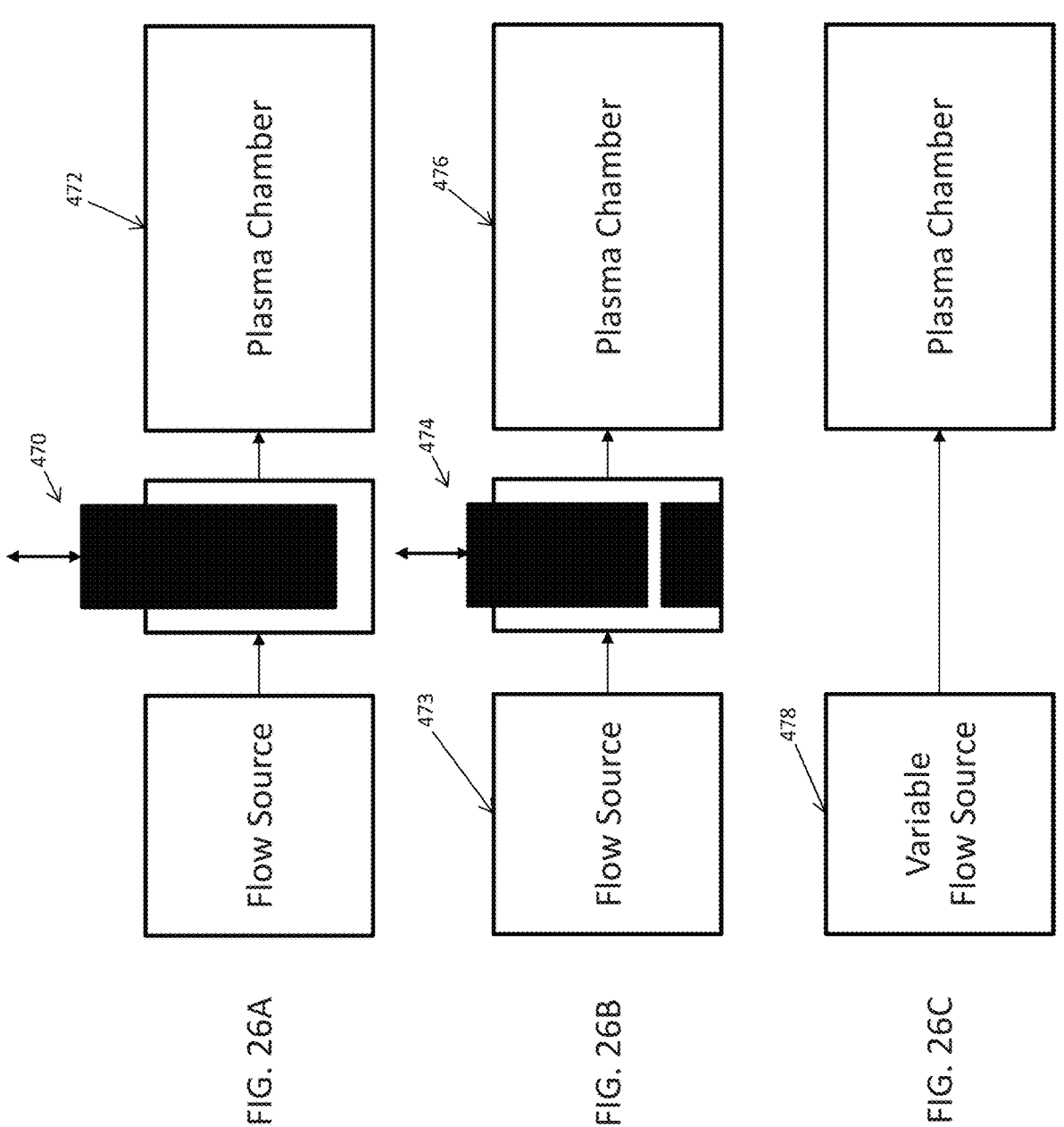
FIGS. 26A, 26B, and 26C are embodiments of flow sources and plasma chambers.

FIGS. 26A and 26B show an $N_2$ and $O_2$ containing gas source with flow path through a valve to a plasma source. In FIG. 26A, the proportional valve 470 does not close further so that there is always some level of flow through the plasma chamber 472. FIG. 26B shows a solenoid valve 474 with a permanent hole that always permits some level of flow. FIG. 26C shows a flow source 478 connected to a plasma chamber where the flow source can be varied in flow rate, pressure or a combination of the two. The flow source could be a rotary pump, piston pump, blower, pressurized vessel, fan, etc. The flow source of FIG. 26C could be controlled in a way that it flows to flush $NO_2$ from the system in-between inspiratory pulses. This flushing could cease after an amount of time, air volume, or when the next inspiratory pulse is detected.

High Voltage Circuit, Plasma Generator, and Electrodes

Figure 27:
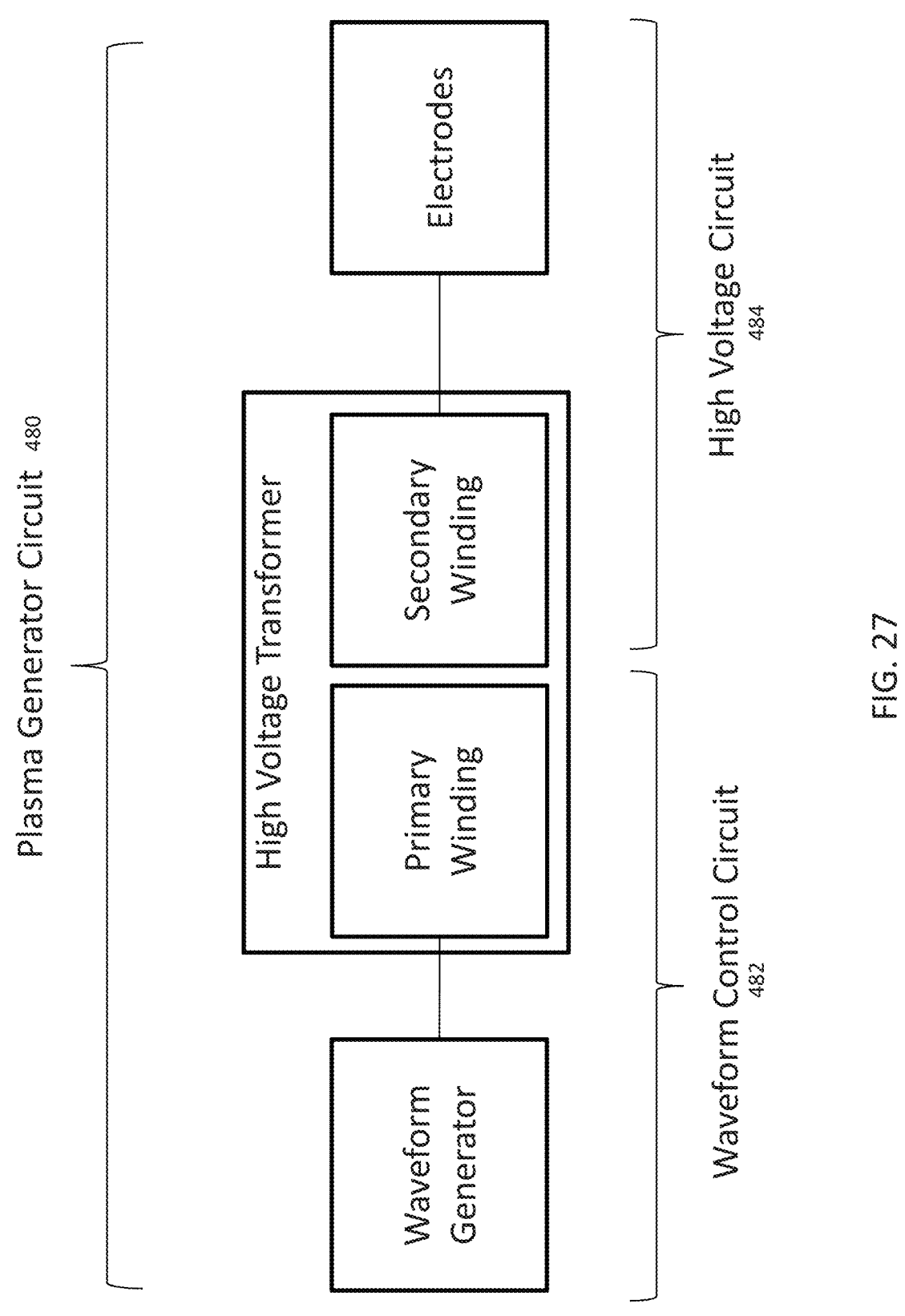
FIG. 27 is a plasma generation circuit including a waveform control circuit and a high voltage circuit.
Figure 29:
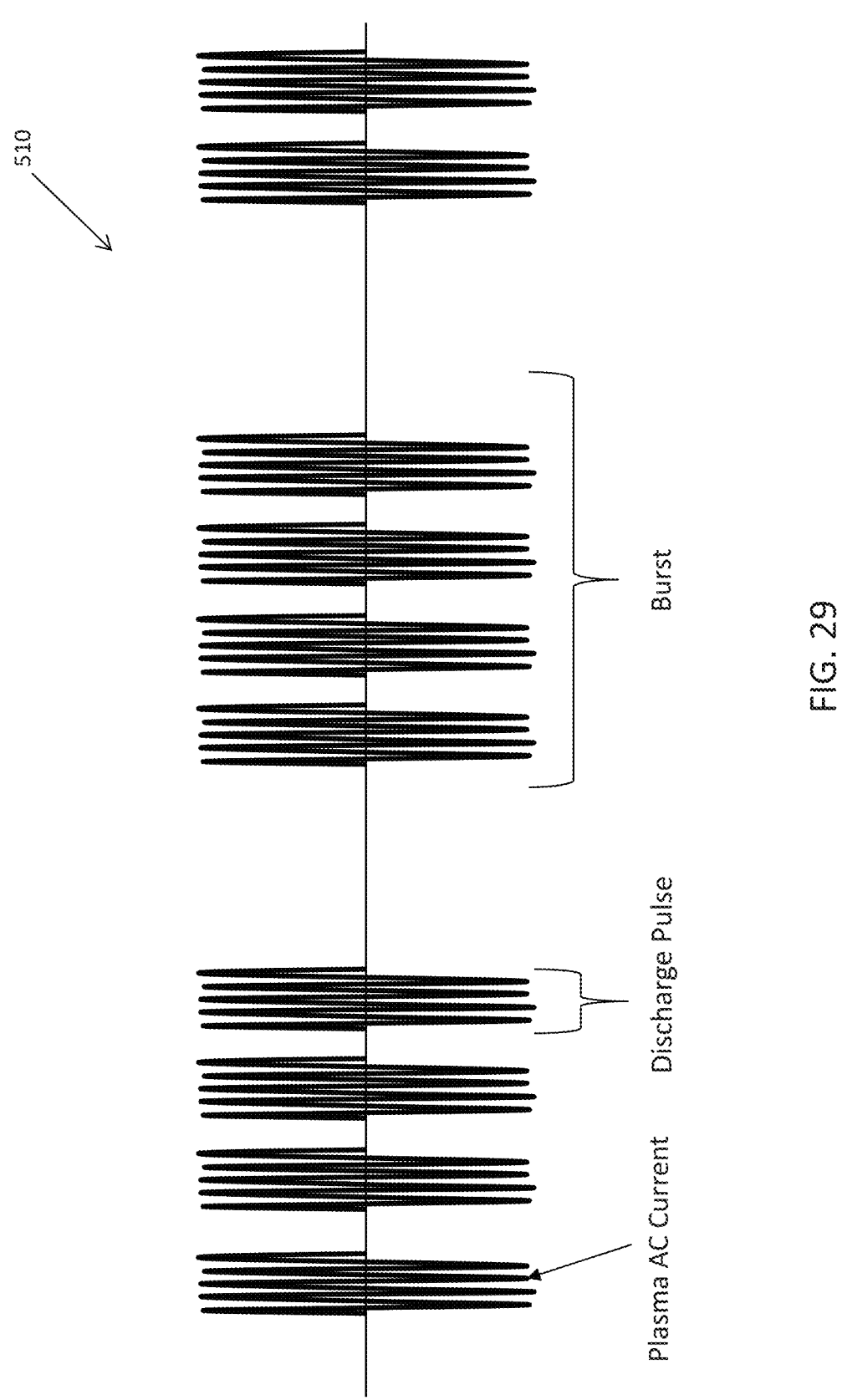
FIG. 29 is exemplary waveform generated by a high voltage controller DSP processor.

In some embodiments, a plasma generation circuit 480 can include a waveform control circuit 482 and a high voltage circuit 484 as shown in FIG. 27. A waveform control circuit 482 generates a continuous, customizable control wave. The control wave contains multiple control parameters, including the plasma AC current frequency and duty cycle, the discharge pulse frequency and duty cycle, and the group frequency and duty cycle. In some embodiments, the control wave is generated by a digital signal processor (DSP). An exemplary waveform generated by a high voltage controller DSP processor is shown in FIG. 29. The high voltage transformer converts low voltage currents into voltage high enough to generate a plasma at the electrode gap according to the input. In some embodiments involving an electrode gap of 2.5 mm, high voltage levels are on the order of 7 kV.

In some embodiments, the system can operate on alternating current (AC) voltage to the electrodes. The presently disclosed embodiments can also operate direct current (DC) voltage to the electrodes. In some embodiments, an AC system can be converted to a DC system by adding additional components to the system. In some embodiments, a halfwave rectifier diode can be included in the system. For example, the rectifier diode can be on the low voltage side or the rectifier diode can be on the high voltage side with a breakdown voltage greater than 15-20 kV. In some embodiments, a 15 kV discharge capacitor is added and can be located after the rectifier to ensure that voltage polarity is not reversed. Redesign of the transformers can be achieved with a much larger turns ratio and current capacity. In an embodiment, a Litz wire can be used. As a DC system does not benefit from resonance, a high voltage level is required. Thus, a high turns ratio in the transformer can be required. A voltage tap can be placed at an appropriate location in the middle of the transformer turns for the AC application. When current is drawn from the voltage tap (AC resonant operation), the unused portion of the secondary windings of the transformer are shorted to prevent excessively high voltages from occurring.

The high voltage circuit can be formed from a variety of components, but in some embodiments the high voltage circuit includes a controller to receive commands, a resonant circuit and high voltage transformer. The HV circuit receives commands from the controller and interprets the commands as plasma parameters and creates pulses of current that are fed to a resonant circuit and generates AC voltage. The AC voltage has a frequency that is tuned to the natural resonance of the high voltage transformer to maximize electrical efficiency. The AC high voltage is applied to the electrodes to make a discharge and is continuous until the pulse ends.

Figure 28:
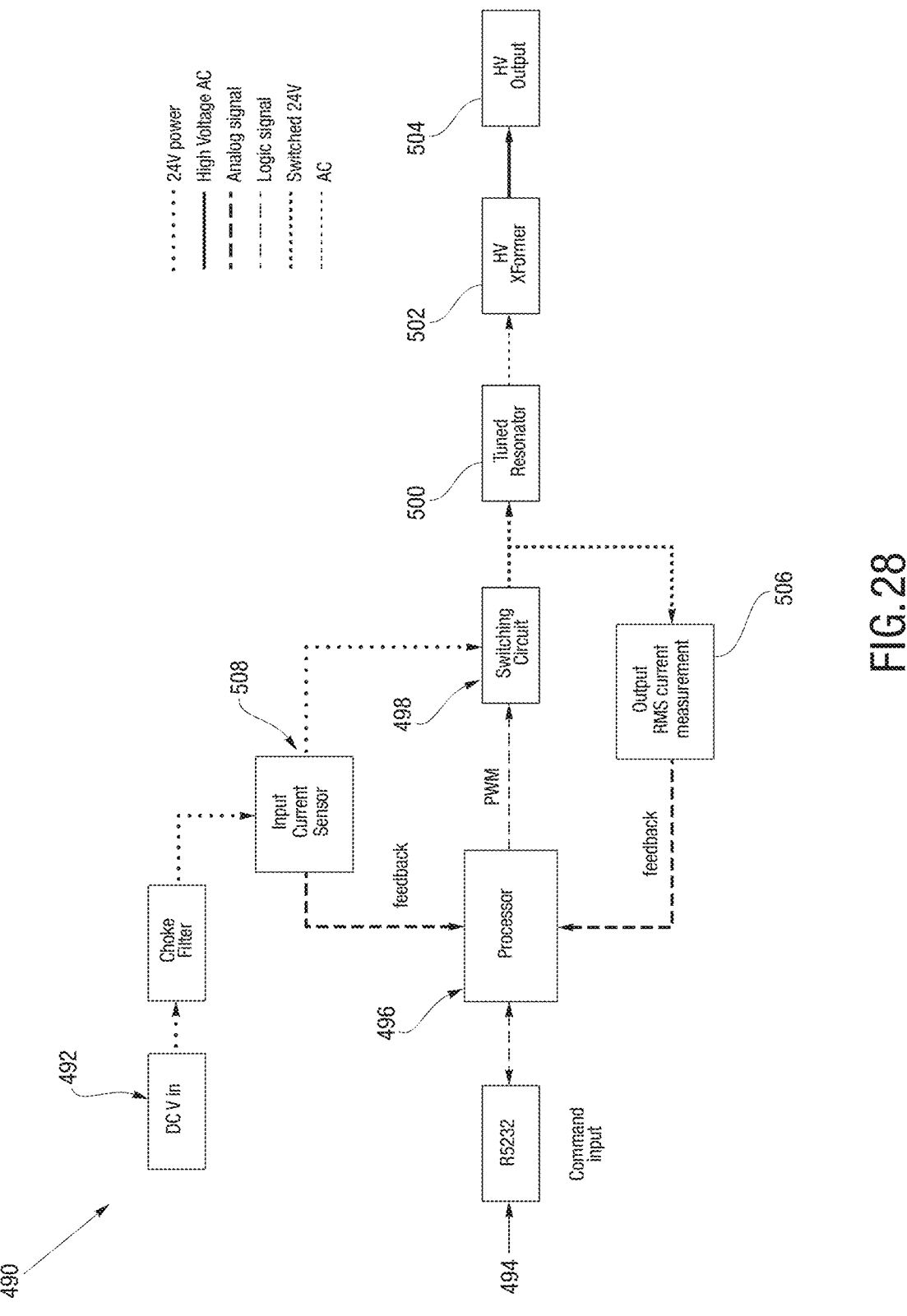
FIG. 28 is an exemplary embodiment of a high voltage trigger circuit.

FIG. 28 illustrates an embodiment of a HV trigger circuit 490. The HV trigger circuit 490 receives DC power 492 and at least one input command 494. A processor 496 supplies a switching circuit 498 with a PWM signal (variable duration) to excite a tuned resonator circuit 500. The resonator circuit 500 excites a HV transformer 502 at a fixed resonant frequency to generate voltage at a HV output 504, for example, the electrodes. Measurement of current 506 to the resonator provides feedback of the plasma function to the processor 496. Additional feedback can be provided from an input current sensor 508.

The HV trigger circuit 490 shown in FIG. 28 can have a number of advantages, including that the resonant tuning improves nitric oxide production efficiency, and it eliminates the need for a discharge capacitor which improves reliability and prolongs component life. AC operation of the HV trigger circuit can prolong the life of the electrodes and can reduce the potential of sputtering metal particles into the airstream. In some embodiments, a filter is used to capture metallic particles within a gas stream. In some embodiments, the filter size is 0.22 micron. In some embodiments, gas is bubbled through a liquid to capture particles after the plasma chamber. The liquid could be water, nitric acid, acetic acid, folic acid, for example.

DSP control of the discharge duration can more precisely regulate the nitric oxide concentration, and DSP control also allows for the automatic "tuning" of resonance to account for manufacturing variation, transformer characteristics, temperature, and electrode status (gap, wear, temperature).

In some embodiments, the system identifies the resonant frequency periodically throughout a treatment to account for changing conditions. In one embodiment, the system determines the resonant frequency only during power-up. In some embodiments, the system stores the resonant frequency and updates this stored value periodically (e.g. bi-monthly) in order to reduce the start-up time. In some embodiments, the system will operate slightly off resonance in order to lower the plasma power to produce low doses of NO. Input and/or output current feedback can automatically sense if the electrode fails to spark, which can allow for autonomous mitigation algorithms. The DSP can control the shape of the AC waveform by controlling its frequency and duty cycle.

In some embodiments, the transformer of the HV trigger circuit is a resonant design where voltage within the secondary side of the transformer increases until a sufficient voltage is present at the electrodes to break down the air gap. The voltage required to break down the air gap can vary with humidity, pressure, gap distance, electrode shape, electrode condition, and other factors. Having a resonant design without a set high voltage level improves reliability of plasma generation in the presence of electrode and environmental variability. In some embodiments, voltages for breakdown are typically in the 8 kV to 20 kV range, however it is desirable to keep voltages to less than 14 kV so that safety standards related to X-ray generation can be applied.

The frequency of the alternating current between the electrodes is the result of the hardware design and, in an embodiment, typically is the range of 50 kHz to 200 kHz. In an exemplary embodiment, the AC current frequency is 135 kHz. In another exemplary embodiment, the AC current frequency is 100 kHz. Pulses can be a fixed frequency for a treatment at roughly 100 to 200 Hz. This rate may vary, depending on the application. For example, a neonatal application would require slower frequencies due to the low amount of NO required. The duration of pulses can also be varied based on the amount of NO desired. For example, for a typical adult, the duration is roughly 250 micro-seconds (a. 25% duty cycle).

The leakage inductance of the primary determines the resonant frequency. The mutual inductance between the primary and secondary determines the resonance of the transformer. The high voltage circuit may be controlled by a 555 Timer, a Complex Programmable Logic Device (CPLD), Field Programmable Gate Array (FPGA), microprocessor, or any analog circuitry. Communication to the high voltage circuit from the control software and control circuit can be done using a wired connection such as a serial bus, I2C bus, or a wireless means such as optical, Bluetooth, WiFi or other means.

The high voltage trigger circuit can continue generating plasma according to instructions until it receives an instruction to either alter or stop plasma production. The system can continue generating nitric oxide in the event of control software failure, user interface failure, and/or control circuit failure.

The system can include a wireless communication module for communicating with various additional components, including but not limited to a hospital patient data system, and other controllers. For example, one system could communicate the status of a patient treatment case to a second system when a cartridge is being transferred between controllers for transport.

In some embodiments, the ventilator cartridge is transferred from one controller to another during transport. Treatment information including but not limited to serial number, lot number, system configuration information, treatment data history, alarm log, patient log, gas analysis data history, treatment settings log, expiration date, flow sensor calibration information and other information can be transferred from one controller to another controller via a memory device within the vent cartridge. The memory device could be communicated via wired connection or wireless means (RFID, Blue-tooth, etc.). Data can be refreshed within the ventilator cartridge at a periodic rate throughout the treatment. In this way, the receiving the system reads the vent cartridge and can pick up patient treatment where the prior system stopped. This sort of transfer could take place during patient transfer from hospital to ambulance, helicopter to hospital, or in the event that a system fails.

In some embodiments, the water trap has a memory device used to store information including but not limited to serial number, lot number, system configuration information, treatment data history, alarm log, patient log, gas analysis data history, treatment settings log, expiration date, flow sensor calibration information and other information. Billing can be in units of minutes of NO treatment, moles of NO treatment, number of treatments, etc.

An enclosure cooling fan can also be included, with or without an encoder to confirm fan operation. The fan operation can also be detected optically or with a flow sensor in line with the fan flow. The fan may also have its own closed-loop control based on a temperature input for modulating fan speed. Fan speed may also be modulated based on enclosure temperature, plasma generation levels, enclosure exhaust temperature, ambient temperature, heat exchanger temperature, and/or other inputs. The fan may source the cooling air from the cartridge or from another filtered inlet in the enclosure. In some embodiments, two fans draw air in through a disposable filter cartridge. In some embodiments, one or more fans source air from within the device enclosure and blow it out. In some embodiments, exhaust gases are blown down out the bottom of the device, addressing fluid ingress concerns.

Various inputs can be used to control the plasma generation levels. In an embodiment, ambient pressure can serve as an input to the control algorithm in determining plasma generation levels for a given nitric oxide output concentration using an ambient pressure sensor. A plasma chamber pressure can be measured within the plasma chamber to determine the amount of $N_2$ and $O_2$ present. An enclosure temperature sensor can be used to detect over-heating in the enclosure. In the event of overheating, the system can respond by increasing enclosure fan speeds, increasing nitric oxide gas flow rates, alerting the user, and/or another other type of notification. An ambient temperature sensor can be located in a location that is isolated from heat generated by the nitric oxide system, and the measurement from the sensor can be used as an input to the plasma generation algorithm since colder air is more dense, resulting in improved NO generation efficiency. A humidity sensor can be used to measure ambient air conditions to provide an input into nitric oxide generation control algorithms and estimates. The humidity sensor can also be used to monitor the humidity in the gas analysis sensor chamber to ensure that sensors are maintained in acceptable humidity conditions, or as an input to controlling sample in temperatures to prevent condensation within the sample line. Gas analysis sensors can either be mounted individually into the controller, or they can be assembled into a sensor pack such that one operation covers all sensors. The gas line handling the sample gases may be made from Nafion, or equivalent, tubing to prevent condensation of moisture and protect sensors from gas that is too dry, depending on the humidity of the gas sample. Gas samples for the analysis sensors can be sourced directly from the plasma chamber, from the exit of the scavenger, from the scavenger cartridge, from the ventilator cartridge, or from a location within the patient inspiratory limb. In an embodiment, gas is sampled from the patient inspiratory limb, just before the patient Y fitting so that gas is analyzed just before it enters the patient without adding additional dead space to the circuit, as would be the case if sampling was made between the Y and patient. In another embodiment, gas is sampled at the exit of the vent cartridge. This presents the advantage of sampling gas that is diluted to patient concentrations while still being in the dry portion of the ventilation circuit, thus not contaminated by humidity, nebulized drugs and other potential contaminants. This option could offer the benefit of not requiring a water trap and filter because it is in the dry portion of the ventilator circuit as well as reducing use steps for setting up the system since there would be no external sample line. It will be understood by a person skilled in the art that any number and any combination of the sensors described herein can be used with the system.

In some embodiments, the system can use an NO sensor to detect nitric oxide levels in the gas immediately prior to patient inspiration. Locating the NO sensor near the patient is desirable so that there is minimal effect of additional NO to $NO_2$ conversion prior to entry into the patient. One or more NO sensors may be used for redundancy and/or closed-loop control of plasma generation based on NO output. In an embodiment, a single NO sensor is used for detecting NO levels out of range and for limited closed loop feedback. For example, the measured NO sensor levels can increase or decrease the plasma activity by a limited amount, such as 10%, to adjust the device output.

In some embodiments, the system can use one or more $NO_2$ sensors to analyze inspiratory gases prior to entry in a patient. The $NO_2$ alarm threshold can vary, but in an embodiment is typically between 1 ppm and 3 ppm of $NO_2$, depending on the application and duration of treatment. In some embodiments, the system can continue operation in the event of an $NO_2$ alarm because a sudden respiratory event is more likely than lung damage at the $NO_2$ alarm threshold levels.

$O_2$ levels can also be measured by the system. A system that sources ambient air to flow through the plasma chamber can dilute gases within the inspiratory limb of a ventilator. This can be of particular interest when a patient has been prescribed 100% oxygen. Thus, it is desirable to inform the user of the actual $O_2$ levels that the patient is breathing post-nitric oxide introduction. For example, the discrepancy in $O_2$ levels between prescribed and actual can be as high as 8% in the 100% $O_2$ case. $O_2$ measurements may also be used as an input to a control algorithm in a system that generates plasma directly within the inspired gases. As $O_2$ and $N_2$ levels approach a Stoichiometric ratio of 50/50, NO production levels improve. Thus, a decreasing amount of electrical power can be required to generate a given amount of NO. Without considering $O_2$ levels in the plasma generation algorithm, the patient is at risk of receiving more or less NO than prescribed. In an embodiment, a membrane, such as one used in an oxygen concentrator, can be used to increase oxygen levels in air prior to entry into the plasma chamber, thereby increasing NO production efficiency.

In some embodiments, a sample gas pump can be located in the system to pull sample gases from the inspiratory flow limb in the ventilator circuit to the gas analysis sensors and on to the atmosphere. Commonly used gas analysis sensors rely on an electrochemical process. The sensors have slow measurement frequencies, typically at 30 to 60 second intervals. Commercially available NO delivery systems pull the gas sample at a constant flow rate. This averages the NO concentration with respect to time. With ventilator flow, however, flow rates and concentrations can vary in time. For example, if the patient received 100 ppm NO during inspiration and inspiration represented 10% of the respiratory period and exhalation took place the remaining 90% of the respiratory cycle, the patient would be receiving on average 100 ppm NO. Gas analysis sensors, however would average the concentration of gas sensed over the entire respiratory cycle and report a concentration of 10 ppm. Thus, a constant flow rate of the sample pump can generate inaccurate gas concentration readings.

One way to improve the accuracy of gas analysis readings is to vary the sample line pump rate as a function of patient inspiratory rate. A reasonable estimate for this is ventilator circuit inspiratory flow rate, however additional considerations for ventilator bias flow may be necessary. In the example above, the sample pump would only pull sample when the patient was inspiring, thus the gases analyzed would be at the same concentration as what the patient inspired, i.e. 100 ppm NO. One way of varying the sample pump flow would be to turn the pump off (zero flow) during patient exhalation and only turn it on during patient inhalation.

Ventilator treatment with bias flow can affect the measured accuracy of inhaled NO as well. If the sample pump is stopped during exhalation (when bias flow is shunting to the expiratory limb and not entering the patient), the concentration of bias flow is not measured, thereby improving the accuracy of the measurement of inspired NO concentration.

In the event that gas analysis sensors require a constant flow of gas, the system could pull sample gas from a source other than the ventilator circuit during patient exhalation. An example of another source would be ambient air. The controller could calculate what the measurement should be based on the known sample time from the inspiratory limb vs. alternative source and concentrations sensed.

In some embodiments, an approach to providing the gas analysis sensors with a gas that is more representative of the gas the patient is inspiring is to have a side-stream accumulator/mixing chamber parallel to the inspiratory limb of the ventilator. Typically, the volume of the mixing chamber is at least equal to the volume of gas pulled by the sample pump in one respiratory cycle so that the sampled gas represents an average of what the patient inspires. In the example above, the device would measure 10% NO. Coupled with the vent flow information, however, the controller would also know that the patient is only inspiring 10% of the time. Thus, the device could apply a factor to the measured data as follows: NO concentration to indicate=measured NO value/% inspiration time, where the measured NO value is the value indicated from electrochemical cells that have averaged the NO level over the entire respiratory cycle and % inspiration is the fraction of respiratory cycle time in units of % that the patient is inspiring.

A sample gas flow sensor can also be provided. A flow of sample gases over the gas analysis sensors can be required for representative measurements of the ventilator circuit gases. It is possible for the sample line to become obstructed or kinked. The system has a sensor to detect a sample line obstruction and proper function of the gas sample pump. The sensor can be a pressure sensor that measures pressure/ vacuum level in the sensor chamber or an actual flow sensor in series with the pump, or the sensor can be a flow sensor within the sample line. In the case of a blocked sample line, the sample line can be purged by running the pump in reverse.

The electrode assembly, or plasma assembly or chamber, can be part of the controller or part of the disposable components such as the cartridge.

In general, the temperatures involved in generating a plasma are at or near the melting point of most metals. In automotive applications and NO delivery system descriptions to date, the voltage applied to the electrodes has been DC, i.e., there is a cathode and an anode. Electrons travel from the anode to the cathode, eroding the anode over time. It follows that in automotive and other applications, high-melting temperature materials are only used on the anode.

In some embodiments, AC current is applied to the electrodes. This evens electrode wear by enabling both electrodes to be the cathode for a fraction of the time. With both electrodes serving as cathode, both electrodes can be comprised of a high-melting temperature material, such as but not limited to iridium, platinum, sintered iridium oxide or an iridium-platinum alloy. The electrode does not have to be monolithic construction of single material but can be alloys or combinations of suitable materials. In some embodiments, an iridium or other noble metal or alloy pad is welded to the end of a metallic, cylindrical substrate. It will be understood that a variety of shapes other than cylinders can also be used to from the electrodes. The substrate material can be of a less-expensive material, such as copper, nickel, carbon steel or iron. This composite approach not only decreases cost, but it also enables additional mounting methods for the electrodes. For example, carbon steel or iron can be used as these materials are non-toxic, thus any arcing that contacts the substrate will remain safe.

In some embodiments, the mass of the iridium electrode pad 0.15 g, which is 360 times greater than a typical automotive iridium pad 0.5 mg. This added mass decreases the temperature rise during plasma generation owing to the larger thermal mass and larger contact patch to the electrode substrate materials. By having a large iridium electrode pad, the electrodes can operate for extended time periods, for example, of one month, two months, three months, four months or longer on a pair of electrodes.

Various electrode shapes and sizes can be used in the plasma chamber. In some embodiments, needle electrodes can be used. Needle electrodes can sometimes wear rapidly, increasing the electrode gap and altering NO production levels. In some embodiments, a flat electrode surface can be used, as an electrode geometry approaching that of a sphere which will erode more slowly since arcs will initiate from more than one location.

Figure 30:
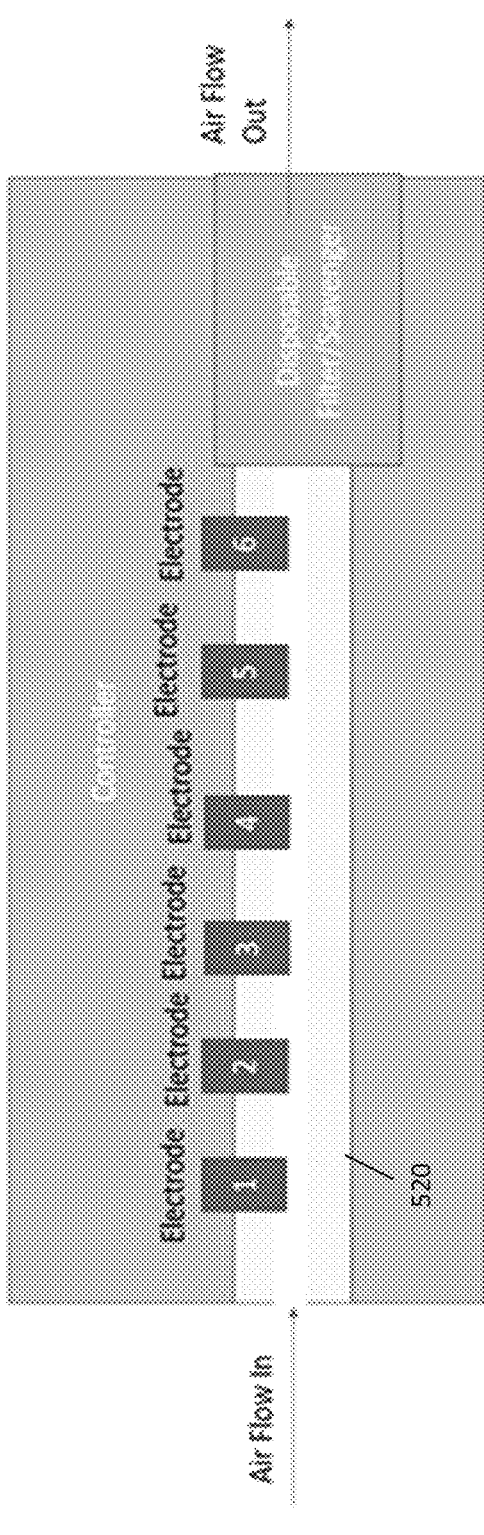
FIG. 30 illustrates an exemplary electrode manifold.

A plurality of pairs of electrodes can also be used in the system. The controller (or plasma chamber, or any other location in which the electrodes can be mounted) can also include one or more electrode pairs to increase run time between services. In some embodiments, these electrodes can be mounted to a manifold so that they are replaced as one unit. In a system that has multiple electrode assemblies, the system can cycle through the electrodes to minimize over-heating. Alternatively, the system can use the electrodes sequentially. Each electrode could have a dedicated high voltage transformer or a switching unit like a distributor could be used to energize each electrode from one HV transformer. FIG. 30 depicts an exemplary embodiment of how an electrode manifold 520 doubles as a heat sink and can have cooling fins on it.

Figures 31A, 31B, 31C:
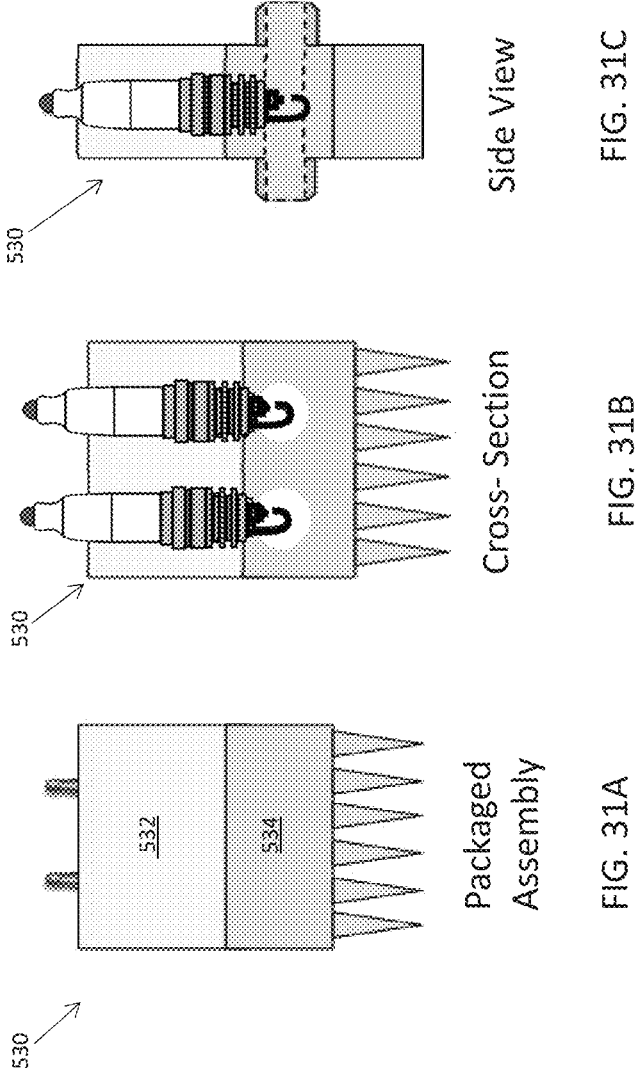
FIG. 31A is an exemplary embodiment of an electrode assembly with independent entry and exit points.
FIG. 31B is a cross-sectional view of the electrode assembly of FIG. 31A.
FIG. 31C is a side view of the electrode assembly of FIG. 31A.

As electrodes can wear, it is possible to position electrodes in the system to increase the ease of replacement. In some embodiments, electrodes can be packaged individually with their own plasma chamber for easy replacement. The assembly can includes other optional features, such as a heat sink. Electrode activity can also generate coatings of sputtered materials on the plasma chamber walls. By making the plasma chamber replaceable with the electrode assembly, decreases in performance due to electrical shorting across sputtered materials can be prevented. In some embodiments, the plasma chamber includes EMI shielding material to minimize radiated emissions from the plasma activity. The EMI shielding material is typically electrically coupled to shielding over the high voltage conductors to the electrodes which, in turn, is electrically coupled to electrical shielding covering the high voltage transformer. In some embodiments, EMI shielding is connected to DC Power supply ground. In some embodiments, the electrode assembly includes pneumatic connections (tubes, fittings and the like) to facilitate connection to the other components of the gas pathway. Gas flow to the electrode could be through the spark chamber with independent entry and exit points as shown in FIG. 31A, FIG. 31B, and FIG. 31C. FIG. 31A, FIG. 31B, and FIG. 31C depict various views of an embodiment of a dual electrode assembly 530 with cross-flow with a potting material 532, a heat sink 534, and a plurality of automotive-style spark plugs. Heat exchanger and gas path can be made from extruded metal. FIG. 32A and FIG. 32B depict various views of an embodiment of a single electrode assembly 540 in which the entry and exit point for gas flow could be the same opening so that gases enter a blind hole in the electrode assembly 540 and travel back out the same entry point. In some embodiments, the broadband EMI generated from the generation of plasma can be mitigated by shielding the electrode assembly by shrouding the electrode in a Faraday Cage.

In embodiments where non-electrically conductive gas passages connect to the plasma chamber (plastic tubes for example), EMI will travel along the length of the gas passage until the passage bends, at which point the EMI exits the side of the passage. Shielding can be placed around the passageway to absorb EMI as it exits the passageway. In some embodiments, an electrically conductive spring connected to ground is placed around the outside of the gas passageway to absorb EMI emitted from the plasma chamber. In some embodiments, a tubular woven structure of electrical shielding is placed around the gas passageway and connected to ground. In some embodiments, electrically conductive tape is wrapped around the gas passageway. In some embodiments, the passageway, itself, is made from a conductive material (stainless steel for example). The minimum length of the shielded portion of the passageway can be from the plasma chamber to the first bend in passageway that has sufficient angle to completely absorb the EMI. It follows that the magnitude of bend sufficient to absorb all the EMI within the passageway is a function of the diameter of the passageway (for round openings). Changing the aspect ratio of the passageway cross-section (ovalizing for example) could maintain similar cross-section, while decreasing the amount of bend necessary to absorb EMI with electrically conductive shielding.

Figure 33:
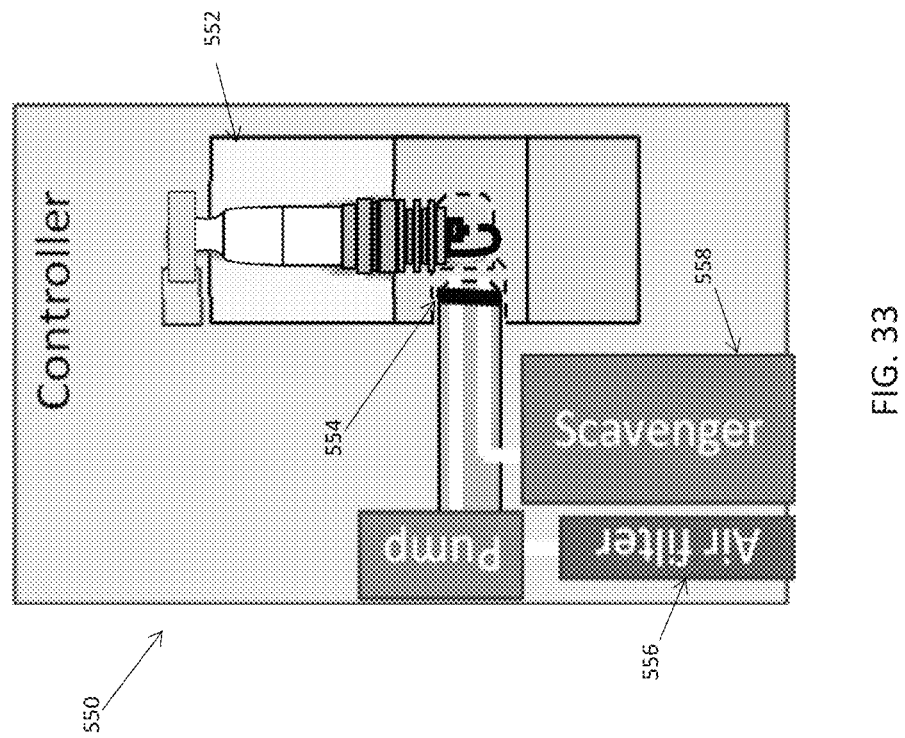
FIG. 33 is an exemplary embodiment of an electrode assembly mounted to a controller.

FIG. 33 depicts an example of an electrode assembly 552 mounted to a controller 550. In the illustrated embodiment, pumped air and NO-containing air are coupled to the electrode assembly 552 with a dual-lumen connector. The assembly includes an O-ring or lip seal 554. The plasma from the assembly 552 is pumped into a filter 556 and a scavenger 558.

Figure 34:
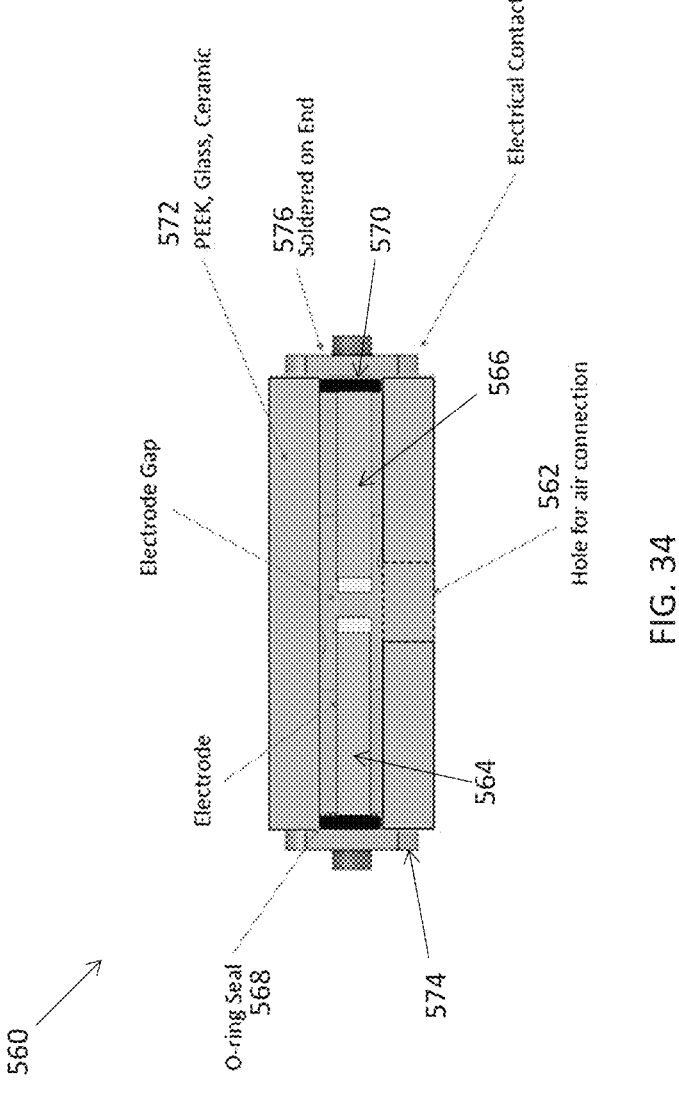
FIG. 34 is an embodiment of an electrode assembly for generating NO in an NO generation system
Figure 35:
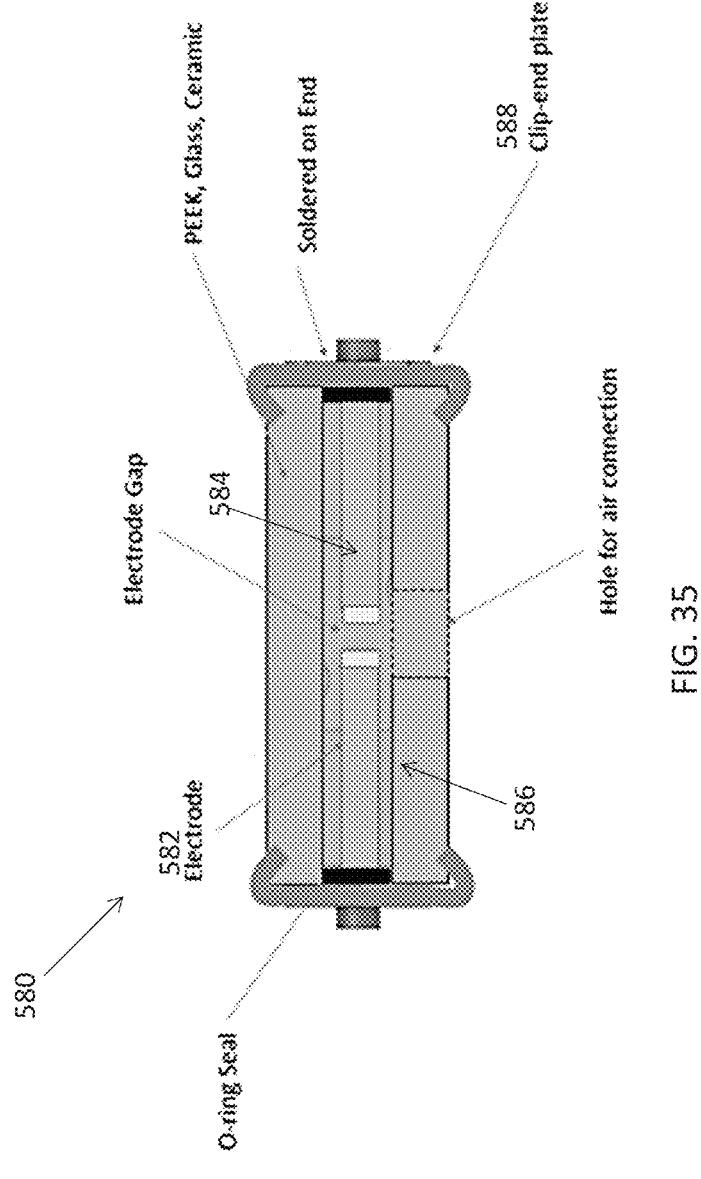
FIG. 35 is an embodiment of an electrode assembly for generating NO in an NO generation system.

Various electrode designs can be used for NO generation. In some embodiments, automotive-style plugs can be used for NO generation, however they can include resistors and more mass and strength than required. An automotive spark plug is designed for strength with a ceramic insulator and heavy metal ground electrode. In the interest of cost and mass, a custom high voltage electrode is desirable. FIG. 34 shows a high voltage electrode that can be manufactured and installed easily. FIG. 34 illustrates an embodiment of an electrode assembly 560 with a blind hole 562 (dashed lines at bottom). Composite electrodes 564, 566 can be inserted into the ends (right and left). In some embodiments, the electrode assembly 560 of FIG. 34 can be manufactured creating composite electrodes by fusing iridium (or other noble metal or alloy) pads to a metallic shaft (for example, copper). O-rings 568, 570 can be inserted into each end of a sleeve. The sleeve 572 can be constructed from PEEK, glass, ceramic or another inert, non-conductive material. Electrodes are inserted through the O-rings from either end into a sleeve. A gap tool is inserted into the hole for air connection. End plates 574, 576 are slid onto each shaft. Electrodes are lightly pressed from either side against the gapping tool. End plates are soldered to the shafts, locking in the gap. The electrodes can be held in place using a variety of techniques, including but not limited to an interference fit, adhesive, threaded fastener, and other means. In some embodiments, the end plate can mechanically snap on to the end of the glass sleeve as shown in FIG. 35, which illustrates an embodiment of an electrode assembly 580 with end plates 588 that clip to the sleeve 586 and solder to the electrodes 582, 584.

Having a single hole for air connection enables the user to insert an electrode assembly from one side with a single action. Various types of retention features can be used, including but not limited to detents, snaps, clamps and other means, to keep an electrode assembly in position within a controller.

A custom electrode assembly can interface with a controller by registering the electrodes with electrical contacts in the controller. A dual-lumen nipple from the controller can be inserted into the hole in the side of the electrode assembly to deliver air and remove NO-laden air.

Figure 36:
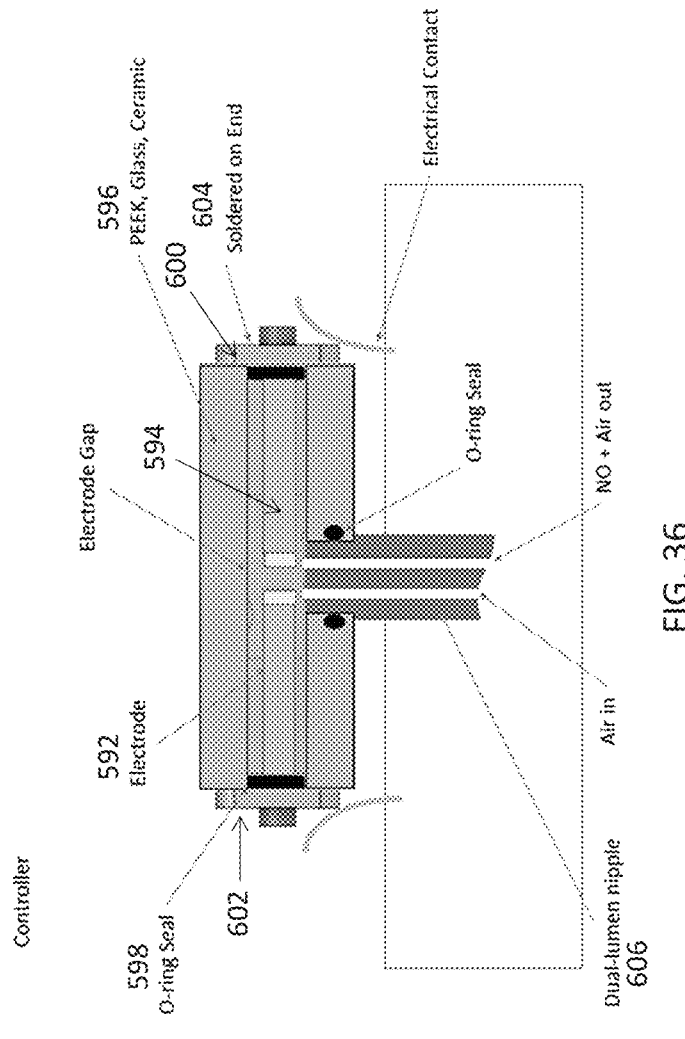
FIG. 36 is an embodiment of an electrode assembly for generating NO in an NO generation system.
Figure 37:
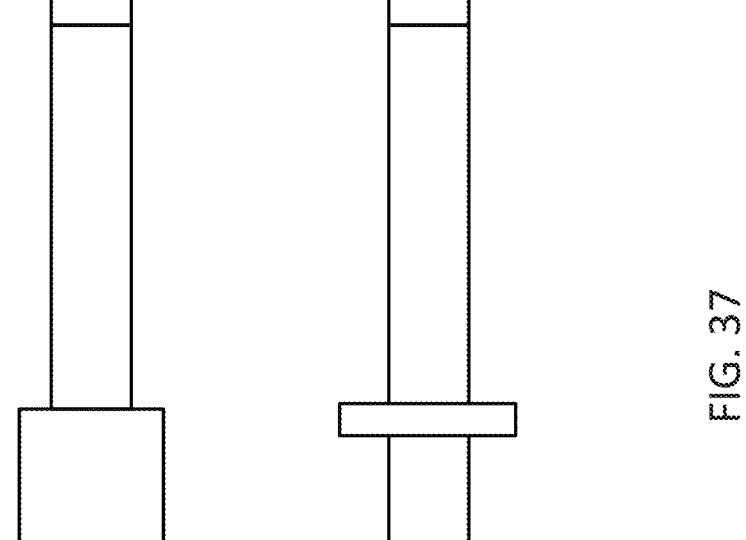
FIG. 37 illustrates various embodiments of electrodes with features for bottoming out.

FIG. 36 illustrates an embodiment of an electrode assembly 590 comprising a sleeve 596, a composite electrode 592 (copper shaft with iridium pad), O-ring seals 598, 600, and end plates 602, 604. The electrode assembly 590 can be inserted into a controller with high voltage electrical contacts contacting each end of the electrode assembly 590 and a dual-lumen nipple 606 inserted into the air connection hole. The composite electrode may have a step in the diameter, flange or other feature that makes the electrode bottom out into a hole at a specific depth. FIG. 37 illustrates embodiments of electrodes with features for bottoming out. During manufacture of an electrode assembly, individual electrodes are fabricated. In the embodiments shown, a high-melting point metal tip is connected to less costly substrate material. This composite approach can reduce cost and improve heat transfer away from the plasma in many cases. To assemble an electrode assembly, in one embodiment, each electrode is pressed into a frame. By providing a shelf or positive stop on the outer profile of each electrode, the electrodes can be pressed into until they bottom out. In other embodiments, the electrodes are pressed into a plasma chamber, manifold or other pneumatic component of the system. In other embodiments, the electrodes are pressed into a frame until a target electrode gap has been achieved. In one embodiment, electrodes are located and held in place within the plasma chamber housing with a press-fit. In one embodiment, the plasma chamber is over-molded onto the electrodes. In one embodiment, electrodes are held in place with a set screw.

Figure 38:
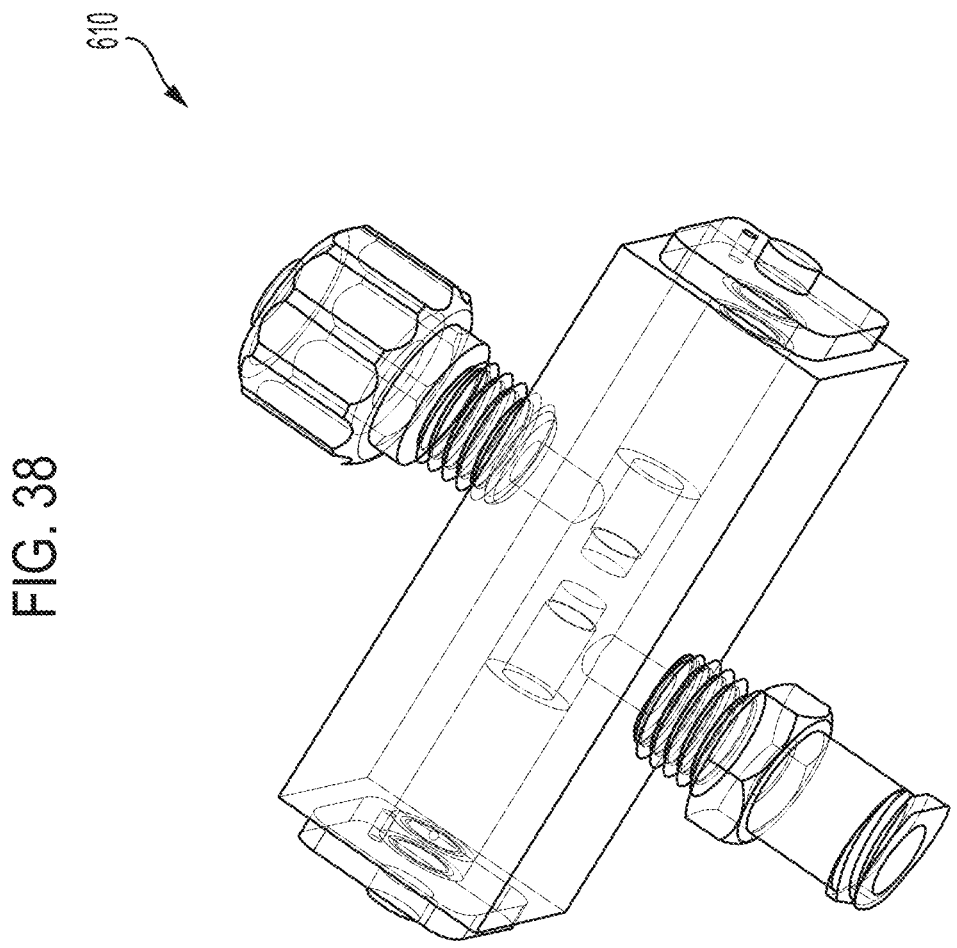
FIG. 38 is an embodiment of an electrode assembly that allows for air flow across an electrode gap.
Figure 39:
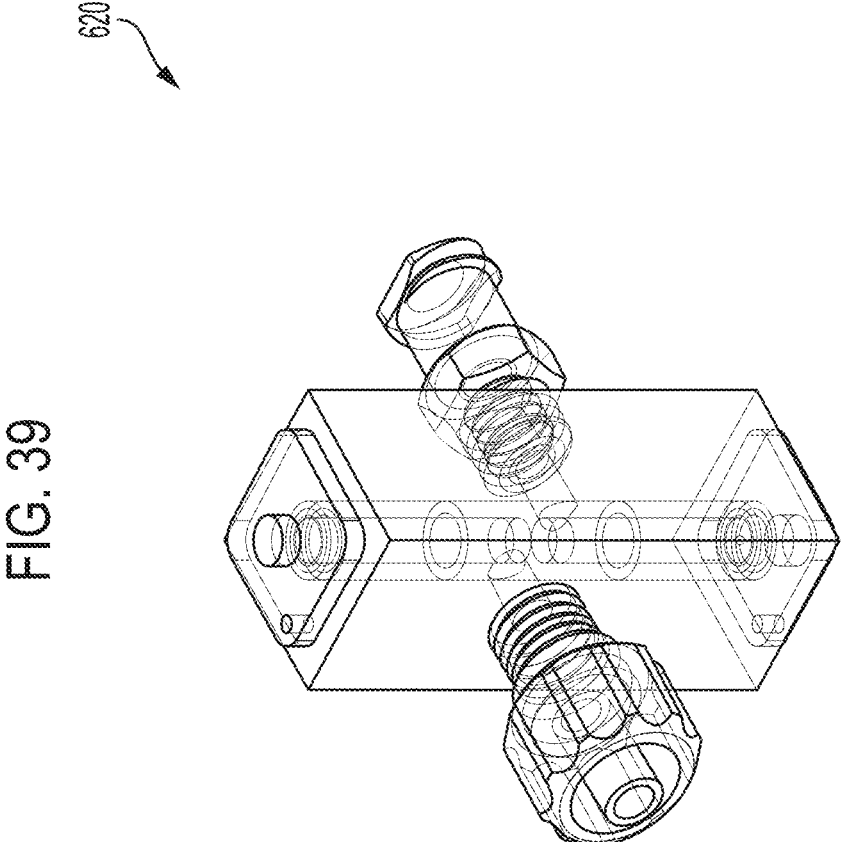
FIG. 39 is an embodiment of an electrode assembly.

In some embodiments, flow of air through the electrode assembly goes across the electrode gap. FIG. 38 illustrates an embodiment of an electrode assembly 610 showing air inlets (bottom left and upper right). Air flows into the electrode assembly on one side and out the opposing side. FIG. 39 illustrates an embodiment of a cross-flow electrode assembly 620 showing end-plate geometry. The hole in the corner of the end plate can be used for soldering a wire to it or fastening the end plate to the sleeve with a threaded fastener. The corners of the end plate can be rounded to reduce the potential of electrical discharge from the end plate.

Air flow within the electrode assembly can be from one side to the other, as shown in FIG. 39. In some embodiments, the flow can be from one side to an adjacent side. In some embodiments, air enters from one side, travels axially in parallel with the electrodes and then exits from the same side. This design shares the benefit of being inserted with a single action. For example, a person installing an electrode simply pushes the electrode assembly onto mating pneumatic connections, simultaneously establishing electrical connections.

There are various ways to accomplish plasma control. In some embodiments, a plasma energy level is controlled by varying the input voltage to the primary coil in the high voltage circuit. A hunting algorithm or a sweeping algorithm can be used that detects the resonant frequency of the HV circuit when the system is first turned on. This accommodates for manufacturing variance in the transformer and electrode variance (for example, gap, wear, corrosion).

Figure 40:
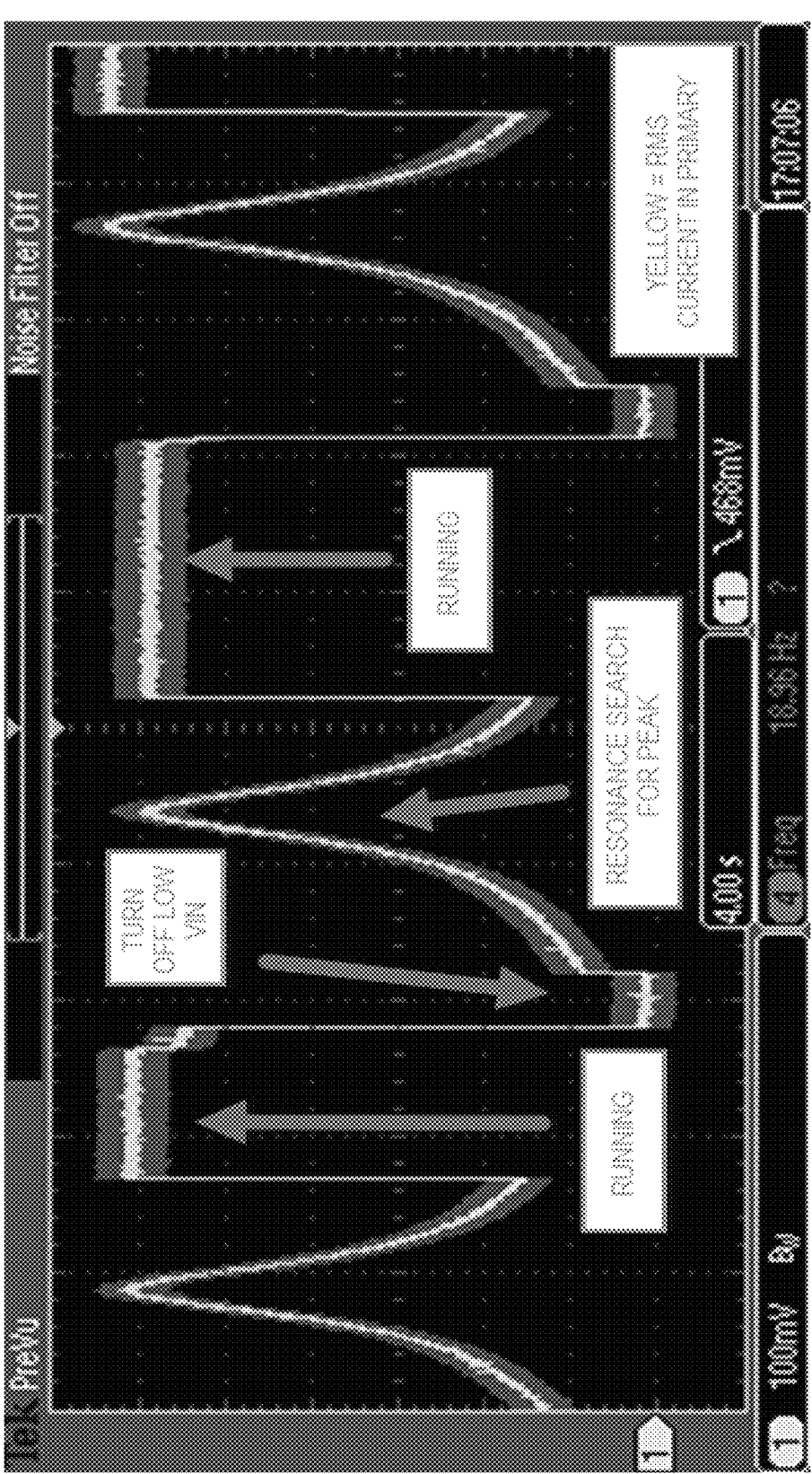
FIG. 40 is an exemplary graph of a spark frequency resonance scan for determining a resonant frequency for a high voltage circuit.

FIG. 40 illustrates an exemplary graph of an approach for determining the resonant frequency for the high voltage circuit. A sweeping algorithm can be used for alternating current frequency (not spark frequency) to find a resonant frequency to accommodate for electrode wear, and can sweep high to low or low to high. It can be possible to detune the resonance when lower NO production is desired. This reduces the amount of energy in the plasma, resulting in reduced NO production.

Figure 41:
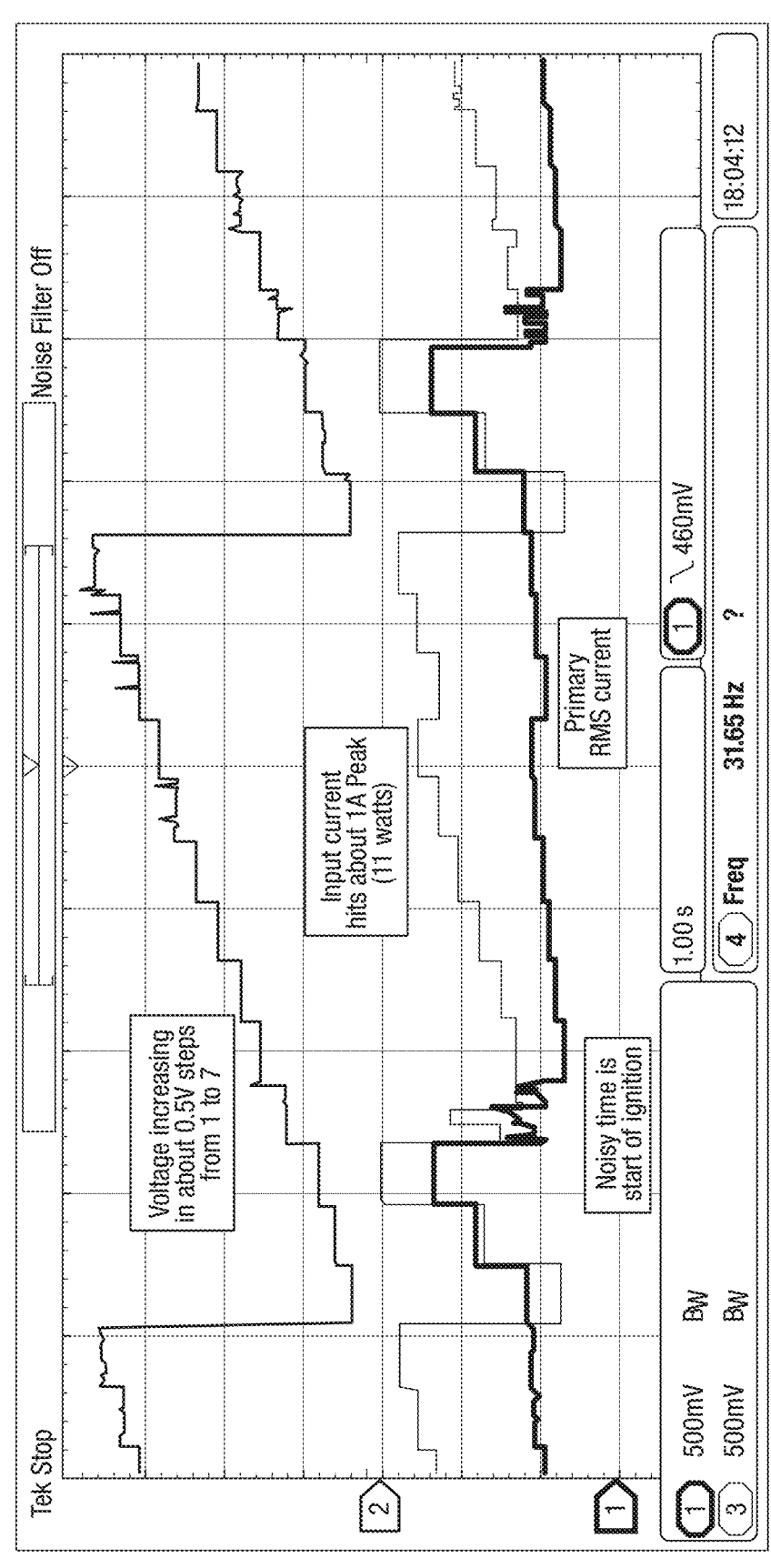
FIG. 41 is an exemplary graph for determining noise in a high voltage circuit to detect plasma.

In some embodiments, a pressure sensor can be used to detect plasma generation. Pressure increases because the plasma heats the air and makes the air expand. In some embodiments, a microphone can be used to detect plasma occurrence. In some embodiments, noise in the current in the primary winding of the HV circuit can be used to detect plasma. FIG. 41 illustrates an exemplary graph showing the use of noise to detect plasma.

The initiation of plasma can require additional energy, increase RFI noise, and increase electrode erosion. Thus, in some embodiments, plasma can be generated continuously and only vary $N_2$ and $O_2$-containing gas flow rate and/or plasma intensity. In addition, continuous plasma generation can create more NO than is needed to treat the patient. To prevent this, the system can have more than one electrode assembly, with each electrode assembly having a different electrode gap. Smaller gaps can be used to generate lower levels of NO, as needed for neonate applications. Larger gaps (2-3 mm for example) can be used to generate higher doses of NO.

The electrode assembly, as noted above, can have a variety of configurations. In some embodiments, a plurality of short-gap spark plugs can be used to reduce electromagnetic interference (EMI) and reduce high voltage requirements. A two-electrode design can be used with a third body that provides a shield for the plasma. A return current from the spark plug can be used as an indication of the status of the electrode, such as loss of the iridium pad or sensing that the performance is waning. Use of color/optical properties of the spark can also be used as an indication of electrode condition.

It is possible that the position of the ground electrode in an automotive-style electrode assembly with respect to air flow can have a 10-12% effect on NO generation. By locating the ground electrode upstream of the electrode gap, there are two significant benefits: A) shielding of the plasma arc, which is susceptible to "bending" in the presence of substantial flow. By using the ground electrode as a flow obstruction, the plasma arc may be produced in a less turbulent region, which may aid in the stable production of NO. B) any particles, specifically iridium oxide, which may be sputtered from the electrode surfaces, may deposit on the ceramic center electrode insulator downstream without creating a shortened creepage/clearance path to the ground electrode. Thus, the electrode assembly can require indexing (i.e. a specific orientation with respect to gas flow) to ensure consistent performance. In some embodiments, a drop-in electrode assembly can be used with an indexing feature. This can work because NO generation does not involve high pressure and temperature, so threads are not required. For example, an indexing feature can include a hexagon shape with a ground-off corner, a peg emanating from the plug (ground electrode, ground electrode shell, insulator, center electrode), a groove in the ground electrode shell, a unique spline design in the ground electrode shell, and/or a unique over-molded shape over the conventional electrode assembly. A visual indicator can be used to assist a user in orienting the electrode assembly correctly. For example, a colored dot on the electrode assembly can aligns with a colored dot on the manifold.

The use of off-the-shelf spark plugs, such as automotive or yard-tool spark plugs, can present a risk to the patient by not generating the appropriate amount of NO and/or introducing toxic materials into the air stream. In some embodiments, a unique electrode assembly interface can be used with the manifold. For example, a thread-less ground electrode shell with one or more of the hexagonal nut corners removed can be used, as shown in FIG. 37. The outer diameter of the thread-less section can be less than the diameter of a threaded spark plug, thereby preventing insertion. The electrode assembly can be retained by a retaining plate that fastens to the manifold and applies a clamping force to the electrode assembly. The electrode assembly shell can have a sealing surface that compresses an O-ring against the manifold.

Figure 42C:
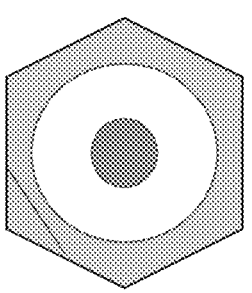
FIGS. 42B-42C illustrate components of the electrode assembly shown in FIG. 42A.
Figure 42B:
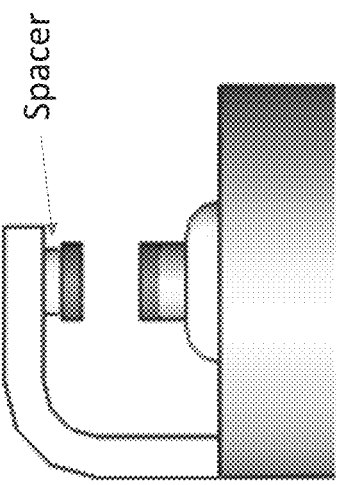
Figure 42A:
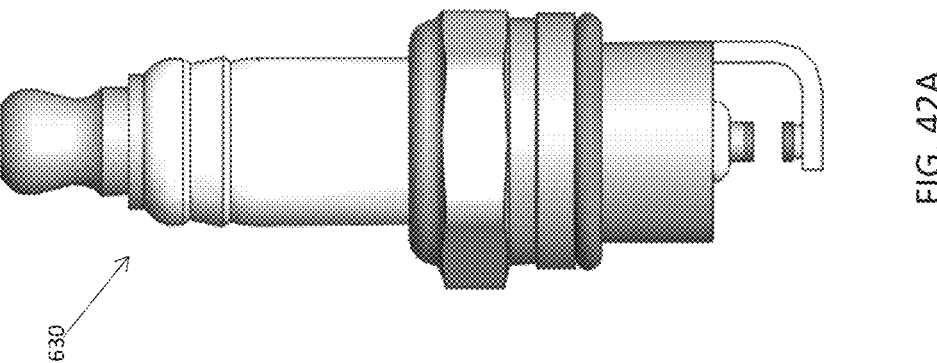
FIG. 42A is an embodiment of an electrode assembly having an o-ring.

The electrode assembly can be sealed to the manifold with a variety of mechanisms. FIG. 42A illustrates an exemplary embodiment of an electrode assembly, and FIGS. 42B-42C illustrates components of the electrode assembly shown in FIG. 42A In some embodiments, as shown in FIG. 42A, an O-ring can be used (Viton, or fluorinated materials are preferred) with an electrode assembly 630. In some embodiments, the O-ring seal, shown in FIG. 42C, is an axial compression O-ring as shown in FIG. 42B, where the clamping force maintains the seal. Compression can be applied by retaining plate that fastens to the manifold. Compression of the O-ring can be controlled by compression limiting features in the plate, plug, or manifold. In some embodiments, a retaining plate can be used and can be electrically conductive in the case of a plastic manifold (Teflon for example). In the case of an electrically conductive manifold, the retaining plate could be non-conductive, such as plastic. In some embodiments, the O-ring seals radially against a bore in the plasma chamber.

Electrode materials can sputter from the electrodes and enter the ventilator airstream, which can be harmful to the patient if the electrode materials are toxic. In some embodiments, electrode assembly ground electrode shell can be made from steel and or iron, which are non-toxic. Iron and steel are also magnetic, thus a magnet could be placed in the system down-stream from the electrode assembly to collect sputtered magnetic electrode particles.

Figure 43:
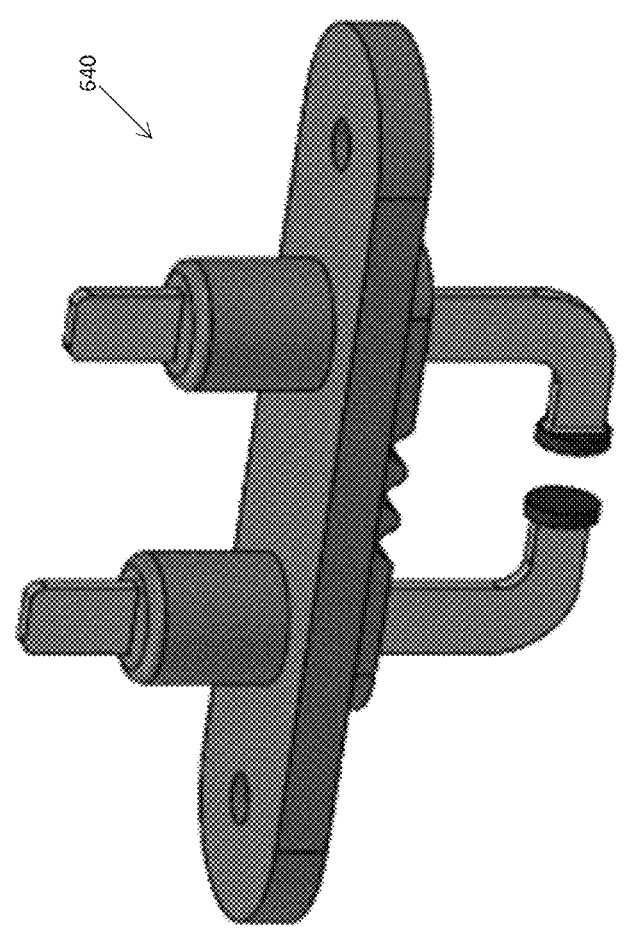
FIG. 43 is an embodiment of an electrode assembly.

FIG. 43 depicts an example of an electrode assembly 640 designed for improved NO gas purity. The noble metal electrode pads are attached on the back surface only so that only the electrode is presented to the plasma. The noble metal could be platinum, iridium, another high-melting point metal or alloy thereof. The metal pads are connected on their back side to an electrically conductive substrate. The substrate holds the electrode pad in the correct location and conducts electricity to the pad. The substrate shown in FIG. 43 is made from sheet metal, which facilitates electrical connection to the assembly via a tab connector. Bosses around the tab connector provide a means for sealing an insulative boot around the connector to prevent electrical creepage. Ridges between the electrodes on the bottom surface increase the surface distance between the electrodes to further minimize electrical creepage potential. The body of the assembly (shown in orange) is made from a non-electrically conductive material such as plastic or ceramic. One or more holes in the body enable the body to be secured to the rest of the system via screws. In one embodiment, the body itself is threaded for engagement into the system.

Figure 44A:
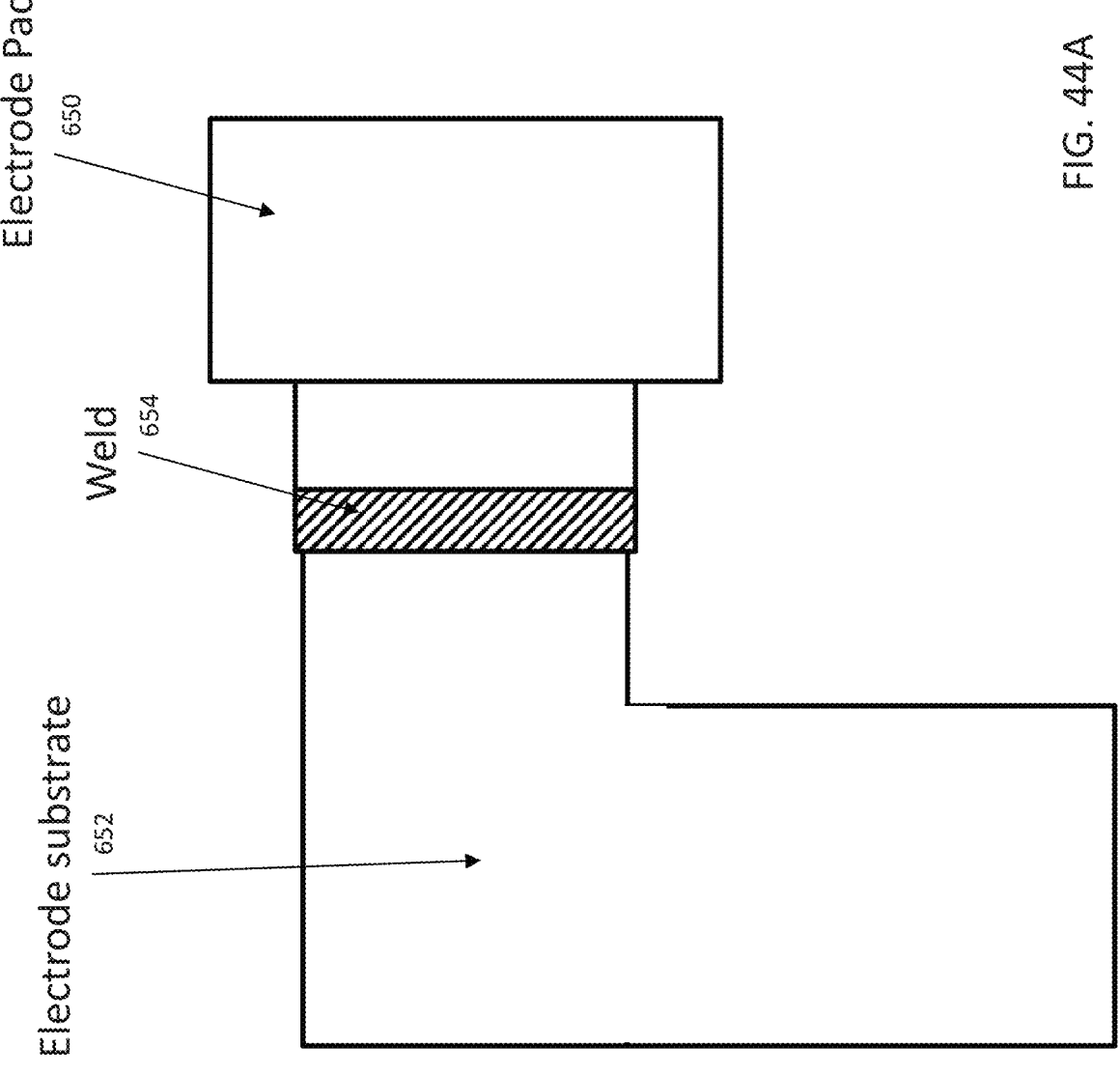
FIGS. 44A, 44B and 44C are embodiments of an electrode assembly.

FIG. 44A presents a drawing of an electrode pad 650 with attachment 654, such as a weld, to an electrode substrate 652. One problem that can occur in plasma generation is that the plasma arc can be emitted from materials adjacent to the electrode pad, depending on their proximity to the arc, thermionic work function, and geometry. During NO generation via plasma, it is desirable to control the plasma so that it is only emitted from the electrode pads. The design in FIG. 44A depicts an electrode pad 650 with a larger area towards the plasma (right in the image) and a smaller end towards the substrate. The smaller end is attached to the substrate via welding, soldering, crimping, press fit or some other means. The electrode pad can be created by turning on a lathe, wire EDM, casting or another process.

The substrate material for the electrode assemblies shown in FIG. 43 and FIG. 44A are typically metallic. Unlike typical spark plugs that have a nickel coating, medical applications require a more inert material. In some embodiments, stainless steel is used, owing to its biocompatibility and weldability to noble metals. In some embodiments, titanium or a titanium alloy is used, offering benefits in thermal conductivity, biocompatibility, weldability (high melting temperature), and absence of nickel and chromium (toxic materials).

Figure 45:
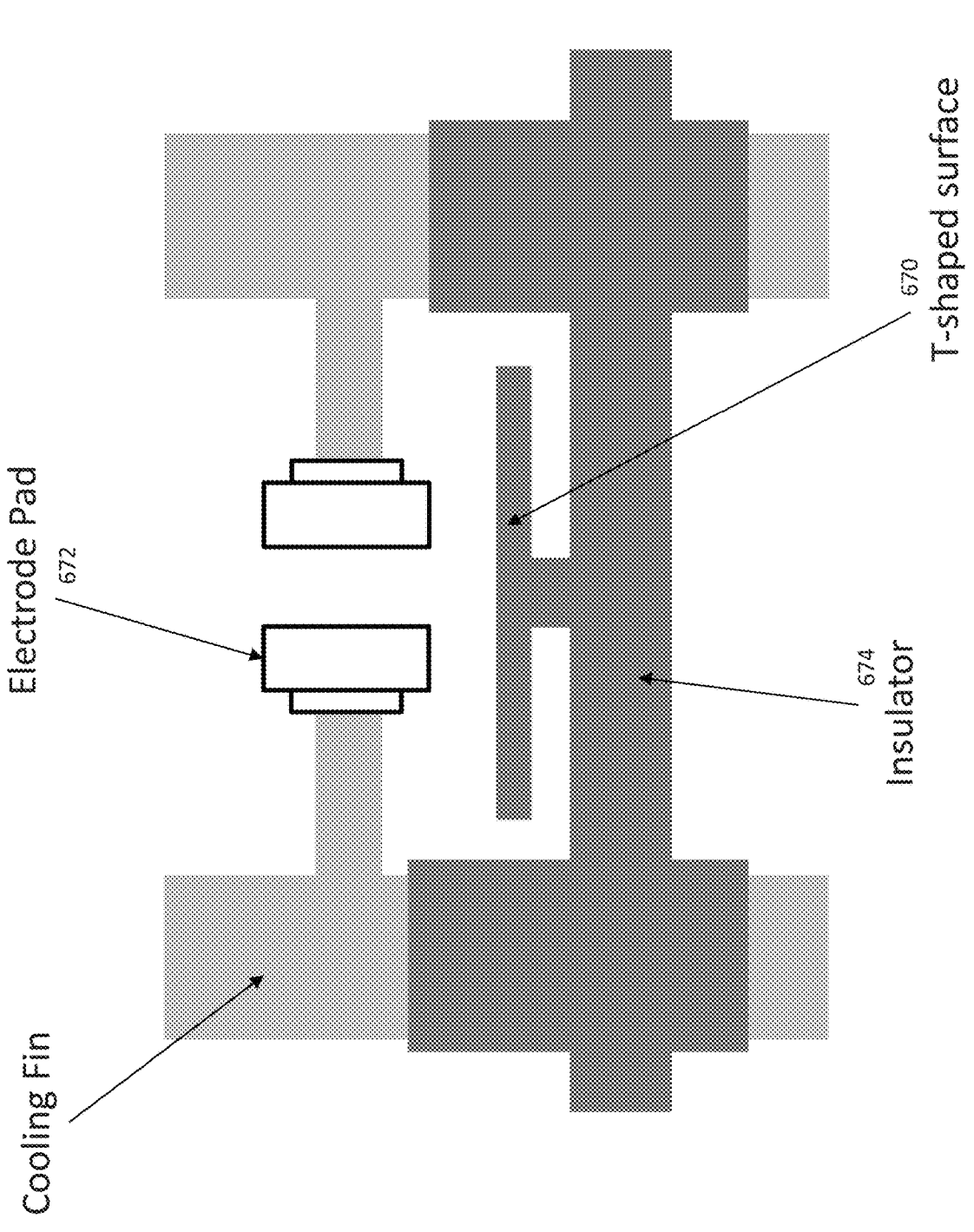
FIG. 45 is an embodiment of an electrode assembly.

FIG. 44A depicts an electrode assembly with a cylinder around the electrode pads. The cylinder provides a surface to capture sputtered materials from the electrodes that can be replaced with the electrodes. Without a surface to capture sputtered materials, the walls of the plasma chamber could build up sufficient sputtered materials to be electrically conductive, thereby presenting a short circuit for the electricity and decreasing NO generation. Other shapes could also serve as a collector for sputtered materials, including a flat surface 670 between electrode pads 672 and the assembly body 674 as shown in FIG. 45, however a closed shape like a tube or square-extrusion is the greatest potential to decrease short circuits between the electrodes. Also shown in FIG. 45 are extensions from the electrodes that serve as cooling features. These cooling features help prevent overheating of the electrode which can lead to increased wear and damage to insulator materials.

Figure 44B:
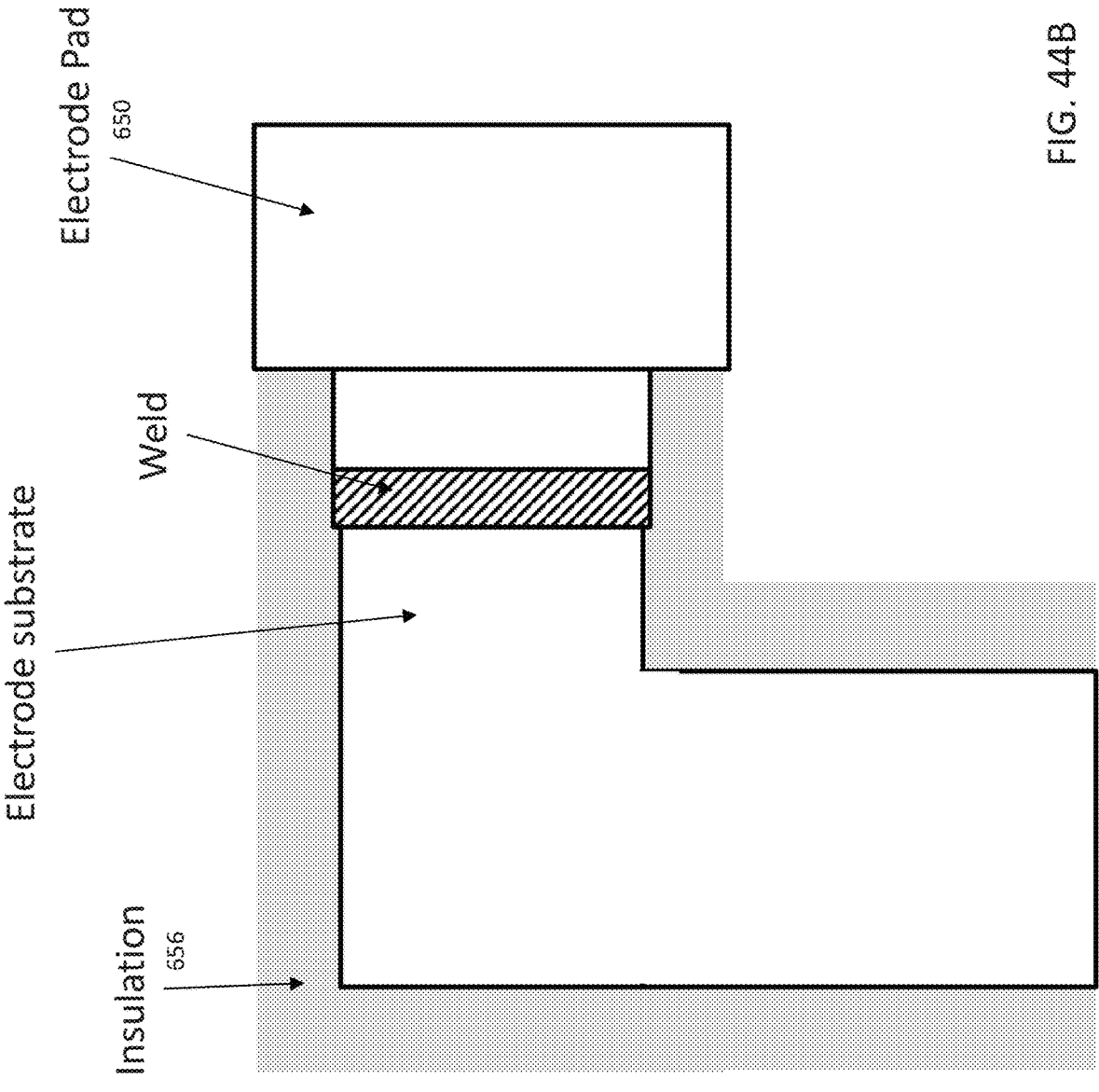

FIG. 44B depicts the electrode assembly of FIG. 44A with insulation 656 around the entire length of the electrode except for the tip. In some embodiments, the tip is made from a noble metal, such as iridium or platinum. Insulation 656 around the electrode prevents the plasma arc from contacting the sides of the electrode when energized, thereby controlling the types of materials that may be sputtered off the electrode. Furthermore, the electrode increases the electrical creepage distance from one electrode to another electrode, thus decreasing the potential for a short circuit.

Figure 44C:
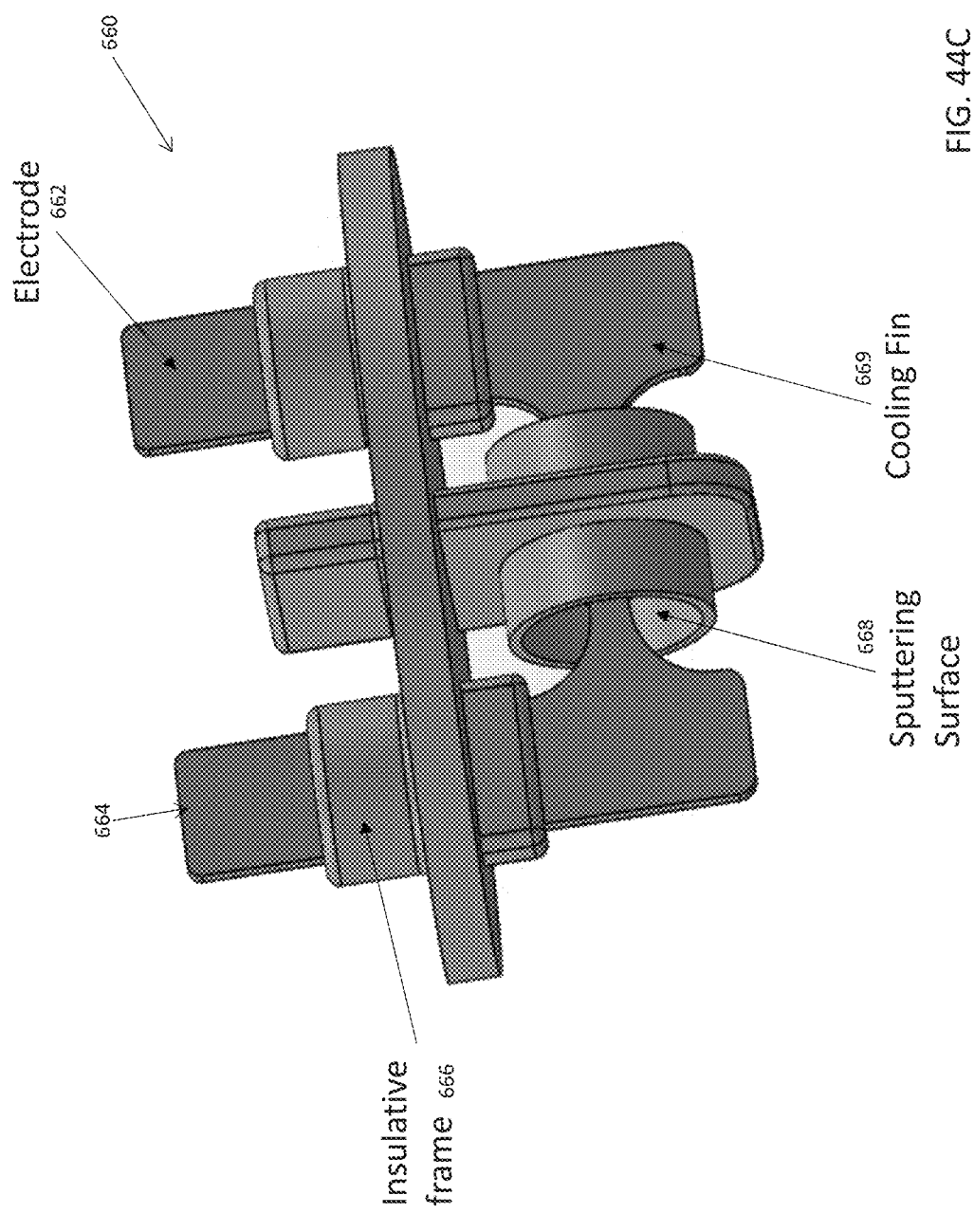

FIG. 44C depicts an electrode assembly 660 for use in an NO generation device. The assembly 660 includes two electrodes 662, 664 made from sheet metal. On one end, the electrodes are shaped like a tab-connector for electrical connection. The insulative frame 666 provides electrical insulation between the electrodes 662, 664 and maintains the electrode gap. Bosses around the electrode tab connectors provide a surface for a boot to seal against when an electrical connection is made. A ridge between the two bosses on the top surface provides additional creepage distance between the two electrodes. On the bottom of the figure, there is a tubular structure 668 around the electrode gap. This tubular structure provides a surface to receive sputtered electrode materials. By providing a sacrificial surface for sputtered materials, sputtered materials do not build up on the plasma chamber wall, increasing the potential for an electrical short due to creepage or arcing directly to the plasma chamber wall. The tubular structure 668 can be made out of either an electrically insulative material or an electrically conductive material if proper clearances are maintained. The bottom edge of the electrodes feature additional material that acts like a cooling fin 669 in the reactant gas air flow to dissipate heat from the electrodes 662, 664 and minimize sputtering.

Figure 46A:
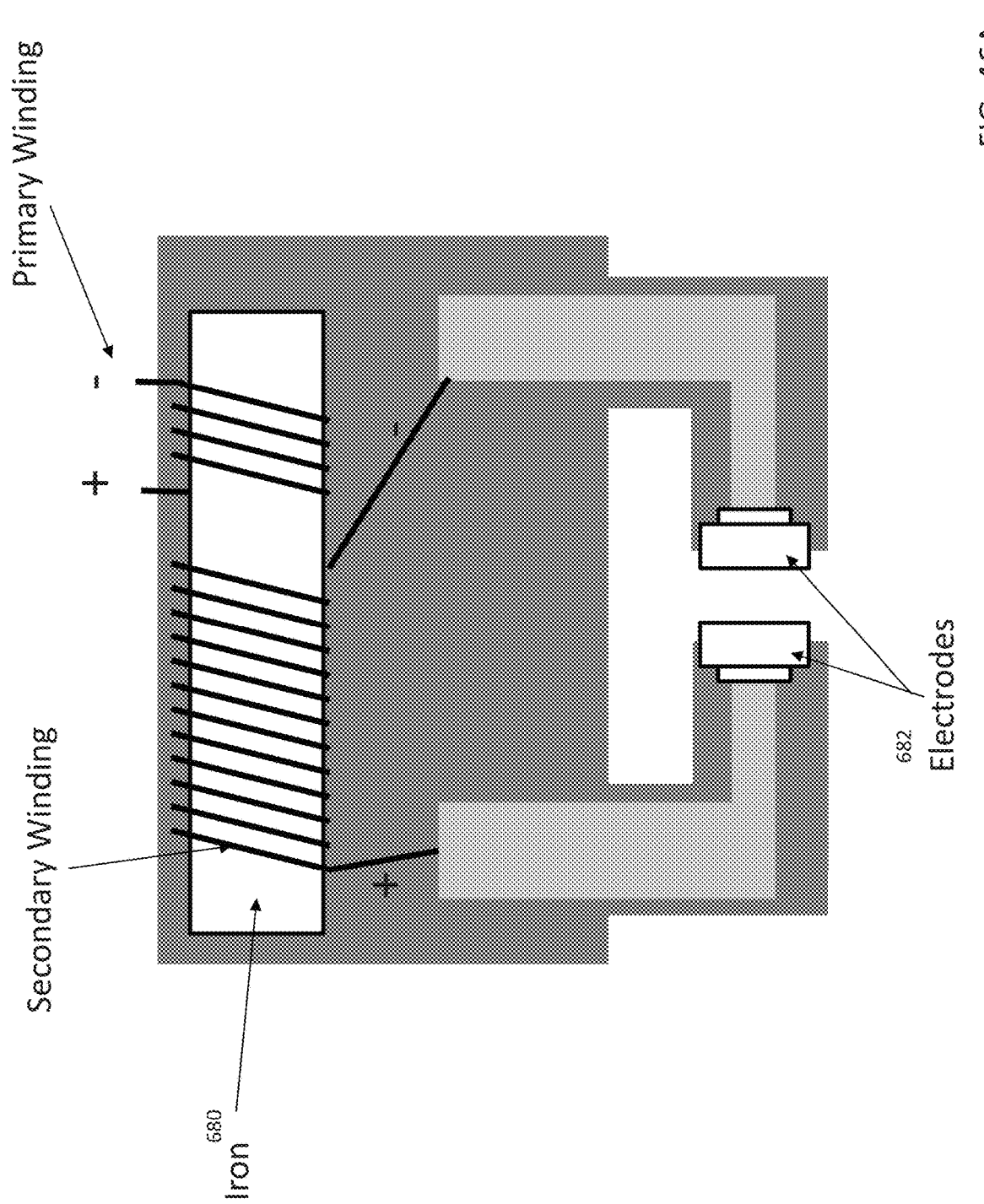
FIG. 46A is an embodiment of an electrode assembly.

Plasma generation can generate considerable electromagnetic radiation. The largest source of emissions is the high voltage circuit and the plasma activity. Shielding the electronic circuit, electrodes and plasma chamber help in minimizing emissions. In addition, shortening the length of wires in the high voltage circuit can reduce emissions. To that end, it is beneficial to combine the electrodes and high voltage transformer so that there is no length of wire between the two that could act as an antenna. FIG. 46A depicts a combination of electrode assembly and high voltage transformer. An iron-core transformer 680 is depicted, but other types of transformers can be combined with the electrodes 682 to reduce emissions. In one embodiment, a central grounding scheme that connects all the chassis shielding elements and ties them to DC ground at a single point absorbs the bulk of the EMI radiation and conducts it to ground without being re-radiated.

Figure 46B:
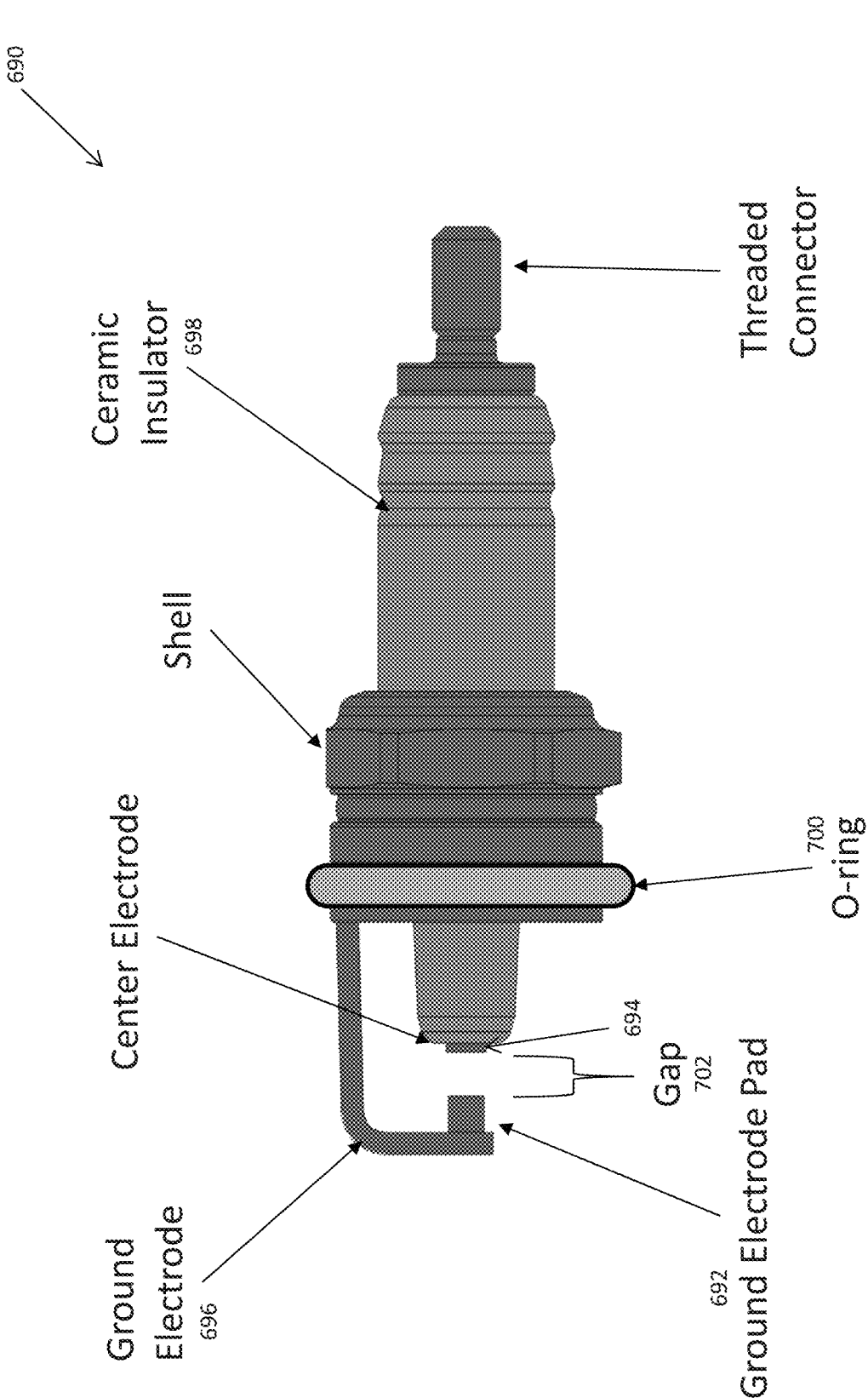
FIG. 46B is an embodiment of an electrode assembly.

FIG. 46B depicts an exemplary electrode assembly 690 with a focus on maximizing creepage and clearance distances. In this embodiment, the ground electrode pad 692 is taller than the center electrode pad to ensure arcing only occurs to the pad. In some embodiments, the ground electrode 696 measures 2 mm in diameter and 2 mm tall. The ground electrode pad 692 is fastened to a ground electrode

696 via welding, soldering or another means. In some embodiments, the ground electrode is made from stainless steel to minimize the potential for nickel particles entering the product gas, however carbon steel, titanium and other high melting point materials have been considered. Both electrode pads are made from a high melting point material, such as iridium, platinum or similar. The center electrode pad can be shorter, such as 1 mm, owing to the fact that there is ceramic insulation 698 around it that prevents arcing to substrate materials.

The shell of the electrode assembly depicted in FIG. 46B is designed to be far from the electrode gap. This is to minimize the propensity for side-sparking. In the example shown, the distance from center electrode to shell is more than 3 times the distance of the electrode gap so that arcing from center electrode directly to the shell is unlikely even in the presence of Iridium-oxide deposition on the ceramic insulator 698. An O-ring 700 provides a seal against a mating surface in a plasma chamber or electrode block.

The ground electrode has an asymmetric cross-section with the long dimension tangential to the shell, thereby maximizing distance away from the electrode gap. The ground electrode is fastened to the electrode shell at the outermost location, further maximizing the distance from the electrode gap. The bend in the ground electrode is a sharp bend to maximize distance from the electrode gap. In some embodiments (not shown), an electrically insulative material such as polymer or ceramic is placed between the electrode gap and the ground electrode. In some embodiments, the insulative material is a tube or coating that covers the length of the ground electrode.

Performance of electrode assemblies with or without embedded transformers may vary in production do to electrode gap, transformer winding variance, conductivity variance and other factors. One solution to address manufacturing variance is to embed calibration information within the electrode assembly via an RFID or other memory device. This calibration information could consist of a resonant frequency.

Performance of the pneumatic manifold within an NO generation device may vary as well. In one embodiment, the calibration information for a manifold is embedded within the manifold and is used by system software as an input to calculating NO generation parameters. The information can be embedded into a manifold by RFID, a processor with Bluetooth, bar code, wired memory device and other means. Calibration information can consist of one or more of the following types of information: a flow restriction value, pressure sensor calibration information, flow sensor calibration information, variable orifice transfer function. The manifold may also have manufacturing and use data embedded and/or written to it, such as serial number, lot number, expiration date, first used date, total amount of run time, total amount of NO exposure, etc.

The purpose of the manifold is to direct the flow of gas through the system without leaking. In one embodiment, the manifold is made of metal, such as aluminum, stainless or titanium, so that the manifold can act as a heat sink and EMI shield. In another embodiment, the manifold is made from a polymeric material such as PEEK or Teflon in order to provide an inert material in contact with the NO, $NO_2$ and air. Polymeric manifolds may be plated or otherwise encapsulated in conductive material for EMI shielding purposes. In one embodiment, the manifold is a split design held together with threaded fasteners with a gasket in between the two halves. The gasket is made from silicone, Tygon, Fluorocarbon (FKM) or other NO-compatible elastomeric material. Gasket compression is protected from over-tightening by positive stops that control the level of gasket compression. Compression of the gasket is done with narrow walls to minimize fastening force on the gasket and provide even gasket compression. In another embodiment, the manifold is constructed from two or more components that are ultrasonically welded together. Other manifold assembly methods may include hot plate welding, laser welding, solvent bonding, RF-welding and UV adhesive, depending on the materials selected.

In some embodiments, side-sparking can occur. Side-sparking is the term used for arcing between an electrode and a non-electrode surface. Side-sparking occurs when the electrical path of the spark to a non-electrode surface becomes a lower impedance then the path to the electrode. When this happens there is a change in the discharge current and the waveform associated with the current discharge. Side-sparking may indicate imperfections in the construction of the electrodes. Side-sparking can also occur as the electrode wears at the end of its useful life. Side-sparking is undesirable for several reasons: 1) Discharge, other than in the electrode gap is non-deterministic. That is, the energy of the discharge is other than expected, and thus the NO and $NO_2$ production are unpredictable, 2) Discharge to points other than the electrodes will sputter other, non-electrode metals into the air-stream. Depending on the materials, the sputtered particles could be potentially toxic, 3) Uncontrolled discharge may cause the generation of unsafe current levels in the control circuit which could potentially damage the circuit.

By detecting the occurrence of side sparking (or non-sparking), undesirable and/or dangerous conditions may be avoided by switching to the backup line. In one embodiment, side sparking is detected by analyzing the frequency content of the input current to the high voltage transformer. The plasma, when sheltered from direct air flow, as in the case of electrode indexing mentioned elsewhere in this text, is more stable and lacking in high frequency structure. Contrastingly, side-sparking can have more high frequency content which can be detected. In another embodiment, a high pass filter is applied to the input current signal. The high pass-filtered signal is half-wave rectified and compared with a known signal. Deviations from the expected are indications of side sparking. In another embodiment, the average input current into the high voltage transformer is compared to an expected range of values. Current below this range can indicate side sparking because the plasma has found a lower resistance path. Current above this range indicates an absence of sparking because the energy generated by the control circuit is not being delivered to the plasma, and so the controller will increase the current to try to force breakdown. In another embodiment, side-sparking is detected by a sudden decline in NO production as indicated by the NO and/or $NO_2$ gas sensors. In some embodiments, the controller, upon detecting side sparking, will turn off the spark in an attempt to reset it. If resetting the plasma discharge is unsuccessful, the controller will switch to the backup NO generation circuit.

Electrode Design

In some embodiments, the system can include first and second individual electrodes. In some embodiments, the system can include user-replaceable electrodes. To facilitate electrode replacement, electrodes can be configured in an electrode assembly. This allows for a preset electrode gap that the user does not have to set or adjust. In some embodiments, the electrode assembly includes a plasma chamber with an inlet for reactant gas and an outlet for product gases.

As electrodes wear, electrode material can sputter onto nearby surfaces. For example, with iridium oxide, the sputtered materials are electrically conductive. This can cause a short circuit that conducts electricity along a surface of the plasma chamber and/or electrode assembly instead of through an air gap. In some embodiments, an electrode assembly can include a surface for collecting sputtered electrode material. This surface is refreshed when the electrode assembly is replaced. In some embodiments, there is a replaceable surface within the manifold that can be changed out as needed. In some embodiments, the plasma chamber is replaceable. In some embodiments, the plasma chamber is integrated into the electrode assembly.

In the event that there is shorting along a surface instead of through the air gap, the control system can detect this type of electrical creepage by analyzing the integrity of the analog DC current signal provided to the switching circuit at the front end of the high voltage generator. During abnormal sparking, current finds a lower resistance path along the sides of the electrode. In some embodiments, the system monitors shifts in the level of the current peaks, in order to detect abnormal sparking events.

Depending on the electrode pad material and electrode substrate material selected, it is possible that the electrode substrate can have a lower work function (i.e. propensity to conduct electricity) than the electrode pad material. In this case, an electrical arc spanning a gap between two electrode pads can travel a longer distance to land directly on electrode substrate material instead of electrode pad material. In some embodiments, the electrode pad length can be sufficiently long that the arc will not reach electrode substrate material. In some embodiments, the electrode pad can be shaped like a mushroom with a large head facing the electrode gap, thereby presenting only electrode pad material to the arc. In some embodiments, a spacer is placed between the ground electrode and electrode pad where the space has a smaller diameter than the electrode pad (FIG. 42). The electrode design shown in FIG. 42 shields the welded interface between electrode tip and electrode substrate from arcing. The spacer is connected to the electrode pad with laser welding, soldering or another means to join the materials. With this design, an arc is less likely to contact the weld and ground electrode substrate material, decreasing the potential of introducing materials into the airstream other than the electrode tip material.

In some embodiments, noble metals can be used for electrode pad material because they have high melting temperatures and generate higher $NO/NO_2$ ratios. In some embodiments, noble metals can be used and connected to other substrate materials, making a composite electrode. A variety of substrate materials can be chosen, taking various factors into account, including but not limited to safety in the event that an arc comes into contact, biocompatibility, weldability and cost.

In some embodiments, the substrate material is made of titanium which offers advantages in biocompatibility and weldability (high melting temperature) over more common substrate materials. In some embodiments, stainless steel is used as a substrate material which offers an advantage minimal to no nickel content.

Electrode Service Life

Electrodes can fail in a variety of ways including excessive wear that increases the gap beyond a usable distance and deposition of electrically conductive materials on adjacent surfaces that can provide a pathway for shorting. In some embodiments, the NO generation system has the ability to detect a failed electrode/electrode set and stop use of an electrode that is not functioning properly.

There are a variety of ways for the system to detect an electrode failure. For example, failure of an electrode can be detected by analyzing the current that travels through the high voltage circuit. The electrical current through the high voltage circuit is typically very noisy (multiple frequencies present) during a normal electrical discharge. Contrastingly, an electrical discharge that travels along a surface (shorting) will have a cleaner signal (less frequency content). This is a detectable event and can be used as criteria for retiring an electrode from service. The wave shape of the discharge current is an indicator of where the discharge landed. In some embodiments, the current wave shape can be used as a trigger for electrode replacement or scheduling maintenance. In some embodiments, the system stops using a particular electrode after a predetermined number of missed discharges or discharges that did not travel across the electrode gap.

High Voltage Circuit

In some embodiments, alternating current (AC) at the electrodes is used. This improves electrical efficiency, reduces weight and evens electrode wear. Furthermore, electrical protection of the user (Means of Operator Protection, MOOP) is reduced with AC voltage because the peak voltage required for electrical discharge with an AC voltage is half the magnitude of an equivalent DC high voltage required. This is because AC voltage has a positive and a negative peak. In some embodiments, a low voltage (~16 VAC) alternating current is supplied to the primary winding of a transformer and the secondary winding creates an output of roughly 7 kVAC. In other embodiments, the input voltage may vary from 6 VAC to 100 VAC.

The frequency of the AC voltage is an additional variable that may be controlled by the system. For optimal electrical efficiency, an NO generation device can sweep through many frequencies to determine a resonant frequency of the high voltage circuit. The advantage of this approach is that it can account for manufacturing variance in the transformer, electrodes, wiring, etc. as well as electrode wear. In one embodiment, the frequency of the AC voltage is determined by selecting the frequency associated with the maximum (resonant) amount of current in the circuit before electrical discharge occurs across the electrodes. The actual resonant frequency varies with the electrical design and level of wear in the high voltage circuit.

In one embodiment, the resonant frequency occurs in the range of 80 kHz to 150 kHz. In one embodiment, a narrower range of frequencies is searched, 115 kHz to 130 Khz for example, to reduce the amount of time to conduct the resonant frequency sweep. The search for resonance of the high voltage circuit can be done at any time when the NO generation system is powered up. In one embodiment, the resonant frequency is determined only at power-up. In another embodiment, the resonant frequency is determined at the beginning of a patient treatment. In one embodiment, the resonant frequency is determined with each patient inspiration. In one embodiment, the system searches for the first harmonic frequency. In some embodiments, the system searches for a harmonic frequency. In some embodiments, the resonant frequency is measured and stored in memory. The resonant frequency does not change significantly from one use to another. Upon the next power-up, the frequency is read from memory rather than re-established, allowing for a quicker start-up. In some embodiments, the resonant frequency is re-established and updated periodically.

Controller

As explained above, the NO generation system includes a controller that is configured to control the NO production by the one or more plasma chambers, for example, by controlling the sparking of the one or more electrodes in the plasma chambers.

The controller is comprised of an enclosure housing various components. It will be understood by of ordinary skill in the art that various combinations of these components can be present in the controller. Also, there may be more than one of some of the components within the enclosure, depending on their criticality to continuous NO production.

The enclosure houses the internal components of the controller and protects them drop as well as mechanical and fluid ingress. In some embodiments in which the system includes one or more cartridges (as will be explained in more detail below), the enclosure can also include features to engage the cartridge. In some embodiments, the enclosure includes at least one cartridge slot that is configured to mechanically interface with the cartridge in a way that ensures the cartridge is removable and positioned correctly in relation to the controller and prevents the cartridge from being inserted improperly, for example upside-down or side-ways. The enclosure and the cartridge slot can include features to protect the cartridge and the cartridge slot. For example, the cartridge slot can include a passive or active door that covers the cartridge slot to prevent mechanical and/or fluid access to the internal portions of the controller. The door can include a spring or other biasing mechanism such that the door can be biased to be in a closed position. In an embodiment, the door can be configured to close entirely when a cartridge is fully inserted in the cartridge slot.

Figures 47A, 47B:
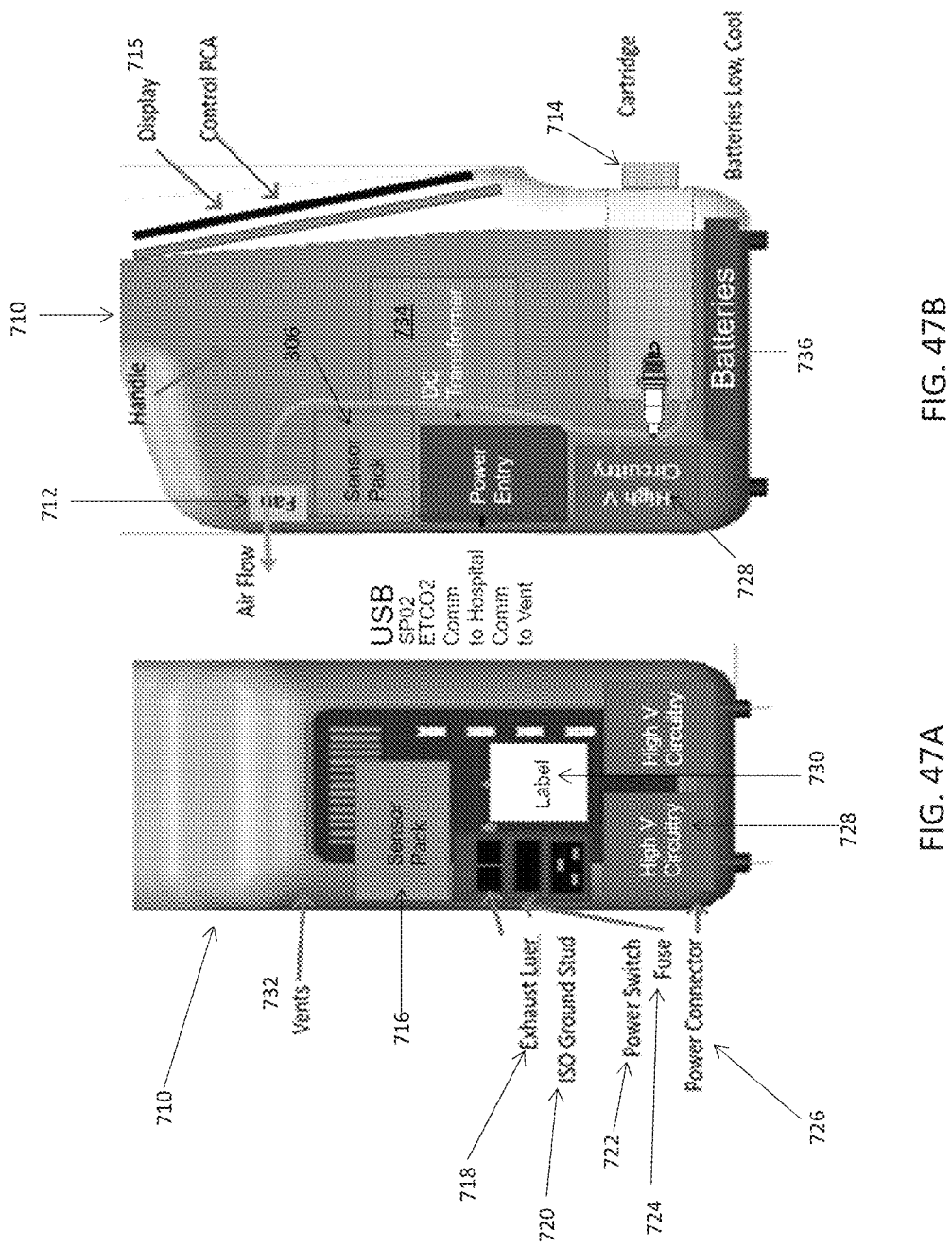
FIG. 47A and FIG. 47B illustrate a back and side view of an embodiment of a controller enclosure.

FIGS. 47A and 47B depict an embodiment of a controller enclosure 710 and its contents. Air flow through the enclosure is moved via a fan 712 that sources air from a cartridge 714. The controller enclosure includes a one or more sensors 716, an exhaust 718 and a vent 732, a power switch 722, a fuse 724, and a power controller 726. Batteries 736 are also included as an additional power source. One or more high voltage circuits 728 and a ground 720 are also included in the controller enclosure 710. The enclosure 710 also includes a display 715 that is configured to communicate and display information to the user regarding NO production and patient information.

The controller accepts AC power from all AC power sources and converts the power into a DC voltage using a standard transformer. The controller as includes a DC power inlet that can accept 12V or 24V to ensure adequate power when operating in a plane, ambulance, or helicopter. The DC power inlet can also be used to receive power from an external battery device for extended patient transport. The external battery can be connected to the controller enclosure to facilitate transport.

The controller can also include one or more batteries for NO generation in the absence of wall power. Multiple batteries, for example, two batteries, can be used for redundancy. For example, the duration of operation for each battery can be 30 minutes.

The controller includes a control circuit that receives and processes information relating to the NO generation system (for example, from a cartridge if one is being used) and the patient being treated with the NO. The controller used this information to determine one or more control parameters that can be communicated to the plasma chamber to control NO concentration in the product gas produced in the plasma chambers. In some embodiments, the control circuit receives and/or processing information relating to sensor information, and received user inputs. The controller circuit can also send and/or receive information to and from a user interface, and can control the production of NO by determining a plasma chamber gas flow rate, and/or a frequency of the waveform control circuit AC, and/or a duty cycle of the waveform control circuit AC, and/or a discharge pulse frequency, and/or a pulse duty cycle of the plasma activity, and/or a burst count, and/or a burst period, and/or a burst duty cycle.

Figure 48:
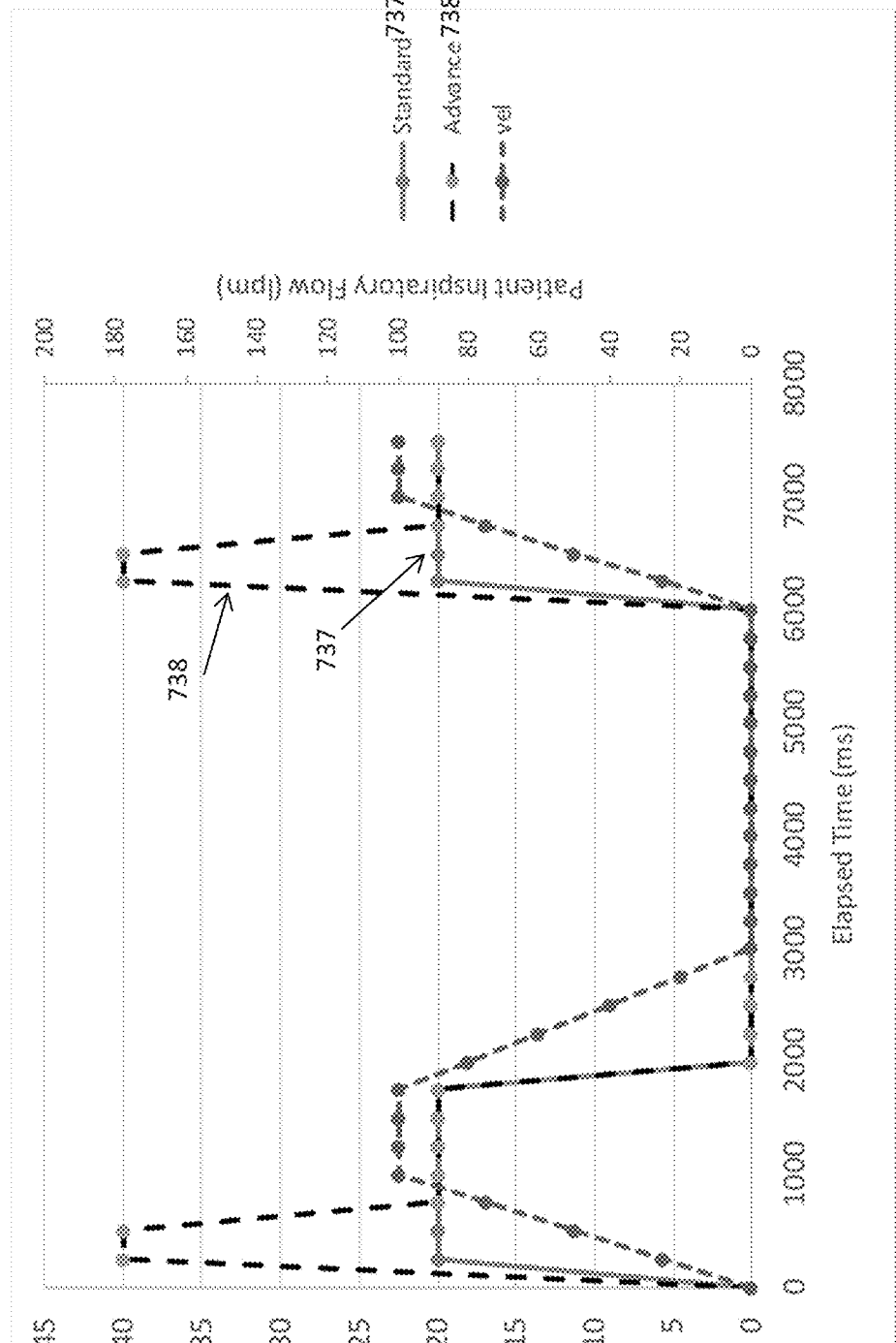
FIG. 48 is an exemplary graph depicting elapsed time versus NO settings.

As shown in FIG. 48, an NO generation and delivery device can provide NO during inspiration using a pulse of constant concentration 737 or a pulse with dynamic concentration 738. In one embodiment using the dynamic concentration 738, the concentration of gases in an initial volume of an NO pulse are higher than the concentration in the balance of the volume in the NO pulse. By varying the concentration within a pulse, the dose delivered can vary within the patient anatomy (lung, airway, etc.). One advantage to this approach is that regions of the lung with greater air exchange that are normally filled first during inspiration would receive preferentially more NO. In one embodiment, the concentration within a pulse is varied by altering the plasma parameters (power, frequency, duty cycle, etc.) with a pulsatile flow through the plasma chamber. In another embodiment, plasma parameters remain constant and flow through the plasma chamber is varied to generate variations in concentration within the product gas stream. In another embodiment, both plasma parameters and flow parameters are varied to produce variation concentration within a delivered NO pulse.

In some embodiments, a watchdog circuit can also be included in the controller and can be used to monitor the function of the control software and the high voltage circuits. The watchdog circuit can create alarms in the event of an alarm event or condition. The creation of an alarm will not stop treatment to a patient as the pause in treatment could potentially harm the patient. Safeguards can be included in the event of a control circuit failure. For example, in the event of control software failure, a piezoelectric buzzer with a dedicated battery is sounded to bring attention to the user. In some embodiments, a system can alert the user if flow through the device is detected and NO has not been initiated. This applies to both the ventilator circuit and the bag circuit.

In some embodiments, a cartridge can include a memory device. The memory device can have a variety of uses. For example, the memory device can include information that identifies the type of cartridge to decrease use errors. Communication to the memory device could be with direct electrical contact to the cartridge or through wireless means, such as RFID. In some embodiments, the information on the memory device and communications to and from the memory device are encrypted to ensure data security and prevent counterfeiting. In some embodiments, an actual microprocessor, sensors, and/or memory could be placed on the cartridge. In some embodiments, a microprocessor, sensors, and/or memory are separate from the cartridge and can communicate with the cartridge wirelessly or through a wired connection.

In some embodiments that utilize a cartridge, the memory can be used to store information relating to the various cartridge options. For example, by knowing what kind of cartridge has been inserted, the controller can use the information stored in memory to look up the corresponding calibration requirements for ventilator flow measurement, cartridge life, NO setting limits, electrode life and other parameters associated with the cartridge. The memory device can be transferred from one controller to another second controller, for example, for transport. The memory device can capture the treatment setting, number of NO molecules flowed through, number of $NO_2$ molecules flowed through, alarm logs, treatment logs and patient history, for example. The benefit of understanding the number of NO and/or $NO_2$ molecules flowed through a scavenger cartridge is that the service life can be more accurately determined than a time-based method, enabling a scavenger cartridge to be used more completely before disposal. In one embodiment, the volume of NO-containing gas flowed through the cartridge is written to the memory device. In some embodiments, the number of plasma discharges that occurred during the time the scavenger has been inserted are written to the cartridge. For scavenger cartridges with more than one scavenger path, the amount of use of each path is stored independently in the cartridge memory device. In one embodiment, the memory device is used to mark whether or not a cartridge has been inserted into a controller.

Various types of information can be written to the memory device during the manufacturing process. For example, the information written to a memory device during cartridge manufacturing can include but is not limited to information relating to part number, manufacturer ID, date of manufacture, expiration date, serial number, lot number, and calibration constants for flow measurement, pressure measurement or other sensing capabilities of the Cartridge. Information written to and read from the memory device during treatment could include but is not limited to count of sparks for a first electrode assembly (A), count of sparks for a second electrode assembly (B), date of first use, accumulated use time, user group information as Neo (Neonatal), Ped (Pediatric), or Adt (Adult), serial number of a first controller cartridge was used in, and serial number of the last controller cartridge was used in. A cartridge RFID can store information that includes but is not limited to used/new state, the last used controller settings, such as desired NO ppm, plasma discharge rate, and/or plasma duty cycle (for transfer to another controller for transport), alarm history for a patient treatment, patient trending data for $FIO_2$, $SpO_2$, NO Level setting, NO level measured, $O_2$ level measured, $NO_2$ level measured, user case notes and annotations (for transfer to another controller for transport). A cartridge recycling program can be implemented to responsibly dispose of cartridges but also to provide data on how the cartridges are used in the field.

Figure 143:
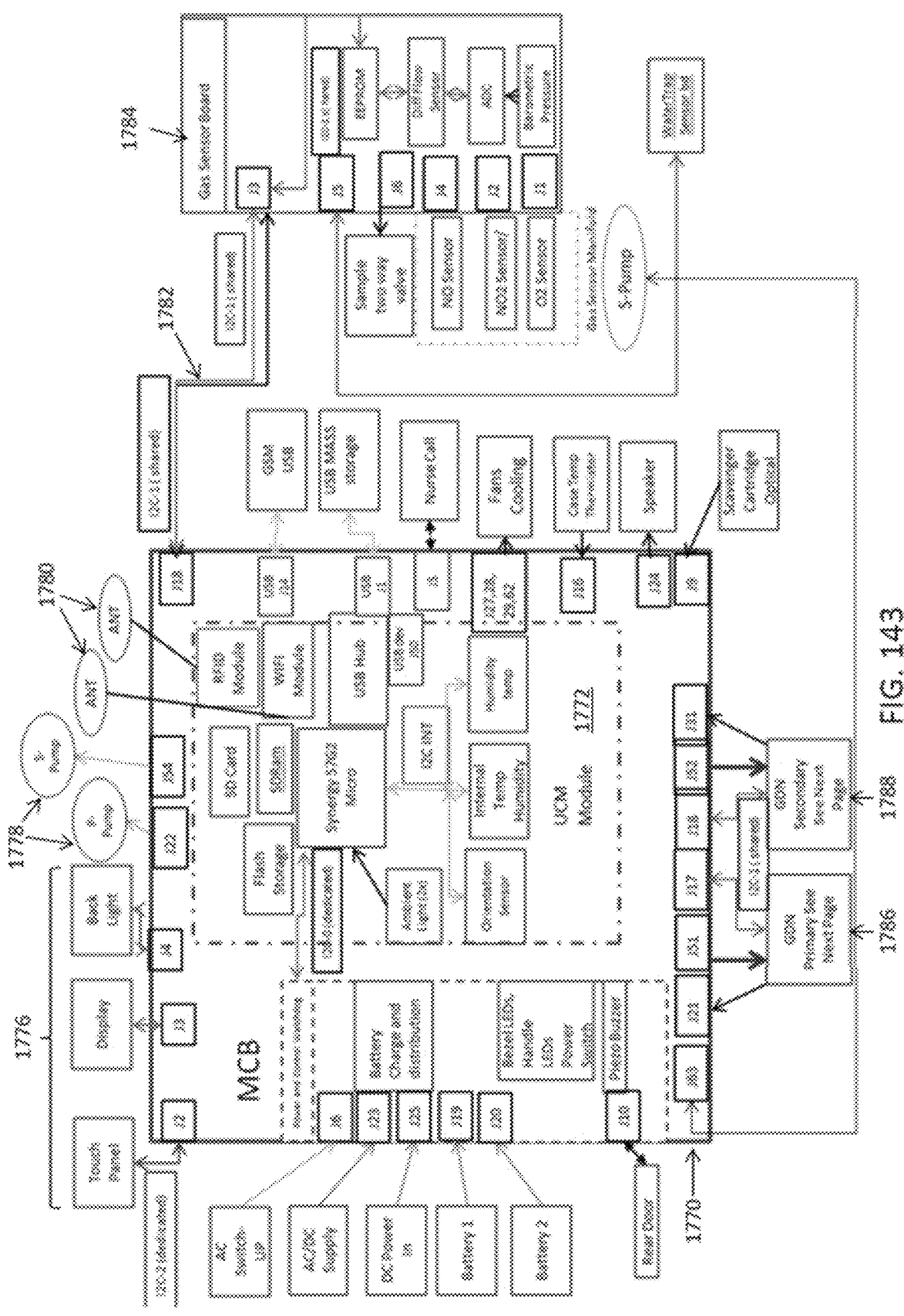

FIG. 143 depicts the hardware architecture of an NO generation and delivery system with redundancy. The main control board (MCB) 1770 has two sub-systems in the form of the User Control and Monitoring (UCM) 1772 and the Power Control and Watchdog (PCW) 1774. The UCM 1772 from top right counter clock wise connects to a touch panel display assembly 1776, system pumps 1778, and antennae 1780 for an RFID subsystem and a WIFI subsystem. There is an I2C bus 1782 that traverses the system controller to the gas sensor pack 1784. This enables the UCM to collect sensor data, water trap data, sensor pack pressure and flow, and provides for control of the sample line pump.

There is a GSM module and USB Module external to the MCB/UCM, a nurse call function, and multiple speed-controlled cooling fans within the system. External to the MCB, enclosure temperature is measured and a speaker is used for audible alarms. At the bottom of the MCB, there are connections for up to two GDN boards 1786, 1788. The left side of the drawing depicts the connectivity to the PCW and the functionality there. There is a service-door-open indication. Two batteries are provided for redundancy that can be charged and drained simultaneously or sequentially. In the event that one battery fails, the system can draw sufficient power from the second battery to continue treatment. There is a DC power in, and AC power in and an indication of switch position. Internal to the PCW module is a piezo buzzer to enables audio alarms during a system catastrophe. There are LEDs for status indicators, the power availability and alarms. A flex circuit containing LEDs (not shown) connects to the MCB and extends up and around the interior surface of the handle to illuminate the light bar within the handle to convey system status.

The internal sensors of the UCM measure ambient light, ambient humidity, orientation, internal temp and internal humidity. There is MMC flash storage and DRAM. A high speed USB 4 port hub is features as well.

Figure 144:
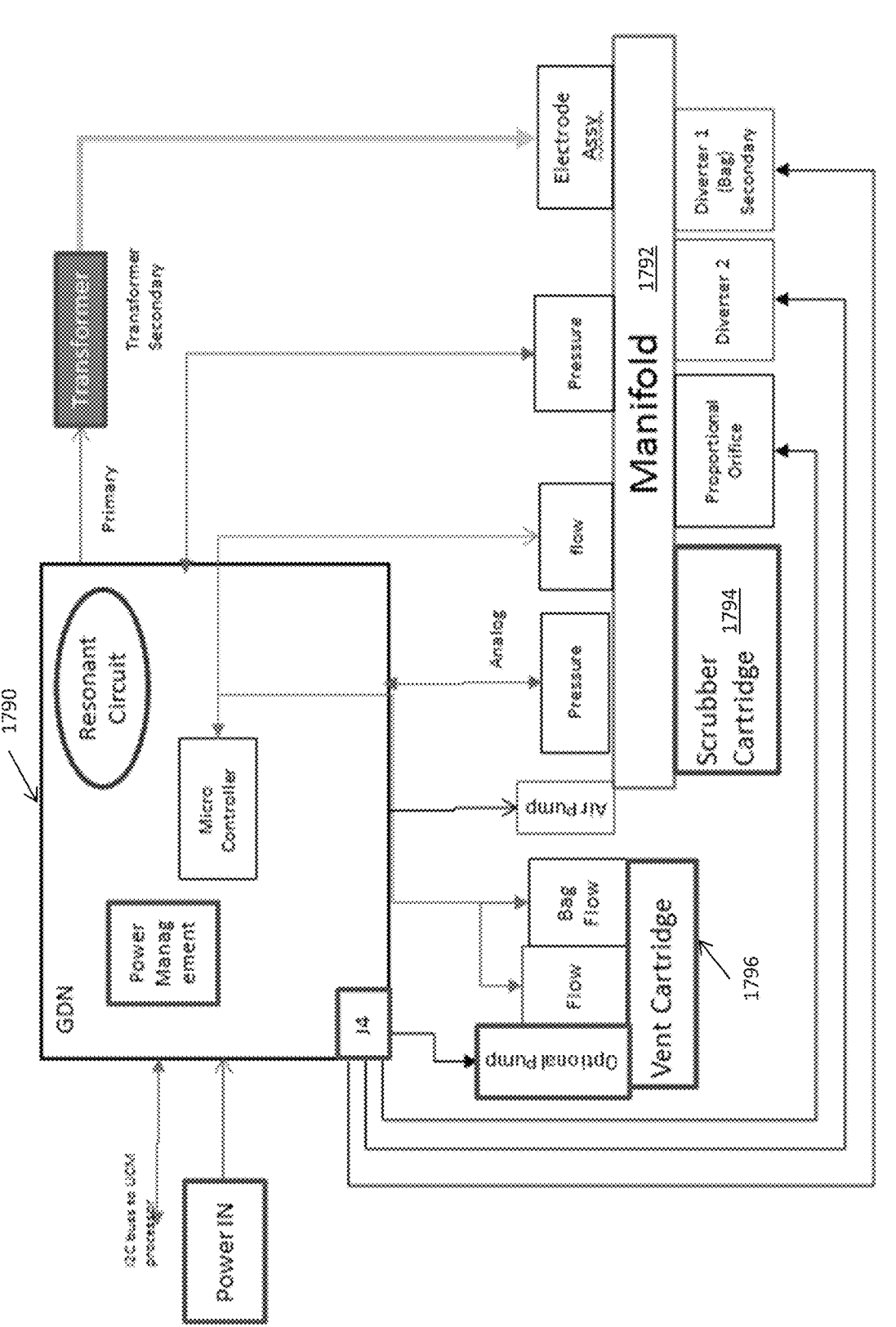

FIG. 144 is an embodiment of a Generate and Delivery NO (GDN) board 1790. From Left to right, the GDN receives commands from the UCM such as treatment settings. The GDN controls over the system reactant gas pump. The GDN provides additional power conditioning for the off-board sensors and system components. The resonant primary circuit connects to the transformer which in-turn connects to the plasma electrodes. The off-board sensors and system components connect to the manifold 1792 to properly control the flow of the various gases. There is a scavenger/filter cartridge 1794 connected to the manifold 1792 that removes contaminants from the system and/or creation of NO. There are sensors in the ventilator cartridge 1796 to measure the flow associated with the ventilators and the manual respiration (bagging).

Control Parameters

As explained above, various information relating the system, including information about the product gas, reactant gas, and patient, can be used by the controller as control parameters to control NO production by the NO generation system.

Plasma parameters that can affect various aspects of NO generation and are controlled by the control parameters, include but are not limited to:

Waveform Control Circuit AC Frequency—This is the frequency of the control signal used to generate the AC current of the plasma. It is used to tune the resonance of the high voltage circuit.

Waveform Control Circuit AC duty cycle—This is the duty cycle of the control signal used to generate the AC current of the plasma. This is used to define the shape of the AC current to control the energy content of a harmonic of the High Voltage Circuit.

Discharge Pulse—a plasma event, also referred to as "Pulse"

Discharge Pulse Frequency—the inverse of the time between discharges (1/pulse period).

Pulse Period—Length of time from the start of one plasma event to start of the next.

Pulse Duty Cycle—Portion of the Discharge Period that the Electrical Discharge is ON.

Plasma Delay—Duration of time between activating high voltage and actual plasma generation. This is the time required for gas between the electrodes to ionize and breakdown. This parameter varies with electrode temperature. By generating bursts of discharges to keep the electrodes hot, the plasma delay can be minimized.

Discharge Power—the product of potential difference (V) and current (A) between the electrodes during a discharge.

Bursts—groups of closely spaced pulses.

Burst count—number of pulses in a burst.

Burst Period—Elapsed time between the start of burst events.

Burst Duty Cycle—Percent of time during a burst period that pulses are allowed to occur. In one embodiment, this parameter is used to generate extremely low levels of NO by decreasing duty cycle (i.e. spacing bursts further apart).

Burst Frequency—Number of bursts per second that occur.

NO Generation Algorithm

The NO generation system can vary the rate of NO molecules/time based on one or more input control parameters. Inputs to the NO generation algorithm can be one or more of the following parameters that can be used to control NO generation/concentration in a product gas produced in the one or more plasma chambers:

Concomitant treatment (ventilator, CPAP, ECMO, anesthesia, manual respiration, etc.) parameters: flow, pressure, gas temperature, gas humidity. These parameters may be measured by the NO generation device or sent to the NO generation device by analog or digital communication.

Patient parameters: inspiratory flow, $SpO_2$, breath detection, tidal volume, minute volume, expiratory $NO_2$, $etCO_2$, Ambient environment parameters: ambient temperature, ambient pressure, ambient humidity, ambient NO, ambient $NO_2$ Device parameters: Plasma chamber pressure, plasma chamber flow, plasma chamber temperature, plasma chamber humidity, electrode temperature, electrode type, electrode gap.

NO treatment parameters: target NO concentration, indicated NO concentration, indicated $NO_2$ concentration. In some embodiments, the NO generation algorithm can use humidity and gas composition sensing of the reactant gas to improve mole flow rate calculations of the reactant gas and/or inspiratory gas.

Outputs to the NO Generation Algorithm

In some embodiments, the system controls the reactant gas flow through the plasma chamber, and all other settings such as plasma frequency, plasma duration, plasma duty cycle, plasma energy, burst count, etc. are constant.

The table below (Table 1) shows some plasma control algorithms. Variable means that the parameter can be adjusted in real time at any point in the treatment. It will be understood that not all possible combinations of control parameters are shown in the table.

TABLE 1

| Parameter | Alg 1 | Alg 2 | Alg 3 | Alg 4 | Alg 5 | Alg 6 |
|---|---|---|---|---|---|---|
| Reactant Gas Flow | Variable | Variable | Variable | Variable | Constant | Constant |
| Discharge Frequency | Constant | Constant | Variable | Constant | Constant | Constant |
| Discharge Duty Cycle | Constant | Variable | Constant | Variable | Variable | — |
| Discharge Power | Constant | Variable | Variable | Variable | Variable | Variable |
| Pulse Duty Cycle | Constant | Variable | Variable | Variable | Variable | Constant |

46

TABLE 1-continued

| Parameter | Alg 1 | Alg 2 | Alg 3 | Alg 4 | Alg 5 | Alg 6 |
|---|---|---|---|---|---|---|
| Burst Count | Constant | — | Variable | Variable | — | — |
| Burst Duration | Constant | — | Constant | Variable | — | — |
| Burst Frequency | Constant | — | Variable | Constant | — | — |
| Burst Duty Cycle | Constant | — | Variable | Variable | — | — |

In some embodiments, the NO generation system selects plasma control parameters to minimize $NO_2$ output. If there is a range of parameters with equal $NO_2$ output, then the parameters are selected based on minimizing electrical energy consumption. In some embodiments, plasma control and/or gas flow parameters are selected so that the output of the NO generation device is at constant NO concentration so that the performance is similar to that of an NO take with constant NO concentration. In some embodiments, plasma control and/or gas flow parameters are selected to that the output NO concentrations of the NO generation device follow a predetermined concentration profile over time.

Inspiratory Flow

In some embodiments, the controller measures the flow of the inspired air in order to calculate the amount of nitric oxide required to achieve the prescribed NO concentration. This can be achieved using a variety of techniques, for example, with the use of an inspiratory air flow sensor. In other embodiment, this flow can be measured by measuring a pressure within the inspiratory limb as a surrogate to flow, having the user input the inspiratory flow rate into the controller, and receiving flow rate information through wired or wireless connection from the ventilator or other device that is generating/measuring the flow.

Flow may be measured in a variety of ways. In some embodiments, flow is measured by a measurement of a pressure drop across a flow restriction within the air flow by a pressure sensor located within the controller. In some embodiments, flow is measured by a measurement of a pressure drop across a flow restriction within the air flow by a pressure sensor located within the disposable cartridge. In some embodiments, flow is measured by a measurement via a heated wire. In some embodiments, flow is measured by a measurement via a heated thermistor. In some embodiments, flow is measured by a thermal mass flow meter that uses a pair of temperature sensors, such as thermocouples, or resistance temperature detectors (RTD).

The system can also include one or more treatment air pumps. Treatment air consists of a flow of air sufficient for NO generation in a sidestream or mainstream application. Treatment air can be a subset of the air a patient breathes and is mixed with main flow of air prior to inspiration by the patient.

Air pumps are needed to source atmospheric air and direct it to the plasma chamber. Measurement of the air flow to the plasma chamber ensures that the air pumps are functional. In some embodiments, this measurement is made with a warmed thermistor, however other flow measurement techniques such as differential pressure across a flow resistance would be equally effective. Target air pump speed may be a function of prescribed NO level, inspiratory air flow rate, air temperature, air pressure, air humidity, and/or other factors. In an embodiment, set gas flow rates appear in one or more look-up tables based on desired NO moles/min desired as well as the variable listed above.

In some embodiments, gas flow rate measured in the ventilator circuit provides an input for determining the air pump speed and/or reactant gas flow rate for NO generation. One advantage to this approach is that it performs well with a patient that breathes spontaneously, ensuring that the system increases NO production to match each breath.

The range of air flow rates can vary, for example, from 0 to 15 lpm with a goal of keeping air flows through the plasma chamber at less than or equal to 10% of the mainstream inspiratory air flow. Air pumps may be of nearly any type, including but not limited to diaphragm, centrifugal, fans, blowers, reciprocating, gear and other designs. In some embodiments, the pump can prevent passive air flow through the pump when the pump is off, which will eliminate the nitric oxide generation system presenting a leak to the ventilator circuit. An example of a pump that satisfies this criterion is a diaphragm pump. In some embodiments, a pump is used to fill a reservoir at flow rates that vary from 0 to 6 lpm while flows exiting the reservoir vary from 0 to 15 lpm. High flow rates exiting a reservoir may be short duration, depending on the volume of the reservoir.

In the event that a pump does not prevent passive gas flow when off, a valve may be placed in series with the pump to block passive air flow from the vent circuit to atmosphere. In some embodiments, the valve would require power to close (open when off) so that any failure of the valve would not prevent the delivery of nitric oxide to the patient. Passive valves, including but not limited to check valves, duck-bill valves, and cross-slit valves could also work in some applications.

In some embodiments, such as delivery of NO through a nasal cannula, a pause in treatment can allow residual NO in the nasal cannula tube to convert to $NO_2$. When treatment is resumed, the residual $NO_2$ would be pushed into the patient. One solution to this is for the air pump to briefly run in reverse when treatment is resumed, pulling potentially $NO_2$-laden air from the nasal cannula into the scavenger. The air pump would run in reverse for sufficient time that the volume of air within the nasal cannula has been exchanged with air. At that point, the air pump could switch to forward flow and being plasma activity to deliver NO to the patient.

It should be noted that some types of pumps such as diaphragm pumps are pulsatile, thereby introducing pulsatility into the air flow. Given that NO production is a function of air density, it follows that higher pressure reactant gas supplies more $N_2$ and $O_2$ within the plasma, thereby generating more NO for a given plasma discharge. When the reactant gas pressure varies, as is the case immediately after a diaphragm pump, NO production levels will also vary with pressure. It follows that a higher level of NO production consistency can be obtained when pulsatility in the reactant gas stream has been minimized. There are pneumatic means to diminish pressure pulsatility downstream from a pump, such as using a critical flow orifice, a diaphragm, an accumulator, or a flexible-walled tube such as an elastomeric tube.

In one embodiment, pump pulsatility or other types of pressure fluctuation within the reactant gas is sensed with a pressure sensor, microphone, force sensor, strain gauge, manometer or other type of pressure sensor and used to determine the timing of plasma activity. In some embodiments, an NO generation system generates plasma at the same time in the pump pulse cycle to make NO production more consistent.

The system can also include one or more gas sample valves. The controller can use a manual or software-controlled valve to select between sourcing gas from the sample line and from the atmosphere to facilitate sourcing clean air for calibration purposes. In some embodiments, a solenoid valve is used to select the source for the gas, however it will be understood that other types of valves can be used to perform this function. In some embodiments, the controller can use a valve to select between sourcing gas from a cartridge or directly from the plasma chamber. Gas sourced directly from the plasma chamber can have NO and $NO_2$ in it at known amounts for calibration purposes.

The system can also compensate for variance in various ambient conditions, including but not limited to humidity, elevation, pressure, and temperature using ambient pressure measurement and/or spark chamber pressure measurement. For example, humid air is less dense than dry air. However, it is more difficult to ionize and discharge an arc in humid air. The net result of these factors would be converted to a sensitivity factor. The controller can use sensitivity factors for each ambient condition, to adjust the NO production in response to current ambient conditions compared with nominal calibration conditions.

Figure 49:
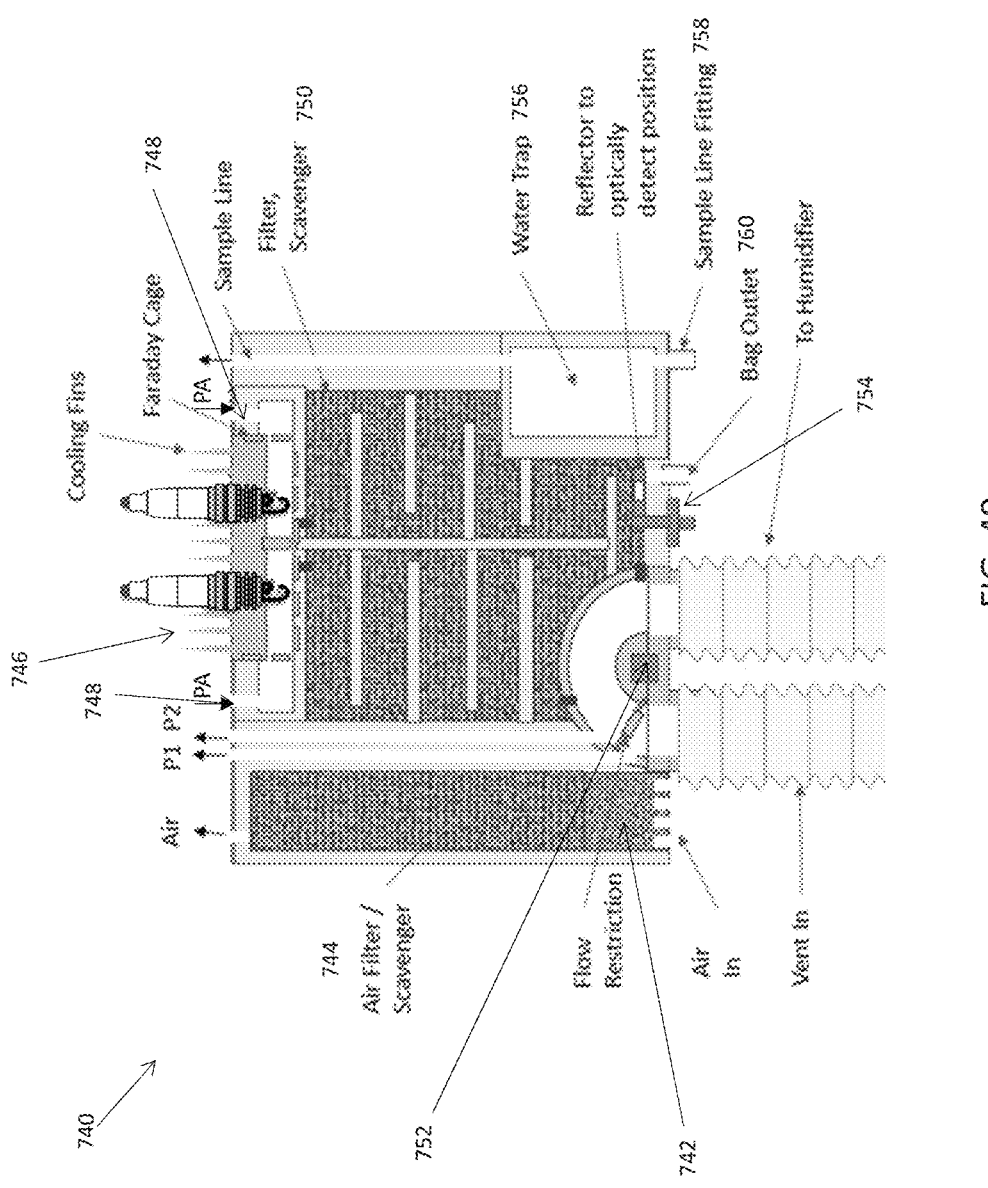
FIG. 49 is a schematic of an embodiment of a cartridge for use with an NO generation system.

A pre-electrode scavenger can be used to make air more consistent for plasma and NO generation. In some embodiments, the pre-electrode scavenger is located within a disposable air filter cartridge and scrubs the air before it enters the pump (FIG. 49). In some embodiments, the pre-electrode scavenger is located after the pump but before the plasma chamber. In one embodiment, the pre-electrode scavenger material is within an air reservoir that serves as an accumulator between the pump and plasma chamber.

In some embodiments, the system can vary air flow through the spark chamber while maintaining a constant spark rate. Plasma activity can be constant (i.e. continuous), periodic, or variable. Achieving a desired NO concentration profile in a patient flow can be done in a variety of ways, including varying one or more air flows in the presence of spark activity. Spark activity can be continuous, intermittent, or variable. In some embodiments, an NO concentration profile can be constant for the entire inspiratory volume. In some embodiments, an NO concentration profile can be constant for every nth breath and zero or a lesser magnitude for the rest of breaths.

The system can use a patient treatment parameter as an input to scale air flow through a spark chamber. For example, inspiratory air flow in a ventilator circuit can be used. In one embodiment, reactant gas flow is $\frac{1}{12}$th of ventilator flow. In another embodiment, reactant gas flow varies from $\frac{1}{20}^{th}$ to $\frac{1}{10}^{th}$ of ventilator flow. The air flow can dilute the oxygen concentration in the ventilator circuit, thus the lowest amount of reactant gas flow/ventilation dilution is desirable. A smaller ratio of air flow to vent flow reduces the dilution of oxygen. Alternatively, gas flow from an oxygen concentrator or from a blender can be used as a patient treatment parameter input.

Closed-loop control of air flow can be used so that flow through the spark chamber is accurate. Various types of control can be used, including but not limited to control of pressure within a reservoir, control of flow from a pump, control of a variable orifice in the presence of a pressure head, and analog or digital modulation (e.g. PWM) of a valve with a known orifice/flow restriction in the presence of a pressure head.

In some embodiments, a system can be provided where the dilution of ventilator gas flow is limited to enforce a user-defined minimum $O_2$ threshold. For example, when a ventilator is delivering 100% oxygen, a target patient $O_2$ concentration of 92% requires diluent flow of less than 10% of the ventilator flow when atmospheric air is the diluent.

In order to increase the air flow through the spark chamber concomitantly with vent flow, the system can be configured to detect the inspiratory pulse in the ventilator circuit as early as possible. In some embodiments, a ventilator tube (for example, roughly 18" long) with a flow sensor on the ventilator connection end can be used so that the system can detect an inspiratory pulse earlier. In some embodiments, pressure in ventilator inspiratory limb can be measured within the vent cartridge to detect spontaneous breathing such that the NO detection system can detect a breath before the ventilator, thereby enabling the system to deliver NO to the leading edge of an inspiratory bolus without the need for a predictive algorithm. In some embodiments, the system can compare vent flow measurements with NO flow measurements to confirm synchronous NO flow timing. The comparison can be performed by subtracting the time of vent peak flow from NO peak flow to calculate a phase offset. In some embodiments, the target delta is offset, in some embodiments it is desirable for the NO pulse to lead the inspiratory pulse, so the offset as defined would be a positive value. In some embodiments, the system uses the timing of a sample (typically a count of 3) of prior inspiratory pulses to predict the timing of a specific inspiratory pulse.

Other Control and Plasma Parameter Considerations

In some embodiments, an open loop with a look-up table based on the prescribed NO concentration indicated by a user is used along with one or more of the following parameters: cartridge type, ventilator flow rate, ambient temperature, ambient pressure, ambient humidity, measured NO values in the ventilator inspiratory line, and any other factor affecting NO production.

Various sensors can also be used in the control of NO production. In some embodiments, partial feedback control from a single NO sensor that can also generate alarms is used. Treatment can only be adjusted (i.e. trimmed) by a limited amount, such as 10%, based on sensor input. In some embodiments, dual NO sensors can be used, with one sensor being used for closed-loop control and the other sensor being used for alarm conditions. The two sensors can be compared to each other to detect a sensor failure. In some embodiment, a triple NO sensor system can be used for closed-loop control. In the event that one sensor differs from the other two, that sensor can be ignored and treatment can continue with the two remaining sensors. In some embodiments, the NO concentration alarm threshold is automatically adjusted when a new NO setting is selected. In some embodiments, the NO alarm setting is determined by a tolerance based on a percentage above and a percentage below the target value. In some embodiments, the NO alarm setting is determined from a look-up table based on the NO target concentration.

Various NO production controls schemes can be employed by the system. In some embodiments, plasma chamber gas flow rate and one or more control parameters are used to control NO production. Plasma chamber gas flow rate can be controlled by a pump speed, reservoir chamber pressure, proportional valve setting, or other means. The plasma parameter can be rate, duty cycle, switching voltage at the primary transformer winding, or energy. In some embodiments, plasma chamber gas flow rate and plasma duty cycle are controlled. In some embodiments, plasma chamber gas flow rate and spark energy are controlled. In some embodiments, plasma chamber gas flow rate and plasma frequency are controlled. In some embodiments, plasma gas flow rate is varied to be a function of respiratory flow rate variation with breath. In some embodiments, the plasma chamber gas flow rate is a constant proportional fraction (10%) of the inspiratory flow rate. In an embodiment, plasma pulse rate can be varied to maintain constant NO concentration throughout the respiratory cycle. In an embodiment, air pump speed is held constant and only plasma control parameters are varied to product required NO concentrations based on patient inspiratory flow. In one embodiment, plasma parameters are held constant and only plasma gas flow rate is varied. In one embodiment, plasma parameters are held constant and plasma gas flow rate is controlled to be a fraction of the inspiratory flow rate. In some embodiments, plasma chamber gas flow rate is held constant and plasma energy is varied. It will be understood that any combination of these NO production schemes can be used.

There can be multiple combinations of plasma chamber gas flow rate and other plasma parameters (for example, pulse rate, pulse width, pulse energy) that generate a given level of NO molecules. In some embodiments, a plasma parameter for a given NO production level is selected based on minimizing $NO_2$ levels in the effluent gas. In some embodiments, plasma chamber gas flow rate for a given amount of NO production is selected based on minimizing $NO_2$ levels in the effluent gas. In some embodiments, the combination of plasma gas flow rate and plasma parameter (rate, duty cycle, or energy) are selected based on minimizing $NO_2$ levels in the product gas.

Spark Energy

In some embodiments, spark energy can be used to control NO production. An increase in spark energy can result in an increase in NO output. Spark energy is a function of high voltage circuit voltage and high voltage circuit current at the electrode gap. Increasing the discharge pulse frequency and/or shortening the pulse duty cycle has the effect of increasing available current in the transformer at the time of discharge. Design elements that have an effect on spark energy include: transformer leakage current (minimized), transformer capacitance (minimized by use of Litz wire and keeping wire dimensionally close to the magnetic core), having a power factor correction unit tuned to deliver resonant alternating current (AC) to the transformer, minimizing transformer temperature by decreasing wire impedance (Litz wire). The system can also operate such that there is continuous NO production. In some embodiments, the nitric oxide generation system can operate with a priority for nitric oxide generation. Thus, the system continues to generate nitric oxide in the event of any single fault. Even when there is an alarm condition, the system can continue NO generation while notifying the user of an issue. The system can be designed with redundancy for several of the critical system elements. Two or more of the following system elements may be present to ensure continuous operation: electrodes, scavenger circuits, air pumps, high voltage circuits, plasma timing circuits, nitric oxide sensors, and batteries.

In some embodiments, an NO generation device can include a pneumatic loop that continuously circulates NO containing gas and scrubs it so that it is available for delivery. After the plasma chamber, oxygen and nitrogen concentration remain virtually unchanged from their atmospheric concentrations of approximately 21% and 78% by volume respectively. Therefore, $NO_2$ is forming from the moment NO is generated in the plasma. Some of this $NO_2$ can be chemically removed after the electric NO generator before the NO-rich gas is mixed into the inspiratory flow. Depending on the detailed design of the pneumatic circuit, and the details of the inspiratory flow rate and NO-therapy, the residence time of the NO-rich, $O_2$-rich gas in the volume after chemical $NO_2$ removal but before injection may be excessive. Excessive residence time leads to greater $NO_2$ formation. This design considers a recirculating loop of NO-rich gas. The gas is constantly circulating, and only a portion is diverted to the inspiratory limb. Recirculation limits residence time, so $NO_2$ formation can be limited. Moreover, gas that returns to the NO source can be "re-scrubbed" to limit $NO_2$ accumulation, as explained in more detail with respect to FIGS. 93-95.

Patients receiving nitric oxide require gradual weaning rather than an abrupt stop, and the system can support weaning a patient in several ways. In some embodiments, the system can provide a weaning reminder to notify the user that the patient has been at a particular dosage for a user-selected amount of time. In an embodiment, the system can automate weaning based on physiological inputs, including but not limited to $SpO_2$ levels. In this mode, the system would lower the NO dose and monitor patient response. If the patient does not respond well ($SpO_2$ levels decrease for example) to the decreased dosage of NO, the NO level could be increased again. In an embodiment, the system can provide a trending screen to show a patient's response to weaning as well as general patient history. The trending screen can display various information about the patient and the treatment, including but not limited to prescribed NO dose, measured NO levels, $SpO_2$ levels, $FIO_2$ levels, and other parameters specific to the treatment or general patient status.

In some embodiments, nitric oxide delivery and generation systems perform measurement of NO, $NO_2$, $O_2$ and other gases from time to time. The gas sensors can be calibrated periodically to ensure adequate measurement accuracy.

Altitude Compensation

The density of air at high elevations is less than at lower elevations. It follows that there are fewer $O_2$ and $N_2$ molecules between an electrode gap at a higher elevation, so that NO molecules are produced at a slower rate than at sea level. The reduction in molecules of all kinds between the electrodes at high elevation also decreases the breakdown voltage for an electrical discharge to occur. In some embodiments, an NO generator can measure ambient pressure as an indication of the status of gas in the plasma chamber. In some embodiments, pressure within the plasma chamber is measured. The controller can alter electrical discharge activity as a function of plasma chamber pressure to ensure accurate quantities of NO are generated. In some embodiments, a variable flow restriction downstream of the plasma chamber is used to control pressure within the plasma chamber. For example, at higher elevations, a proportional valve can be adjusted to restrict flow and increase pressure within the plasma chamber thereby increasing NO output. In some embodiments, changes to the high voltage parameters are not required at high elevation because the pressure within the plasma chamber is maintained at a constant level.

Variance in Ambient Conditions

In some embodiments, an NO generation system includes a means of compensation for variance in ambient conditions (humidity, elevation, pressure, temperature) since these conditions can affect the number of NO molecules generated for a given electrical discharge. Compensation can be in the form of altering one or more of the following parameters: the duration of electrical discharges, the frequency of discharges, the voltage of discharges, the duty cycle of electrical discharges, the pressure within the plasma chamber, the flow rate through the plasma chamber, the discharge burst count or other parameters known to affect NO production rates. In some embodiments, the NO generation system measures one or more of the following parameters: ambient pressure, plasma chamber pressure, ambient temperature, plasma chamber temperature, ambient humidity, plasma chamber humidity.

Continuous Variation of Flow

Patient respiration can be voluntary or induced by machine. In either case, the flow rate is dynamic as a patient inspires. This presents a challenge to an NO generation device to provide a constant concentration of NO to the patient.

In inline (mainstream) configurations where the plasma occurs within the inspiratory gas, plasma parameters alone can be varied in real time to dose the inspiratory gases appropriately. In some embodiments, the controller senses a pressure and or flow measurement that serves as the controlling input.

In side-stream configurations, plasma is generated in an $N_2$ and $O_2$ containing gas source that is independent of the patient inspired gas. For example, a side-stream NO generation device sources $N_2$ and $O_2$-containing gas from an external source, converts a portion of the gas to NO and introduces that NO-containing gas to a ventilator circuit. In this example, the NO generation device must generate a variable amount NO in proportion with ventilator flow in order to achieve constant NO concentrations in the inspired gas. In one embodiment, the NO generation device delivers a constant flow of NO-containing gas to the ventilator circuit and only varies one or more plasma control parameters.

Pressure variance within the ventilator circuit presents a resistance to the introduction of NO-containing gas into the ventilator stream. In some embodiments, running a pump at a constant rate can result in a situation where no NO is introduced into the ventilator during inspiration due to the high pressure that occurs during the inspiratory pulse. In some embodiments, a small orifice can be used at the NO injection location to keep product gas pressure higher than the pressure within the ventilator circuit, ensuring that there is always NO flow into the ventilator circuit.

In some embodiments, reactant gas flow through the NO generation device is varied as a function of ventilator flow. In one embodiment, air flow through the NO generation device is varied as a linear proportion to the flow rate of the patient inspiratory flow. In one embodiment, the linear proportion is 1-10%, however ratios as high as 20% have been contemplated.

Varying reactant gas flow continuously in real time through the NO generator as a function of an input parameter offers advantages: 1) The quantity of NO molecules increases with increasing flow through the plasma, thereby increasing NO generation when it is needed, 2) Pressure within the NO generation system increases as inspiratory flow pressure increases, thereby ensuring that product gas continues to flow into the inspiratory flow, 3) Changes in plasma control parameters or not necessary in order to deliver constant NO concentration to the patient, 4) High reactant gas flow rate minimizes the transit delay and residence time of NO-rich gas in the controller.

The input parameter can be an indication of the patient inspiratory cycle timing and/or flow rate. The sensed parameter could be one or more of the following: pressure, flow, temperature, strain, acoustic, ultrasonic, optical or other means. The parameter could be sensed directly by the NO generation device or measured by another device and communicated to the NO generation device via wired, wireless, optical, or other means. In one embodiment, Inspiratory flow rate is measured by the NO generation system. In one embodiment, ventilator flow rate is measured by the NO generation system. In one embodiment, a trigger event is marked by a ventilator and communicated to the NO generation device. In one embodiment, patient chest wall strain and/or diaphragm EMG activity are communicated to the NO generation device. In one embodiment, NO generation is controlled based on one or more of an input of patient inspiration acoustics (microphone measurement), inspiratory circuit pressure, inspiratory flow temperature (exhaled gases are warm).

NO/NO$_2$ Ratio Optimization During Generation—Ozone

The ratio of NO$_2$ to NO generated during an electrical discharge can vary. One of the mechanisms for forming NO$_2$ is when O$_3$ combines with NO. O$_3$ is formed from electrical corona which can occur as electrical potential builds in the electrodes prior to discharge. The production of NO is maintained by the control signal from the high voltage control circuit. In one embodiment, this consists of a wave made up of AC pulses. The term "wave" refers to the control signal going to the circuit that drives the primary coil of the high voltage transformer. When the wave is high (during the high part of a pulse), the primary circuit drives the transformer with AC current. When the wave is low (pulse off), the primary circuit is inactive. In general, the amount of NO generated is proportional to the percentage of time that the pulses in this wave are ACTIVE (i.e generating NO). At the start of a pulse, the voltage builds until plasma breakdown across the electrode occurs. This slight delay reduces the time within the pulse that the pulse is active. If the pulse is relatively short, the voltage build-up could be a significant portion of the pulse and thus significantly reduce the effective ON time, and thus reduce the production of NO. Hot electrodes ionize the gas between them. Thus, a breakdown delay is decreased if the time between pulses is reduced because the electrodes do not have time to cool significantly between pulses. In one embodiment, pulses are grouped close together to reduce the breakdown delay. In one embodiment, space is introduced between groups of pulses to keep the NO production from climbing too high and to maintain the average effective time that the wave is active.

In some embodiments, after the initial plasma breakdown, the control wave voltage may be reduced to maintain the spark at a lower energy until the pulse ends. For example, for a 2.5 mm gap, it can require 6-12 kV to breakdown the gap and create the plasma, it only requires 500-1000 volts to maintain it. Reducing the control voltage reduces the current in the plasma, and thus the energy, allowing the formation of low energy plasma which enables the production of low doses of NO. A reduction of the plasma energy also improves the electrical efficiency of the controller.

In some embodiments, the system uses bursts of discharges (a series of discharges in rapid succession) to keep electrodes hot, thereby reducing plasma delay in subsequent discharges after the first discharge. In one embodiment, the system varies the pause between bursts to control NO output levels. The pause between bursts also provides time for electrodes to cool the reactant gas flow. In one method, anti-corona insulator materials are used on and around the electrodes to decrease O$_3$ formation from corona.

Production of NO per watt can have optimal control parameters. During the development of an NO generation device, optimal plasma parameters are determined and used as defaults for commercial designs. In one embodiment, the device sweeps some or all of the spark parameters to determine optimum settings before or during the early stages of a treatment. A capacitive high voltage storage device was not selected for reliability reasons.

Energy optimization and NO$_2$ minimization often do not coincide. In some embodiments, plasma control parameters are selected to optimize electrical efficiency. In some embodiments, plasma control parameters are selected to minimize NO$_2$ production. In some embodiments, plasma control parameters are selected to optimize a combination of NO$_2$ levels and electrical efficiency, recognizing that neither parameter is optimized.

NO$_2$ Management

NO oxides in the presence of oxygen and will entirely oxidize into NO$_2$ given sufficient time. NO$_2$ is unhealthy to breath because it forms nitric acid when it contents moisture, as is found in the lining of the lung. It follows that NO generation systems should minimize the amount of NO$_2$ delivered to the patient. NO$_2$ levels are reduced by inclusion of a scrubber, however additional algorithmic approaches can reduce NO$_2$ delivery further.

In one embodiment, the NO generation system continues to run the reactant gas pump for a period of time after plasma activity ceases. This purges the pneumatic paths and scavenger of the device. Cessation of plasma activity could be when treatment is terminated. Cessation of plasma activity could also be breath to breath. In one embodiment, the NO generation system can reverse the direction of flow through the scavenger, directing NO$_2$ to the system exhaust port instead of the patient. In one embodiment, product gas is exposed to UV light with a frequency in the range of 300 nm to 420 nm to convert NO$_2$ to NO prior to injection into an inspiratory stream. In one embodiment, the inspiratory stream is exposed to UV light with a frequency between 300 nm and 420 nm post NO-injection.

Dose Management

Trim Adjustment

Treatment set-ups for NO delivery vary with patient size (vent tubing diameter), humidifier type, patient tubing length, auxiliary concomitant treatments (nebulizers for example) and other variables. It follows, that the transit time from NO generation to the patient will vary in turn which can cause variance in the amount of NO conversion to NO$_2$. Additional transit time occurs as sample gases travel from the gas sampling location in the inspiratory limb to the gas analysis sensors. As a result, the amount of NO indicated by the gas sensors may be different (typically lower) than the amount of NO requested. In one embodiment, an NO generation device has a trim feature that enables fine adjustments in the NO production to be made so that NO measurements at the gas sensors match the target NO level. In some embodiments, an NO generation device has a trim feature that enables fine adjustments in the NO production to be made so that measurements at the gas sensors are equal to the target NO concentration+the NO amounts lost due to transit from the sample collection point to the sensors.

Manual Trim Adjustment

A manual trim feature enables a User to overcome variances in the patient set-up that alter the amount of NO delivered to the patient. Increases in NO production using the trim feature will increase both NO and NO$_2$ production. The trim feature does not alter NO and NO$_2$ alarm levels, so that safety features are unchanged. In one embodiment, the trim feature is presented on a touch screen interface. In one embodiment, the trim feature is a physical knob.

Automatic Trim Adjustment

In one embodiment, the system uses gas sensor data to automatically increase or decrease NO production to match the target NO delivery level in a closed-loop fashion. In one embodiment, the automatic trim adjustment is limited to a particular magnitude of adjustment. In one embodiment, the level of trim adjustment is limited to a set number of ppm of NO. In one embodiment, the level of trim adjustment is limited to a percentage of the target NO level (for example, 10%). In some embodiments, an automatic trim feature compensates for NO losses that occur during transit within the sample line so that it is controlling NO concentration at the sample collection point.

Multiple Doses of NO

In some embodiments, it is possible to use multiple doses of NO to provide a multi-stage NO therapy. For example, a first dose of NO can be used to dilate a pulmonary vessel or an airway, and a second dose of NO can be used to sustain dilation. In some embodiments, an NO generation and delivery device delivers a high dose for a set amount of time (1-2 minutes for example) before automatically lowering the dose to the target dose. In another embodiment, a high dose is delivered for a certain number of breaths (10 for example) before changing to the target dose. The transition from the high dose to the target dose can be a step function or a continuous decline (linear, logarithmic, etc.). In some embodiments, the high dose is a set value for all patients. In some embodiments, the high dose is a function of the target dose (2 times the target dose, for example).

User Interface

Figure 50:
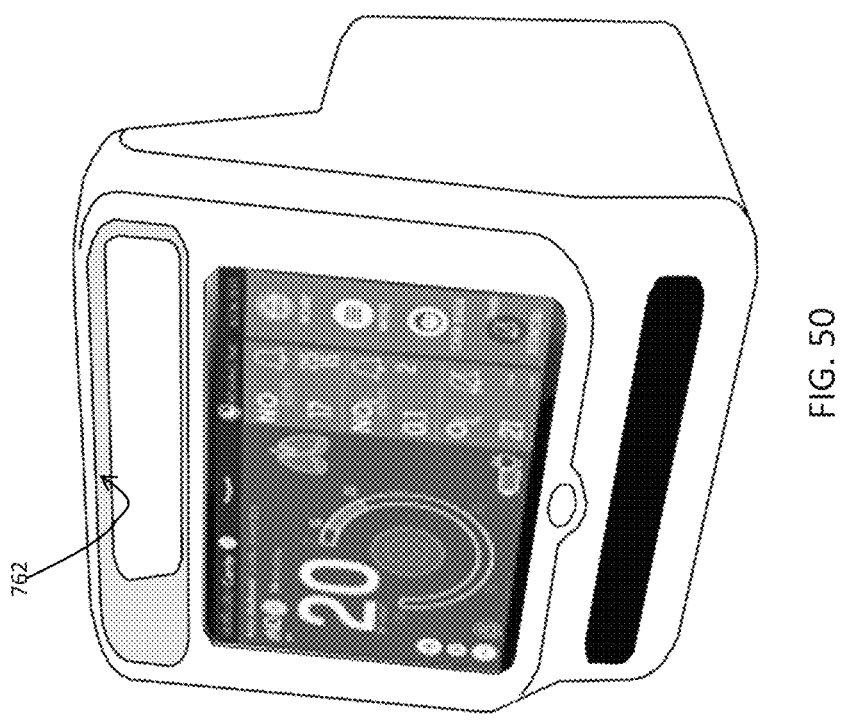
FIG. 50 is an embodiment of an NO generation system with a visual alarm status component.

In some embodiments, the system can include a user interface (UI) in communication with the controller and configured to display information relating to NO production, treatment settings, alarms, annotations, gas concentrations, and patient status. The user interface can be configured to display trending data, the trending data being a time history of generated NO, measured NO, $SpO_2$, $O_2$, a respiratory rate, a heart rate, and EKG, or a capnograph. In one embodiment, a light bar is inset within the device handle, locating alarm lights high on the enclosure for visibility. In one embodiment, windows in the side of the handle enable alarm lighting to project out the sides of the handle as well. FIG. 50 shows an example of an alarm light bar 762 illuminated flashing red for a high-level alarm. The light bar can be illuminated in other colors, such as flashing yellow for warning, solid green for self-test complete, solid blue for NO delivery active, and flashing white for bag-mode active. In one embodiment, LEDs for illuminating the light bar are located on the edge of the UCM board. In one embodiment, a PCB is located in the upper portion of the handle to shine light down into the light bar.

Various types of information can be presented to a user on a graphical user interface. In some embodiments, an NO delivery system can provide a trending graph or table that shows the time history of one or more of the following: prescribed NO, measured NO, $SpO_2$, $O_2$, EKG, respiratory rate, heart rate, capnography, $NO_2$. In some embodiments, an NO delivery system can have quick NO settings such as 80, 40, 20, 10, 5, 4, 3, 2, 1. In some embodiments, an NO delivery system can display an animated lung that indicates that treatment is in process. In some embodiments, an NO delivery system can determine patient respiratory parameters such as respiratory rate or tidal volume from measured flow in the patient inspiratory limb and present the information on the interface. In some embodiments, the background color of the UI can be changed to indicate therapy is running. In addition, bezel of the screen has an indicator stating 'eNO' that lights up with treatment is running and NO is being delivered to patient.

Figure 52:
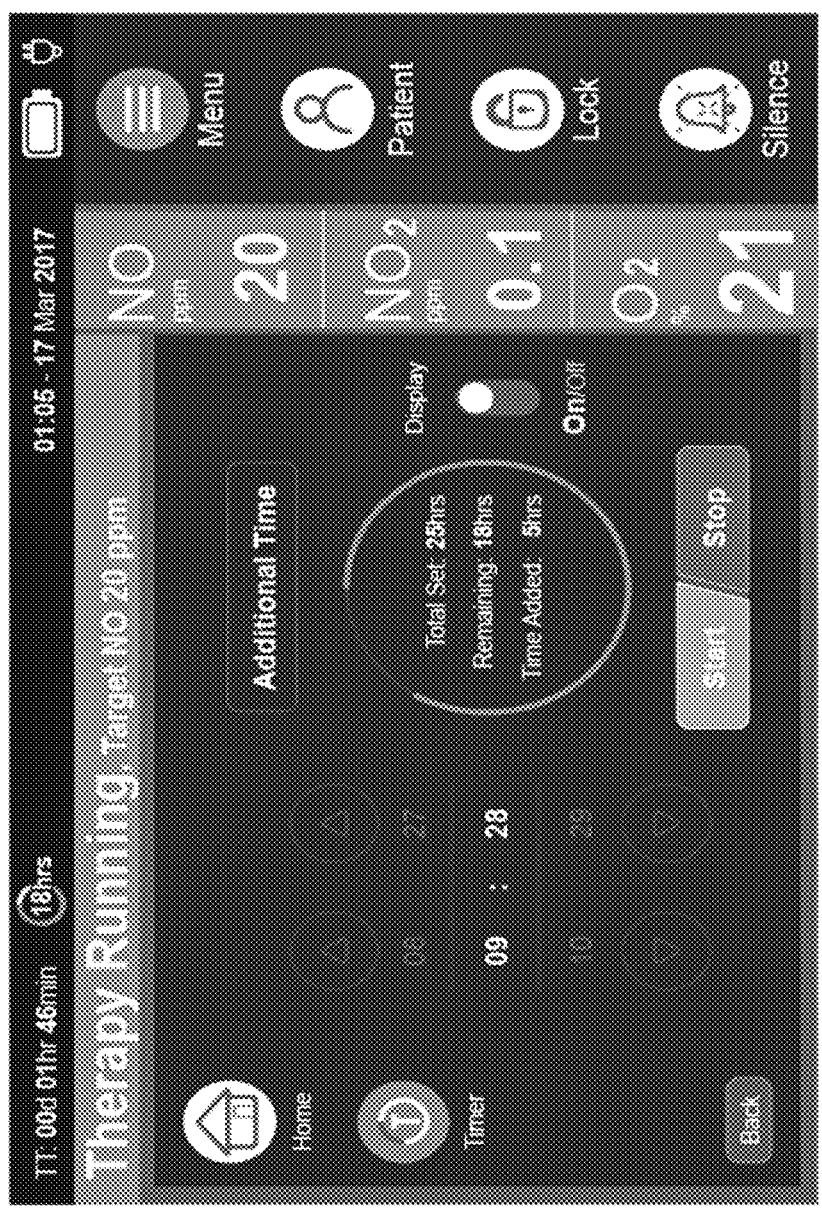
FIG. 52, FIG. 53, FIG. 54, FIG. 55, FIG. 56, FIG. 57, FIG. 58, FIG. 59, FIG. 60, FIG. 61, and FIG. 62 are embodiments of a user interface of an NO generation system.
Figure 53:
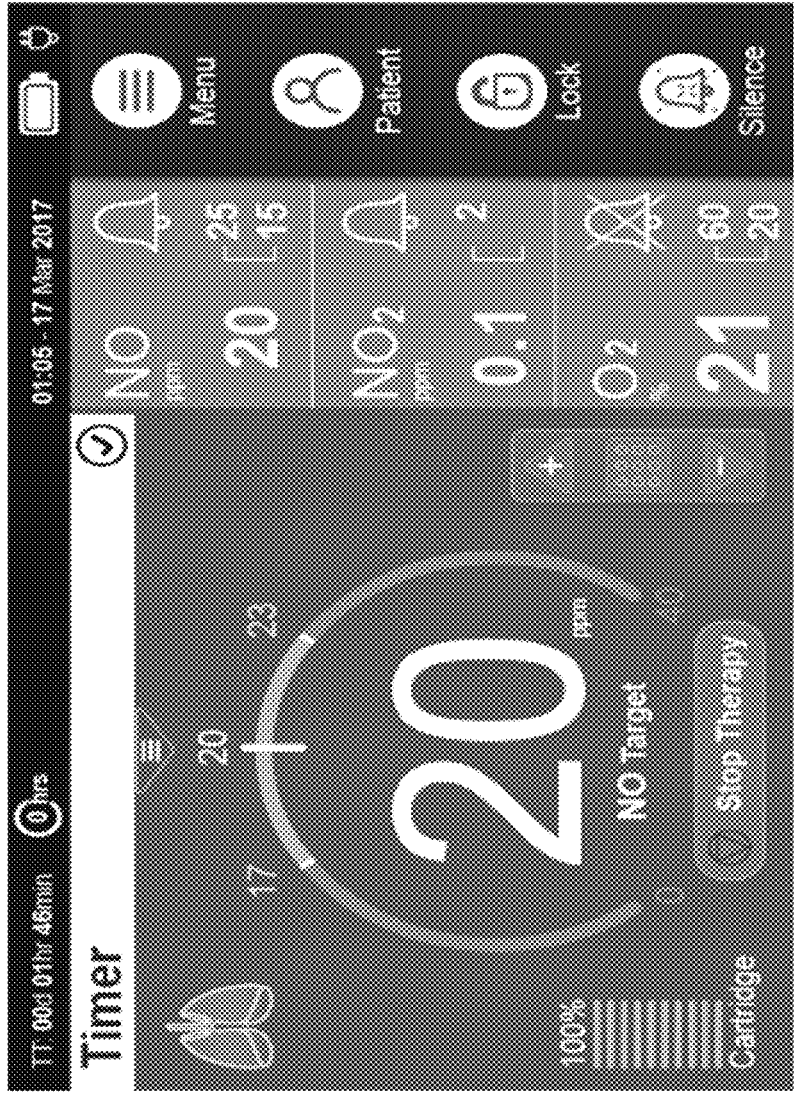

In some embodiments, an NO generation system can provide the user with a reminder of when the patient is ready for the next weaning step to decrease NO levels, as shown in FIGS. 52 and 53. The timer can also be used to remind the user to check patient shortly after initiating therapy, i.e. 10 mins to 24 hours, to check whether the patient is responding to therapy. The reminder can also be used as a reminder to replace disposable accessories like disk filter periodically based on hospital protocol. When the set time is up the device can remind the user as an alarm or a notification using visual and/or audible signals. The reminder can be based on time, $SpO_2$, or other physiological variables.

Figures 51A, 51B:
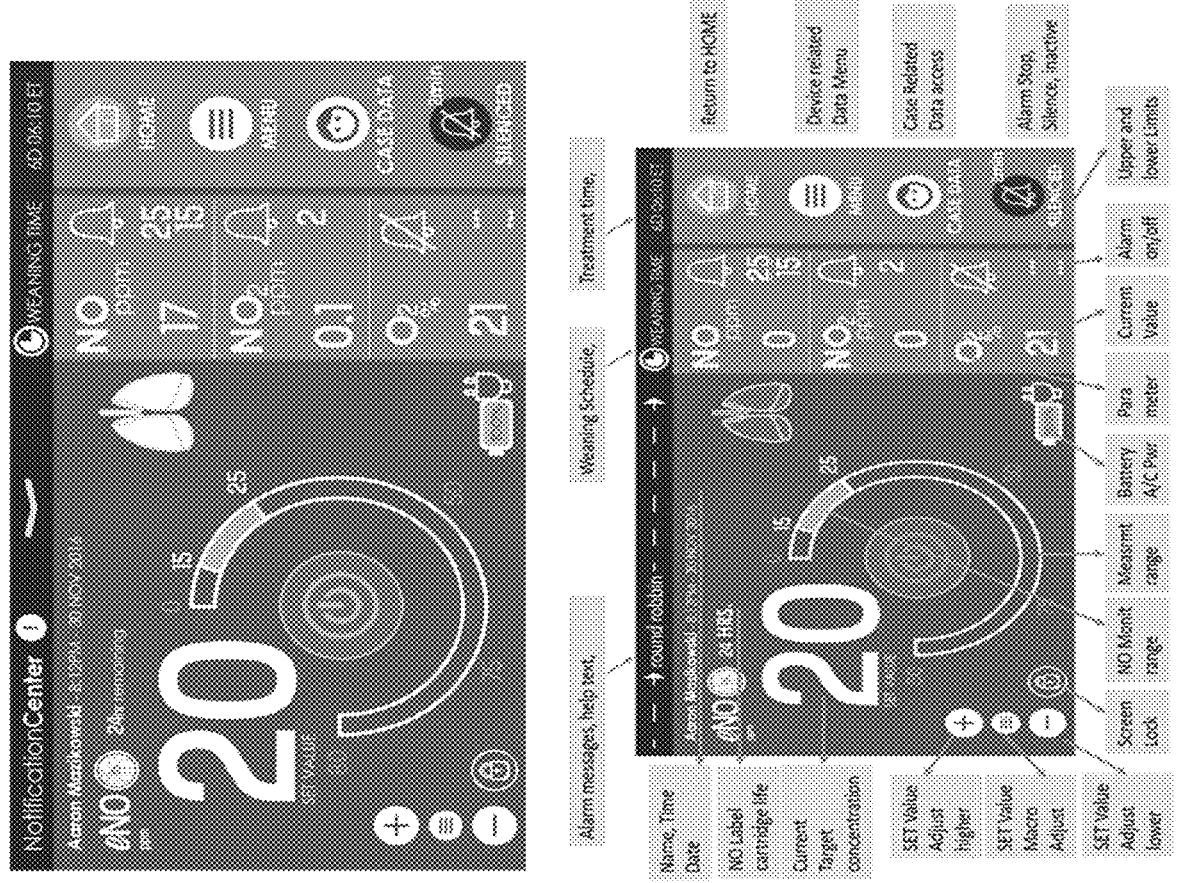
FIG. 51A, FIG. 51B, FIG. 51C, FIG. 51D, FIG. 51E, FIG. 51F, and FIG. 51G are embodiments of a user interface for displaying information related to NO production to a user.
Figure 54:
Figure 55:
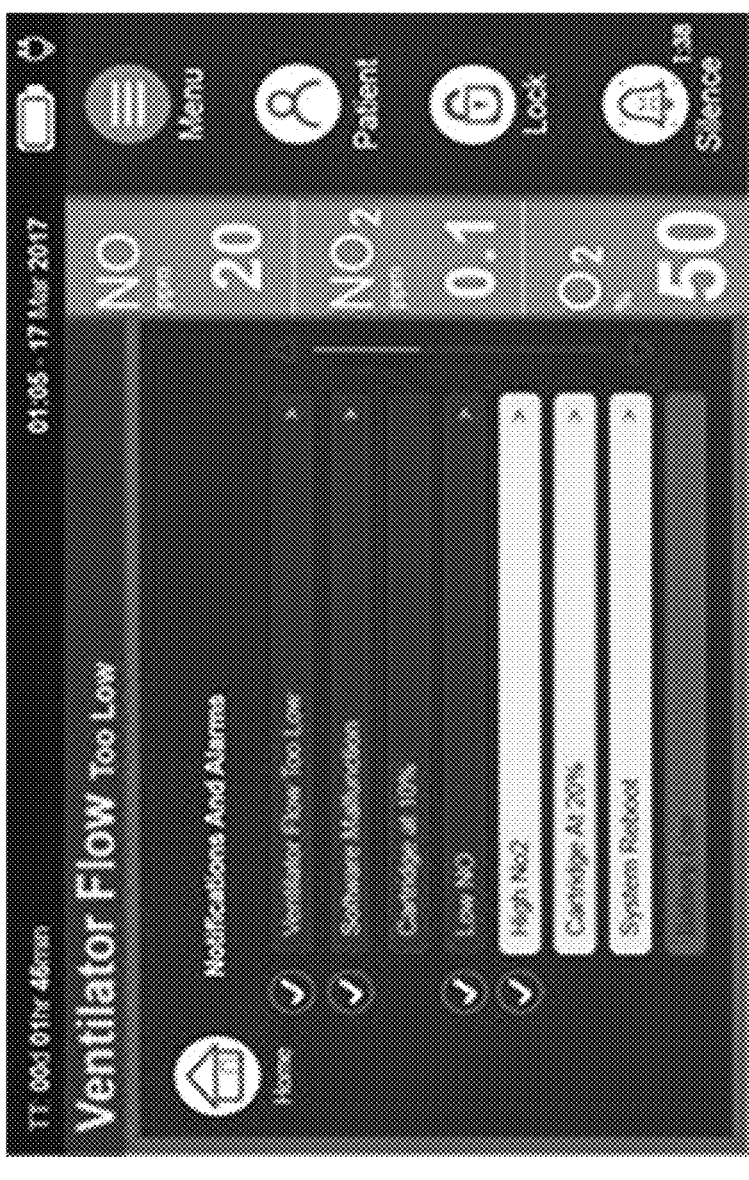

FIG. 51A depicts an exemplary embodiment of a user interface. As shown in FIG. 51A, the user interface of a clinical screen can be divided into 5 main regions: a status panel, a notification center, a treatment panel, a gas analysis center, and a control panel. The notification center can present messaging and information related to a patient, system status, and user instructions. A downward pointing chevron under the notification center can be pressed and dragged downwards to expose additional information. Instead of a precise press on chevron, a swipe down gesture anywhere in the ventilator treatment panel can also expose additional information. The additional information could include all the active alarms and troubleshooting instructions for each of active alarms. The user interface allows for scrollable screen by swipe up and down gestures. Any time a new alarm is active and a UI closes all pop ups and submenus and returns the user to main clinical home screen, as shown in FIGS. 54 and 55. The status bar displays real time information such as timer status, cumulative treatment time, patient info, battery status and battery remaining in percentage, ac power status, wireless connection status, date and time. In some embodiments, elapsed time from initiation of treatment is shown as well. The cumulative treatment time is the total time of when treatment was given to the patient since the device was turned on where as elapsed time is the total time since the last time treatment was started. It will be understood that various other types of information can be displayed to a user in status bar and notification center.

Figure 51C:
Figure 56:
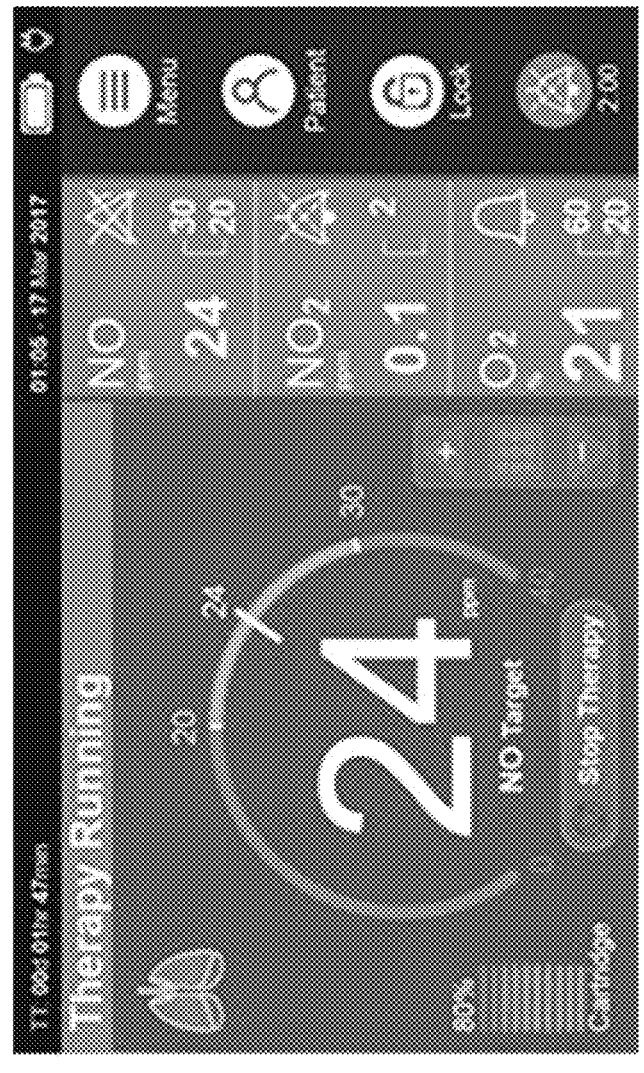
Figure 57:
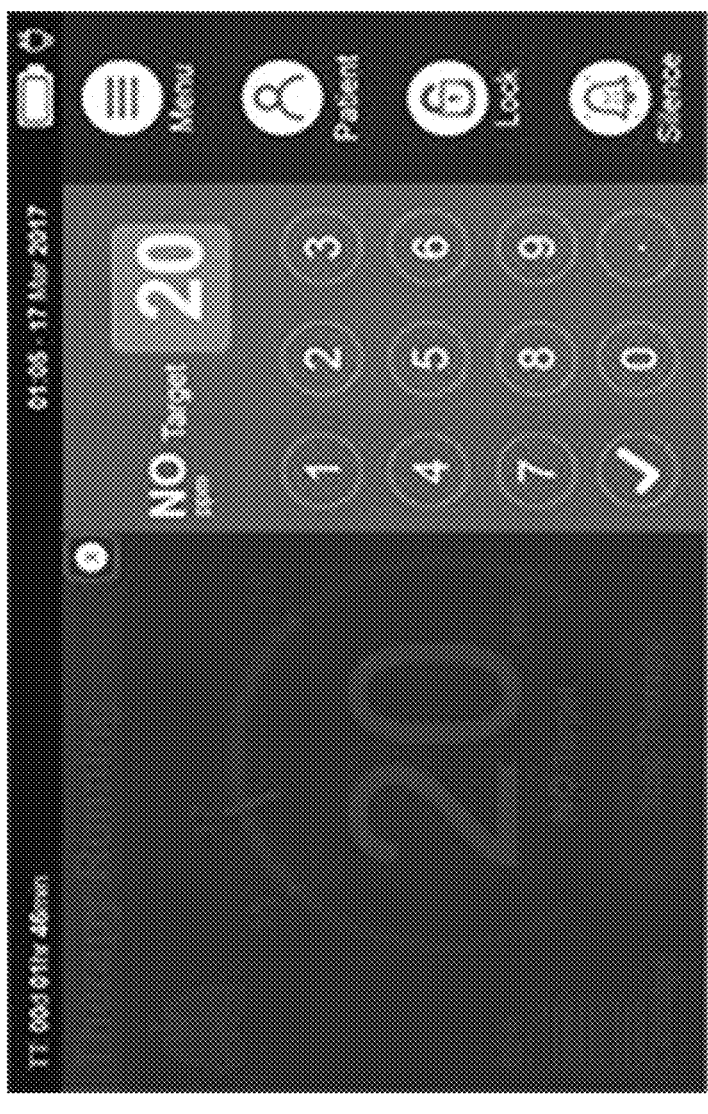

FIG. 51B illustrates an embodiment of the ventilator treatment panel of the user interface. As shown in FIG. 51B, the ventilator treatment panel shows an animation to show system activity (for example, a lung image), the prescribed amount of NO (20), means to enter manual mode, scavenger cartridge remaining useful life meter (lower left corner), measured gas values, alarm limits (15, 25), and treatment setting adjustments (3 buttons on lower right corner). The plus sign increments the prescribed amount in increments that are proportional with the value. For example, from 1 to 10 can be incremented in 1 ppm increments, but beyond 10 the increments are 5 ppm. The minus button decreases the prescribed amount in similar decrements. In some embodiments, the NO target can be changed by touching the NO target value and sliding a finger up or down until an NO target value is changed to the desired value. FIG. 51C depicts how the center button with a keypad in it pops up a quick setting menu to enable the User to rapidly select the desired NO concentration. When a keypad for NO target or an alarm settings pops up, the ventilator treatment area can be semi-transparent and active to allow user to see the current treatment status at all times. In some embodiments, touching the large NO target number can also open a quick setting menu, as shown in FIGS. 56 and 57.

An arc, or a radial or linear gauge, on the treatment panel shows the range of possible NO concentrations, highlighting the current range of operation. In some embodiments, the scale represented by the arc can be adjusted by patient type, for example 0 to 40 for a neonate and 0 to 80 for an adult. A start button can be located at the center of the arc, and can toggle to a pause button when treatment is active. The interface can also include a button to enter manual mode. A highlighted region on the arc depicts the alarm limits/ acceptable tolerance around the set concentration. In the event that NO concentration goes above or below this bracket, an alarm is generated. In one embodiment, the user interface is a touch screen that enables a User to touch the arc in the location of the alarm limit they desire. In one embodiment, the User can touch the screen and drag the alarm limit along the arc to the desired level.

Figure 58:
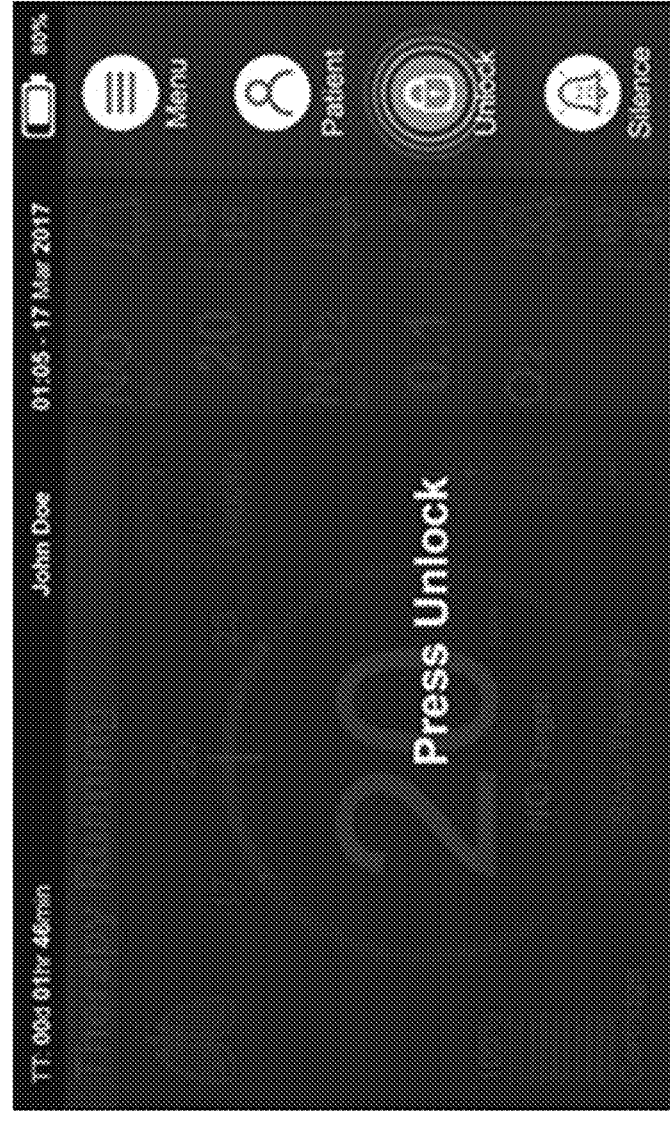

The gas analysis panel can present the current measured values for NO, $NO_2$ and $O_2$ as well as set alarm limits. Pressing a gas panel can pop up alarm range settings menu for respective gas to enable user to rapidly change the alarm range to desired value. The quick settings also allow user to change the alarm status of each gas measurement to active, inactive or audio indefinitely paused. In some embodiments, the NO level displayed is equal to the NO level measured by the gas analysis sensors plus the amount of NO lost in transit from the gas sampling point to the sensors. The amount of NO lost, being calculated as a function of NO concentration, $O_2$ concentration and transit time from. Transit time is a function of sample line internal volume (length, ID, etc.) and sample pump flow rate. In some embodiments, the $NO_2$ level displayed is equal to the $NO_2$ level measured minus the amount of NO lost in transit from the gas sampling point to the sensors. The control panel is static and present on all pages of the user interface and can include a menu, patient info, screen lock, and alarm silence. The menu enables the user to go back to a menu home page, view deeper menus, and review case data. The lock button lock and unlocks the screen to prevent accidental touches. When screen is locked pressing anywhere on screen enables an unlock animation to alert the user that screen needs to be unlocked. The home button in any of the sub menu enables the user to go back to the main clinical home screen from any screen. An exemplary user interface screen is shown in FIG. 58.

Figure 51D:
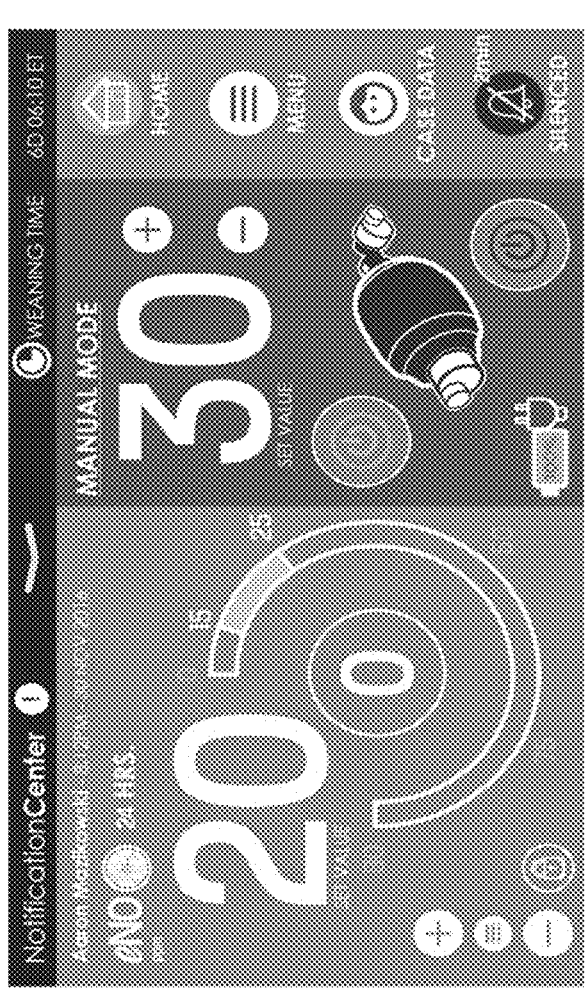
Figure 59:

FIG. 51D illustrates an embodiment of the manual mode screen, which displays to the user that the system has manual mode initiated. The desired NO concentration is displayed. Plus and minus buttons enable the user to adjust NO concentration quickly while the key pad button pops up the quick setting to allow user to manual enter the desired setting, as shown in FIG. 59.

Figure 51E:
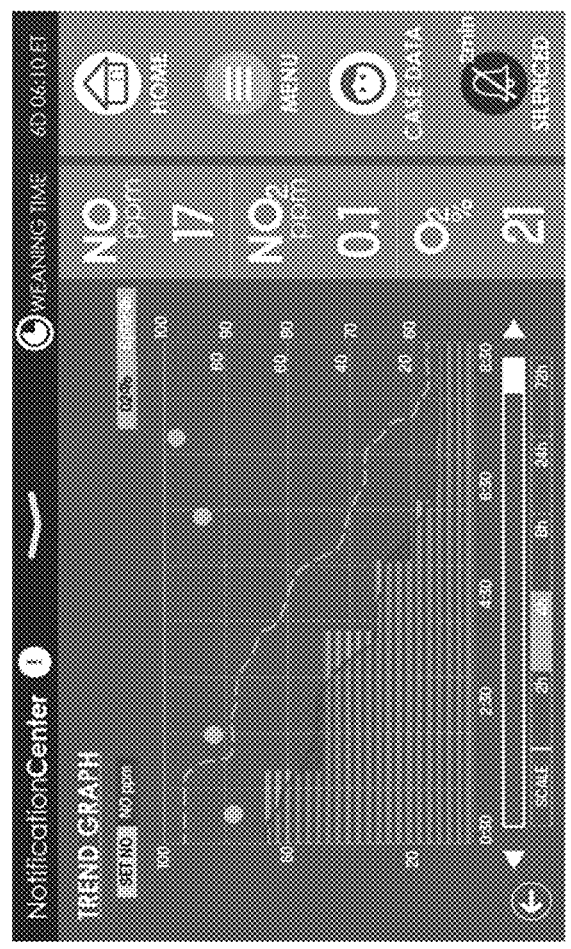
Figure 51F:
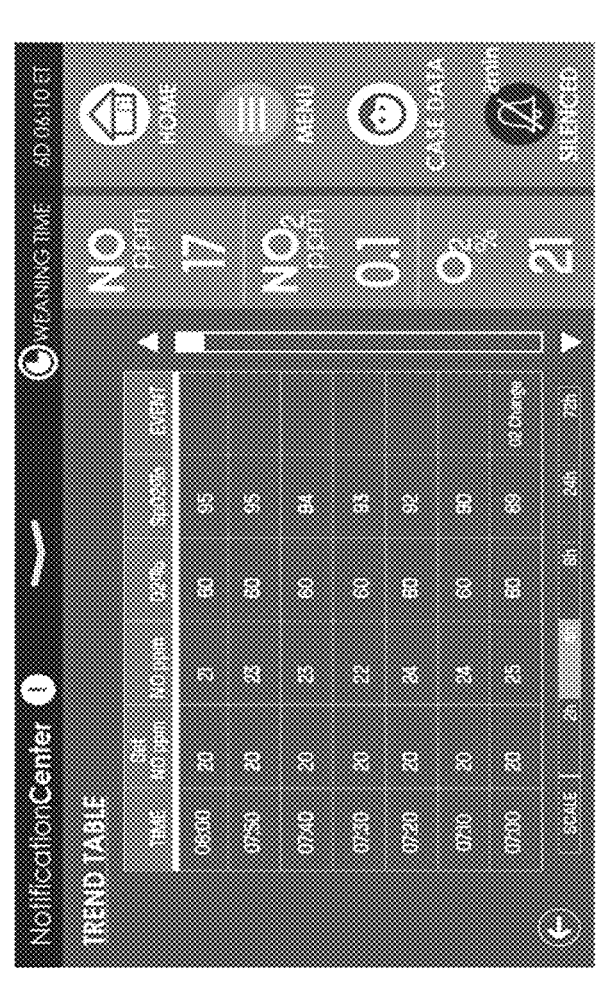
Figure 60:
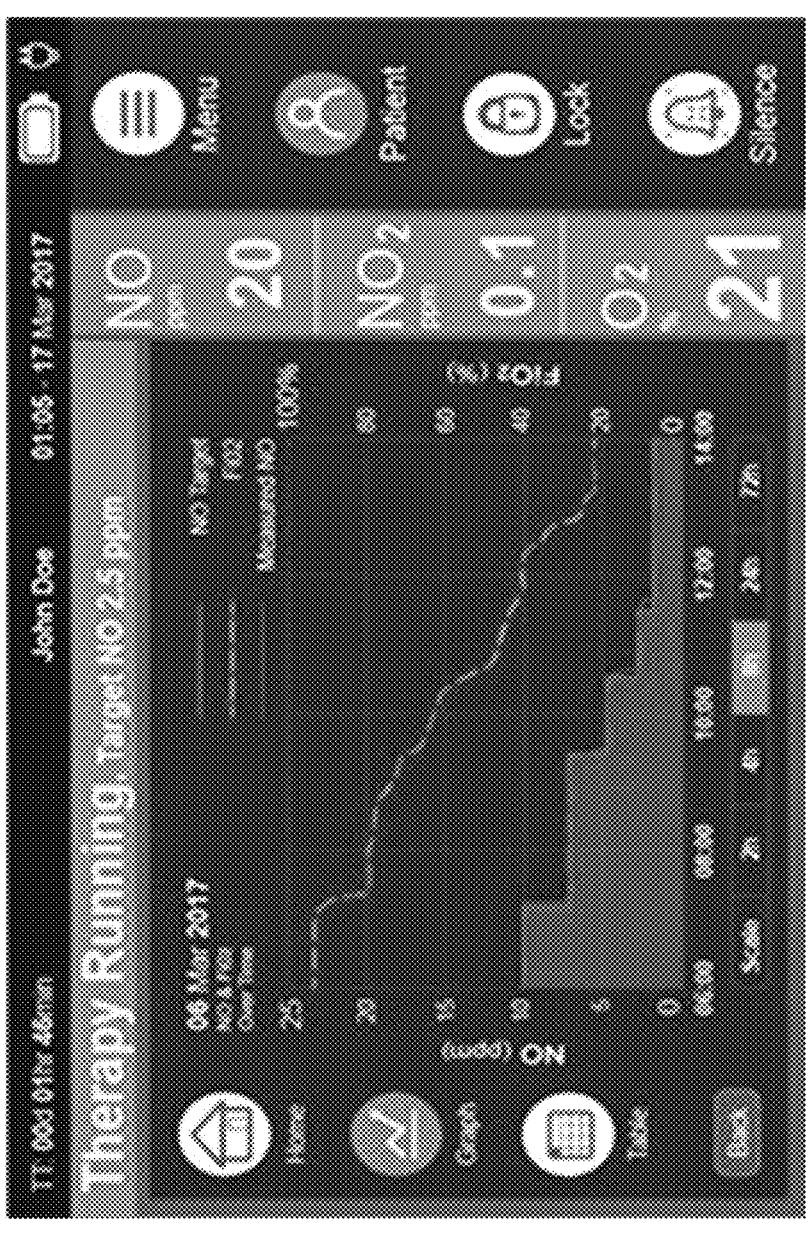
Figure 61:
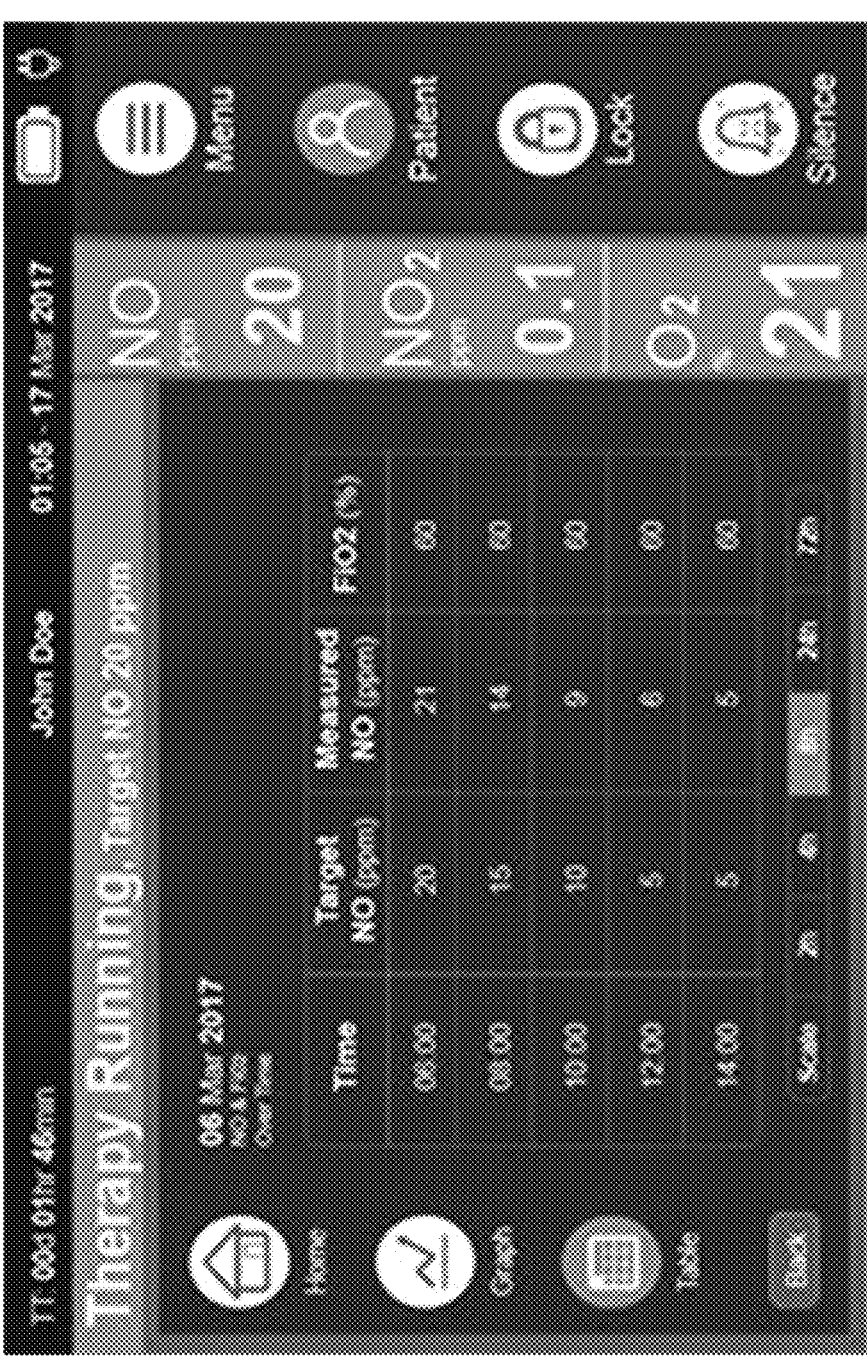

FIG. 51E depicts an embodiment of a trending screen that can display historical NO settings, actual NO measurements, $NO_2$ measurements, $O_2$ measurements, $SPO_2$ measurements, user entries/annotations, $CO_2$ (capnography), respiratory rate, EKG, pulse rate and other physiological and environmental measurements. The amount of time displayed in the trending graph can vary, but in an embodiment the graph displays 72 hours. In some embodiment, the trend graph can be swiped left to display historical data collected for current therapy beyond the time represented in x-axis, as shown in FIG. 60. A user can change the X-axis, for a subset of the 72 hours. The trending screen enables a physician to see what happened to a patient over a period of time, for example a weekend. FIG. 21F depicts an embodiment of a trending screen displaying the trending data in tabular form, which can be swiped up to display historical data, as shown in FIG. 61.

Figure 51G:
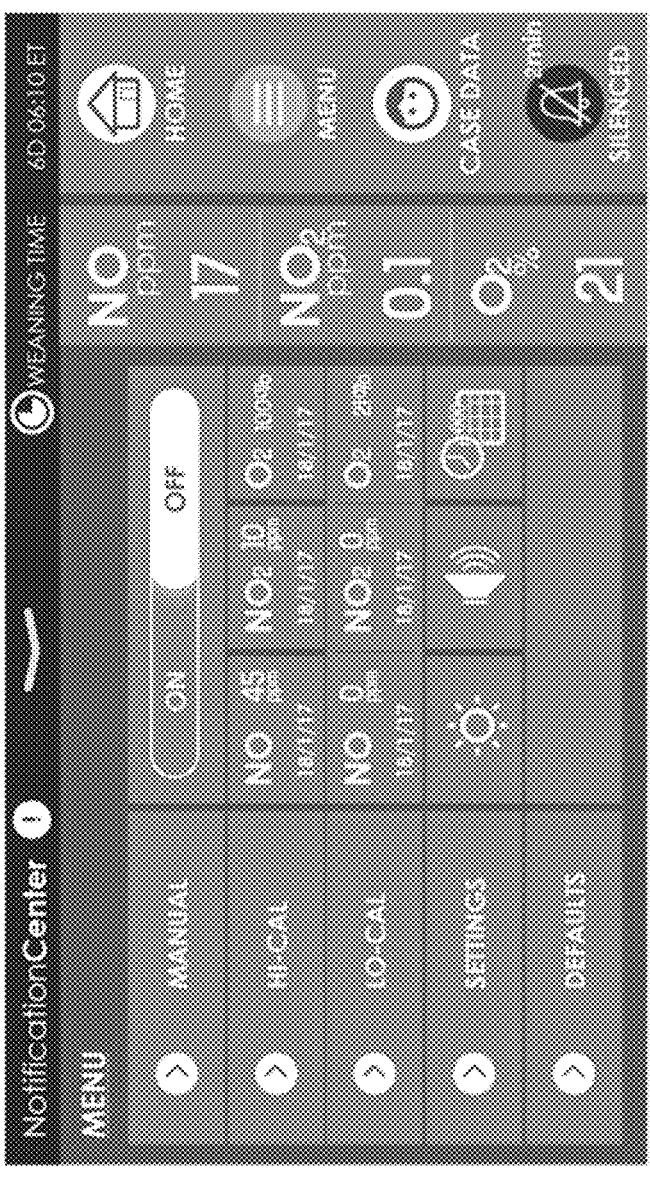
Figure 62:
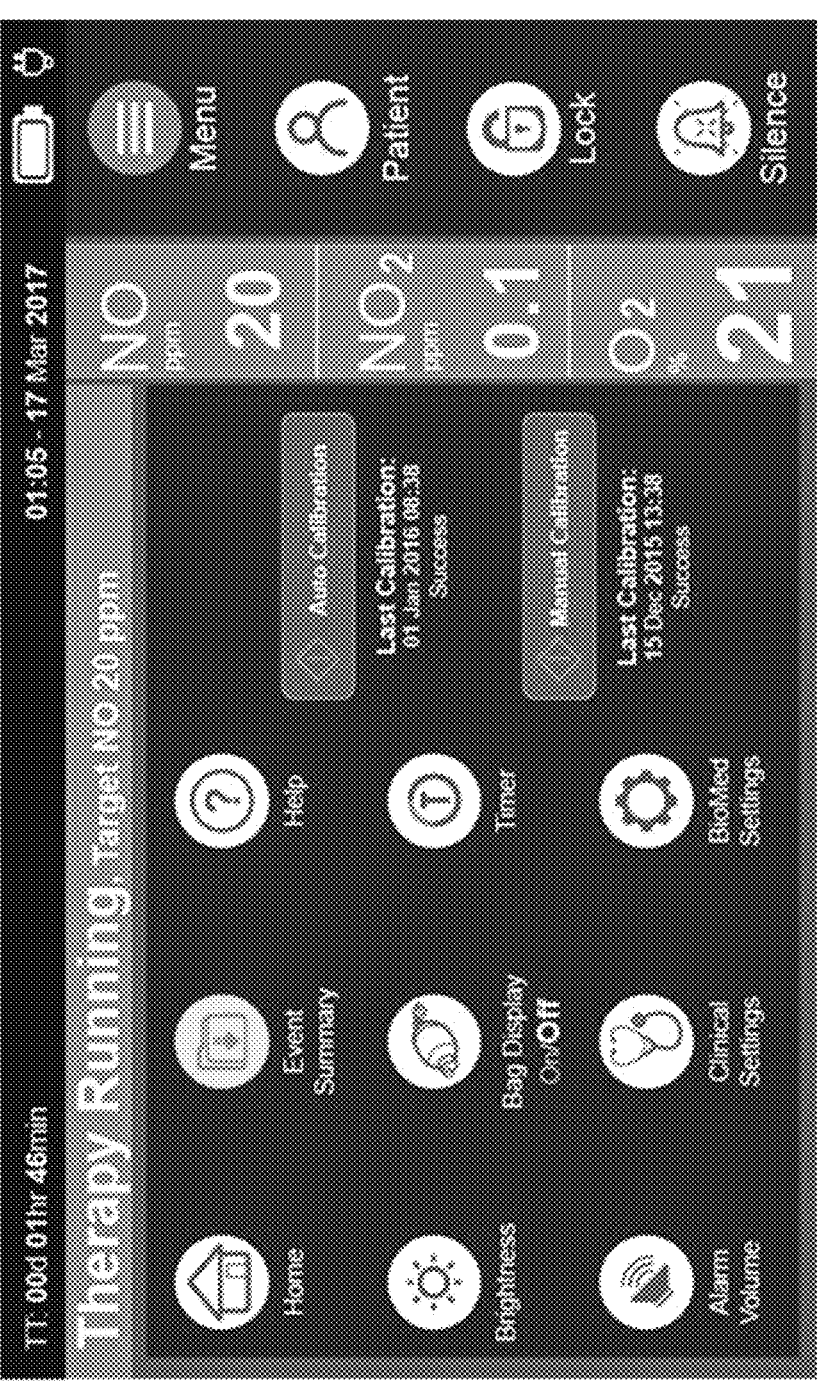

FIG. 51G depicts an embodiment of a menu screen. When the menu button is pressed, the user has access to manual ventilation mode button display settings, manual HI-calibration, manual low calibration, auto-calibration, settings and defaults. A help feature can also be made available where there a FAQ. A searchable IFU can also be made available in Help. The entry to clinical and biomed settings can be password protected to restricted or can be programed to give access to an individual or group of user IDs. In some embodiments, the settings could include ability for user to generate and customize presets for alarms, timer, alarm limits, NO target defaults, etc. based on patient type or patient disease state or department. An exemplary user interface screen in shown in FIG. 62.

During normal use, the user interface can be static or animated. The animation on the screen can alert the user to the fact that that the system is functioning properly. In an embodiment, the animation is in the form of a lung image with arrows or dots representing NO gas entering the lung. NO gas existing in the lung can also be displayed. In some embodiments, the lung animation could accurately represent the bpm in real time. In manual mode a bag animation on screen can alert the user to the fact that the system is in manual mode and the system is functional properly. The bag animation could be a flashing animation toggling between colored bag representing bag filled with gas to uncolored bag representing empty bag or an animation showing gradual inflation and deflation of the bag.

The user interface can also display tidal volume of the patient, as measured by integrating the gas flow measurements in the ventilator flow path. To improve the accuracy of the calculation of tidal volume, the system can use the measured flow rate within the inspiratory line during patient exhalation as an indication of ventilator bias flow.

The user interface can include various displays and features. In some embodiments, a lung animation can be used with drug going down into the lung and back out. For example, the displayed lung can be initially colored black on the insides. As a drug enters the lung, shading in the displayed lung can change from top to bottom to make the lung a color (such as pink). As the patient exhales, the pink shading retreats and the displayed lung can become black again. The display can also include an animation of NO flowing through a bag to indicate NO delivery to a bag. For example, a gradient can be shown moving from one end to the other of a bag image. The bag can be empty (black) or colored to indicate the presence of a drug.

When a patient is taken off respiratory assistance with an automatic ventilator and transitioned to manual ventilation (i.e. bagging), there is a risk that the NO concentration delivered changes from the first mode to the next. This could lead to adverse effects to the patient. One concept to prevent a rapid change in NO concentration delivered is for an NO generation system to automatically set the NO concentration for manual respiration to the same level as it was in ventilator respiration. The opposite is also applicable, when NO delivery changes from bag to ventilator delivery. The system also doesn't allow a user to switch between modes if no flow is detected in the desired mode.

Scavenger

The scavenger path can vary in size, shape, and design. In some embodiments, a scavenger path with a round profile with about 0.25 inch inside diameter can be used. It will be understood that other small cross sections can also be used, depending on the gas flow rate. In an example, standard commercially available scavengers (United Filtration P/N DIA-BNMB) measures 2 cm in ID, 3 cm in length and has 6 g of scavenger material. It has a 0.25 inch barb fitting on each end for gas entry and exit. By decreasing the cross-sectional area, it can be ensured that all of the scavenger material was contacted by gas, even at low flow rates. This allowed for a marked improvement in scavenger efficacy, reducing the $NO_2$ ppm in the exiting flow, and increased the longevity of the scavenger. Longevity of the scavenger can be determined by subjecting the scavenger to a simulated clinical scenario until $NO_2$ levels reach a clinically relevant threshold, for example 5 ppm. In some embodiments, the cross-sectional area of the scavenger is kept small, which provides greater control over the path length for gases to travel and improves scavenger efficacy. The benefit of having a relatively small cross section is that gas passes with greater velocity, more actively mixing and contacting scavenger material.

In some embodiments, the system has two independent scavenger paths. The first scavenger path is for ventilator NO delivery and the second scavenger path is a back-up for ventilator delivery or a manual ventilation device.

The scavenger can include one or more paths through the scavenger material. Since a gas will take the shortest path, a long scavenger path with small cross-sectional area is used rather than a short path with large cross-sectional area. In order to package a long scavenger path into a more compact space, the scavenger path can have a switch-back design, resembling a maze. Many configurations of the scavenger path can be used, including but not limited to a spiral to the tube for compact packaging.

The scavenger can be made from a variety of materials. In some embodiments, the scavenger material is soda lime, which is a combination of sodium hydroxide, potassium hydroxide, and calcium hydroxide. Soda lime is available in multiple physical form factors, including cylinders and half-spheres.

Figure 63:
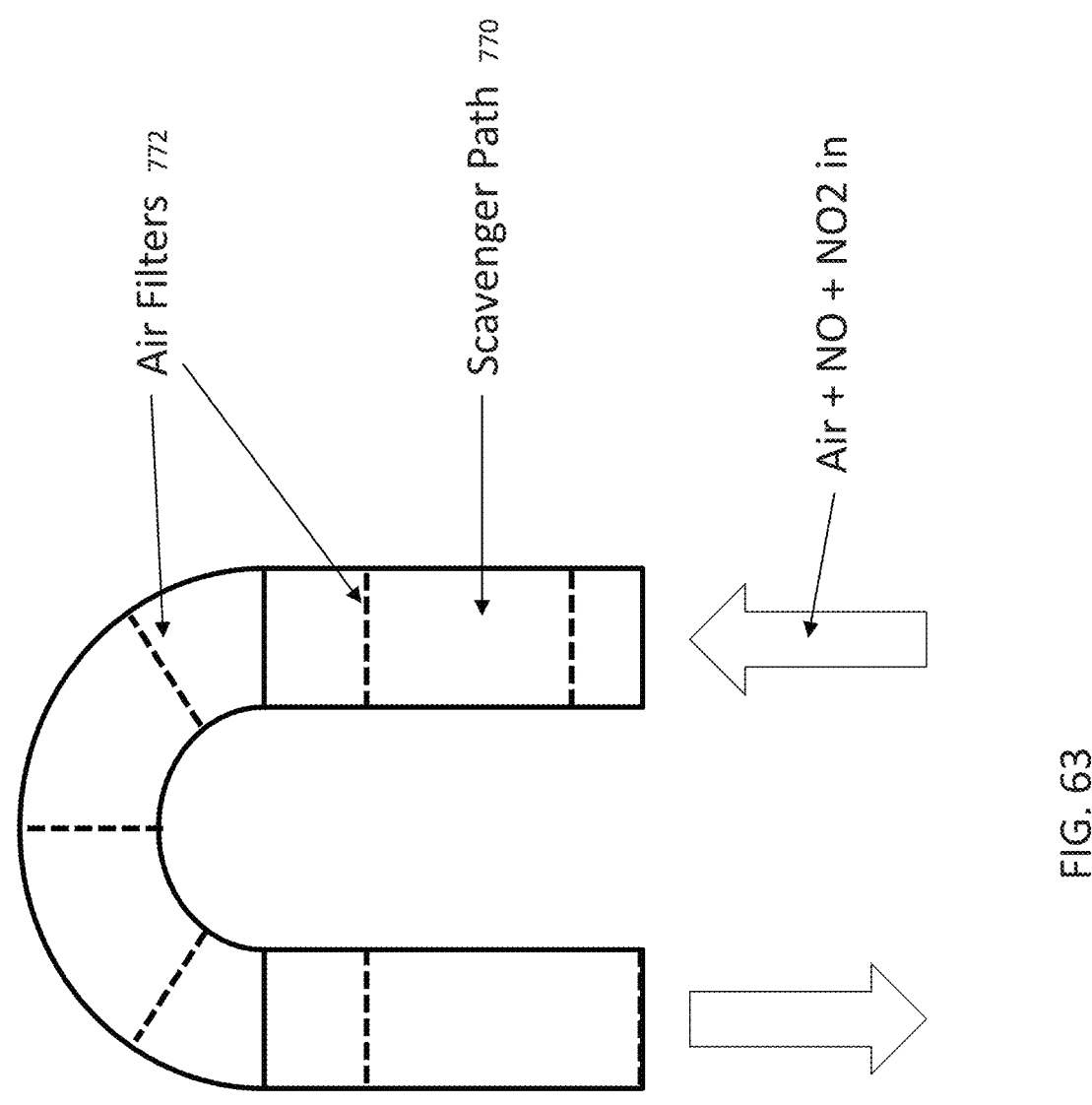
FIG. 63 is an embodiment of a scavenger path.

Soda lime is brittle and can fracture during handling. When soda lime fractures particles of soda lime can travel through the scavenger path and clog the filter at the exit. In one embodiment shown in FIG. 63, the scavenger path 770 has multiple particle filters 772 spaced along the flow path to capture soda lime particulate. This design limits the amount of particulate matter that can collect in any one filter.

In some embodiments, soda lime is compounded or mixed with a material that increases its toughness while maintains $NO_2$ absorption. In some embodiments, soda lime is blended with sugar to increase toughness. In some embodiments, a flexible polymer shell that is permeable to $NO_2$ is placed around one or more soda lime particles. In some embodiments, a flexible substrate is coated with soda lime to prevent soda lime fracturing. In some embodiments, the flexible substrate is a tube with soda lime coating the interior wall. In some embodiments, soda lime particles are embedded in a porous structure (open cell foam). The foam protects the soda lime from compression and shear while maintain an open gas pathway and ability to collect particles. In some embodiments, soda lime is packaged in a rigid walled tube to protect granular material from crushing. In some embodiments, soda lime pellets are mixed with elastomeric or relatively soft pellets within a volume so that the soft pellets protect the soda lime pellets when displacement and/or vibration is applied. In some embodiments, the gas flow through a bed of soda lime particles is vertical with respect to gravity so that particles settle to the bottom of a chamber when gas flow rates are sufficiently low or nonexistent.

In some embodiments, the product gas flow path within an NO generation device is designed to sequester soda lime particulate to prevent particulate from clogging a filter. In some embodiments, the air flow path at one or more locations within the scavenger has a sharp turns, typically measuring 90 degrees or more. As air flows around the bend, high mass particles travel to the outside of the turn due to centrifugal force where they collect. In some embodiments, particles collect in a pocket or chamber pneumatically connected to the air path. In another embodiment, particles collect on an adhesive surface. In some embodiments, particles embed into an open-cell foam.

Figure 64:
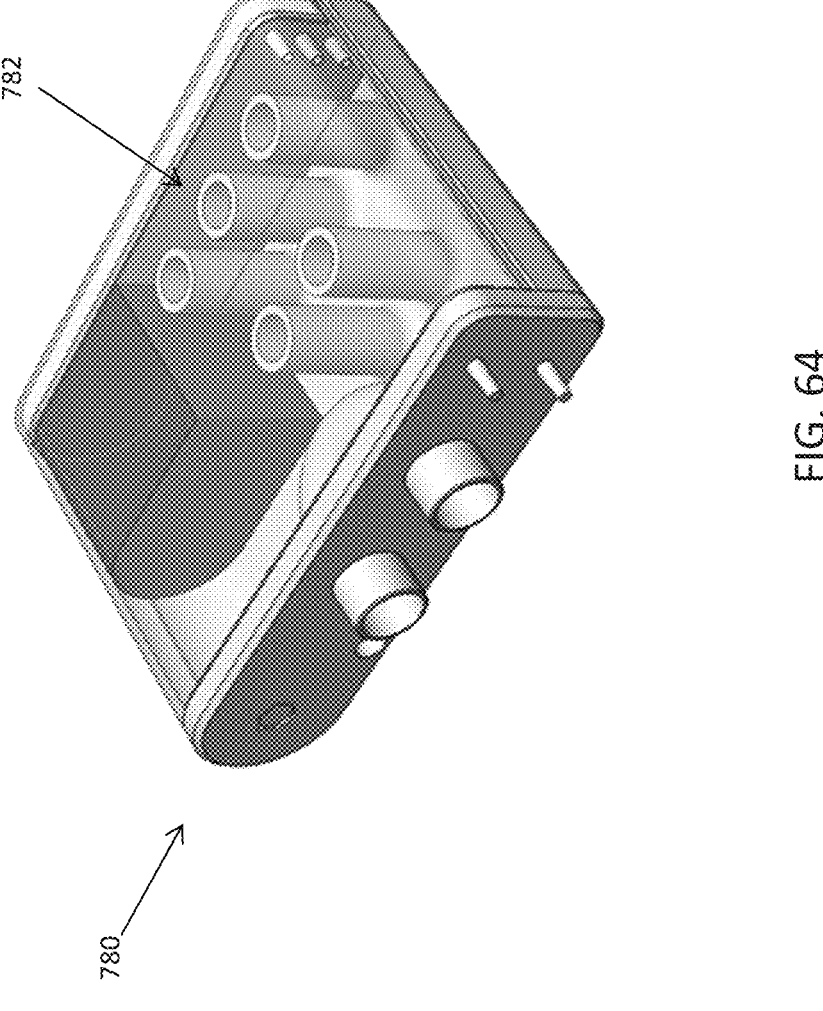
FIG. 64 is an embodiment of a cartridge housing with multiple cylinders therein for managing scavenger tubes.

It can be important to fill the scavenger path and maintaining continuous filling of the path with scavenger material. For example, if a 2-D path is used and it is oriented in a horizontal plane, the scavenger material can settle to the bottom of the path, leaving an unobstructed gas path above the scavenger material. In an embodiment, the air space at the top of the maze path is filled with a closed-cell foam or other compressible filler material that is compatible with NO to prevent gas from avoiding the scavenger material. In an embodiment, a 2-D path is used with the plane of gas travel oriented in a vertical orientation such that the gas is forced to travel through the scavenger material as it travels down below obstructions in the gas path. The benefit of this approach is that settling of the scavenger material due to gravity and vibration from transit does not affect the efficacy of the scavenger. In an embodiment, the scavenger path travels in 3 or more directions so that settling of scavenger material does not introduce a gas flow path that avoids travel through scavenger material. In an embodiment, a long, slender scavenger path can also be created by filling a tube with scavenger material. The tube can be spiraled, wrapped, folded, or otherwise routed as part of a disposable device. Molded-in cylinders or other shapes can be added to the cartridge to provide a structure for wrapping scavenger tubes to package them in a tight space without kinking the tube. Referring to FIG. 64, a cartridge housing 780 is illustrated with five cylinders 782 for wrapping scavenger tubes. The tubes may be formed from a variety of materials, including elastomeric material such as Tygon, or a more rigid material such as stainless steel or Teflon.

In some embodiments, a scavenger path comprises a 2D switchback path or maze oriented in a vertical plane to ensure gas contact with scavenger. In an embodiment, a scavenger path comprises a 2D tortuous path oriented in a horizontal plane with impervious filler material at the top to prevent gases from not flowing through the scavenger material. In an embodiment, a scavenger path comprises a path that flows in 3 orthogonal directions (or additional directions) to ensure that gas flows through the scavenger regardless of cartridge orientation. In an embodiment, a scavenger path comprises a tube (for example, a rigid tube or an elastomeric tube) located within a cartridge housing. In some embodiments, a scavenger path has a cross-sectional area less than 0.5 cm$^2$, which can increase the scavenger life by ensuring that a gas contacts all of the scavenger. In some embodiments, a cartridge can have the ability to redirect gas flowing in one scavenger path to another scavenger path. In some embodiments, the scavenger material is compressed by a spring so that the scavenger material remains packed after encountering fracturing and settling due to impact, handling, and/or vibration. In some embodiments, a system can be used that is capable of generating NO from two or more independent plasmas, sending NO down two or more independent scavenger paths and merging the NO flow into one patient airstream.

In some embodiments, the scavenger can include a reusable scavenger housing that enables the user to remove scavenger material and add new scavenger material. By removing and replacing the scavenger material, this allows the remaining components to stay in place while only scavenger material is disposed of at the end of treatment.

Nitric oxide is very chemically reactive, thus the material selection for the cartridge and other parts of the system that are exposed to NO is important. In some embodiments, polymers such as polyethylene and polypropylene are used. Alternative polymers may be used as well. One way to protect the polymer is to protectively coat the polymer surface with metal, ceramic, glass, or scavenger material to prevent NO reaction. In some embodiments, a scavenger path with walls constructed from scavenger material.

Various parameters are used to determine the length of the scavenger path. In some embodiments, the scavenger path length required to reduce $NO_2$ concentrations to acceptable levels depends on the initial $NO_2$ concentration, flow rate, scavenger path length, scavenger size, scavenger cross-sectional area, the number of parallel scavenger pats, temperature, and/or pressure. For example, an adult being treated with a face mask, receiving 60 lpm of air with a 40 ppm NO would require two, ¼" ID, roughly 70 cm long scavenger paths flowing at 2 lpm with 300 ppm NO in order to last 1 week. On the other hand, neonatal patients breathing 20 ppm at 0.5 lpm, require only a 6 cm length of ¼" ID tubing for a scavenger that lasts at least one week. Thus, an array of scavengers can be produced that match the flow rate, NO concentration, and duration requirements of the users.

In some embodiments, a single cartridge can have multiple scavenger paths with varying length. For example, the cartridge can include a scavenger path with a long path for primary adult applications and a scavenger path with a shorter path for manually ventilating the patient and a back-up for the primary NO generation circuit. The back-up path could also be applied to manual ventilation.

In some embodiments, a cartridge can include multiple scavenger paths with each path having molded-in gates blocking air flow into and out of them. Depending on the application that the cartridge is intended for, tabs in the injection molded part are broken out during manufacturing to permit gas to flow through particular scavenger paths.

A scavenger path for manual ventilation can also serve as a back-up circuit for ventilator NO delivery if there is a failure in any part of the ventilator NO circuit. A selector valve enables the user to choose between manual mode and ventilator mode for the second circuit. Actuation of the valve can be manual, automatic, or software-controlled. For manual action, levers, rotational knobs, push-pull valves, sliding controls, or any other manual mechanism can be used. Software controlled options involve solenoid actuation of the valve either physically engaging a mechanism on the cartridge or applying an electromagnetic force to an iron slug within the cartridge valve mechanism. In some embodiments, a manual/ventilator selector can be biased towards ventilator support. For example, the selector can only remain in the manual position when an actual manual ventilation device is connected to the system. In an embodiment, an optical sensor within the controller can detect the position of the selector and display to the user that manual mode has been enabled on a screen or display. Enabling the manual ventilation device circuit to also support ventilator function prevents the need for a third scavenger path in order to provide both redundant ventilator support and a manual feature.

The cartridge can include one or more valves at the exit point of the scavenger paths to prevent ventilator circuit contents from entering the scavenger. The valves can be active (such as a solenoid-actuated valve) or passive (such as a duck-bill valve). It will be understood that any type of valve or other connection can be used at the exit point of the scavenger path to prevent back flow from the ventilator circuit connected to the cartridge.

One or more outlet filters can be positioned between the scavenger material and the spark chamber to prevent migration of scavenger material into the spark chamber. A filter can also be positioned between the scavenger and the ventilator circuit to prevent migration of scavenger material into the ventilator circuit.

Under certain conditions, $NO_2$ can be converted back into NO. In one embodiment, the NO generation device exposes NO+air to a heated molybdenum feature that catalyzes the $NO_2$ to NO conversion. In another embodiment, $NO_2$-containing gas is exposed to a heated metal carbide surface that converts $NO_2$ back into NO. In another embodiment, a UV light source with approximately 380 nm wavelength is used to convert $NO_2$ in the gas stream back into NO. In another embodiment, plasma intensity and exposure length is sufficient to convert all oxygen in an air sample to NO, thereby leaving trace amounts of oxygen to oxidize the NO. In some embodiments, that converts a high proportion of available oxygen to NO, it is possible that a scavenger to remove $NO_2$ may not be required if initial $NO_2$ generation levels are sufficiently low.

Pneumatic Design

An NO generation system includes various tubes and manifolds to route reactant and product gases through the system. In one embodiment, a single manifold provides the pneumatic routing for one or more of the following pneumatic features: Air reservoir, Reservoir pressure measurement, proportional valve (i.e. flow controller), reactant gas flow measurement, the plasma chamber, electrode assembly mounting interface, plasma chamber pressure sensor mounting, Flow director mounting, bleed valve mounting, routing from plasma paths to gas analysis sensors, routing of product gas to a scavenger path, routing of product gas through a flow director that selects between bag and ventilator, routing of product gas to a ventilator cartridge, etc.

In some embodiments, the pneumatic pathways handled by more than one manifold. In one embodiment, there is a manifold for each redundant pathway.

In some embodiments, there are three scavenger paths: a first ventilator path, a second ventilator path, and a manual ventilation (bag circuit) path.

In some embodiments, the pneumatic path is split sequentially, with smaller manifolds of reduced scope handle the reactant and product gases in series. In one embodiment, one manifold handles one or more of the following: reactant gas reservoir pressure, proportional orifice mounting, reactant gas flow rate measurement, plasma chamber pressure. In some embodiments, a manifold functions as part of the air reservoir housing; as an endcap, plug, or the air reservoir housing itself, for example.

In one embodiment, the electrode assembly includes a manifold with a reactant gas inlet and product gas outlet. In one embodiment, the manifold is metallic to provide electromagnetic shielding. The electrode assembly/manifold can be replaced as a unit by the User as part of routine service. One design philosophy is to route gases to the electrodes rather than route electricity to the electrodes. This is because gas is easily routed within a system using tubing. Electricity is easy to route too with wires, however the high voltage required for plasma generation generates EMI. Thus, electrical conductor length should be minimized. In one embodiment, the plasma chamber is located within a faraday cage with gas paths running into and out of the faraday cage. In one embodiment, the electrode assembly/manifold resides in the same faraday cage as the high voltage circuit and electrical conductors from high voltage circuit to electrode assembly.

In one embodiment, a single manifold handles the pneumatic passages and connections for the following features: plasma chamber pressure measurement, proportional valve for altitude compensation, bleed valves for shunting flow to gas analysis sensors, flow director(s) for directing product gases to sensors, flow director(s) for routing product gases to specific treatment paths (ventilator treatment vs. manual bag ventilation, for example), routing gases to a scavenger path, routing gases from a scavenger path to a NO injection path, routing gases to an NO injector, routing gases to a vent cartridge, etc.

FIGS. 65-68 illustrate various embodiments of pneumatic circuits.

Figure 65:
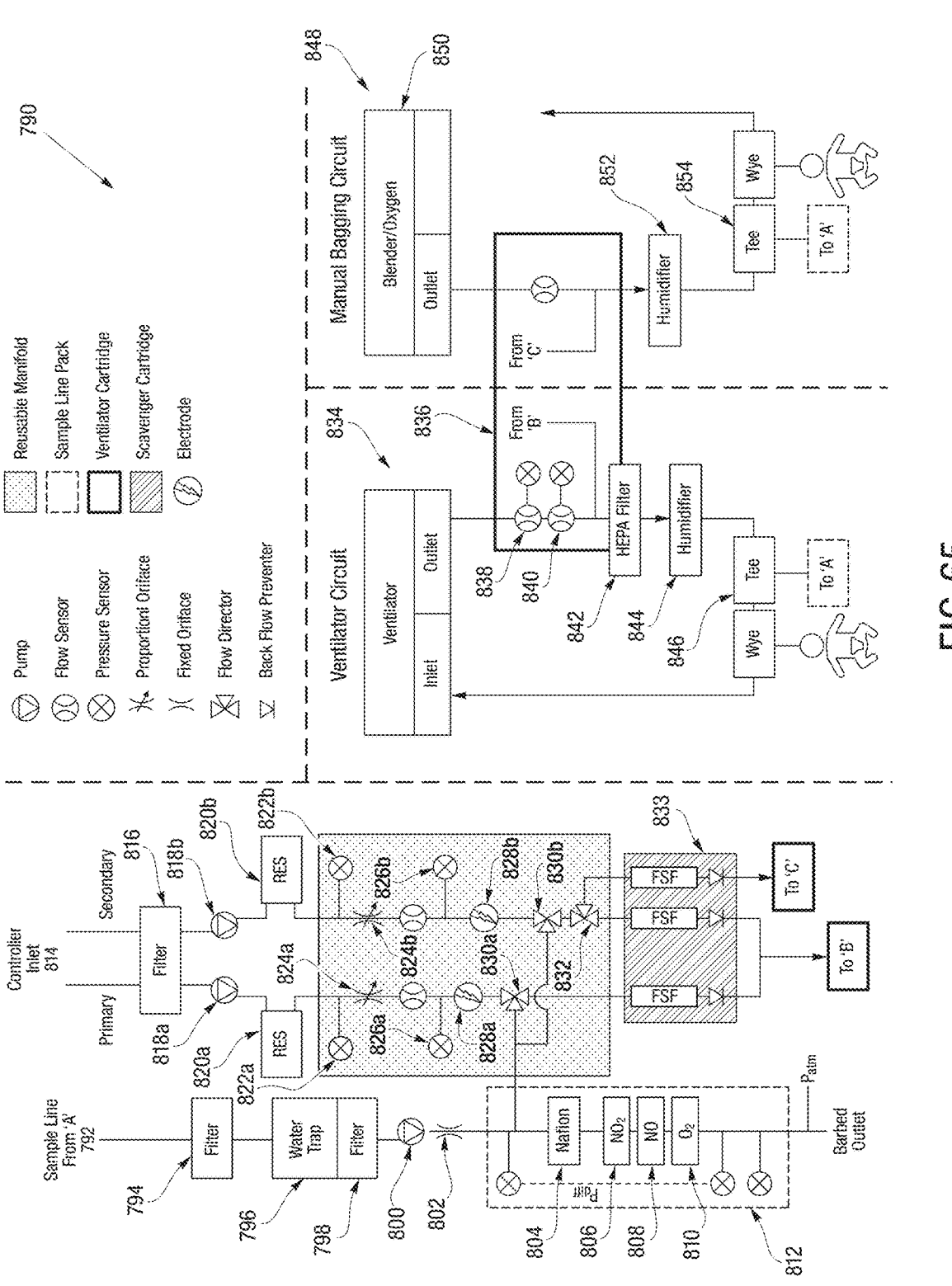
FIG. 65, FIG. 66, FIG. 67 and FIG. 68 are embodiments of pneumatic circuits.

FIG. 65 depicts an exemplary pneumatic design 790 for an NO generation and delivery system. In the upper left of the diagram, sample gases 792 originating in the treatment circuit (lower right of the figure labeled 'A') enter the system through a filter 794 and travel through a water trap 796. In some embodiments, this filter 794 is disposable so that user can replace it as needed when it clogs. An additional filter 798 after the water trap 796 protects the gas analysis sensors for contaminants. Sample gases then flow through a pump 800 and then through a fixed orifice 802 that limits the gas flow rate through the sensors and diminishes pulsatility in the sample gas flow. Gas then flows through Nafion tubing 804 to add humidity to the sample from the atmosphere in the event that sample gases are very dry. Next, the sample gas flows through one or more gas analysis sensors. Sensors 806, 808, 810 for NO, $NO_2$ and $O_2$ are shown. A differential pressure sensor shown on the left side of the sensor manifold block is used to measure the flow rate through the gas sensor manifold 812. This flow rate can be used to ensure that the sample pump is functioning. An absolute pressure sensor near the end (bottom) of the sensor manifold is used to measure atmospheric pressure. Gases exit the sensor manifold and flow through a T-fitting, where one leg is connected to atmospheric pressure and the other leg is connected to an external port in the device. The first leg is connected to atmosphere to prevent hospital vacuum from affecting the flow rate through the gas sensor manifold and potentially affecting patient treatment. The external port can be connected to hospital vacuum or just vented to atmosphere.

Moving to the right in FIG. 65, at the top of the diagram there is an inlet 814 to receive reactant gas into the system. In some embodiments, this is a 22 mm medical air connection. Incoming reactant gas flows through a filter 816 to remove particulate then bifurcates into two parallel NO generation paths. Each path consists of a pump 818a, 818b, a reservoir 820a, 820b, a reservoir pressure sensor 822a, 822b, a proportional flow valve 824a, 824b, a fixed orifice, a plasma chamber pressure sensor 826a, 826b, and a plasma chamber 828a, 828b. After the plasma chamber 828a, 828b, each flow path has a flow director 830a, 830b that can direct gases to either the gas sensor manifold 812 or towards the patient inspiratory air. These side paths to the gas sensor manifold 812 enable a system to evaluate the gas produced and/or redirect gases within the plasma chamber away from the patient. After the gas analysis side paths, one of the gas paths utilizes a flow director 832 to select whether product gases will flow to a ventilator circuit (B in the figure) or to a manual bag outlet (C in the figure). Gases then flow through three parallel scrubber passages in a disposable cartridge 833. The scrubber passages consist of a filter, scrubber material, a second filter and a one-way valve. The one-way valve ensures that pressures and materials outside of the system do not enter the cartridge and controller.

In the lower right corner of FIG. 65, a treatment setup is depicted. In a ventilator circuit 834, inspiratory gases exit the ventilator and enter a ventilator cartridge 836. The gases flow through two flow sensors 838, 840. In some embodiments, the flow sensors measure pressure, humidity and temperature in addition to flow. NO-containing product gas is merged with the inspiratory flow after the flow sensors. Inspiratory flow continues through a HEPA filter 842, a humidifier 844 and on to a "T" fitting 846, where sample gases are pulled, then on to the patient.

Also shown in the lower right corner of FIG. 65 is a manual bagging circuit 848. Inspiratory gases are sourced from a blender/wall outlet/cylinder 850 and enter the ventilator cartridge 836. Flow is measured within the ventilator cartridge 836 prior to adding NO-containing gas. Gases flow through an optional humidifier 852 and on to a "T" fitting 854 where sample gases are pulled and then on to the patient.

Figure 66:
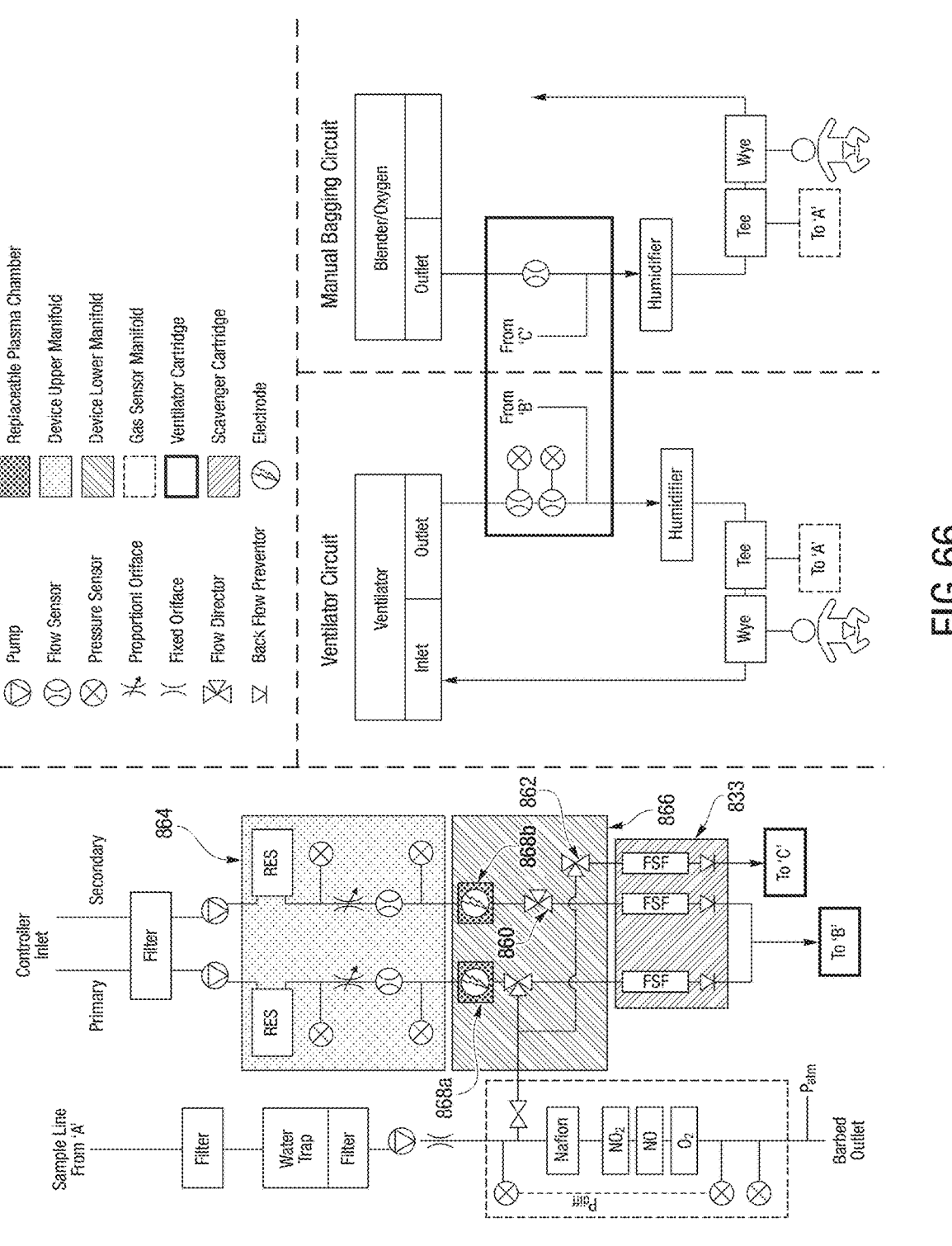

The system depicted in FIG. 66 is similar to the system depicted in FIG. 65 with the exception that a first flow director 860 within the secondary NO production line selects between flow to the inspiratory limb and flow to manual respiration/gas sensors, then a second flow director 862 selects between flow to the manual bagging circuit and gas sensor manifold. One advantage to this configuration is that the flow restriction of the primary and secondary NO generation lines are identical. Another feature of this system is a valve at the entry of the gas sensor manifold from the shunt lines can be actuated in combination with the flow director valves to create a closed volume that can be tested for leaks during a system self-test. The closed volume includes pneumatic pathways between the pump and the gas sensor manifold, including the plasma chamber.

FIG. 66. also depicts an embodiment of the reusable portion of the system where the manifold is divided into an upper manifold 864, a lower manifold 866, and replaceable plasma chambers 868a, 868b. Separating the functions of a manifold into multiple manifolds facilitates manifold fabrication and eliminates and or minimizes the need for gaskets and plugs which could present a leak in the system. The upper manifold 864 is near or part of the reservoir. In one embodiment, the manifold serves as an end-cap to a tubular reservoir. In another embodiment, the reservoir is a volume within the upper manifold. The lower manifold 866 houses removable plasma chambers and directs gases to the scavenger cartridge 833. In this embodiment, the scavenger cartridge pneumatically connects directly to the ventilator cartridge for reduced NO transit time and reduced pneumatic connections. FIG. 66 depicts a system without a HEPA filter at the exit of the NO generation system.

Figure 67:
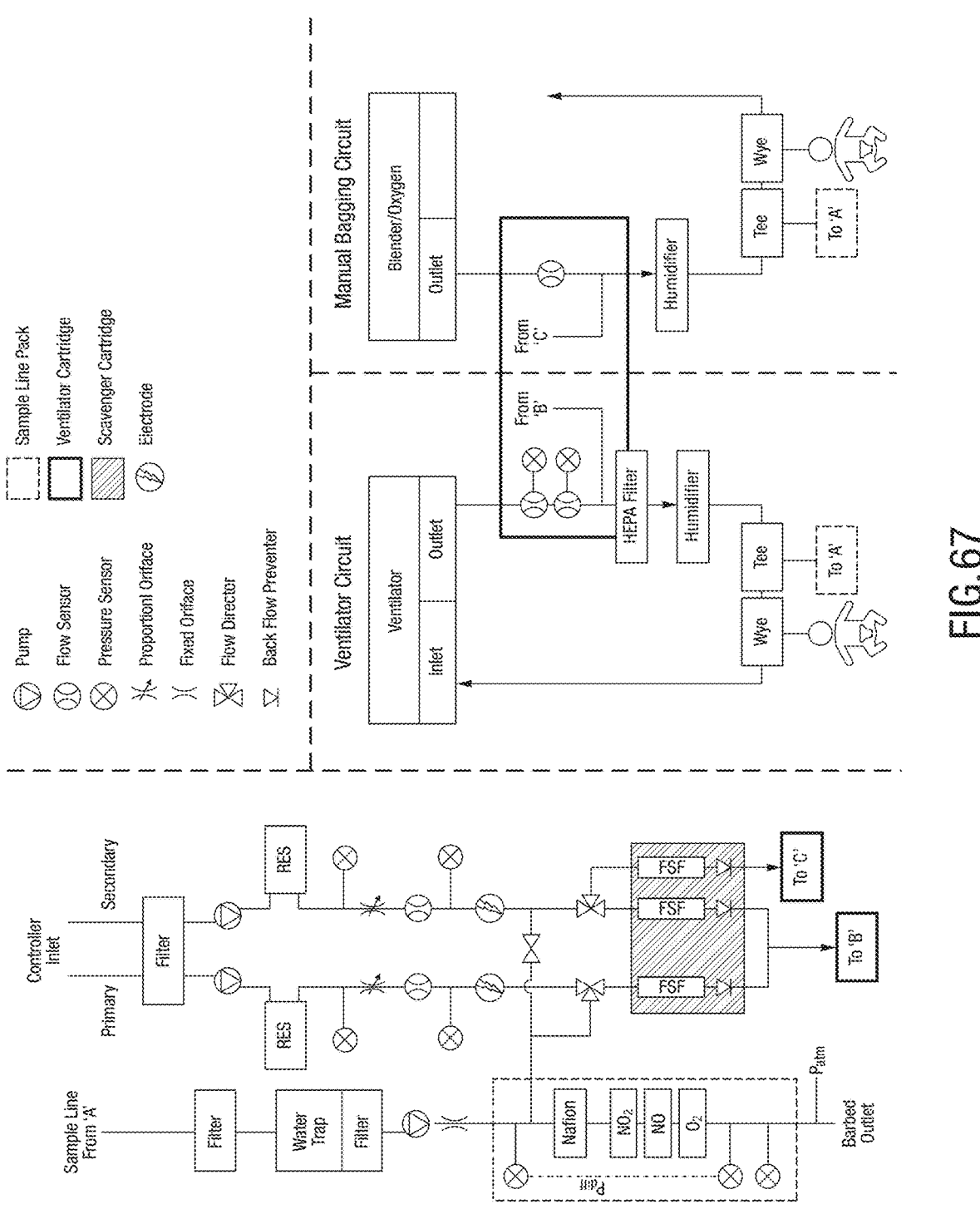

FIG. 67 depicts a system embodiment that largely similar to the systems depicted in FIG. 65 and FIG. 66. One difference is in how gas for sensor analysis is redirected. Sample gases from the primary pathway are redirected with a flow director while gases from the secondary pathway flow through a valve within the gas sensor pathway. This design offers a benefit in that the flow restriction for the primary and secondary flow paths will be identical thereby decreasing variance in performance between the redundant NO generation pathways. Another unique feature of this system is that it has no reservoirs and relies solely on pressure generated in the line between pump and proportional valve. Generally, this is a small volume making this design most applicable to neonates and patients with low NO pulsatility.

Figure 68:
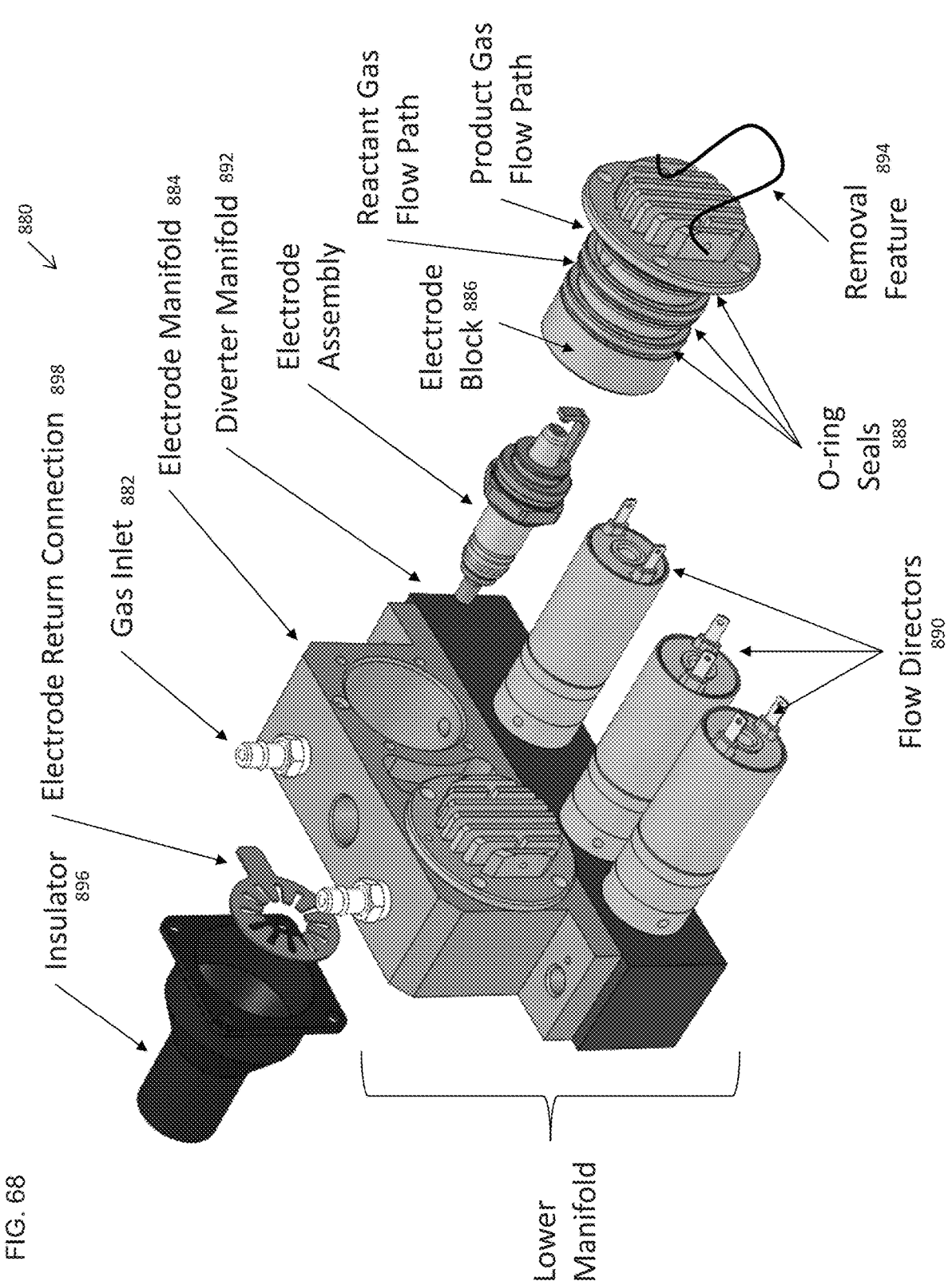

FIG. 68 provides additional detail of a lower manifold. Reactant gas enters the manifold through a gas inlet 882 in the top. The gas passes through the wall of an electrode manifold 884 and into a groove on the outside of an electrode block 886. The groove is sealed to a bore within electrode manifold using O-rings 888. The groove exists around the circumference of the electrode block to prevent a blind passageway that could hold stagnant gas flow that could turn into $NO_2$. Gas flows from the groove into the void within the electrode block that serves as the plasma chamber. An electrode assembly mates with the electrode block to seal the chamber with an O-ring seal. The electrode block is indexed so that it only enters the electrode block in one orientation. After passing through the plasma, product gas exits through a hole in wall of the electrode block into a second circumferential groove. Gas exits the groove into the electrode manifold and then into the diverter manifold where it passes through a flow-diverters as described above. The electrode manifold is fastened to the diverter manifold with threaded fasteners and O-rings provide seal for each pneumatic connection.

Figure 92:
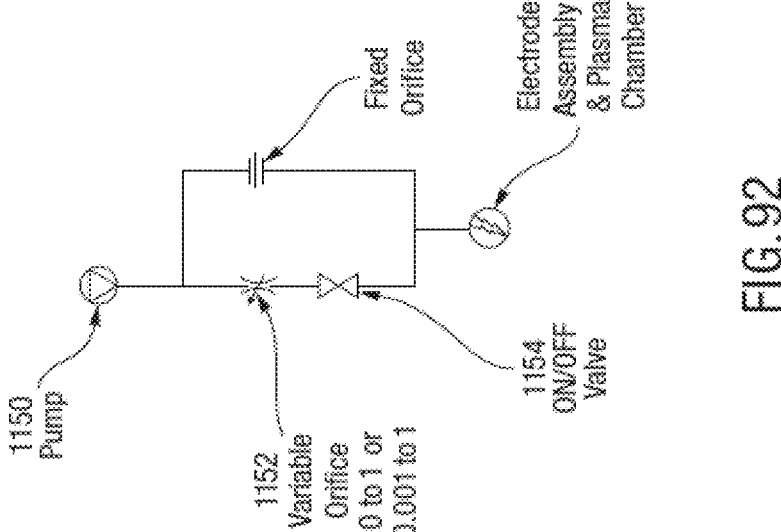
FIG. 92 is an embodiment of an NO generation system having a single pump and
flow path.

As mentioned before, the electrode block seals to the electrode manifold with three O-rings. The electrode block can be made from either polymer or metal. In one embodiment, it is made from aluminum, owing to its high thermal conductivity to aid in cooling. Cooling fins on the closed end of the electrode block provide additional surface area to aid in removal of heat from the plasma chamber to the convective cooling air within the device enclosure. A removal feature on the end of the electrode block consists of a wire form that can be grasped with a finger and pulled to remove the electrode block from the electrode manifold. One benefit to this design is that the electrode block is replaceable in the event that it is damaged in use or receives sufficient sputtered materials that electrode activity is affected. The electrode block is fastened to the electrode manifold with screws, a clamp, or some other feature. In one embodiment, no tools are required to remove the electrode block. One benefit of the embodiment depicted in FIG. 92 is that the electrode assembly can be removed from an access panel in the back of the NO generation device by removing the electrode block, replacing the electrode assembly and re-inserting the electrode block.

On the far side of FIG. 68, an insulative boot 896 is shown to prevent foreign materials from shorting the electrode assembly. High voltage is applied to the center electrode of the electrode assembly by means of an electrical contact. An electrode return connection 898 contacts the ground shell of an electrode assembly to complete the high voltage circuit.

Introduction of No Flow to an Inspiratory Flow

NO Injection into Inspiratory Stream

An NO generation system requires a period of time to sense inspiratory flow, adjust NO generation parameters, generate NO, scrub for $NO_2$ and deliver NO to an inspiratory stream. This reaction time delay creates a phase offset between NO demand and NO delivery. If NO delivery lags demand, the concentration within the inspiratory stream can be low at the beginning of an inspiratory pulse and high at the end of an inspiratory pulse.

In some embodiments, NO is introduced to the inspiratory flow as a jet with higher velocity than the prevailing inspiratory flow. This enables the NO entering the inspiratory flow to offset the phase delay and "catch up to" the inspiratory flow.

For example, a bolus of NO intended to dose a bolus of inspiratory air can be entered after the inspiratory bolus has passed the NO injector, but can catch up with the inspiratory bolus by having a greater rate of speed.

In some embodiments, NO flow is injected through a small diameter tube, concentric with the tube conducting the inspiratory air flow. The small area increases the speed of NO-rich product gas as it enters the inspiratory flow. In some embodiments, the NO flow rate selected is based on the lag time of the system. A proportional valve is one way of adjusting the NO flow. In some embodiments, an axis-aligned jet that is significantly smaller than the delivery tube to create a jet of NO to make up for system lag with the objective to create a well-mixed controlled concentration.

NO Injection

Pressure within an inspiratory circuit varies. An NO generation device generates product gases at a pressure greater than the pressure within an inspiratory circuit for there to be flow from the NO generation device to the inspiratory circuit. In one embodiment, a large and responsive pump is used to vary gas pressure and flow, as needed, to ensure forward flow of NO into an inspiratory stream. In another embodiment, a smaller pump is used to fill an air reservoir to a pressure that is higher than within the inspiratory circuit. The volume of the reservoir is selected based on the inspiratory circuit maximum pressure and maximum NO bolus volume to be required. In this reservoir approach, the system can deliver high flow and high pressure for a brief amount of time that is sufficient for dosing a bolus of inspiratory gases with NO. Between breaths, the air reservoir is recharged so that it is ready to dose a subsequent inspiratory bolus.

Owing to the fact that NO has a half-life within the physiology that lasts longer than a breath, it is not necessary to dose every breath in order to maintain the desired physiological response. In one embodiment, the NO generation device doses a subset of inspirations. In one embodiment, NO delivery is set to every other breath. In one embodiment, NO delivery is based on delivering a set number of NO molecules per unit time.

In some embodiments, the NO generation system increases gas pressure upstream of the NO injector and releases a pulse of gas at a specific time in the inspiratory cycle. In one embodiment, the high-pressure gas is stored within the plasma chamber prior to release.

In some embodiments, high-pressure reactant gas is stored within a reservoir located before the plasma chamber. In one embodiment, a means of flow control is located between the air reservoir and plasma chamber to vary the flow of gas through the plasma chamber. In another embodiment, a means of flow control is located after the plasma chamber so that the plasma chamber is at the same pressure as the air reservoir.

In one embodiment, a gas reservoir containing product gas is located after the plasma chamber. A means of flow control (proportional valve for example) is located between the gas reservoir and NO injector.

The release of pressure can be in response to a sensed inspiratory event, in anticipation of an inspiratory event based on the timing of prior events, based on measurement of a physiologic parameter, based on a trigger signal from a peripheral device (ventilator for example), based on a data stream from a peripheral device.

By adjusting the pressure upstream of the NO injector, the system can modulate the flow rate of the NO gas that enters the inspiratory stream.

NO Recirculation

Figure 69B:
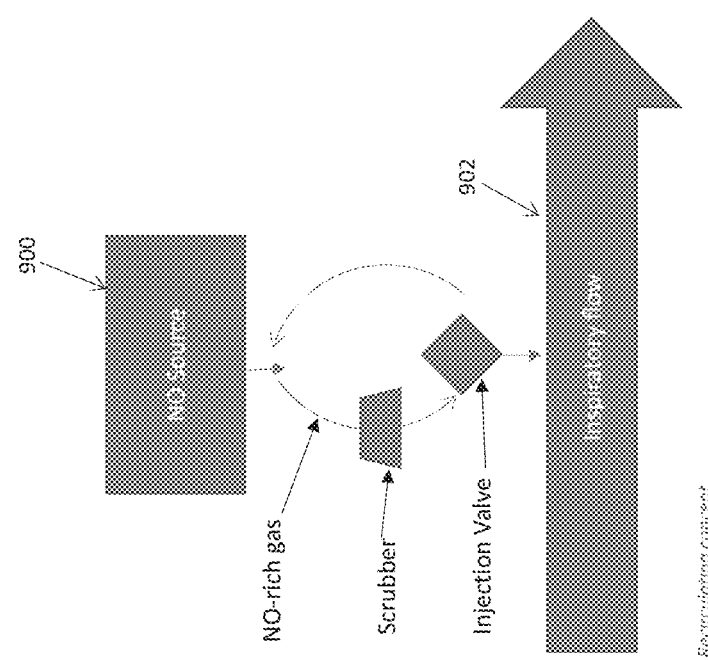
FIGS. 69A and 69B illustrate embodiments of movement of NO in a single direction pathway and recirculation of NO.
Figure 69A:
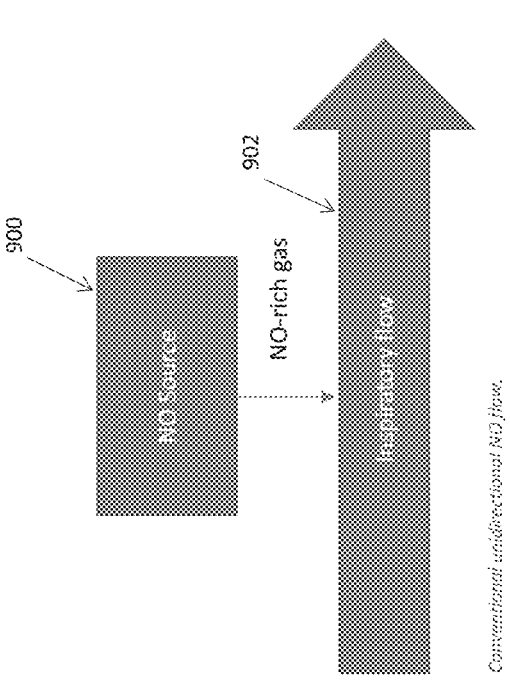

In some embodiments of inhaled nitric oxide therapy systems, the pneumatic pathway conducts gas in a single direction from the NO source (i.e. tank or generation unit) to the point where the NO-rich gas is injected into the flow in the inspiratory circuit (FIG. 69A).

In some embodiments, recirculation of gas between the NO source 900 and the point of injection 902 can be achieved (FIG. 69B). This can be used with all types of NO generation systems described herein, including ambulatory systems and acute applications, for example, with a remote NO-injector.

At standard temperature and pressure, nitric oxide reacts with the oxygen to form nitrogen dioxide ($NO_2$). $NO_2$ is a toxic pollutant to which human exposure should be limited. The rate of oxidation of NO is the rate of formation of $NO_2$. The reaction rate increases when the NO concentration is higher, or the oxygen concentration is higher. The reaction is not very sensitive to temperature near standard temperature and pressure. During inhaled NO treatment, it is necessary to maintain a constant concentration of inhaled NO, while minimally diluting the inspiratory flow. Therefore, the NO source is typically a reasonably high concentration (~500-1000 ppm). If the NO source is a tank of compressed gas, and the balance gas is an inert species such as nitrogen, the only significant $NO_2$ formation occurs in the inspiratory circuit after the NO-rich gas is mixed in the correct proportion with the inspiratory flow to achieve the desired dose concentration.

In some embodiments, an electric arc is used to generate nitric oxide from ambient air. The nitric oxide (NO) is present in concentration on the order of 50-5000 ppm depending on the desired dose and inspiratory flow. However, leftover oxygen and nitrogen remain virtually unchanged from their atmospheric concentrations of approximately 21% and 78% respectively. Therefore, $NO_2$ is forming from the moment NO is generated in the arc. Some of this $NO_2$ can be chemically removed after the electric NO generator before the NO-rich gas is mixed into the inspiratory flow.

Depending on the detailed design of the pneumatic circuit, and the details of the inspiratory flow rate and NO-therapy, the residence time of the NO-rich, $O_2$-rich gas in the volume after chemical $NO_2$ removal but before injection may be excessive. Excessive residence time leads to greater $NO_2$ formation.

In some embodiments, there is a recirculating loop of NO-rich gas. The gas is constantly circulating, and only a portion is diverted to the inspiratory limb. Recirculation limits residence time, so $NO_2$ formation can be limited. Moreover, gas that returns to the NO source can be "re-scrubbed" so to limit $NO_2$ accumulation.

Figure 70:
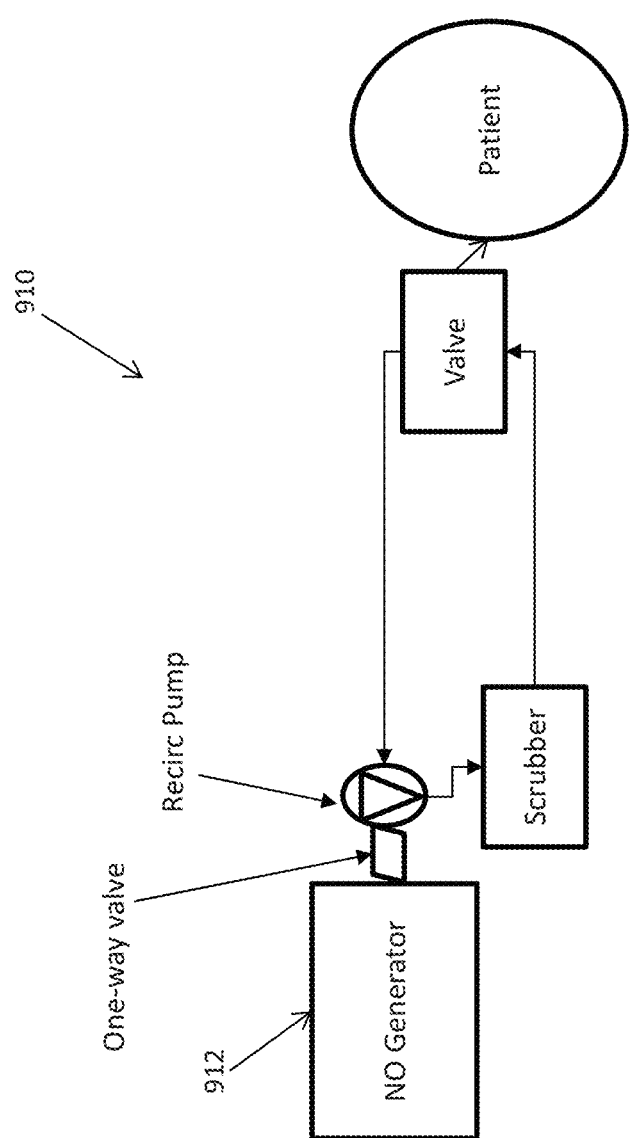
FIG. 70 is an embodiment of a recirculating loop that continuously removes $NO_2$ from stores NO-containing gas.

FIG. 70 illustrates an embodiment of a recirculating loop 910 that continuously removes $NO_2$ from stores NO-containing gas. A valve opens to inject NO containing gases as directed by the NO generator 912. In some embodiments, the valve opens open patient inspiration.

Figure 71:
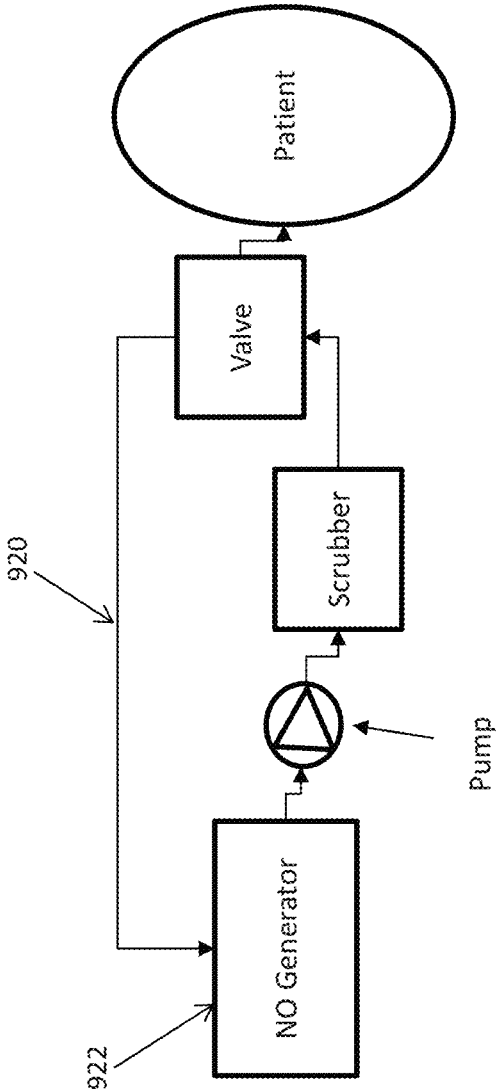
FIG. 71 is an embodiment of a system where recirculated gas flows back through the NO generator.

FIG. 71 illustrates an embodiment of a system where recirculated gas 920 flows back through the NO generator 922. This is acceptable because only a fraction of $N_2$ and $O_2$ is converted to NO in the plasma chamber. Thus, additional NO can be generated from the same air.

The flow of NO-rich gas can be directed to the inspiratory limb by closing the injection valve on the return leg, otherwise NO-rich gas is continuously recirculating in the loop.

Self-Test (Calibration)

There are various approaches that can be used to ensure that the NO generation system is functioning as expected, ensure that the gas sensors are functioning as expected, and/or calibrate the system. It will be understood that calibration and self-testing are interchangeable, and in some embodiments refer to testing NO production and sensor responses. Some of these approaches can significantly decrease the time and complexity of calibration. In some embodiments, a calibration cartridge is used, and in some embodiments, a calibration gas shunt internal to the therapy controller device is used. Both embodiments take advantage of the fact that a controlled plasma generates known quantities of NO. The plasma is controlled by taking into account one or more of the following: ambient air pressure, ambient temperature, humidity, spark rate, spark duty cycle, air flow rate. It will be understood that other factors can also be considered when controlling plasma and calibrating the system. The calibration approaches described here-in can provide up to a 70% time savings due to a decrease in user involvement and the ability to check NO and $NO_2$ sensor function as well as gas production simultaneously.

Figure 72:
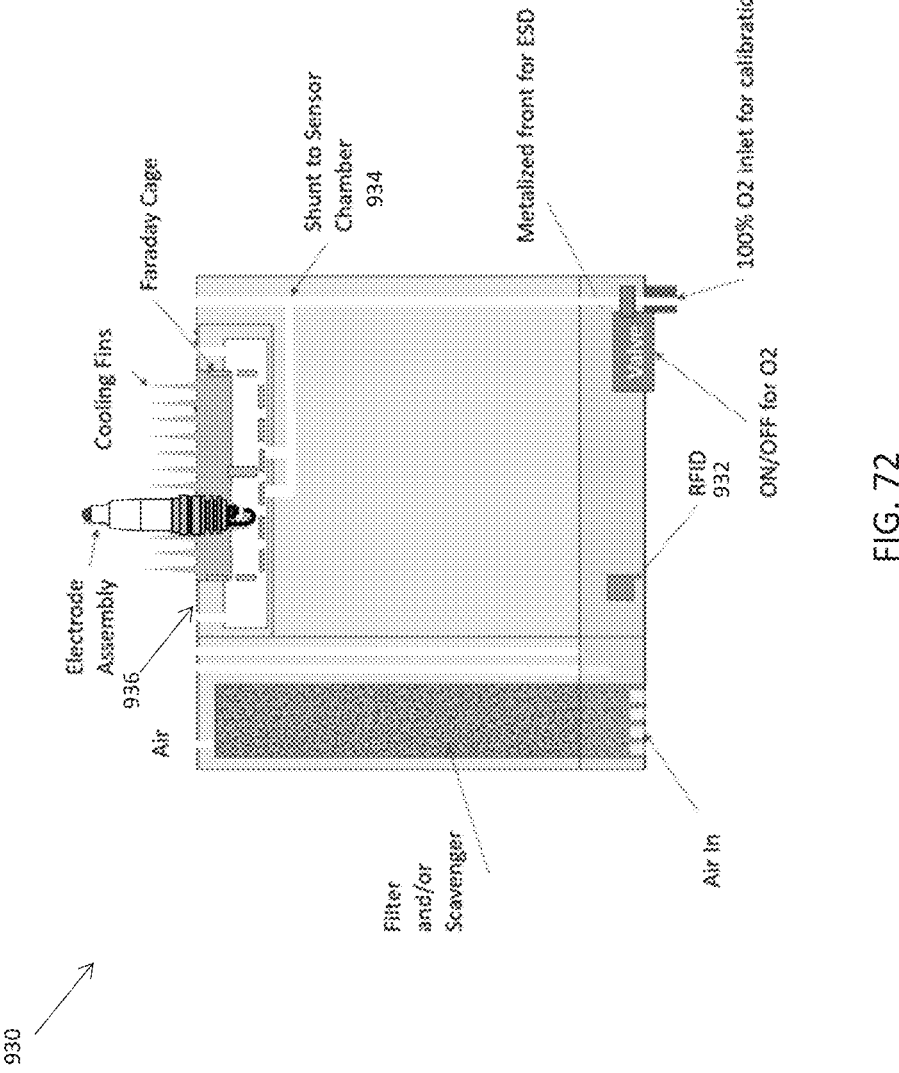
FIG. 72 is an embodiment of a calibration cartridge.

In some embodiments shown in FIG. 72, a calibration cartridge 930 directs output $NO/NO_2$-containing gas flow from a plasma chamber 936 through a shunt 934 to the sensor chamber input prior to scavenging for $NO_2$. By controlling plasma activity according to environmental conditions and desired NO and $NO_2$ concentration levels, the sensors can be exposed to known high or low values for sensor calibration. Although the accuracy of this approach is not at the same level as a calibration with traceable calibration gas, this test can detect system performance issues with minimal user effort. FIG. 72 illustrates an embodiment of a calibration cartridge 930. The calibration cartridge 930 can include an RFID chip 932, a bar-code, and a unique mechanical interface or other means of automatic identification by the controller. The system can automatically enter calibration mode when a calibration cartridge 930 has been inserted and detected. The RFID chip 932 can also include calibration constants for a specific cartridge, if cartridge to cartridge variance is sufficient to warrant this level of control. It will be understood that other identification mechanisms can be used in place of or in conjunction with the RFID chip, including but not limited to a 2D bar code.

In some embodiments, the calibration cartridge also includes additional features, such as a carbon filter to remove NO from ambient air, which can assure that zero levels for low calibration do not have an offset due to environment NO levels. The calibration cartridge includes a gas connection, and in an embodiment it has a gas connection on the front surface for the addition of $O_2$, NO, or $NO_2$ gas for manual calibration with an external source of calibration gas. The gas connection is controlled by a valve, stop-cock, solenoid, or other means. In some embodiments, the gas connection valve can be in the same location as the manual/ventilator selector on a standard cartridge for increased ease of use.

In some embodiments, in a system that has electrodes located within the controller, output gases from the plasma chamber can be directed to the sample chamber through a pathway entirely within the controller, not passing through a cartridge (FIGS. 65, 66, 67, 68). This allows for calibration of high or low values at any time without requiring additional equipment in the form of a calibration cartridge or compressed gas cylinder. One or more shunts from a plasma chamber output of a plasma chamber to the gas sensor chamber can be controlled by a software-controlled valve, manual valve, pump, or any other means of flow control. In some embodiments, the response of the gas sensors and NO production of one NO generation path can be checked simultaneously while another NO generation path is delivery NO to a patient.

A sensor response test (high calibration) can be performed by generating plasma at a rate that produces a known amount of NO and $NO_2$. Low calibration can be performed by stopping the plasma generation and exposing the sensors to ambient air. Alternatively, low calibration for NO and $NO_2$ can be performed at the same time as high calibration for $O_2$ since $O_2$ calibration gas does not contain NO or $NO_2$.

Sample Lines

The system also includes one or more sample lines. The sample line can be a disposable component that is used to convey gas samples from the ventilator inspiratory limb to the gas analysis sensors. In some embodiments, the sample line is a tube with one or more lumens. The sample line can include additional features that can be incorporated into the design to facilitate use, plan for humidity effects, and accommodate viscous materials that could enter the sample line. In an embodiment, a sample line includes a fitting for installation of the sample line into a ventilator circuit. For example, the sample line can include a "T"-fitting at the patient-end to facilitate rapid installation into a ventilator circuit. The "T" fitting can be sized for the ventilator tubing size expected, such as 22 mm for adults. In an embodiment, the gas sample is pulled from the center of the ventilator flow instead of the wall of the "T" fitting, thereby decreasing the potential for moisture or other materials within the ventilator line from entering the sample line.

Between the "T" fitting and the cartridge/controller runs a sample line tube. The sample line tube can have a variety of shaped and sizes. In an embodiment, the tube measures 10' (3 m) in length, but other lengths can be used. In general, a shortest possible length of the tube is best to minimize NO to $NO_2$ conversion in the sample line and provide the gas analysis sensors with a timely sample.

The sample line tube connects to a sample line filter. The sample line filter can have a variety of shapes and sizes. In an embodiment, the sample line filter is a 0.2 μm, hydrophilic, 50 mm diameter filter with Luer connectors on either end. The filter is hydrophilic so that moisture in the sample line passes through to the water trap. Other diameters are possible and will directly relate to how long a filter can be used before it clogs and requires replacement. Any type of connectors can be used in place of the Luer connections, including but not limited to other small-bore push/pull and threaded connectors, as long as they make an air tight seal.

In some embodiments, the sample line can include a dehumidification section, which can have many forms. For example, it can be a length of Nafion tubing to help convey humidity from the gas sample to the ambient surroundings. In an embodiment, the sample line can have a triple lumen tube, where one lumen is used to pull the sample gases from the patient. The other two lumens can be used to measure the patient inspiratory flow rate. The sample line with three lumens allows for gas samples and flow rates to be measured in the sample place, providing gas sample and flow data that are synchronized in time. This approach also can decrease complexity within the cartridge.

Water Trap

Figure 73:
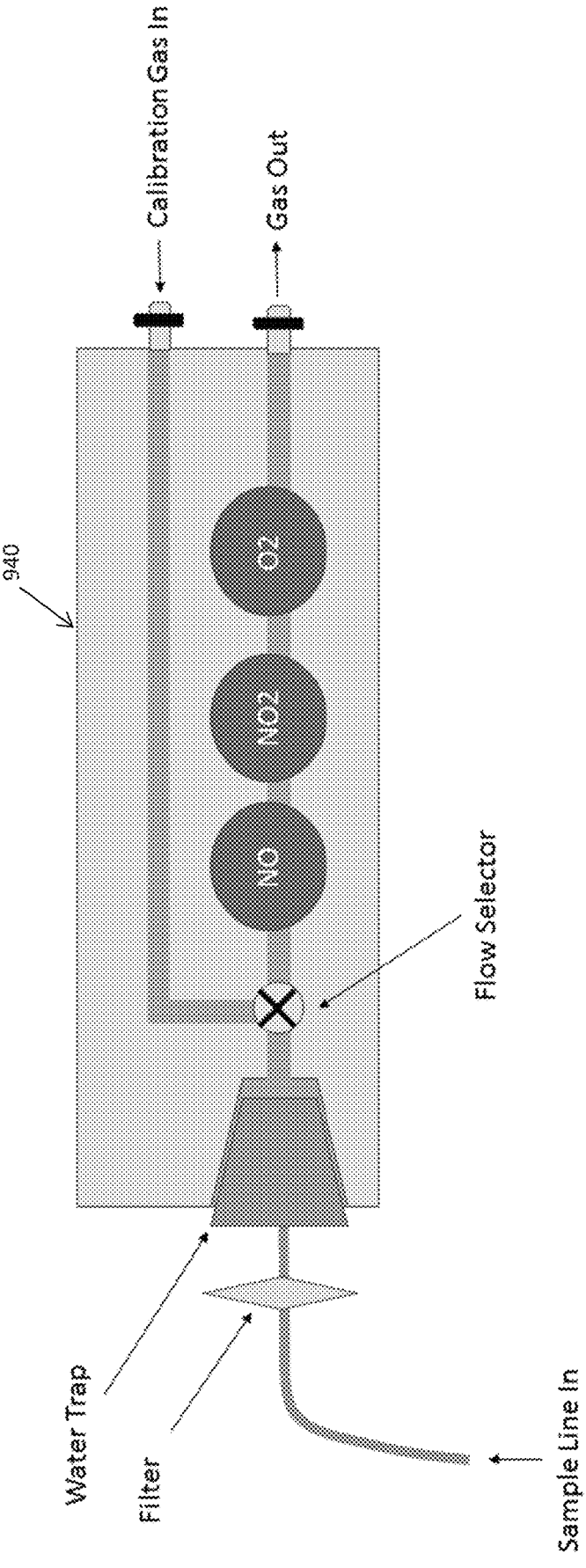
FIG. 73 is an embodiment of a sensor pack having a water trap.

The water trap, as noted above, fills with condensate and other materials from the inspiratory line. In some embodiments, the user can be notified that the water trap is nearly full before there is no flow through the water trap. The fluid level in the water trap can be detected in a variety of ways, including but not limited to optically, ultrasonically, conductively and capacitively. The water trap can be associated with one or more sensors, and a water trap 942 can be located within a sensor pack 940 (as shown in FIG. 73) or within the controller. In some embodiments, the water trap can be located near a heat source to help evaporate water trap contents out of the reservoir. In some embodiments, a dye can be added to the water trap to increase the opacity of fluid that collects within the water trap, making it easier to detect optically.

The water trap may be used with a portable NO generator that could experience lateral accelerations from motion and/or orientation with respect to gravity. In one embodiment, an open-cell foam or sponge is placed in the bottom of the water trap to prevent splashing or migration of fluid. In another embodiment, super-adsorbent polymer (Sodium Polyacrylate) is placed in the reservoir to control migration of fluids from the water trap reservoir. In one embodiment, the super-adsorbent polymer is housed within a package to prevent migration. In one embodiment, the package is a gel-pack. In another embodiment, the package is a perforated pouch.

In some embodiments, the water trap consists of a 1 micron hydrophilic filter, a water separator, a reservoir and a 0.22 micron sensor protection filter. In one embodiment, the reservoir is separable from the water separator for ease in emptying. In one embodiment, there is a syringe-activated small-bore fitting on the reservoir for draining the reservoir. In another embodiment, a stop-cock or other manually-activated valve is connected to the water reservoir for ease in draining. In one embodiment, the water separator consists of a coalescing filter. The coalescing filter may be wrapped in a hydrophobic filter material to protect it from fluid splashes from the reservoir. In another embodiment, the water separator uses centripetal acceleration to separate water droplets from the air by flowing the air around a turn in a flow path. In one embodiment, there are baffles within the reservoir to prevent fluid splashes contacting a coalescing filter. Obstruction of either filter can be detected by sample line pressure and/or sample line flow.

As explained in more detail below, a cartridge can include a water trap that has a hydrophobic barrier that sample gases pass through. Liquid water can collect on the bottom of the water trap while sample gases with water vapor pass through. The water trap can hold various volumes of liquid. In an embodiment, the water traps can measure roughly 10 ml in volume, but this volume can require draining and/or replacement multiple times within a treatment. In an embodiment, the water trap can measure a volume that holds enough liquid such that the water trap does not need to be drained. For example, the water trap can measure 60 ml in volume so that the water trap does not require draining under normal circumstances.

In some embodiments, the water trap is located near a warm area of the controller, such as the high voltage power supplies of the electrode assembly. The heat from the controller can warm the water trap contents and can drive the liquid contents of the water trap into vapor form such that the vapor can exit the controller through a gas sensor chamber.

In some embodiments, the level of liquid in the water trap can be visible to the user, for example, when viewed from the front of the controller. The visibility of the water trap contents can facilitate trouble shooting when an alarm relating to the water trap is generated, for example, by a gas analysis sensor generating an air flow alarm. Fluid level within the water trap can be detected in a variety of ways, including optically, ultrasonically, conductively, and with other means. In some embodiments, detecting a fluid level in the water trap is achieved by detecting a drop in pressure within the gas sensor chamber.

In the event that the water trap is full or needs to be drained, the user can drain the water trap with a valve connected to the water trap. In an embodiment, a syringe-activated Luer fitting can be used, but it can be understood that any kind of stopcock, spout, or valve can be used to drain the water trap. In some embodiments, the controller can automatically empty the water trap via a liquid pump. The pump can transfer the water trap contents to a drain or larger reservoir.

Water traps fill during treatment. In some embodiments, the water trap is removable so that a reservoir can be drained of water. In some embodiments, there is an outlet in the reservoir to enable draining of the water trap without removal of the reservoir from the system. The outlet may have a small-bore connector like a luer fitting or barb fitting. Fluid flow through the outlet can be controlled by a stop cock, tubing clamp, syringe activated valve, etc. In some embodiments, the level of fluid in the water trap is measured by the system. This enables the system to alert the user about an impending full water trap condition before the water trap is completely full. The system can also measure gas flow through the sensor bench. In the event that the gas flow diminishes, the system generates an alarm for the user to check the water trap.

Gas Sensors

Various mechanisms can be used to measure the concentration of the gases in the system. Oxygen sensors can often last longer than NO and $NO_2$ sensors. In addition, the amount of $O_2$ in the ventilator circuit does not significantly change between the time gas leaves the NO device and reaches the patient. Thus, in some embodiments an $O_2$ sensor can be located in the cartridge or controller, instead of the sensor pack. This keeps sample gas for the $O_2$ sensor dry and without hydrocarbons and sulfur compounds present in nebulized medications that could affect its longevity. $O_2$ dilution does not change after the cartridge.

Pneumatic connections can be a source of leak which could send corrosive $NO_2$ into the device. In some embodiments, the pneumatic connections can be decreased by using a sensor pack for the acute device that receives the water trap/filter assembly into one end and passes gases out the other end. The sensor pack can be installed by sliding in from the front of the system. In some embodiments, the sample line can include the water trap.

In some cases, gas sensors have very poor resolution. In some embodiments, another digit of resolution can be obtained by measuring the percent of time that the final digit flickers high vs. low. In addition, $NO_2$ can be corrosive, thus the sensor line pump can wear our prematurely from corrosion. In some embodiments, a pump can be included in the sensor pack so that it is replaced at the same schedule as the gas analysis sensors. In some embodiments, the sensor pack includes a length of Nafion tubing to allow humidity in the atmosphere to enter the gas sample in the event that the gas being sampled is dry. This protects the gas analysis sensors from being dried out. In one example, the Nafion tubing is 30 cm long.

No Generation Cartridges

Cartridges are used in an NO generation and delivery system to facilitate replacement of consumable elements of the system. In one embodiment, all of the consumable elements are integrated into one NO generation cartridge. In other embodiments, referred to as "Multiple Cartridge embodiments," consumable elements such as the scavenger material, water trap, inspiratory flow path, inspiratory flow sensor, electrode assembly and spark chamber are independent so that they can be replaced on independent schedules.

An NO generation cartridge can include a variety of features for the production of NO. The electric generation of nitric oxide can consume electrode material and scavenger material as well as obstruct filter materials. Thus, it is necessary to provide a means of scavenger, electrode and air filter cleaning/refurbishment/replacement.

In some embodiments, a disposable cartridge can include a housing, the incoming plasma air filter, ventilator flow inlet, ventilator flow conduit, ventilator flow outlet, incoming air scavenger material, enclosure air filter, plasma chamber, electrode assembly(s), air pump, ventilator flow measurement, a manual ventilation device flow inlet, a manual ventilation device flow outlet, manual ventilation device circuit flow measurement, manual/backup selector, sample line connection, water trap, water trap drain, dual $NO_2$ scavenger paths, a water trap drain, outlet check valves, outlet filters and a memory device. Other embodiments may include one or more of these elements or a subset of these elements.

FIG. 49 illustrates an embodiment of cartridge 740 that includes an air inlet filter 742, an air scavenger 744, vent flow measurements (P1, P2), air inlets 748 into plasma chambers 746, dual scavenger paths 750, a memory device 752, a manual mode selector 754, a water trap 756, and a sample line connection 758. A bag outlet 760 is also included and allows a ventilator bag to be coupled to the cartridge.

The cartridge includes a housing that is configured to encapsulate the various features of the cartridge, facilitating the handling and set-up of the system. The cartridge housing is designed with features to facilitate proper placement of the cartridge into the controller of the system, for example, a unique cross-section and/or markings to prevent insertion upside-down or side-ways. In some embodiments, the housing can be plated or painted with conductive and/or EMI shielding materials to prevent electromagnetic emissions from leaving the system. The housing may be disposable or reusable. In a reusable design, the cartridge housing can be opened so that electrodes, filters, and/or scavenger material can be replaced prior to the next treatment.

In some embodiments, features presented on the user interface of the system align with mechanical connections to the cartridge. For example, the target and measured NO values for the ventilator circuit can be located above the ventilator connections. The same can be done for manual ventilation device measurements and controls being located in the vicinity of manual ventilation device connections and gas analysis measurements being near the sample line connection.

In some embodiments, the incoming plasma air filter is hydrophobic to prevent ingress of cleaning solutions including isopropyl alcohol (IPA) into the air flow path. The filter can have a variety of sizes, but in an embodiment, the incoming filter is typically 0.3 μm or less to prevent entry of infectious materials.

In some embodiments, the incoming plasma air scavenger can include soda lime for removal of $NO_2$, $CO_2$, and/or other contaminants from the air prior to plasma generation to minimize the potential of unwanted byproducts. Environmental levels of NO can reach 5-8 ppm, potentially creating an offset in NO concentrations in the system output. In order to provide improved NO output accuracy, the incoming scavenger can include a filter, such as a charcoal filter, for removal of NO and other organic compounds that could alter plasma generation products.

An enclosure air filter for the controller can be used to remove lint and other large particles from the air used to cool the enclosure. This prevents build-up of material on the high voltage surfaces within the controller which could decrease effective electrical creepage distances. It also ensures adequate air flow through the controller enclosure for cooling purposes. By including the enclosure air filter within the disposable cartridge, the number of user steps can be reduced and the presence of a clean air filter is ensured. In an embodiment, air for plasma generation is sourced from air that has already passed through the enclosure air filter such that the incoming plasma air filter is less likely to be clogged with large particles. In a cartridge that includes an electrode assembly, it is beneficial to direct the enclosure cooling air over a heat-sink thermally connected to the electrodes.

A ventilator flow conduit, or ventilator tubing, can be connected to the cartridge using various connections, such as a standard 22 mm connection. Other exemplary connections include but are not limited to a 10 mm conical, 15 mm conical, and ¼" barbs. It will be understood that the ventilator tubing can be connected to the controller instead of the cartridge. The ventilator flow conduit can also have various shapes and sizes. In an embodiment, the ventilator flow conduit has a smooth U-shape which allows the conduit to maintain laminar flow of the vent gases and improves the accuracy of ventilator flow measurement. In an embodiment, the conduit can have a T-shape, where the NO is delivered through the stem of the T.

In some embodiments, the ventilator flow conduit can be removable from the cartridge to enable cartridge replacement without opening the ventilator circuit. The conduit can connect to the cartridge in a variety of locations, including the front, sides, or bottom of the cartridge, but in an exemplary embodiment the conduit can be connected to the front of the cartridge for ease of use and to decrease interference with peripheral equipment.

Figure 75:
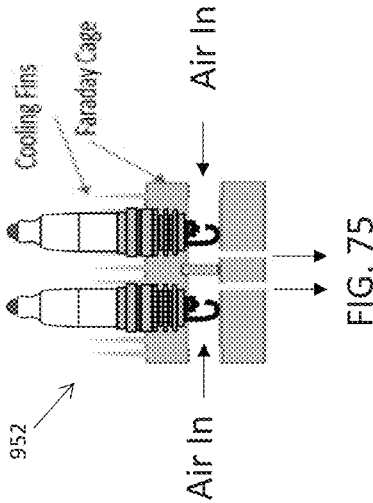
FIG. 75 is an embodiment of a solid metal plasma chamber.
Figure 74:
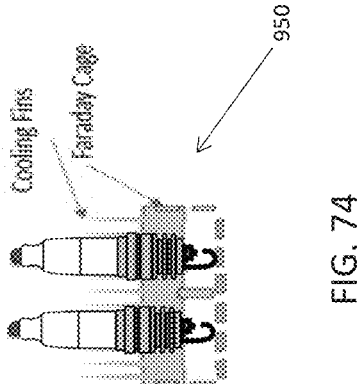
FIG. 74 is an embodiment of a Faraday cage plasma chamber.

The plasma chamber houses the one or more electrodes and serves as a conduit for air. The plasma chamber can be formed from a variety of materials, but in an embodiment the plasma chamber is metallic in order to provide conductive cooling to the electrode assemblies as well as electromagnetic shielding. The chamber can be made of solid metal, covered with metal, or parts of it may be simply screen to act like a Faraday cage. In some embodiments, the metals block electromagnetic radiation, such as ferrous metals or Mu Metal. In the unlikely event that flammable materials enter the plasma chamber, the plasma chamber can act as a flame arrestor by providing sufficient cooling through thermal mass and restricted air flow to choke a flame via a screen or mesh. In some embodiments, the plasma chamber is electrically connected to a ground electrode and a chassis ground. The plasma chamber can also include integrated cooling fins for convective cooling. FIG. 74 depicts an embodiment of a Faraday Cage plasma chamber 950 and FIG. 75 depicts an embodiment of a solid metal plasma chamber 952.

The geometry of the plasma chamber can be used to increase the production efficiency of NO. For example, increased pressure within the plasma increases the number of $N_2$ and $O_2$ molecules that will be affected, thereby increasing the NO production per joule of energy applied. In an embodiment, creation of a flow restriction at the exit of the plasma chamber can increase the pressure within the plasma chamber which can increase NO production efficiency. In an embodiment, pressure within the plasma chamber can be increased intermittently with a valve at the exit of the plasma chamber or surges in air flow rate, timed to coincide with plasma activity in an optimal way.

A cross-sectional area of the gas flow path by the electrodes in the plasma chamber can also affect the NO production. Necking down the cross-sectional area at the plasma so that a greater portion of the gas contacts the plasma can increase NO production efficiency.

When an automotive-style electrode is used, the orientation of the ground electrode with respect to the air flow can have an impact on NO production and efficiency. In an embodiment, it is desirable to orient the ground electrode in a repeatable fashion within the spark chamber. This can be done by controlling the orientation of the ground-electrode to threads during manufacturing of the electrode assembly. In an embodiment, the orientation of the electrode assembly with respect to the plasma chamber could be controlled with a jam-nut, high friction interface (pipe thread for example), or a clamping mechanism.

The electrode assembly can include one or more electrodes. In some embodiments, two independent electrode pairs are present within two independent gas flow paths.

In some embodiments, the electrode pairs are mounted within a metallic housing that serves to thermally conduct heat away from the electrodes, and provides electromagnetic shielding. The metallic housing can have cooling fins on its surfaces to increase convective transfer of heat to either the enclosure cooling air or the plasma air. The metallic housing can be made from a variety of material. In an embodiment, the metallic housing is made from ferrous materials or Mu metal for electromagnetic shielding. In an embodiment, the metallic housing is made from aluminum for high thermal conductivity and electromagnetic shielding is achieved by another component, such as a coating, paint, or Faraday cage surrounding the electrode assembly. The coating, paint, or Faraday cage could be part of the disposable cartridge or part of the controller.

The cartridge can include an air pumping mechanism, such as a diaphragm pump, that is pressed by a solenoid within the controller. The configuration allows the air intended for the patient to stay within the disposable cartridge.

The cartridge can provide a means for measuring flow rates of the supplied gases from a ventilator and/or manual ventilation device circuit. By means of adaptors, other therapies may be addressed from the same connections on the cartridge, such as NO delivery to a face mask, nasal cannula, anesthesia circuit, high frequency ventilator, oxygen generator, and other treatments.

In some embodiments, flow is measured by a sensor, such as a reusable differential pressure sensor, within the controller. The cartridge presents a flow restriction to the subject gas flow and provides a pressure tube on either side of the restriction to measure pressure drop. Pneumatic connections are made between the cartridge and the controller to convey the pressure signals to the pressure sensor. In some embodiments, an electrical pressure sensor is placed within the cartridge and electrical connections are made between the cartridge and the controller to convey pressure signals to the controller microprocessor. This allows for decreased pneumatic connections that could leak but introduces additional cost to the disposable cartridge.

The sample line connects to the cartridge with a sample line connection. In an embodiment, the sample line connection can be a detachable, air-tight connection. This connection could be a Luer, a barb, a push pull connection, or any other connection. In some embodiments, a "pig tail", or short length of tubing is placed between the cartridge and the sample line connection to move the sample line connection and a sample line filter away from the face of the cartridge. This can provide additional working room for making connections to the cartridge without increasing the actual area of the face of the cartridge.

In some embodiments, a HEPA filter is located at the gas outlet of the cartridge (FIG. 89) to serve as a redundant particle filter to capture potential particulate introduced to the airstream from either the NO generator or the inspiratory air source and to protect the cartridge from potential contamination from the patient and/or downstream components. In some embodiments, the HEPA filter is integrated into the cartridge, but in other embodiments, the HEPA Filter is individually replaceable. In some embodiments, the interface between HEPA filter and cartridge is proprietary so that the user cannot connect a ventilator circuit without using the HEPA filter.

Multiple Cartridges

Figure 76:
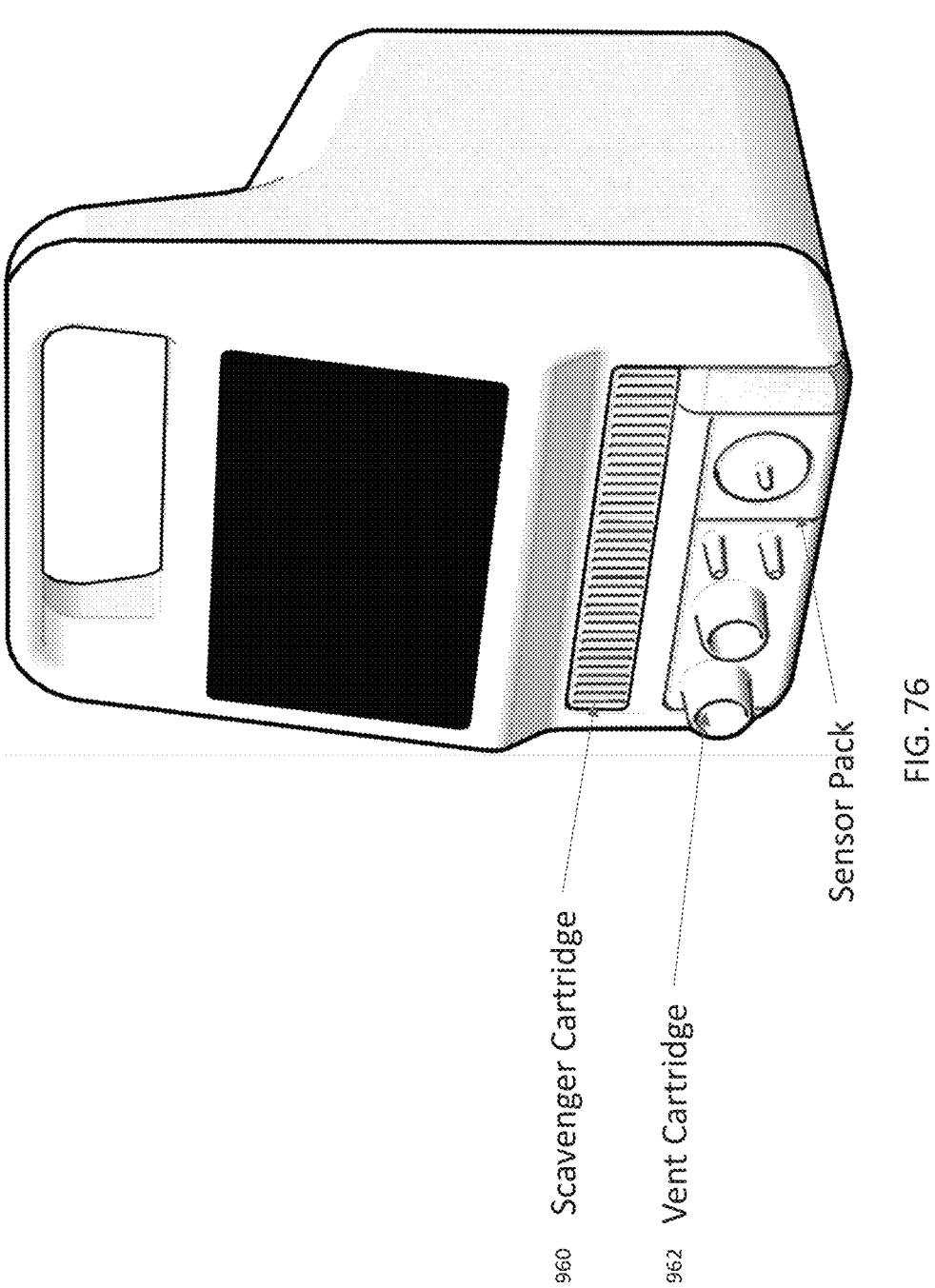
FIG. 76 is an embodiment of an NO generation system with a vent cartridge and a scavenger cartridge.
Figure 77:
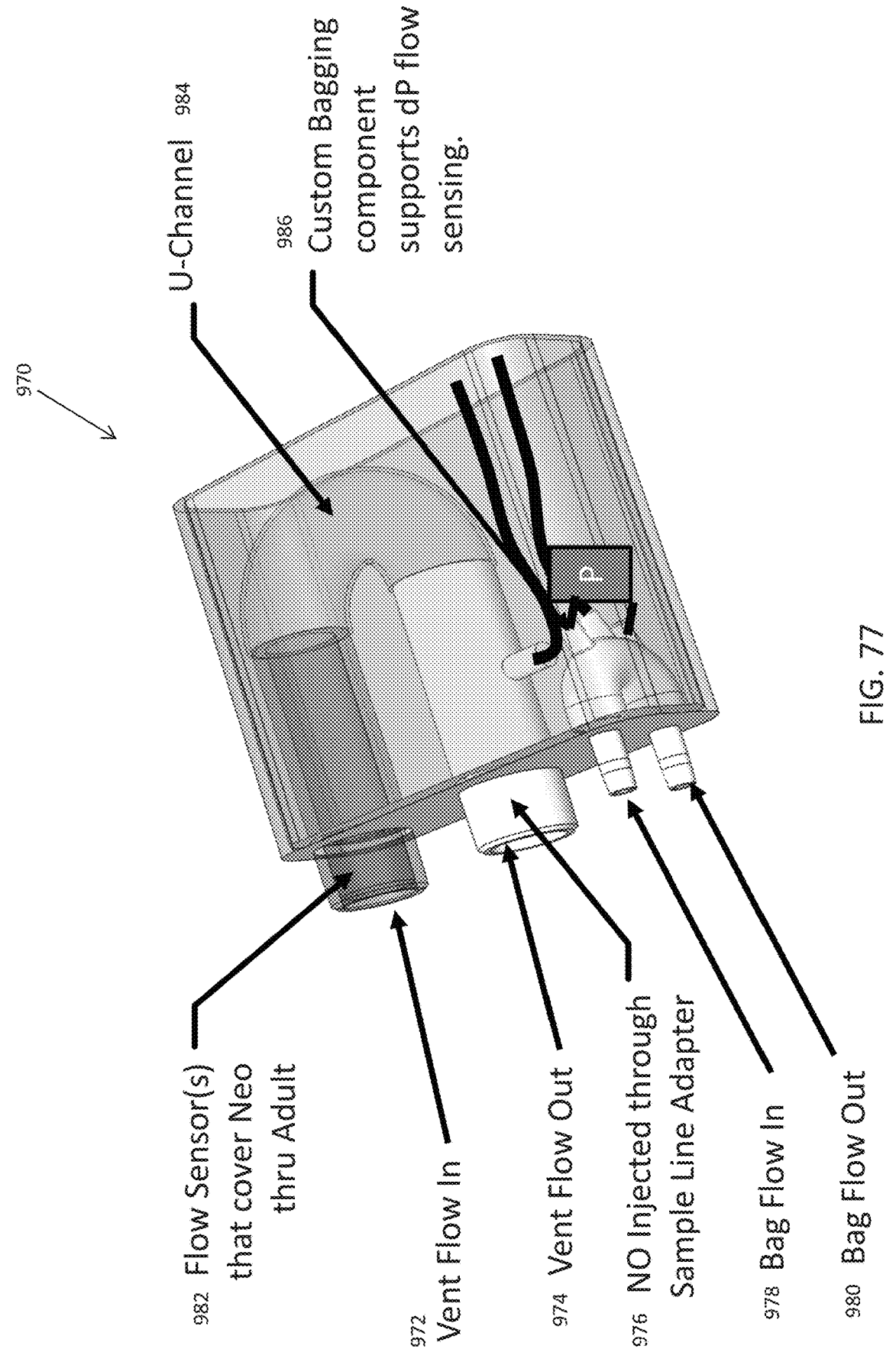
FIG. 77 is an embodiment of a vent cartridge.
Figure 78:
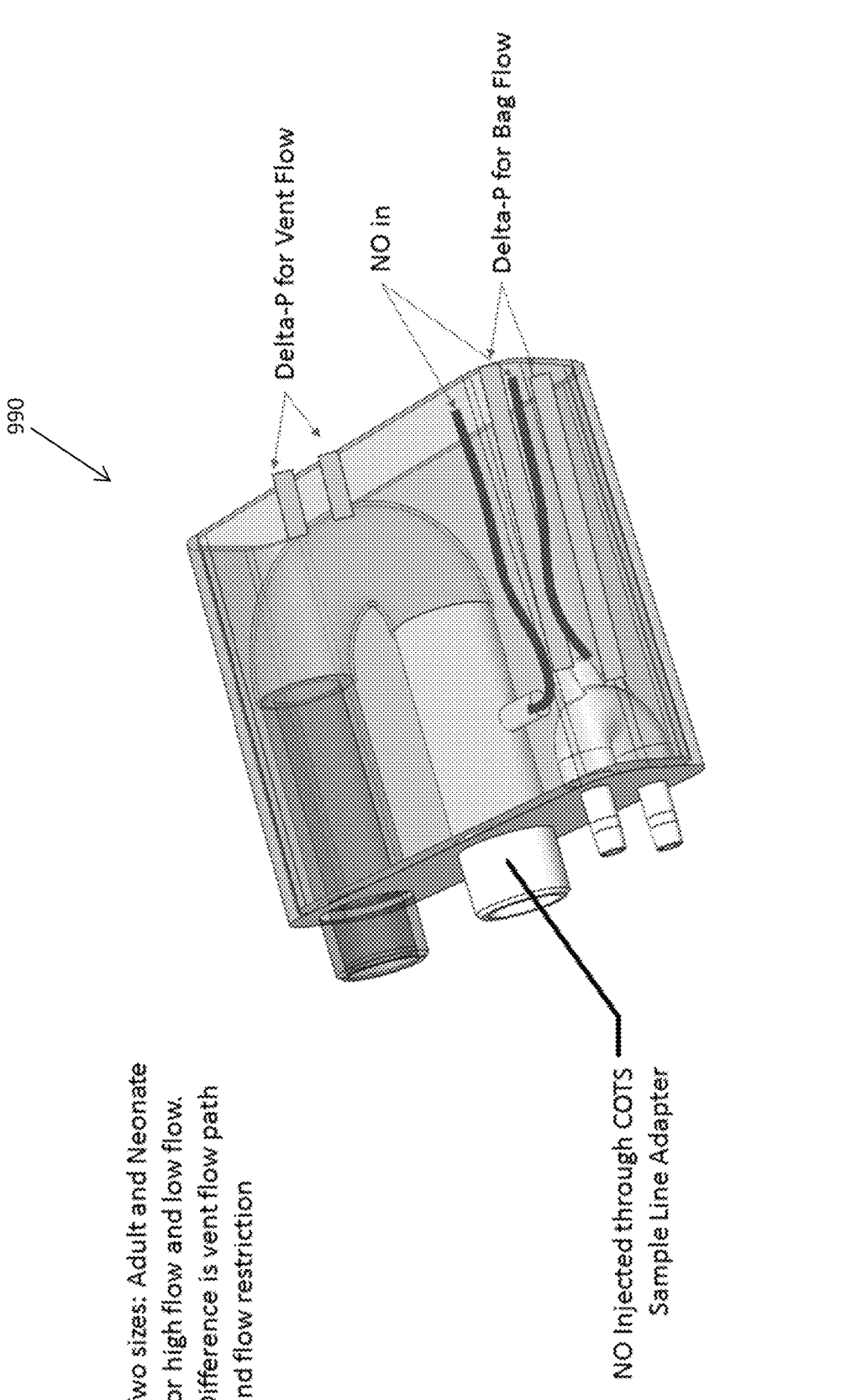
FIG. 78 is an embodiment of a vent cartridge.
Figure 79:
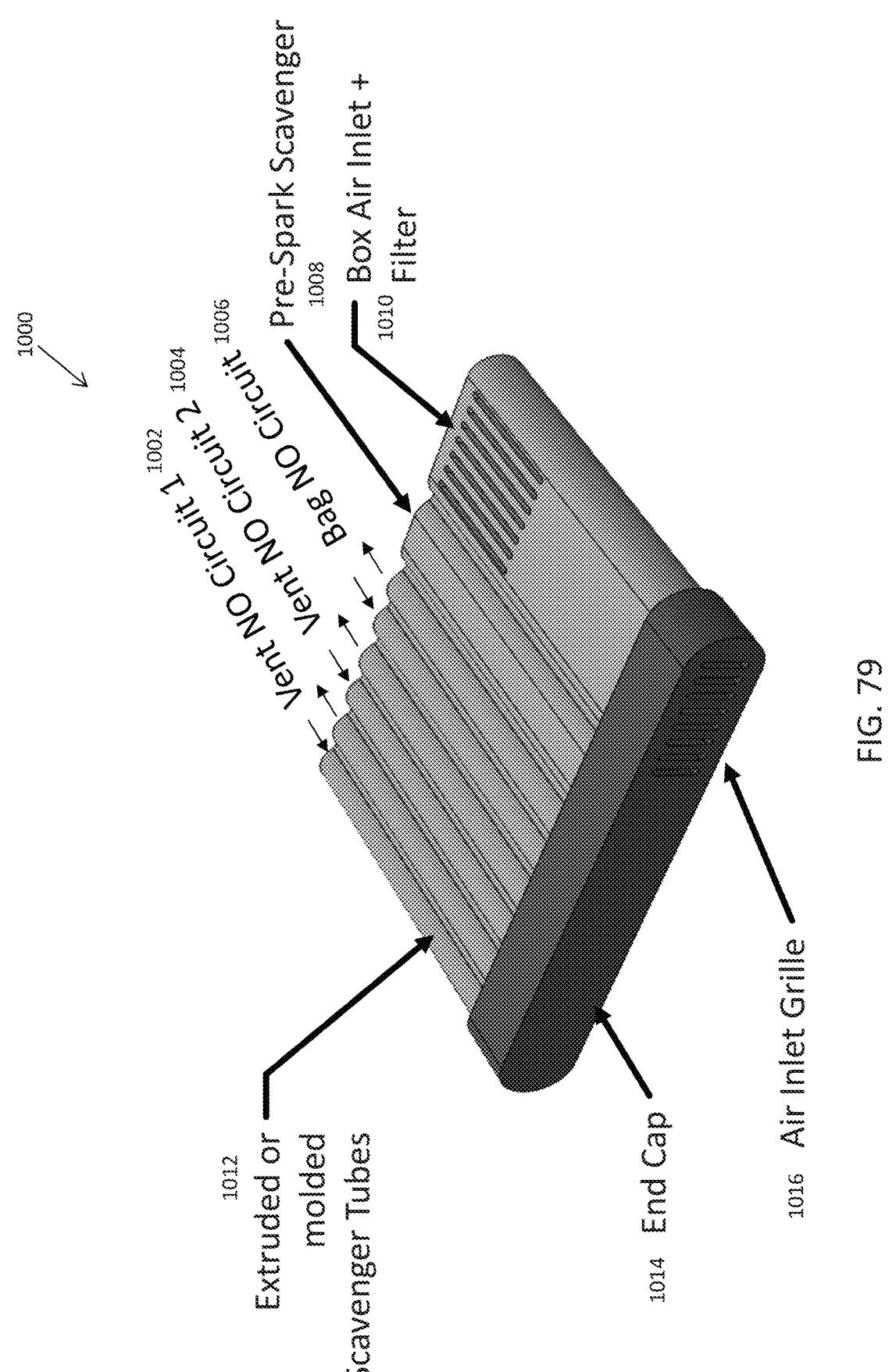
FIG. 79 is an embodiment of a scavenger cartridge.

In some embodiments, an NO generation system can include more than one cartridge. For example, there can be separate ventilator and scavenger cartridges 960, 962, as shown in FIG. 76. Separate cartridges can be used to reduce pneumatic connections within the system, which can assist with issues involving insertion forces, tolerances required, and flow sensor issues as well as minimizing the potential for pneumatic leaks. The scavenger material is usually the most common component that needs replacement, so it follows that having a separate scavenger cartridge decreases the cost of NO therapy by enabling the user to replace the scavenger material more frequently than other components of the system. Exemplary ventilator cartridges 970, 990 are shown in FIG. 77 and FIG. 78, and an exemplary scavenger cartridge is shown in FIG. 79. One of the most significant benefits of having a separate ventilator cartridge and scavenger cartridge is that the ventilator circuit is not opened during scavenger cartridge change because the vent cartridge can remain in place.

Ventilator Cartridge

A ventilator cartridge can include one or more of the following, as shown in FIG. 77: a ventilator flow inlet 972, ventilator flow outlet 974, bag flow inlet 978, bag flow outlet 980, NO flow inlet for ventilator 972, NO flow inlet for bag, an NO injector for ventilator 976, an NO injector for a bag, means for measuring ventilator flow, and means for measuring or supporting the measurement of bag flow. There can be a variety of rationale for having a ventilator cartridge. In some embodiments, the ventilator cartridge can house flow sensors that can fail from time to time. Flow sensor failure triggers ventilator cartridge replacement, rather than a more invasive repair. Flow sensors can be electronic sensors within the ventilator cartridge or pneumatic tubes within the ventilator cartridge that connect with differential pressure sensors within the main device. In some embodiments, one or more electronic flow sensors with pressure and humidity sensing are located within the vent cartridge. In some embodiments, dual flow, pressure and humidity sensors are manufactured into one assembly that is mounted within a ventilator cartridge. In general, electronic connections to a ventilator cartridge are preferred over pneumatic connections because they are simpler to test during a system self-test, they are more reliable, and they don't require as much connection force as pneumatic connections. In some embodiments, more than one size of ventilator cartridge can be provided to the user. This adjusts for different size ventilator connections, different treatment operating ranges (flow rates, pressures, etc.), and/or different internal volume requirements. In some embodiments, as sensor technology evolves, the ventilator cartridge design can be iterated, rather than the entire system. In some embodiments, the system only needs one ventilator cartridge because flow sensors with a wide measurement range can be implemented (not high flow and low flow). In some embodiments, users and ambulances do not have to have both cartridges. In some embodiments, there can be less chance of contamination from a ventilator line entering the controller. In some embodiments, when a flow sensor with wide flow range is used, user steps to set up the device are reduced if the user does not have select a particular size of ventilator cartridge (for example, neonate, pediatric, adult).

A ventilator cartridge is typically used in the dry portion of a ventilator circuit (i.e. upstream from the humidifier). In the event that a humidifier is used upstream of a vent cartridge, there is a potential for humidity to condense within the ventilator cartridge, potentially decreasing humidity to the patient and damaging electronic components within the NO generation and delivery device or within the ventilator cartridge. In some embodiments, a ventilator cartridge is heated to prevent condensation from occurring. In some embodiments, a humidity sensor within the ventilator cartridge can detect humidified gases entering the system and generate an alarm.

In some ventilator cartridge embodiments, there are only barb fittings for connecting to a respiratory bag or face mask, as could be applicable in catheter lab applications where the patient is briefly evaluated with NO and is not connected to a ventilator. The cartridge does not have the 22 mm vent tube connections. It follows that a controller could have a specific software mode for catheter lab applications. In one embodiment, the catheter lab mode presents the user with buttons for present NO values, 20, 40 and 60 ppm, for example.

The vent cartridge is in series with the patient inspiratory flow. Many hospitals replace and/or disinfect all tubing between the ventilator and the patient after a patient is treated. This would include the vent cartridge. In one embodiment, a HEPA filter is placed at the exit of the vent cartridge to prevent contamination of the vent cartridge from reverse flow within the inspiratory limb. In some embodiments, the HEPA filter is removable as a separate unit from the vent cartridge. In some embodiments, the HEPA filter connects to the output of a vent cartridge with a proprietary connection to prevent use of the system without the HEPA filter. In another embodiment, the vent cartridge can be disinfected via ethylene oxide (EtO), autoclave, alcohol soak, dry heat, wipe down or another means. In order to protect the electronic sensors within the vent cartridge, soaking can consist of filling the air flow path within the vent cartridge with disinfectant, rather than fully submerging the vent cartridge. Post-soaking, a drying fixture may be used to hasten the drying process. In one embodiment, the drying fixture draws air through the vent cartridge under vacuum. Use of vacuum reduces the pressure within the vent cartridge, increasing the potential of alcohol droplets to evaporate. Reversing the direction of flow can also be used to dislodge droplets. In one embodiment, the vent cartridge is heated to hasten evaporation. In another embodiment, warm air is flowed through the vent cartridge during the drying process. A fixture can be used to soak the vent cartridge, dry the vent cartridge, or both steps in one automated process. In some embodiments, the electronic sensors are installed in the device and not part of the ventilator cartridge. This allows thorough disinfection or sterilization of the ventilator cartridge without the risk of damaging electronic sensors.

In the event that a ventilator cartridge is exposed to fluids outside of the air flow path, fluids may damage electronic components within the vent cartridge. In some embodiments, a paper tag with ink on it is placed within the vent cartridge housing. In the event that fluids contact the ink, the ink spreads leaving a record of the fluid exposure.

In some embodiments, the function of the ventilator cartridge and the scavenger cartridge are combined into a single cartridge. In some embodiments, the scavenger cartridge connects directly to the ventilator cartridge to reduce pneumatic connections and decrease NO transit time while maintaining the ability to replace a scavenger cartridge without opening a patient's inspiratory circuit.

Owing to the fact that the rate of NO to $NO_2$ conversion is faster with higher levels of NO, it can be advantageous to dilute NO-containing gas into the inspiratory flow path as soon as possible. In one embodiment, NO-containing gas is added to the inspiratory path prior to scrubbing the gas for $NO_2$. In one embodiment, there is a scavenger/HEPA filter insert at the inspiratory air exit of the vent cartridge. The scavenger/HEPA filter insert can have a unique connection so that a conventional ventilator tube cannot be connected to prevent errors in assembling the system that could result in the absence of the scavenger/filter insert.

Scavenger Cartridges

The scavenger material in an NO generation and delivery system is consumed rapidly compared to other components of a system. That being the case, the scavenger material can be packaged in a container for easy replacement by a user. A scavenger cartridge can include of one or more of the following elements: a housing, one or more product gas inlets, one or more product gas outlets, one or more product gas flow paths, one or more filters before the scavenger material, one or more filters after the scavenger material, and one or more filters mid-path within the scavenger material. In some embodiments, the scavenger cartridge also contains filters that clean the incoming air for plasma generation and/or cooling the overall system. In some embodiments, most elements, like the housing, scavenger paths, and connections are reusable and only the scavenger material is replaced between uses.

FIG. 79 depicts an embodiment of a scavenger cartridge 1000. The cartridge 1000 is constructed from an extrusion 1012 and an endcap 1014. The extrusion features eight lumens. Pairs of lumens in connection with the end cap create "U"-shaped paths filled with scavenger material to scrub product gases for a first ventilation circuit 1002, a second ventilation circuit 1004 and a bag circuit 1006. A seventh lumen 1008 is used to filter and/or scrub incoming air from outside the system. An eighth lumen 1010 has a grille 1016 on one end and filtration material within. Air from outside the system is drawing through the eighth lumen and used to cool the system enclosure. The end cap is bonded or otherwise affixed to the extrusion with an air-tight seal. Connections on the other end of the cartridge consist of holes that register with pneumatic fittings within the Controller when the cartridge is inserted. O-rings, lip-seals or a similar approach seal between the reusable portion of the system and the cartridge. In some embodiments, the cartridge housing and pathways are made from polymers, such as ABS, teflon, polypropylene, nylon, and/or polyethylene. Scavenger material is held within the paths within cartridge housing with filter plugs that are pressed into each of the six scavenger paths. The filter plugs have a dual purpose to prevent migration of the scavenger material and filter out particles that may arise from fracture of the scavenger material. In one embodiment, the filter plugs have some elasticity and are inserted in a manner that compresses the scavenger media to prevent relative motion and prevent settling that could open a passage around, rather than through, the scavenger material.

Software Modes

Figure 80:
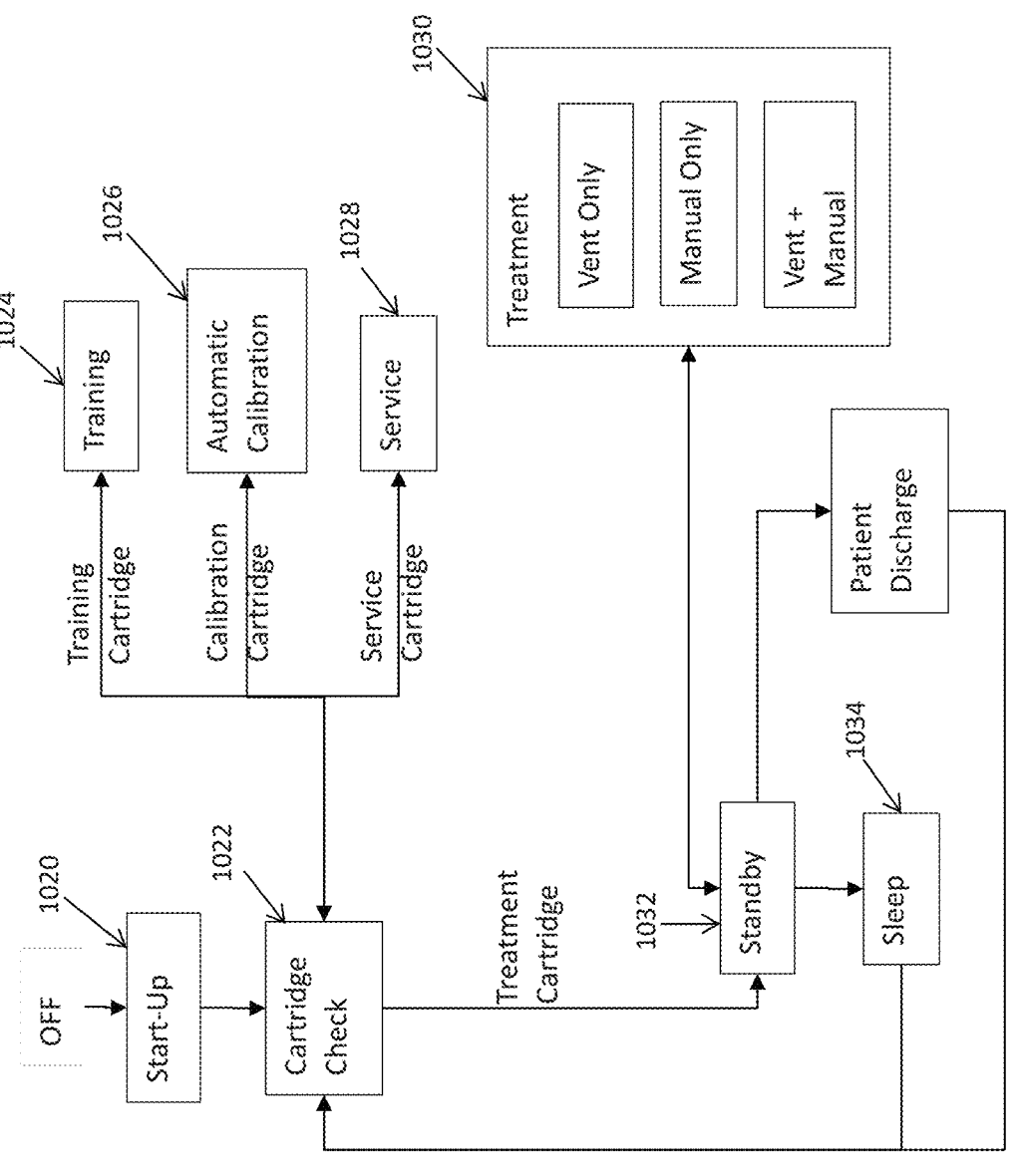
FIG. 80 is a flowchart of an exemplary embodiment of software modes of an NO generation system.
Figure 81:
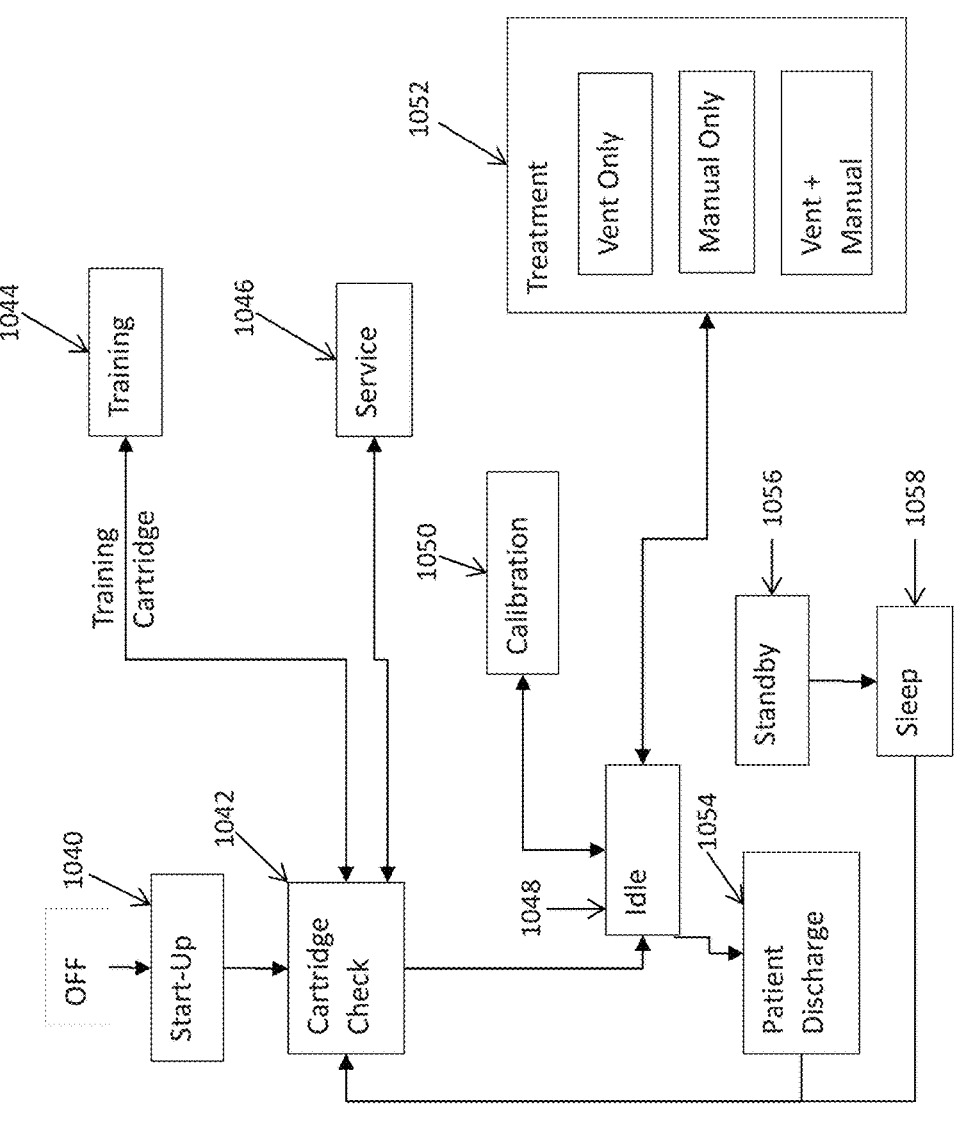
FIG. 81 is a flowchart of another exemplary embodiment of software modes of an NO generation system.

The system can have a variety of software modes. In some embodiments, the system software can include a start-up mode in which the system boots and performs a self-test. A cartridge check mode can allow the system to wait for a cartridge to be inserted and then checks the viability of the cartridge and advance to the next state or mode based on the type of cartridge. A training mode can be entered when either a training cartridge is inserted or based on touchscreen inputs. In the training mode, the system permits the user to enter all screens and displays, however no plasma is generated. A calibration mode is entered when either a calibration cartridge is inserted or based on touchscreen inputs. The system either automatically performs calibration based on plasma generation or instructs the user in how to perform a manual calibration. A service mode is entered when either a service cartridge is inserted or based on proprietary touchscreen inputs, for example, from a service technician. The service mode is used to make adjustments to the software, hardware and internal settings to the system. A standby mode can be entered when a viable treatment cartridge has been inserted. The system tests the high voltage circuit(s) upon entry into standby mode to confirm that all systems are working properly. A treatment mode can be entered when the user initiates treatment on the user Interface. A sleep can be automatically entered after a set time period of no user activity in standby mode. The system enters cartridge check mode after a sleep mode to ensure that the cartridge is still inserted and has not expired. For systems that include more than one cartridge, the insertion and/or expiration status for each cartridge is checked during cartridge check mode. A patient discharge mode can be entered upon a user indication that the patient treatment is complete. The system instructs the user on how to close out the patient data file and dispose of the cartridge. FIG. 80 illustrates a flowchart of an embodiment of software modes and the way in which the system moves between modes during system use. After start-up 1020, a cartridge check 1022 is performed. There is a treatment mode 1030 for use with a cartridge, as well as standby and sleep modes 1032, 1034. There are also training, calibration, and service modes 1024, 1026, 1028. FIG. 81 illustrates a flowchart of another embodiment of software modes and the way in which the system moves between modes during system use. After start-up 1040, a cartridge check 1042 is performed. There is a treatment mode 1050 for use with a cartridge, as well as standby, idle, patient discharge, and sleep modes 1056, 1048, 1054, 1058. There are also training, calibration, and service modes 1044, 1050, 1046.

In some embodiments, manual mode is entered by a user pressing a manual ON button or the detection of the position of a manual selector in the cartridge with a sensor, for example an optical sensor or a contact sensor. Manual mode can be selected from the menus of the user interface, or manual On/Off can be controlled by voice-activation to decrease the amount of contact the user makes with the NO generation system. Once the system enters manual mode, the controller enables a manual ventilation device circuit and redirects the ventilator flow towards the manual ventilation device.

The presently disclosed embodiments can flow either air or air with NO. Thus, when manual ventilation treatment paused, the system can continue flowing air through the system to purge the system of NO prior to stopping the air pump. This eliminates the need for the user to purge the system prior to manual ventilation, saving time and reducing treatment complexity.

Figure 82:
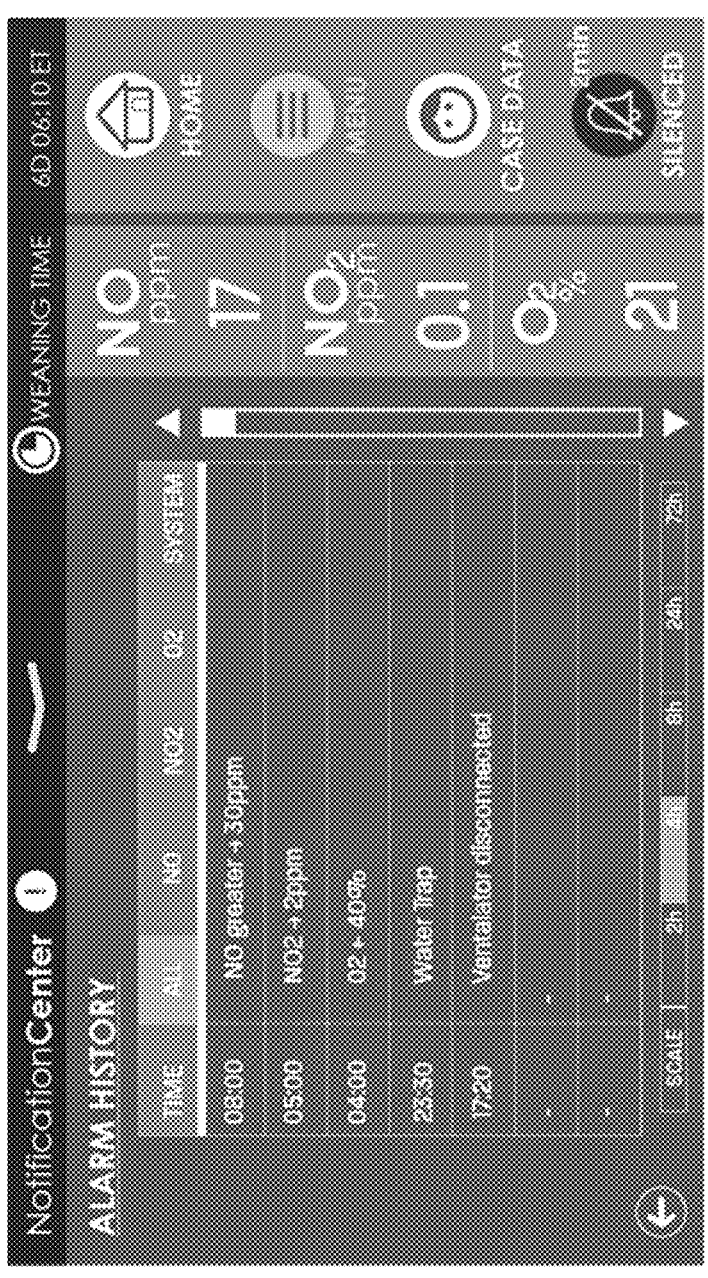
FIG. 82 is an embodiment of a user interface for displaying information related to alarm history.

In some embodiments, the system can provide continuous NO delivery to the patient in the event of any single fault. In the event of an NO sensor failure, the system can continue treatment by using the $NO_2$ measurement as a surrogate for NO input. If $NO_2$ is present, the system can be certain that NO is still being produced. The system can also log all information, warnings, and alarms that are presented to the user throughout a treatment. FIG. 82 depicts an embodiment of an alarm log that can be viewed as a screen on the GUI. The information displayed in the log can also be included in the data files for a particular treatment.

Table 2 illustrates an embodiment of a system installation.

TABLE 2

| Step | Description |
|---|---|
| 1 | Remove Controller from Box |
| 2 | Remove power cable from bag |
| 3 | Insert power cable into back of controller until it "clicks" |
| 4 | Plug Controller into a wall outlet |
| 5 | Turn on mains power switch |
| 6 | Wait for system to boot up |
| 7 | Press TBD to enter BME mode |
| 8 | Enter Hospital Name |
| 9 | Enter preferred default settings for NO tolerance, alarm level, privacy mode, and security code. |
| 10 | Press TBD to save and exit |
| 11 | Remove the calibration cartridge from it's pouch |
| 12 | Insert the calibration cartridge into the cartridge slot until it "clicks". |
| 13 | The system will automatically enter calibration mode and confirm NO and $NO_2$ calibration |
| 14 | Once system completes calibration and makes a "beep" sound, press the cartridge release button to eject the cartridge. |
| 15 | Store the cartridge in a cool, dry location |
| 16 | Leave system ON and plugged into AC power for TBD hours until the internal battery is fully charged. |
| 17 | Unplug AC power cable and wrap it around the winding feature on the back of the device. |

Table 3 illustrates an embodiment of mounting to a pole or rail.

TABLE 3

| Step | Description |
|---|---|
| 1 | Remove Controller from Box |
| 2 | Remove power cable from bag |
| 3 | Insert power cable into back of controller until it "clicks" |
| 4 | Plug Controller into a wall outlet |
| 5 | Turn on mains power switch |
| 6 | Wait for system to boot up |
| 7 | Press TBD to enter BME mode |
| 8 | Enter Hospital Name |
| 9 | Enter preferred default settings for NO tolerance, alarm level, privacy mode, and security code. |
| 10 | Press TBD to save and exit |
| 11 | Remove the calibration cartridge from it's pouch |
| 12 | Insert the calibration cartridge into the cartridge slot until it "clicks". |
| 13 | The system will automatically enter calibration mode and confirm NO and $NO_2$ calibration |
| 14 | Once system completes calibration and makes a "beep" sound, press the cartridge release button to eject the cartridge. |
| 15 | Store the Cartridge in a cool, dry location |
| 16 | Leave system ON and plugged into AC power for TBD hours until the internal battery is fully charged. |
| 17 | Unplug AC power cable and wrap it around the winding feature on the back of the device. |

Table 4 illustrates an embodiment of initiating treatment.

TABLE 4

Use Case 3: Set-up for ventilator use by Nurse/RT
Initial Condition: Installed Controller mounted to rail/pole in Sleep mode.

| Step | Description |
|---|---|
| 1 | Press the Power button on the front panel of the Controller to "wake up" the system. |
| 2 | Remove the pouched cartridge from its box |
| 3 | Remove the cartridge from it's pouch by tearing the vacuum-sealed pouch |
| 4 | Orient the cartridge with the ventilation tubes towards you and the air filter on your left. |
| 5 | Insert the cartridge into the Controller cartridge slot |
| 6 | At the end of the cartridge travel into the slot, grasp the sides of the Controller enclosure and press the cartridge in with both thumbs until there is an audible "click" |
| 7 | Confirm that the Controller recognizes the cartridge. |
| 8 | Using the provided, short ventilator tube, Connect Ventilator Inspiratory line to the cartridge inlet (left) |
| 9 | Connect the ventilator expiratory line/humidifier line to the cartridge exit (right) |
| 10 | Connect the Inspiratory Line T-fitting to the patient inspritory line beside the Patient Y. |
| 11 | Connect the filter of the sample line to the cartridge and tighten by hand. |
| 12 | If the default setting of 20 ppm is not desired, press the up/down buttons to alter the prescribed NO level. |
| 13 | Press the Case Data key to enter patient information. NOTE: This step can be done after treatment begins if there is insufficient time. |
| 14 | Press the Start button to begin delivering NO |

Table 5 illustrates an embodiment of adjusting settings mid-treatment.

TABLE 5

Use Case 3: Adjust settings mid-treatment by Nurse/RT
Initial Condition: System is actively treating a patient

| Step | Description |
|---|---|
| 1 | NOTE: Treatment does not need to be stopped in order to alter treatment settings. |
| 2 | Press the up/down buttons corresponding the change in treatment desired. NOTE: The preset button can also be pressed for larger changes. |

Table 6 illustrates an embodiment of a system tear down, post treatment.

TABLE 6

Use Case 4: Tear down system - post treatment by Nurse/RT
Initial Condition: System is actively treating a patient

| Step | Description |
|---|---|
| 1 | Press "Stop Treatment" on the User Interface |
| 2 | Disconnect the sample line from the T-fitting in patient inspiratory line. |
| 3 | Plug the sample line connection for continued use. NOTE: T-fitting is discarded with the patient Y and inspiratory line. |
| 4 | Disconnect ventilator tubing at the ventilator |
| 5 | Disconnect ventilator tubing at the cartridge exit. |
| 6 | Press the Cartridge eject button |
| 7 | Discard the cartridge (TBD) |
| 8 | The controller will automatically go to sleep after 15 minutes with no input. |

Table 7 illustrates an embodiment of a system calibration with a calibration cartridge.

TABLE 7

| Use Case 5: Calibrate system by Biomedical Engineer<br>Initial Condition: System is ON and in Idle mode. | |
|---|---|
| Step | Description |
| 1 | Insert calibration cartridge into the Controller |
| 2 | Wait for the Controller to perform the automated sensor calibration process for NO and $NO_2$ |
| 3 | When the calibration process is complete, the Controller will emit a sound and show the calibration status on the User Interface. |
| 4 | Press the cartridge eject button to remove the calibration cartridge. |

Table 8 illustrates an embodiment of reviewing historical data.

TABLE 8

| Use Case 6: Review of Historical Data by Nurse/RT<br>Initial Condition: System is in either Idle mode<br>or actively treating a patient. | |
|---|---|
| Step | Description |
| 1 | Press the Trend button on the GUI. |
| 2 | Press the X-adjust button to change the time range, as needed. |
| 3 | Press the Done button to return to the main screen. |

Table 9 illustrates and embodiment of responding to an alarm condition.

TABLE 9

| Use Case 7: Respond to alarm condition of low NO<br>Initial Condition: System has detected an alarm condition<br>but has not stopped treating the patient. | |
|---|---|
| Step | Description |
| 1 | Press the "Silence Alarm" button. NOTE: Alarms are silenced for 2 minutes |
| 2 | Read the alarm message on the User Interface |
| 3 | Follow the device instructions to resolve the alarm condition |
| 4 | NOTE: The system continues to deliver NO during most alarm conditions. |

Table 10 illustrates an embodiment of a use case of patient transport.

TABLE 10

| Use Case 8: Patient Transport<br>Initial Condition: System is mounted to a ventilator and<br>treating a patient that is about to be transported | |
|---|---|
| Step | Description |
| 1 | Unplug the AC Power cord |
| 2 | Wrap the AC Power cord around the wrapping features on the Controller enclosure |
| 3 | Prepare ventilator and other peripheral equipment for transport. |
| 4 | Transport patient. NOTE: During long transports, use Auxiliary power inputs when available to preserve battery charge. |
| 5 | Upon arrival at the new location, plug the AC power cord into a wall outlet. |

Table 11 illustrates an embodiment of a use case of controller cleaning.

TABLE 11

| Use Case 9: Controller Cleaning<br>Initial Condition: Controller plugged into AC Power and Idle. | |
|---|---|
| Step | Description |
| 1 | NOTE: Do not clean the Controller while it is being used to treat a patient. |
| 2 | Unplug the Controller from AC Power |
| 3 | Using a damp cloth, wipe down the external surface of the Controller.<br>NOTE: Do not spray fluids into the controller enclosure.<br>NOTE: Do not clean the inside of the cartridge slot. |
| 4 | Plug in AC Power. |

Table 12 illustrates an embodiment of a use case for initiating manual mode.

TABLE 12

| Use Case 10: Initiate Manual/Bag Mode<br>Initial Condition: System actively treating a patient in Vent mode.<br>Assumption: System has Bag air inlet<br>and Bag air outlet and measures flow. | |
|---|---|
| Step | Description |
| 1 | Connect source of bag air to cartridge bag inlet |
| 2 | Connect bag to cartridge bag outlet |
| 3 | Turn Bag selection knob on cartridge to "Bag" mode |
| 4 | Press "Bag" on the touch screen to initiate flow of NO. |
| 5 | NOTE: The default bag NO concentration is 20 ppm. This level can be adjusted on the settings page. |
| 6 | NOTE: The System will continue delivering NO to the vent circuit until no flow is detected in the vent circuit. |

Table 13 illustrates an embodiment of a use case for stopping manual mode.

TABLE 13

| Use Case 11: Stop Manual Mode<br>Initial Condition: System actively generating NO on the Bag Circuit<br>Assumption: System has Bag air inlet<br>and Bag air outlet and measures flow. | |
|---|---|
| Step | Description |
| 1 | Press the "Bag" button on the screen to disable Bag mode. |
| 2 | Disconnect the bag from the cartridge. |
| 3 | Disconnect the air source from the cartridge. |
| 4 | Turn the Bag selection knob to the "Vent" setting. |

The system can convey alarm status in 360 degrees around a room. This facilitates evaluating treatment status from a distance, sparing the user from walking up to the device. In an embodiment, this involves illuminating the handle with a light bar that can change colors depending on treatment status, such as green for OK, yellow for warning and red for error.

Figure 83:
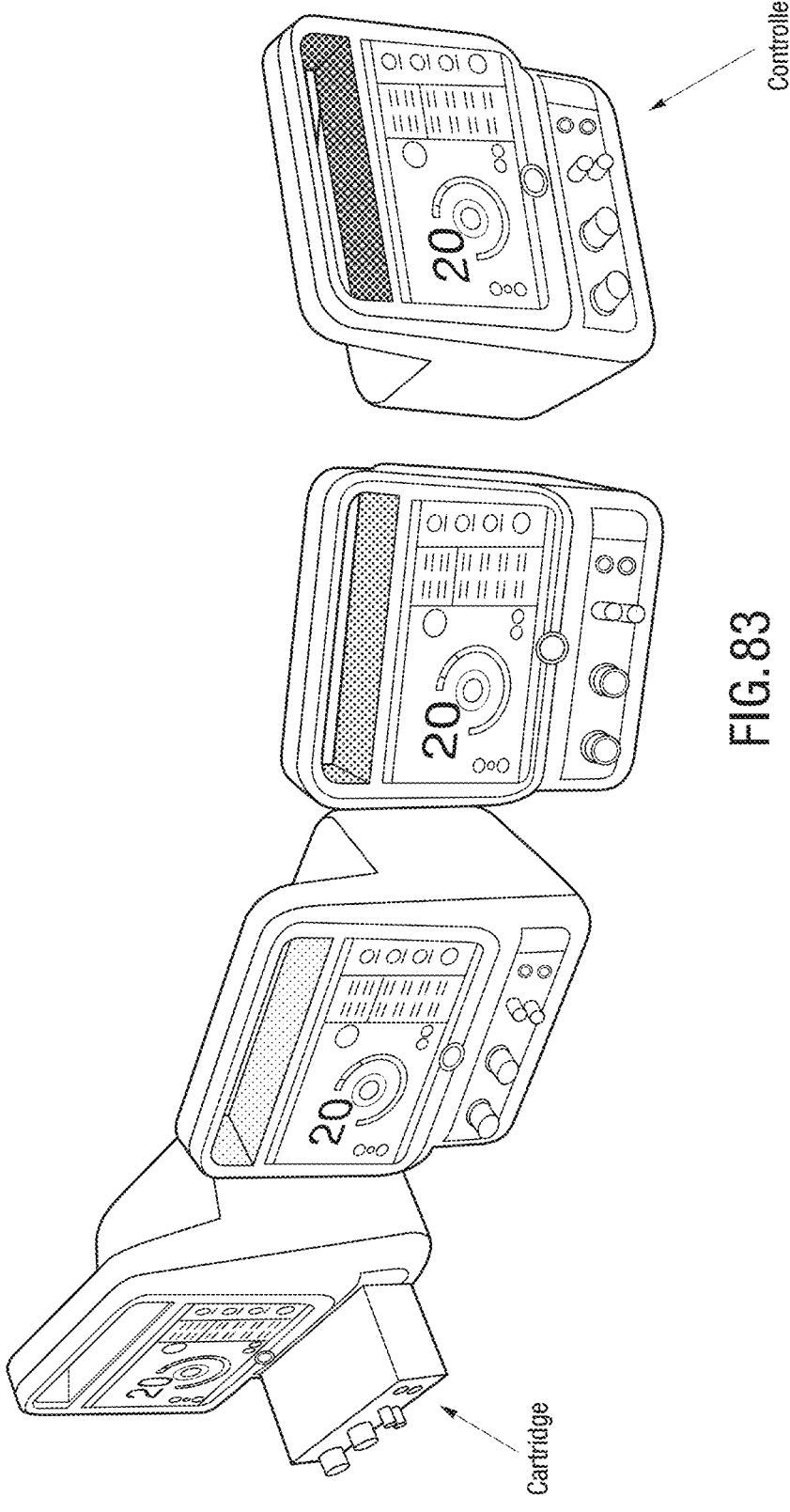
FIG. 83 is another embodiment of an NO generation system with a visual alarm status component.

FIG. 50 and FIG. 83 depict embodiments of the NO generation system with alarm status indicators. In an embodiment, the alarm status indicator can be in the form of a light pump of other illumination element in a handle of the device to display system status. The light bar in can be positioned in the docking station and/or around the user display on the generator. Various colors of light can be used to indicate the status of the system. For example, a blue color can indicate that there are no alarms, and a blinking blue light can indicate that battery charging in process. A blinking yellow light (sometimes accompanied by a periodic audible beep) can indicate a warning situation, such as a low battery or a cartridge near end of life. A red blinking light (sometimes accompanied by continuous audible sound) indicates that a serious alarm state exists, such as cessation of NO delivery. It will be understood that an audible alarm can accompany any of the visual alarm states, and or that an audible alarm can be used without any visual alarm status. It will also be understood that any color scheme of light or pattern of light flashes can be used to indicate the various states of the device.

Cartridge Design

As explained above, the cartridge can include scavenger material. In some embodiments, the scavenger flow-paths can be constructed from Teflon tubing, filled with scavenger material and filters pressed into the ends. Humidity increases the efficacy of a soda lime scavenger by roughly 20%. In some embodiments, the air is bubbled through water pre-spark or post-spark and pre-scavenger to add humidity. Using this approach, humidity can increase by 40% relative humidity, resulting in a roughly 20% improvement in $NO_2$ absorption. It should be noted that in some dry environments, humidity may need to be added to the incoming air to have sufficient $NO_2$ scavenging for patient safety. In addition, electrochemical gas analysis sensors can be adversely affected by dry air, thus humidity may need to be added for them to function accurately.

Flow Measurement

Regarding the measurement of patient inspiratory flow, the range of flow rates within the ventilator circuit can vary significantly. This range can exceed the range of an individual flow sensor. In some embodiments, a flow restriction can be used within the flow path with two or more differential pressure sensors in a parallel configuration measuring the same differential pressure. The pressure sensors can have different ranges for high and low ventilator flow rates. In some embodiments, an elastomeric region can be present in the vent flow path that can be deformed from the outside to create an additional flow restriction when flows are low. This can increase the pressure drop so that pressure sensors can accurately measure the flow. In some embodiments, a cylinder or other obstruction to the vent flow can be introduced to increase the pressure drop during low flow. For example, a cylinder translated by a solenoid can be used.

System Configuration

Figure 84:
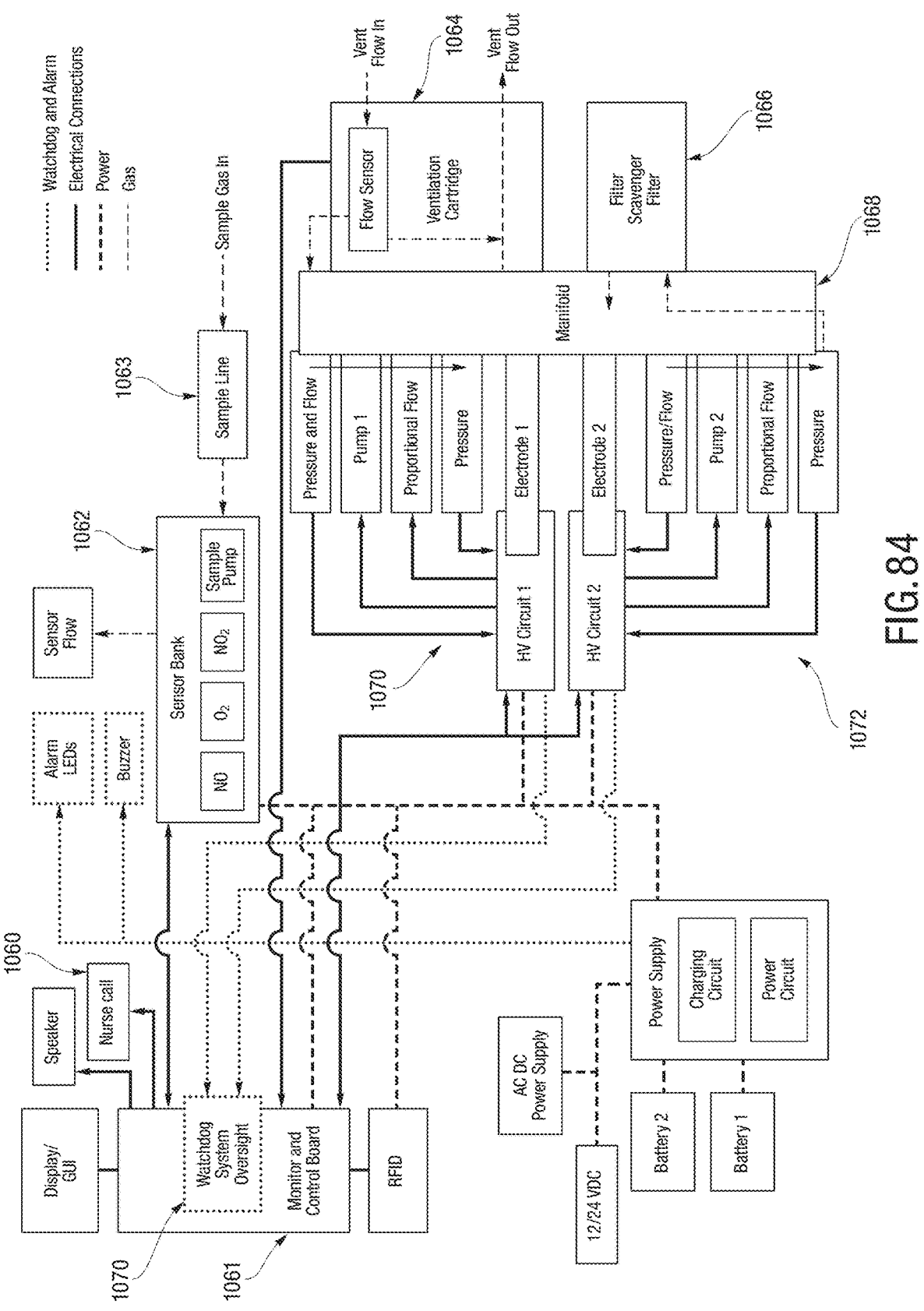
FIG. 84 is an embodiment of an NO generation system.

FIG. 84 is an exemplary embodiment of a system for generating NO. In order to have fully redundant operation in the event of a control software fault, the HV Circuits 1070, 1072 have additional functionality that allows for vent flow measurement and spark chamber pressure measurement. A power circuit as shown in FIG. 84 can be separated from a control board so that it can be double-sided, making it smaller and easier to locate within the controller enclosure. The system can include a nurse call feature 1060 in communication with a monitor and control board 1061, a sensor bank 1062 with a pump that receives sample gas from a sample line 1063, and an added external DC power from an ambulance/automobile/aircraft. The system can utilize redundant plasma assemblies and separate scavenger and ventilator cartridges 1066, 1064 that connect to the manifold 1068. A watchdog component 1070 monitors the control software and high voltage circuit software activity. In the event that software fails, the watchdog circuit can reset the software. After multiple attempts, the watchdog circuit can initiate an alarm (audible and visual) to notify a user that the system has been compromised. The watchdog circuit and its alarm are powered by independent battery so ensure operation in the event of power failure as well.

Electromagnetic interference (EMI) can introduce digital communication errors and erroneous sensor readings. In one embodiment, the system times sensor readings to occur when there is no plasma activity. In some embodiments, the system times digital communications within the system to occur when there is no plasma activity.

Given that the system can continue NO delivery in the event of a user interface failure or control software failure, it is important to notify a user that NO is still being delivered even though the display may be frozen or blank. In some embodiments, a separate indicator can be provided that signifies NO delivery, such as a blue LED. In some embodiments, separate blue LEDs are used to represent NO generation in each of two plasma chambers. In cases where the watchdog alarm is triggered, the visual alarm can be flashing red (indicating alarm) and blue (indicating NO is being delivered). Furthermore, voice alarms can notify a user that NO is being delivered by playing a voice recording in the appropriate language.

The cartridge or cartridges used with the system can have various configurations and combination of components. In some embodiments, a cartridge with only scavenger and water trap can be used. Vent flow can go through the controller only, which enables better flow measurement, a cheaper disposable, and fewer gas connections. In some embodiments, the scavenger and water trap can be separated. The water trap can be part of the sample line and connect directly to the sensor pack. This can decrease the number of pneumatic connections in the system without adding any user steps to set up the system.

It is possible that the pressure in the ventilator circuit can increase when air is pushed to the patient by the ventilator. This increased pressure can stall flow through an NO delivery device. In some embodiments, a venturi can suck NO into the vent flow like a carburetor sucks gas in. Thus, increased vent flow increases NO flow. In some embodiments, a flow restriction can be included after the plasma to keep the NO-containing gas pressure high in the spark chamber and increase NO output. This flow restriction can be useful for altitude compensation. In some embodiments, a flow restriction can be included at the end of the scavenger so that NO-containing gas is at higher pressure than the inspiratory limb of the ventilation circuit and can flow into the vent flow at all times, including when the vent flow is at high pressure. In some embodiments, a feedback control on the pump can be used to maintain constant pressure in a spark chamber. This can account for variance in ambient pressure and pre-scavenger resistance. Spark chamber pressure can also be used as an input into the NO generation control algorithm. In some embodiments, a variable orifice can be included downstream of the plasma chamber to allow pressure to build up, and the orifice can open to increase NO flow during an inspiratory pulse. In some embodiments, the system can include two pistons/chambers. One chamber can fill during patient inhalation and deliver gas to the bias flow within the ventilator circuit during patient exhalation. The other chamber can fill during patient exhalation and deliver gas to the ventilator circuit during patient inhalation. In some embodiments, a single piston with chambers on either side can be used. As the piston moves one direction, it delivers air for bias flow. As the piston moves in the other direction, it delivers air for inspiratory flow. In some embodiments, the piston can deliver both bias flow and inspiratory pulse gas in one direction before reversing direction and delivering bias flow and inspiratory pulse gas.

Figure 85:
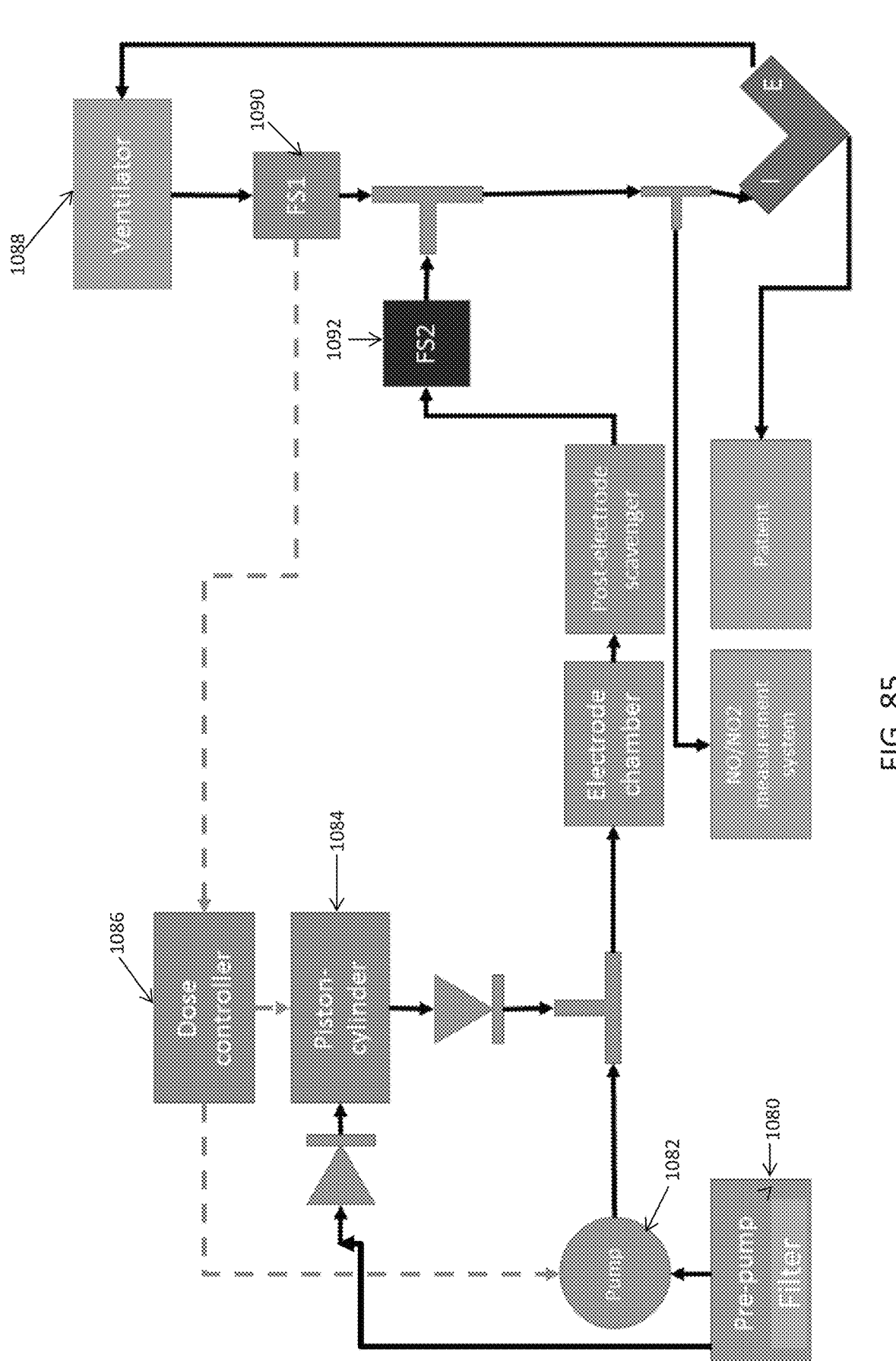
FIG. 85 is an embodiment of a piston-pump configuration.
Figure 86:
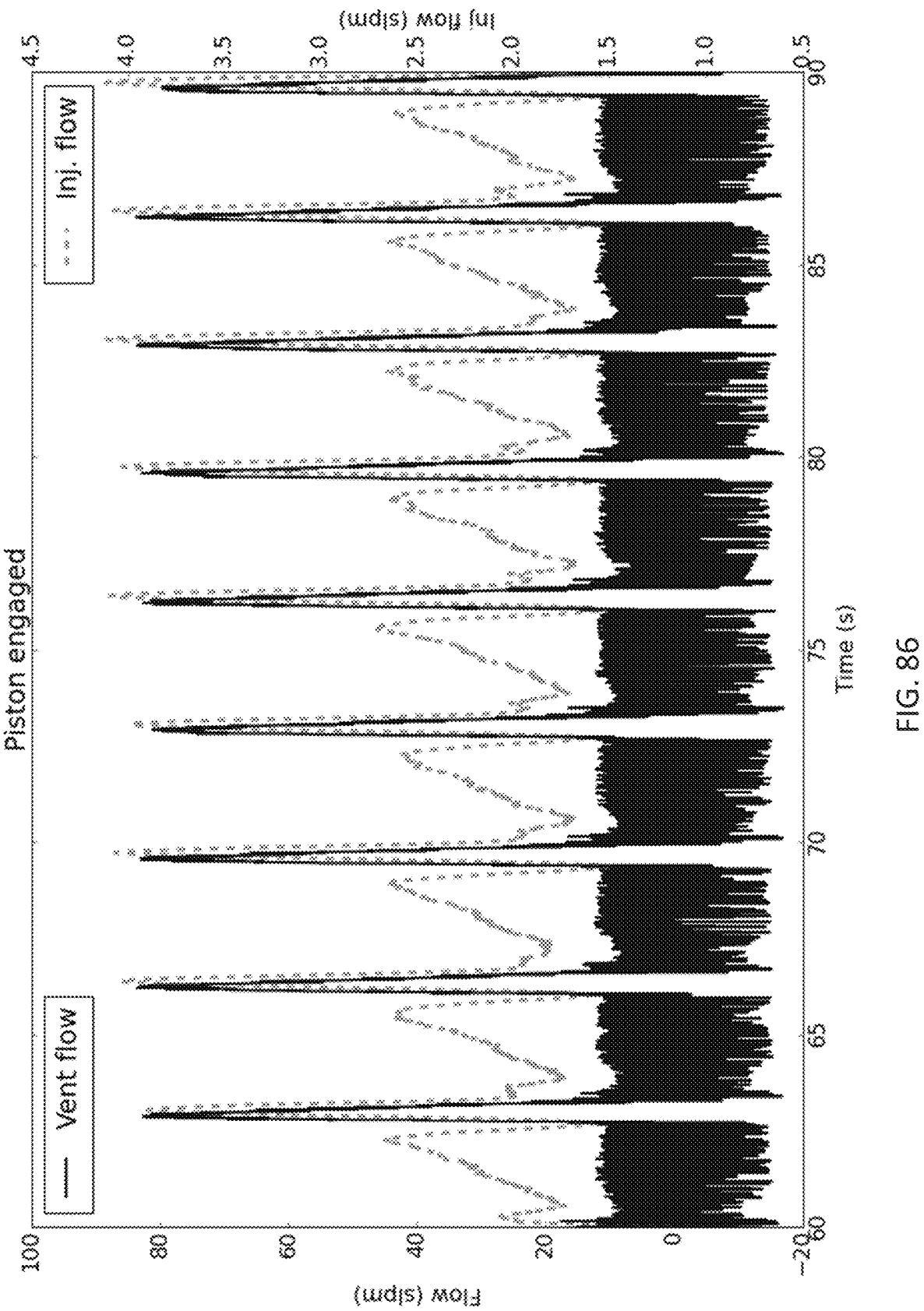
FIG. 86 is an exemplary graph comparing ventilator flow and injection flow using a piston-pump configuration.
Figure 87:
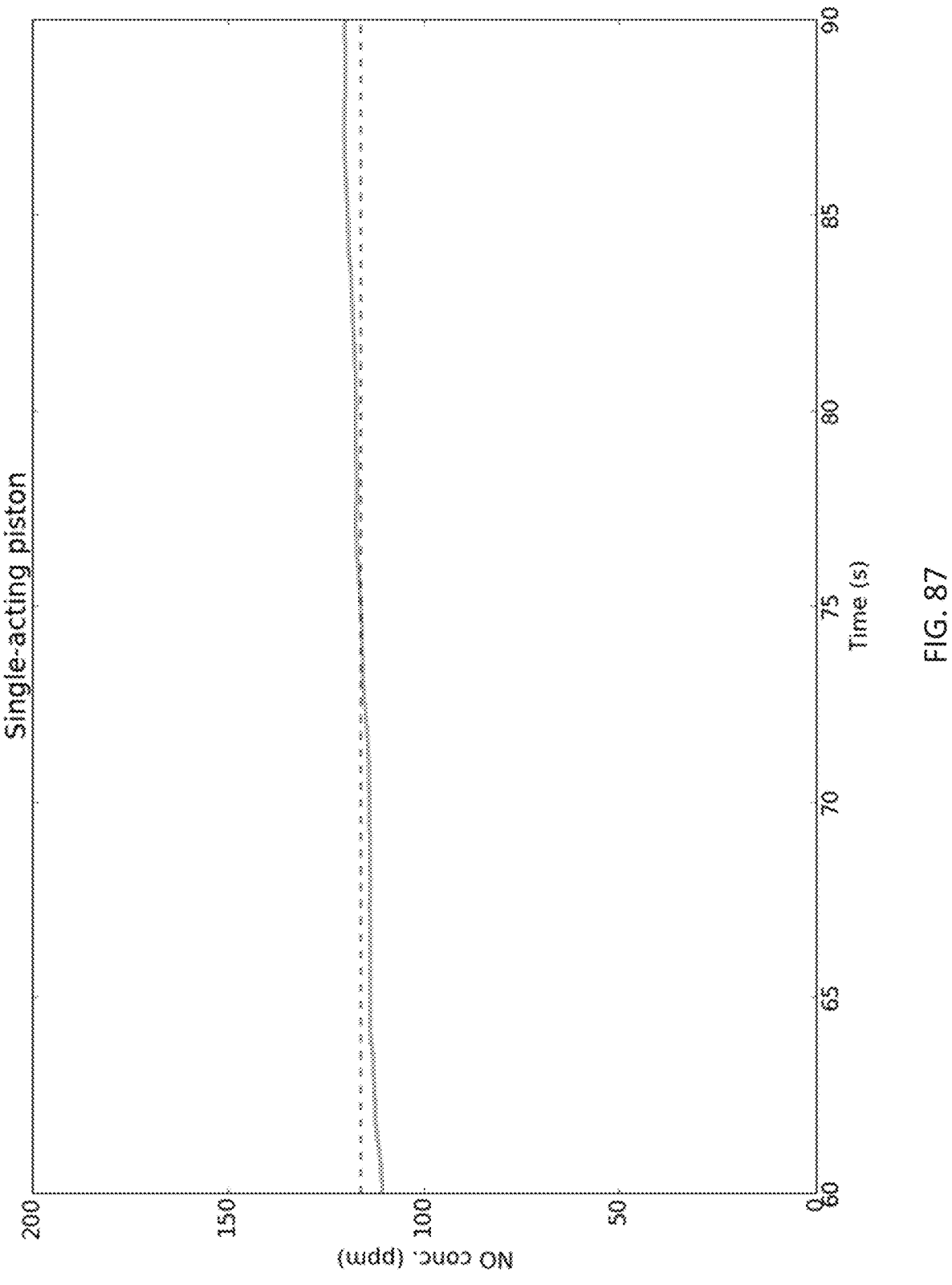
FIG. 87 is an exemplary graph of NO concentration over time when a single-acting piston is used.

FIG. 85 illustrates an embodiment of a piston-pump configuration, and FIG. 86 illustrates a graph demonstrating synchronization of inspiratory events in the ventilator flow and injection flow using the piston-pump configuration of FIG. 85. Air is drawn into the system through a filter 1080 and flows to either a piston cylinder 1084 or a pump 1082. FS1 1091 measures the flow within the patient inspiratory limb to provide timing information to a dose controller 1086. FS2 1092 measures the flow rate out of the system for closed-loop feedback of the NO-containing gas flow. FD2 can be located anywhere along the NO flow path between the intersection of pump and piston-cylinder flow and the intersection between NO generation device flow and patient inspiratory flow. The pump can be used to create a constant flow rate to match the bias flow of the ventilator 1088, and the piston 1084 can be used to create a bolus to match the inspiration bolus of the ventilator 1088. The function of the piston is timed with the ventilator. While the piston shown in FIG. 85 is positioned to adjust the flow before the spark that generates the NO, the piston can also be positioned in other locations in the system, including after the generation of NO. FIG. 87 illustrates a graph of NO concentration versus time during the experiment depicted in FIG. 86, showing that constant NO concentrations can be delivered to the patient.

Figure 88:
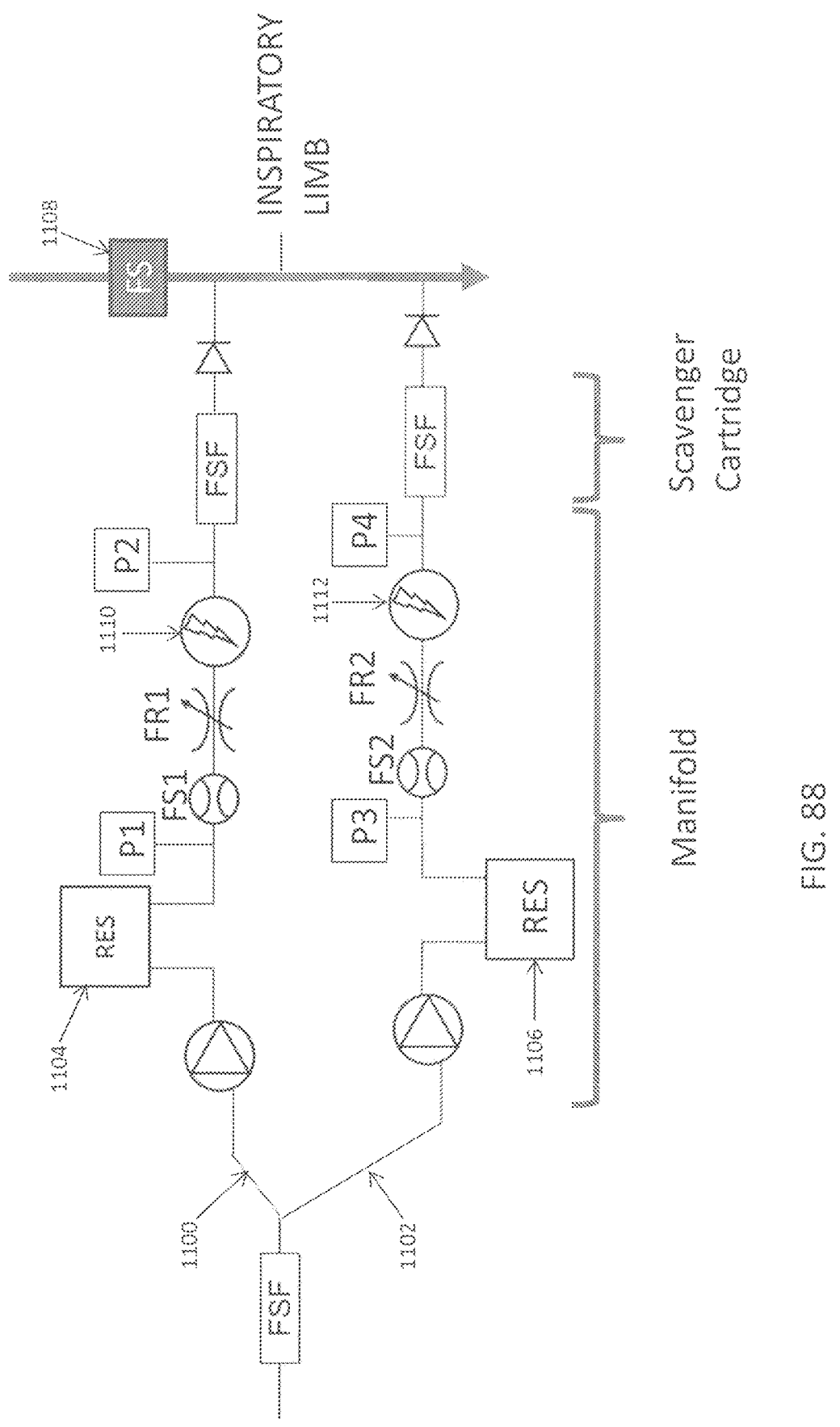
FIG. 88 is an embodiment of an NO generation system using at least one reservoir.
Figure 89:
FIG. 89 is an exemplary graph comparing ventilator flow, plasma air flow, and NO levels.

FIG. 88 illustrates an embodiment of a reservoir configuration and FIG. 89 illustrates a graph comparing ventilator flow 1120, plasma air flow 1122, and NO levels 1124. This configuration involves two redundant flow paths 1100, 1102. Each flow path includes a pump that fills a reservoir (RES) 1104, 1106 and first pressure sensors P1, P3 to sense pressure within the reservoir. A feedback loop exists so that the pumps are controlled based on the pressure of their respective reservoir. A variable flow restrictor FR1, FR2 are used to adjust the flow rate of the gas from the reservoirs through the spark chamber based on flow measured in the ventilator inspiratory limb flow sensor 1108. Flow sensors FS1, FS2 are used for feedback to the control system for adjusting the variable flow restrictor setting. Flow rates can vary, for example, from 0 to 4 lpm. Additional pressure sensors (P2 & P4) measure the pressure within the plasma chamber 1110, 1112 as an input into the overall NO generation control algorithm. Air flows from the plasma chamber located in the manifold, a reusable portion of the controller, to the scavenger cartridge where it flows through a filter/scavenger/filter (FSF) as shown. Check-valves in each path ensure that pressure transients in the ventilator inspiratory limb do not reverse the flow in the NO generation paths.

Figure 90:
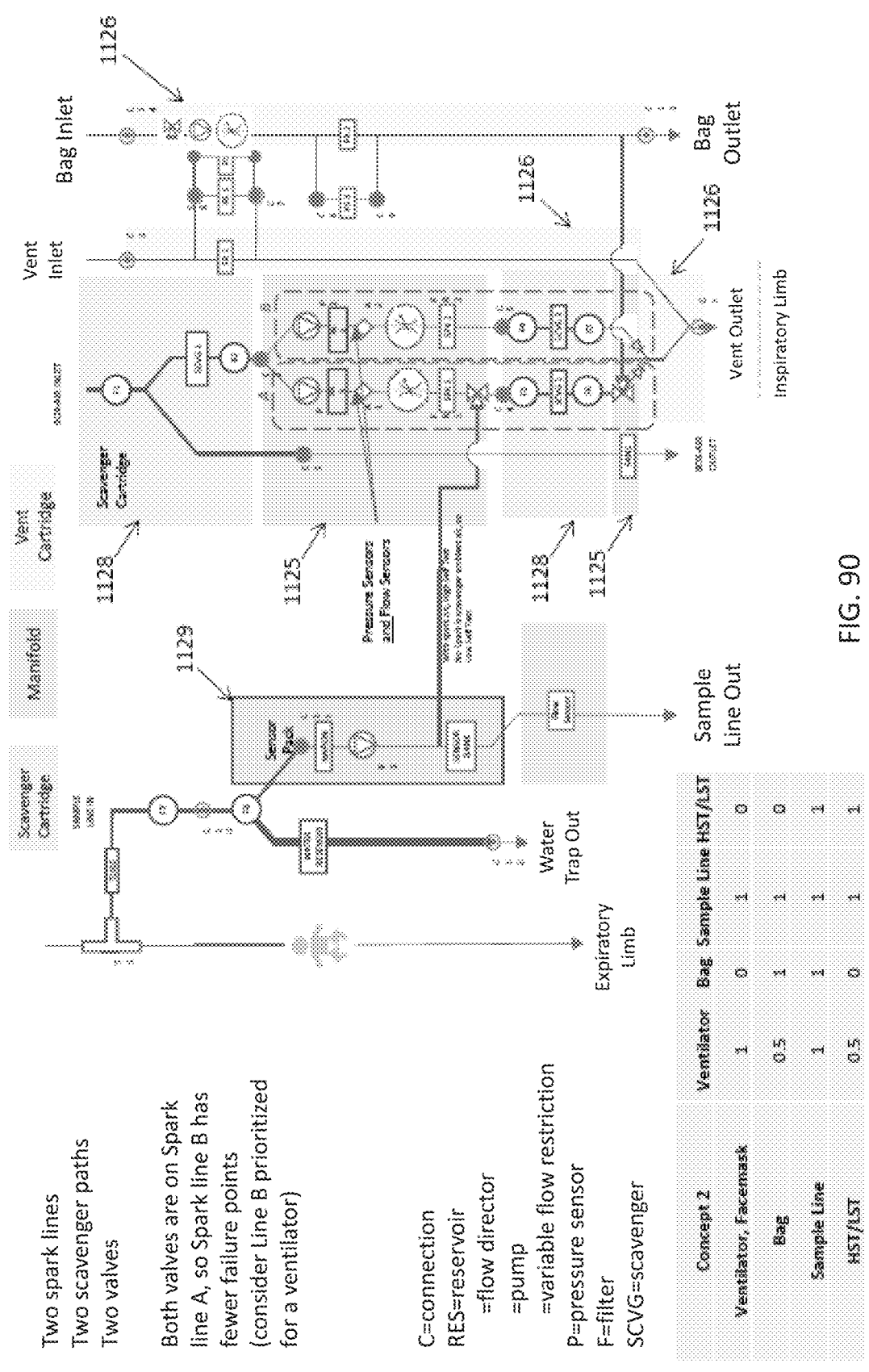
FIG. 90 is an embodiment of an NO generation system using at least one reservoir.

FIG. 90 depicts an embodiment of a similar system to the embodiment shown in FIG. 88 with the following exceptions. Flow directors are shown in flow path A. The first (upper) flow director can direct flow to either the gas analysis sensors for calibration purposes or to the vent flow. The second (lower) flow director can direct flow to either the ventilator flow or to the bag flow. The thick lines represent disposable paths and features while the sensor bank, flow sensor, flow directors, pumps, Nafion tubing, fan, and spark chambers are reusable components within the controller. Ventilator and bag flow are shown as vertical lines on the right side of the illustration. In some embodiments, flow is measured by two pressure sensors within the controller. The two pressure sensors may be identical for redundancy, or they may have different ranges of accuracy to enable the system to measure a wider range of ventilatory flows. Shaded zones 1125 identify components connected to the controller manifold. Shaded zones 1126 identify components within the ventilator cartridge. Shaded zones 1128 identify components within the scavenger cartridge. Shaded zone 1129 identifies the sensor pack.

Figure 91:
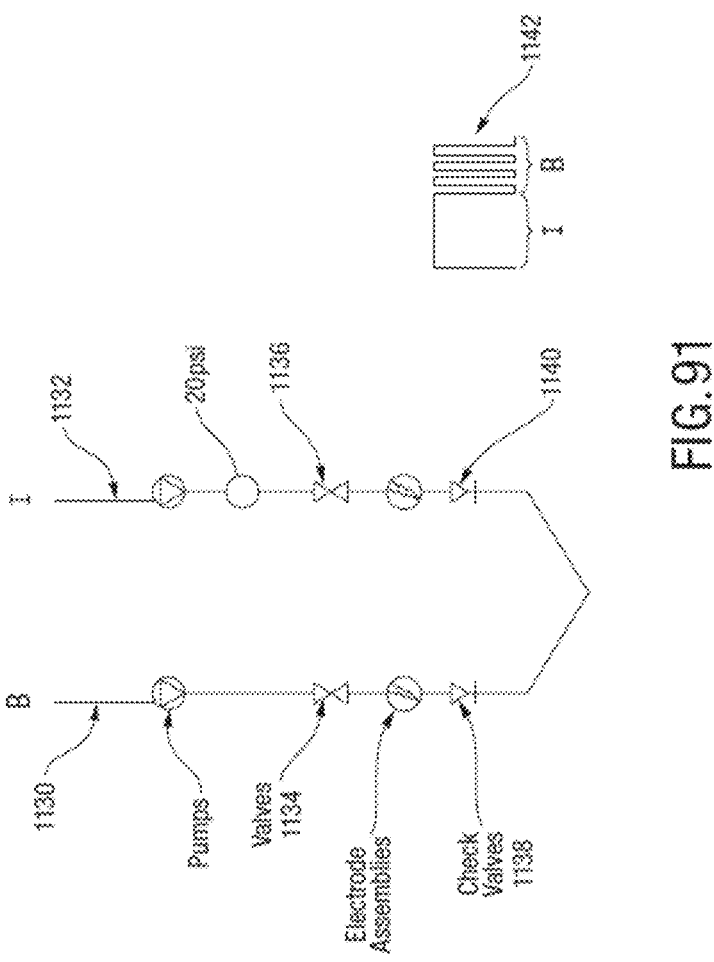
FIG. 91 is an embodiment of an NO generation system having dual-flow paths.

FIG. 91 illustrates an embodiment of a system with dual flow paths 1130, 1132. Under normal, ventilator treatment, one channel labeled "B" (bias flow path) is tuned to deliver a constant amount of NO based on the ventilator bias flow. The other channel labeled "I" (inspiratory flow path) provides pulsatile flow to deliver NO in proportion the inspiratory bolus from the ventilator. Valves 1134, 1136 in each path can close off air flow when a flow path is not active. Flow through each path can be varied by pump rate and the amount of time each valve is open. Plasma activity in a flow channel is typically constant when air is flowing so that the only variable in NO production control is air flow. Check valves 1138, 1140 at the end of each flow path ensure that ventilator flow does not flow back into the system during moments of high inspiratory pressure. A graph 1142 illustrates how a valve can be open 100% of the time during inspiratory flow and intermittently during bias flow so that a single flow path can provide all the NO for a treatment. In another mode of operation, one flow path could be used for bias flow and the other flow path used for inspiratory flow to even the wear on each flow path. Pulses 0.4 seconds in length with a duty cycle of 50% are not detectable at the patient Y due to mixing that occurs along the length of the inspiratory limb as the NO flows through the patient humidifier and vent tubing. It is possible that each individual flow path can be used for both bias flow and inspiratory flow if one of the paths fail.

FIG. 92 illustrates a sample flow path with a single pump 1150 providing air flow. In some embodiments, the pump can run continuously. The flow path bifurcates with a single fixed orifice used to elevate pressure within the system and provide NO during bias flow. In some embodiments, the pump rate and the fixed orifice are tuned for bias flow. A variable orifice 1152 is tuned to provide the desired flow rate during inspiratory pulses within the ventilator circuit. A valve downstream of the variable orifice controls when flow travels through the inspiratory flow path. The variable orifice 1152 can close down to zero flow or a low flow rate. At the bottom of the illustration is the plasma chamber. In some embodiments, the valve 1154 enables the system to quickly turn ON and OFF the inspiratory flow. In some embodiments, the valve is not required owing to a very vast acting variable orifice. The entire flow path shown in FIG. 92 can be duplicated within a device for redundancy or for dosing a ventilator circuit, calibration, and/or a bag circuit simultaneously.

Figure 93:
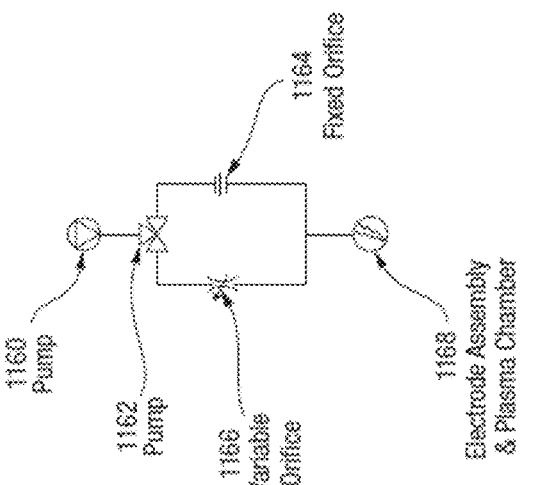
FIG. 93 is an embodiment of an NO generation system having a flow path with a pump and a flow director.

FIG. 93 illustrates an embodiment of a flow path consisting of a pump 1160 and a flow director 1162. The flow director 1162 switches flow between an orifice 1164 set for bias flow and a variable orifice 1166 set for the sum of inspiratory flow and bias flow. The variable orifice can be adjusted mid-inspiration to further tune the air flow, as needed. The plasma chamber 1168 is shown at the bottom of the image.

Figure 94:
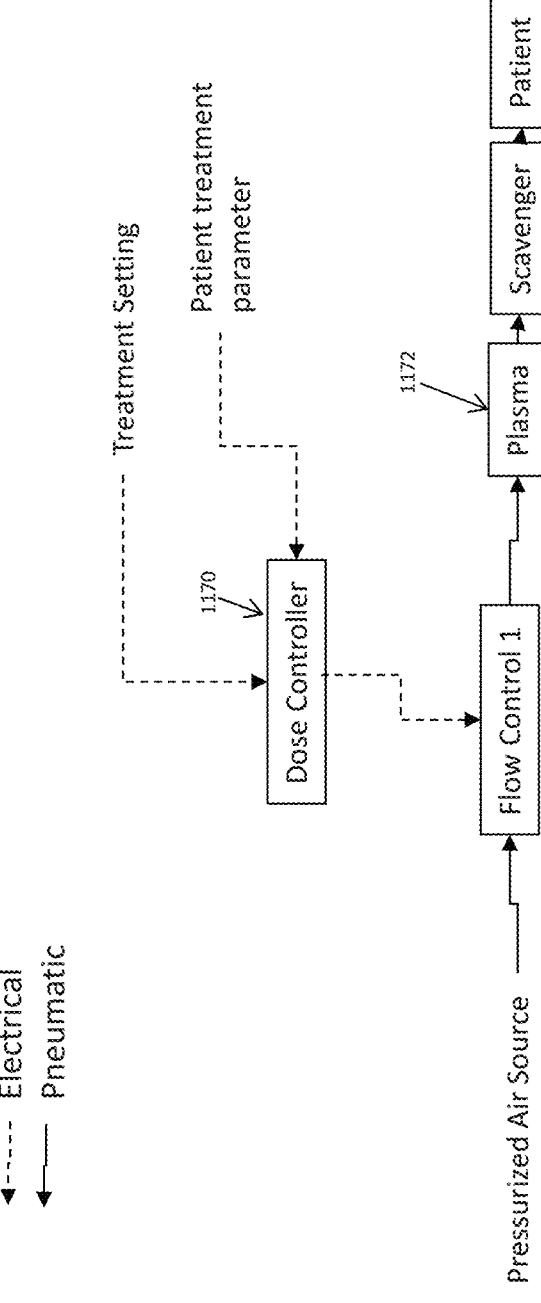
FIG. 94 is an embodiment of an NO generation system that varies air flow through the system.

FIG. 94 illustrates an embodiment of a system that varies air flow through a plasma chamber 1172 to provide an accurate dose of NO to a patient. A target dose is selected by a user or physician. A patient parameter can be sensed and used by a dose controller 1170 to indicate the timing and/or magnitude of a patient inspiration. Examples of patient parameters include but are not limited to patient inspiration detection, ventilator circuit pressure, ventilator circuit flow, nasal cannula pressure, thoracic wall strain, diaphragm EMG, oxygen generator pressure, and oxygen generator flow. Air or another $N_2$ and $O_2$-containing gas is sourced from a pump or compressed gas source. The dose controller 1170 can control the flow of the pressurized gas. This can be done in a variety of ways, including by varying the size of an orifice or the duty cycle of a valve. In some embodiments, as shown in FIG. 94, a pressurized air source serving a single flow controller can require a fast-responding flow controller and an air source that can keep up with demand.

The patient dose can be defined in many ways. The most conventional means is to provide the patient with a particular concentration of NO at all times. More sophisticated approaches calculate a target number of NO molecules to be delivered per unit time based on the size of the patient's lungs (typically ideal body weight is used as a surrogate). With this approach, the system generates and delivers only enough NO to keep the lung lining appropriately dosed. NO delivery may be intermittent to achieve the target number of molecules per minute. The system is programed with the ideal number of molecules per minute based on the patient's ideal body weight. The system can vary the NO concentration per breath from zero to a maximum value (typically 80 ppm) with each breath so that the moving average of molecules delivered per unit time is accurate. This approach provides the lining of the lung an appropriate amount of NO molecules, despite variation in breathing that can occur based on activity level and respiratory rate.

Changes in dose can be controlled by varying plasma activity and/or air flow rate. In one embodiment, these two parameters are varied to achieve a constant concentration of NO-containing gas before dilution into a patient airstream. In another embodiment, air flow is varied in proportion to patient inspiratory activity (e.g. inspiratory air flow rate, ventilator flow signals, breath detection) while plasma activity (pulse width or pulse frequency or pulse power) is varied to generate the target NO concentration in the NO-containing gas.

In some embodiments, the source of the pressurized gas shown in FIG. 94 is controlled by the dose controller is controlled in addition to the flow controller. In another embodiment, the dose controller only controls the source of the pressurized gas.

Figure 95:
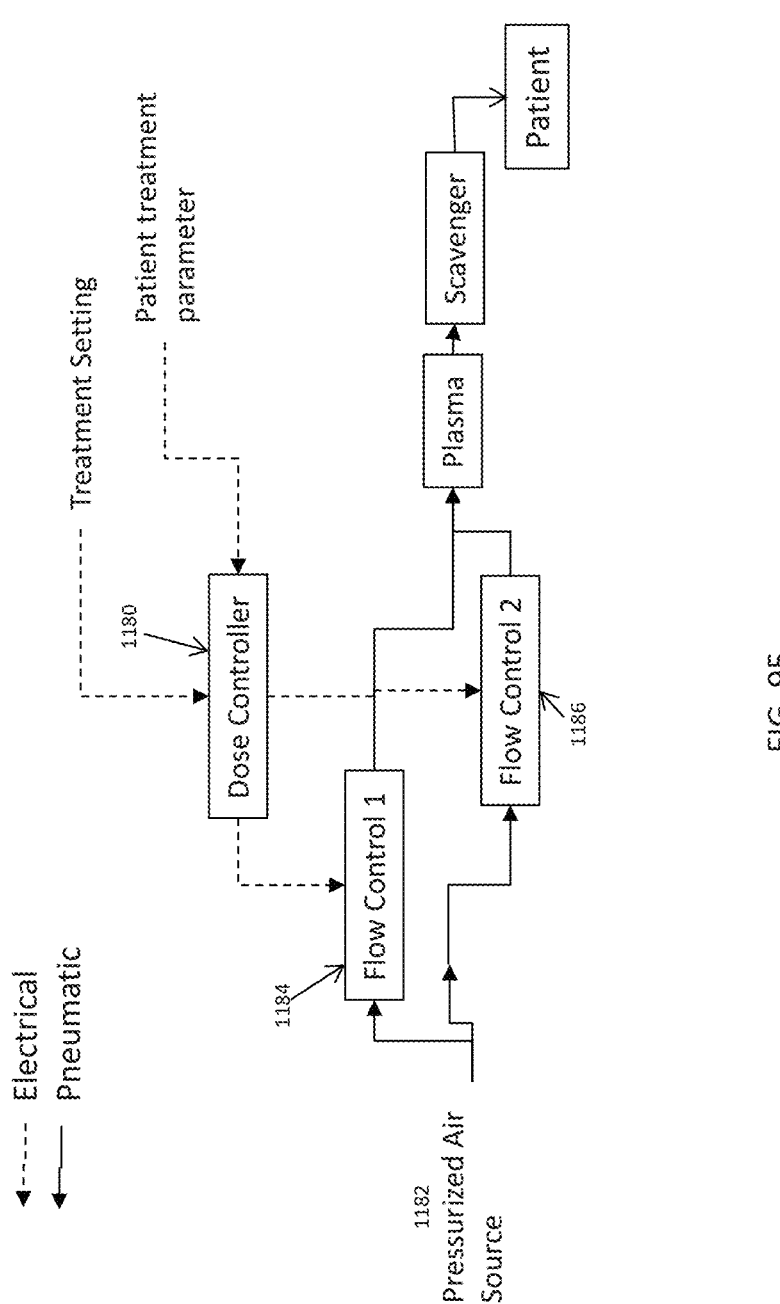
FIG. 95 is an embodiment of an NO generation system that utilizes a plurality of controllers to control flow through the system.

FIG. 95 illustrates an embodiment of a dose controller 1180 that varies treatment based on a patient parameter and treatment setting. In some embodiments, a pressurized air source 1182 is connected to two or more flow controllers 1184, 1186. The dose controller 1180 can control the status of each flow controller, i.e. the orifice size and flow rate (from 0 to wide open). One pressurized air source servicing a plurality of flow controls permits the use of slow dynamic response flow control elements because each flow controller remains at a relatively constant set point (the dynamic response is less important). In this case, the single pressurized air source must still address rapidly varying air demand.

Figure 96:
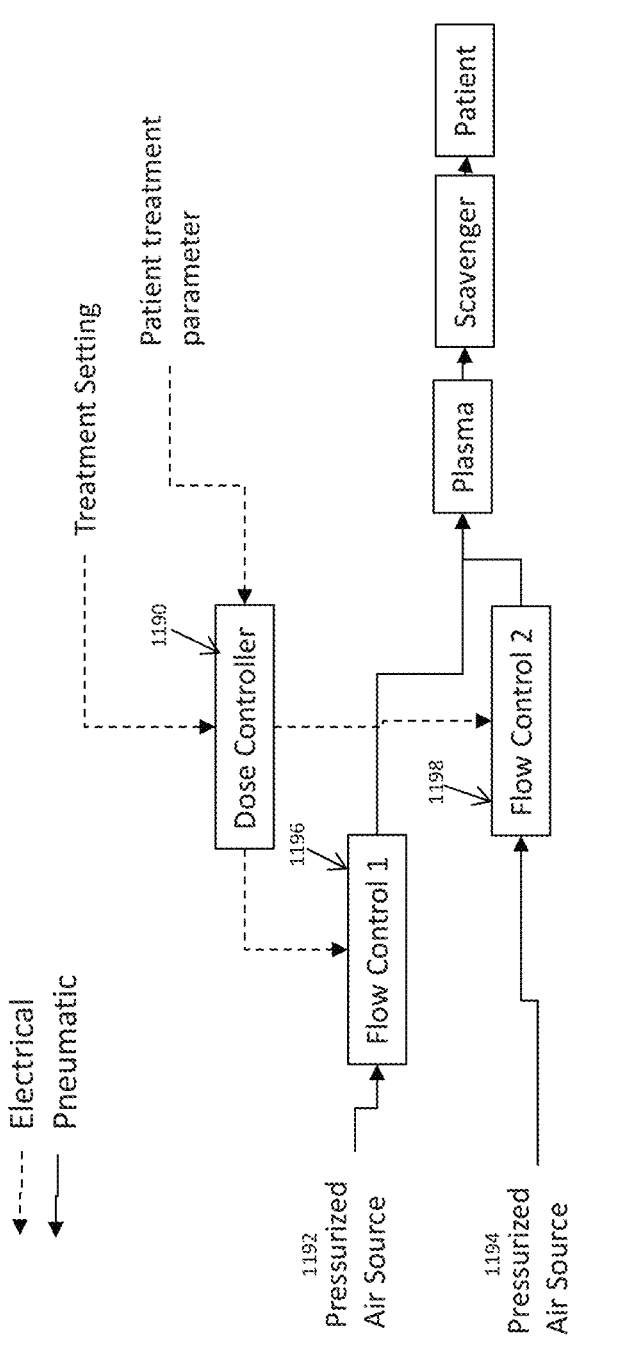
FIG. 96 is an embodiment of an NO generation system that utilizes more than one air source.

FIG. 96 illustrates an embodiment of a dose controller 1190 that varies treatment based on a patient parameter and treatment setting. In some embodiments, more than one pressurized air source 1192, 1194 is used to send air through more than one flow path. Examples of pressurized air sources include but are not limited to compressed gas reservoirs, air pumps, and house air services. Use of a plurality of pressurized air sources (pump, etc.) servicing a plurality of flow controllers 1196, 1198 permits each air source and flow controller to operate at relatively constant operating levels. Thus, no pressurized air source is required to address rapidly-changing demand.

Figure 97:
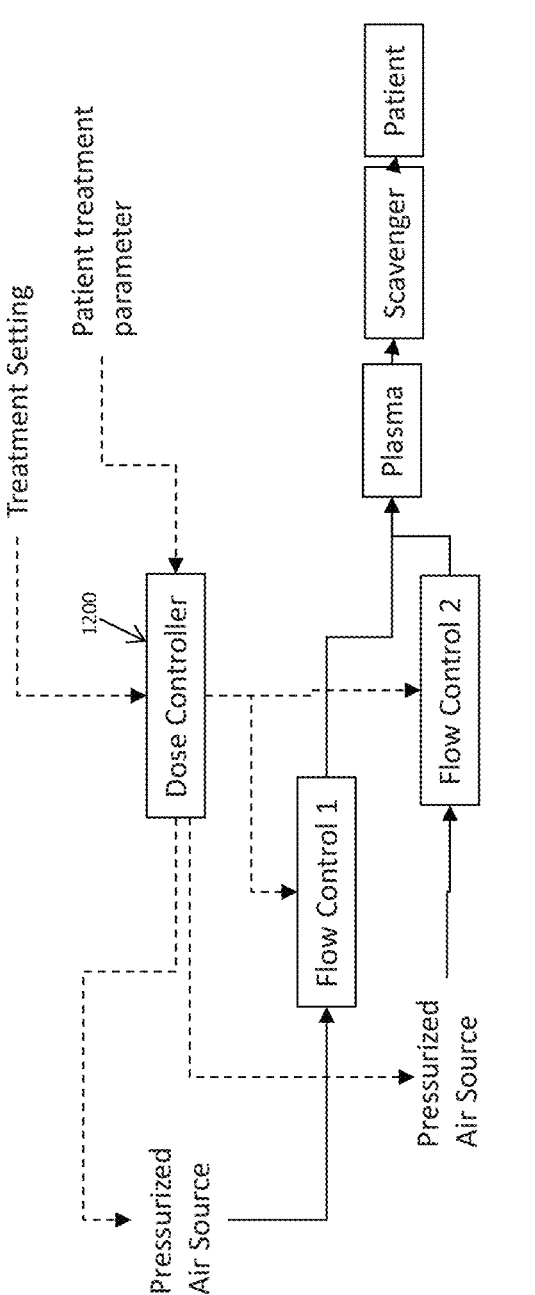
FIG. 97 is an embodiment of an NO generation system that utilizes a dose controller to control a plurality of air sources.
Figures 98A, 98B:
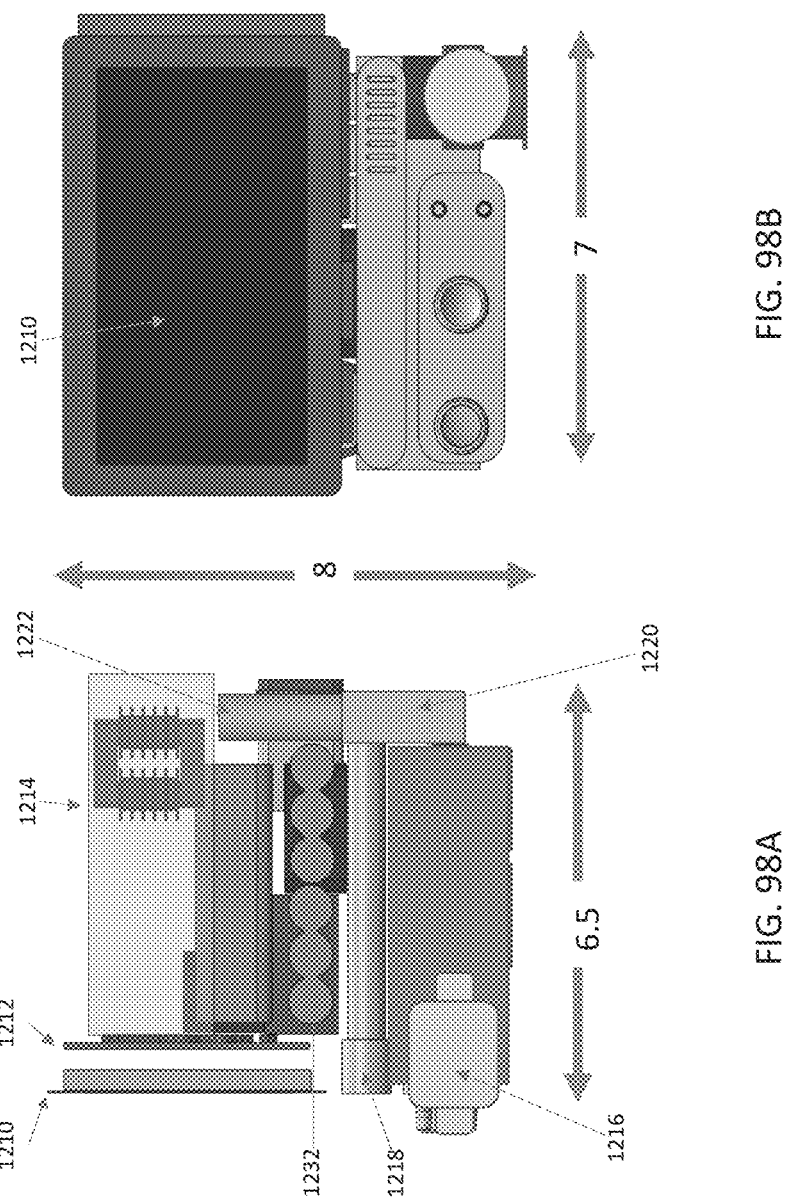
FIGS. 98A, 98B, 98C, and 98D illustrate multiple view of an embodiment of a system for generating NO.
Figure 98D:
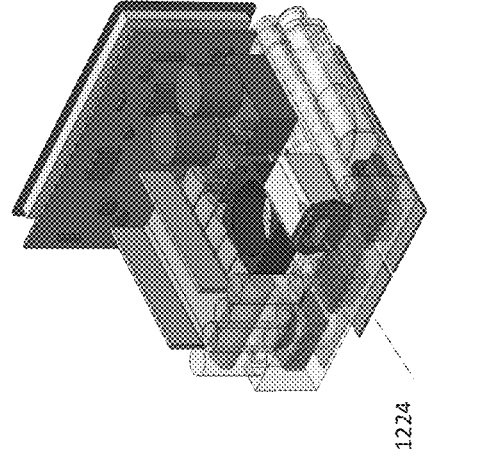
Figure 98C:
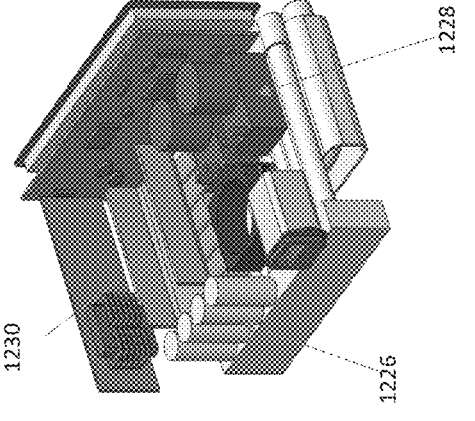

FIG. 97 illustrates an embodiment similar to FIG. 96 where the dose controller 1200 has additional control over the pressure source. Each pressurized air source can be tuned to the flow required for its flow path. For example, the pressure in a gas reservoir can be adjusted with a regulator, or a pump speed could be adjusted. Use of a plurality of pressurized air sources (pump, etc.) servicing a plurality of flow controllers (for example, flow control 1 and flow control 2) permits each air source and flow controller to operate at relatively constant operating levels. Thus, no pressurized air source is required to address rapidly-changing demand. In some embodiments, for example where pumps and blowers are used, the dose controller 1200 can vary the pump effort, thereby effecting flow rate and exit pressure. In some embodiments where the source is compressed gas, the dose controller 1200 can regulate the pressure of the gas source.

FIGS. 98A-98D illustrate multiple views of an embodiment of a system for generating NO. The system can include a touchscreen interface 1210, a main circuit and power board 1212, a high voltage & treatment control circuit board 1214, a water trap 1216 from a sample line, a scavenger cartridge 1218, a manifold 1220, an electrode assembly 1222, a power entry module 1224, flow directors 1226, an air pump 1228, an AC/DC power transformer 1230, and batteries 1232.

The system can use a flow-director to redirect flow from one of the plasma chambers to the gas analysis sensors for calibration. The system can use a flow-director to redirect flow from one of the plasma chambers to the bag flow circuit for NO delivery during manual ventilation.

The system can use a vent cartridge that includes a vent flow path and a bag flow path. Vent flow can be measured as it flows through the vent cartridge. This can be done by a sensor within the vent cartridge or by one or more pressure sensors within the controller that are pneumatically connected to the vent flow with an appropriate flow restriction between locations sensed. For vent cartridges that contain sensors, calibration information for the sensors can be written to a memory device within the vent cartridge. Additional data written to the vent cartridge can include any of the following: serial number, lot number, whether or not it has been installed, treatment data, settings log, alarms log, and user-entered notations. Given that the vent cartridge is integral to the inspiratory flow path, it is desirable to transfer a vent cartridge from on controller to another in the event of a system malfunction or transfer a patient from one facility to another. By writing the treatment history and settings to the vent cartridge, the treatment can continue seamlessly in the next controller. The system can also function with two or more types of vent cartridges. Vent cartridges can vary by tubing connections, tubing diameter, and/or flow restriction (for flow measurement). In some embodiments, the vent cartridge can include the electrode assembly. The low flow vent cartridge can have a small electrode gap for lower NO production. The high flow vent cartridge can have a larger electrode gap (for example, 2-3 mm) for higher NO production.

An NO generation system needs to quickly calculate the dose for NO delivery based on measured flow levels, generate that dose and deliver it to the main airstream. Some aspects that contribute to a system being able to respond quickly are using look up tables, fast processors, one or more quick acting proportional valves, low flow restriction scavengers, short pneumatic pathways and a high pressure gas source (reservoir, pump). Despite these efforts to respond quickly, a system can still lag sufficiently that a specific of bolus of NO may be introduced to the gas flow behind the bolus of gas it was meant for. By introducing the NO-containing flow in the center of the mainstream gas flow and at a higher velocity than the mainstream gas flow, it is possible for the NO-containing bolus of flow to actually catch up with the gas bolus that it was intended for. The velocity of the exiting NO flow is varied by the orifice size in the injector, gas pressure and gas flow rate.

Another approach to dosing a bolus of patient gas sufficiently is to account for system lags by overshooting on the dose to deliver. For example, if a bolus of mainstream flow is detected that requires 20 ppm NO, the system may set the plasma and/or flow parameters to generate 40 ppm for a brief amount of time so that the system responds more quickly to the demand. As the actual dose delivered crosses the 20 ppm threshold, the system could change its settings to deliver 20 ppm.

In some embodiments, the system can include three electrode assemblies and NO paths and three scavengers, with two for vent NO delivery and one for bag NO delivery.

Figure 99:
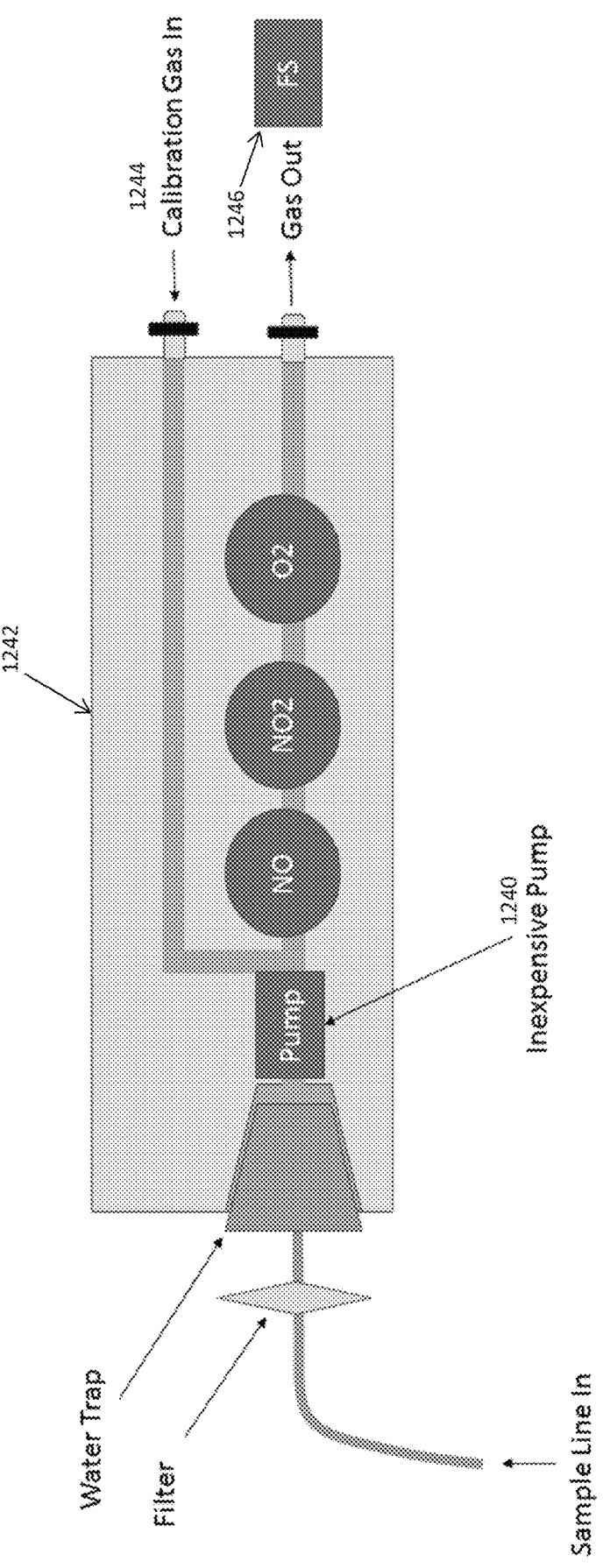
FIG. 99 is an embodiment of a sensor pack having a water trap and a pump.

Sample sensors can receive flow from either the patient inspiratory limb, a calibration gas cylinder connected to the sample line connection, or the NO generation device for calibration, and the source of NO can be selected. In some embodiments, as shown in FIG. 99, a pump 1240 within the sensor pack 1242 can be positioned between the sample line connection and intersection between sensor path and self-calibration gas source 1244. A reusable flow sensor (FS) 1246 is shown to the right of the sensor pack and is part of the overall NO generation device. Gases from the sensor pack 1242 flow through a manifold, to the flow sensor and on to an exit port. In another embodiment (not shown), a ON/OFF valve is in the location of the pump in FIG. 65 to block flow from the sample line connection so that flow pumped from the controller can pass through the sample sensors. In some embodiments, as shown in FIG. 73, a flow selector can be within the sensor pack that can choose between a sample line and a self-calibration gas source path.

Safety

Various safety features can be incorporated into the system to solve a variety of issues. For example, the system can have a scavenger at the patient Y before sample collection that is configured to absorb any $NO_2$ formed due to long inspiratory circuits or high $O_2$ levels.

NO delivery to a patient can be done in emergency situations, thus time to NO delivery can be important. If the device requires a lot of time to prime the pneumatic pathway, this could present a delay in patient treatment. In some embodiments, the system can have a mode to rapidly prime the cartridge with NO before connecting it to the vent circuit after cartridge replacement. In some embodiments, the system primes itself by pumping air at a rapid rate through a plasma in the plasma chamber and the scavenger cartridge before directing the flow to the gas analysis sensors. This priming can take place for a set amount of time or until NO is detected at the NO sensor. Then, the system can decrease the pump speed and direct the flow to the vent cartridge for treatment. This can result in a decrease in the amount of time required to prime the system, thereby decreasing the time that the patient is without NO.

It can be important to restrict operation of a hospital device to people that are authorized and trained to operate the equipment. In some embodiments, an RFID label can be associated or attached to an ID card of user, with the RFID having a unique number within it that is used to identify the user. In some embodiments, the same RFID reader within the controller can be used to identify the disposable components (for example vent cartridge, scavenger cartridge, and/or sample line) as the user ID badge. An RFID reader can be positioned in various locations, but in some embodiments an RFID reader can be on the side of the controller so that it can read the RFID tags on the cartridges on one side and the hospital ID on the external-facing side of the reader. An RFID tag can also be attached to the controller within the field of view of the RFID reader. This enables the software to test the RFID reader because there should always be an RFID tag in the field of view. It also enables the software to know which controller is performing the treatment. Other information could be placed in the controller RFID tag, such as the controller serial number, last service date, date of manufacture, error codes, run time of the system, run time of various components, service logs, and other information that could assist with patient treatment, diagnostics, and/or service and repair.

Sometimes, clinical personnel have to write by hand the NO drug indication into their records. In order to improve accuracy and safety, in some embodiments the system can show a bar code on the user interface that can be scanned into the hospital system.

In some embodiments, the system can receive compressed air from an external source, such as the hospital air supply or a compressed gas cylinder. This approach can also serve as a back-up air supply in the event that an internal pump/blower fails.

Infection Control

When used with a ventilator circuit, the NO generator is typically located between the ventilator and the humidifier, i.e. the dry portion of the circuit. There is still potential, albeit small, for infectious materials to travel from the patient to the NO generator and contaminate components of the NO generator. This presents a risk of cross-contamination when the NO generator is used to treat a different patient.

In some embodiments, a HEPA filter is located at the outlet of the NO generation device. In systems utilizing a vent cartridge, the HEPA filter would be located on the exit of the vent cartridge. For the purpose of preventing contamination, the filter must be located in series between the NO generator and the patient. In some embodiments, the filter is connected to the humidifier and does not directly contact the NO generator. In addition to preventing transfer of infectious materials from the ventilation circuit to the NO generation device, a HEPA filter between the NO generation device and patient serves to capture any metallic particles or scavenger material particles introduced to the air stream by the NO generator.

Service Life

Each component of an NO generation system has a service life. The enclosure, for example is designed to last 10 years of more. Alternatively, valves are designed for a certain number of cycles. In one embodiment, the NO generation system counts the number of cycles that a valve has undergone. Based on the acceptable number of cycles, the NO generation system can recommend replacement of the valve prior to the service life being exceeded. Similar logging can be done for pump run time, proportional valve cycles, electrical discharge count, and actions that wear components.

When a component is nearing the end of service, the NO generation system can use the back-up NO generation system, leaving the worn component as a back-up rather than the primary thereby prolonging the use of the system with a functional back-up. In one embodiment, the system uses its one or more redundant systems evenly throughout the service life so that components wear at a similar rate across one or more flow paths.

In one embodiment, an accelerometer with in the NO generation system is used to detect vibrations in the system. Vibrations are used as indicators that components are functioning properly. They are also indicators that components have worn and/or are not functioning properly. In one embodiment, the system uses an accelerometer to detect vibrations that are indicative of a worn pump.

In one embodiment, a microphone within the system is used to verify that various components are functioning properly by detecting the sound of various components. Detection of components could be done sequentially as each component is powered or actuated during the power-up-self test.

Gas Analysis

In one embodiment, NO and/or $NO_2$ content within the product gas is measured using spectroscopy. In one embodiment, the spectroscopy is based on infra-red absorption.

System Power-Up Self-Test

In one embodiment, the system directs product gases from the plasma chamber to the gas analysis sensors during power-up self-test to confirm that the gas sensors are functioning and the NO generation system is functioning. In one embodiment, the accuracy of the NO production during power-on self-test is accurate enough that gas sensors can be calibrated. In one embodiment, an alarm prompting gas sensor replacement is generated when either NO or $NO_2$ indicated levels are not consistent with $NO/NO_2$ production settings during self-test NO production.

In some embodiments, the system can be configured with pressure sensors and valves to perform an internal pressure test to sense the pneumatic integrity of the system. In such a self-test, valves are configured to close off air flow. The pump pressurizes all or a portion of the pneumatic pathway. In one embodiment, the pump stops and a leak-down test is conducted by monitoring the drop in pressure within the system over time. In another embodiment, the pump continues operating and the flow through the system is measured, with flow above a certain threshold indicating a leak.

Digital Communications

Electrical discharge events and high voltage can emit electromagnetic emissions that interfere with electrical signals. This can affect analog sensor readings as well as digital communications. In one embodiment, a NO generation system reads sensors and performs digital communications between plasma events. In one embodiment, one part of the NO system generates signal that discharge is about to occur. In one embodiment, the high voltage control circuit sends signal that discharge is about to occur. In one embodiment, the NO generation device uses differential communication signals to provide a level of immunity from EMI.

Power Management

Electrical discharge events can draw high levels of instantaneous power. This can cause current spikes which present challenge to battery powered devices. In one embodiment, current spikes are addressed by hold-up capacitors. In another embodiment, current spikes are addressed by a pre-regulator. In some embodiments, an intermediate power factor correction stage is used to make the NO generation load look to the batteries like a load that the supply can deliver. In some embodiments, Power Factor Correction (PFC) is used to manage the load on one or more batteries to an acceptable level.

Alternative Applications

There are a variety of applications for use of an NO generation system, including for use with patients requiring defibrillation to improve oxygenation and likelihood of heart restarting or regaining normal rhythm. In addition, there is an application of NO for patients experiencing an asthma attack to improve oxygenation, or for sports performance enhancement in various fields, including cycling, football, snow skiing, high elevation compensation, and aviation.

Cloud Connectivity

An NO generation device can benefit from connecting to the internet. Connections may be made by GSM, WiFi, ethernet cable or other means. Once connected the system can exchange information with servers for technical assistance, treatment assistance, billing and other data exchange purposes. The cloud can also be used to transfer treatment data, settings, alarm logs, user comments, service logs, scavenger cartridge status, and other information from one controller to another controller.

Ambulatory Device

There can also be systems and methods for portable and compact nitric oxide (NO) generation that can be embedded into other therapeutic devices or used alone. The portable NO generation device allows NO to be generated and delivered to a patient in any location or setting as the device is small enough to be mobile and used anywhere, including in a home of a patient or during travel. The size and portability of the ambulatory NO generation system allows a patient use the system on-the-go outside a hospital and to have the benefit of NO delivery through a respiratory gas delivery device without having to be in a hospital, clinic or other medical setting. In some embodiments, an ambulatory NO generation system can be comprised of a controller and disposable cartridge. The cartridge can contain filters and scavengers for preparing the gas used for NO generation and for scrubbing output gases prior to patient inhalation. The system can utilize an oxygen concentrator to increase nitric oxide production and compliment oxygen generator activity as an independent device.

The generated NO can be delivered to the patient in a variety of ways. In some embodiments, the NO is delivered through a nasal cannula. The gases exit an array of holes in the vicinity of the nose of the patient and mix in the space between the cannula and the nose. The cannula can include a variety of configurations.

Figure 100A:
FIG. 100A and FIG. 100B are an exemplary embodiment of a nasal cannula prong design for use with an NO generation system.
Figure 100A:
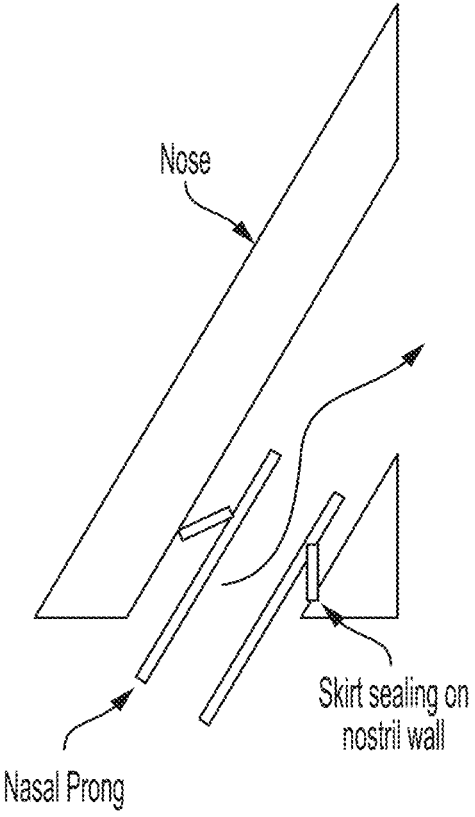
Figure 100B:
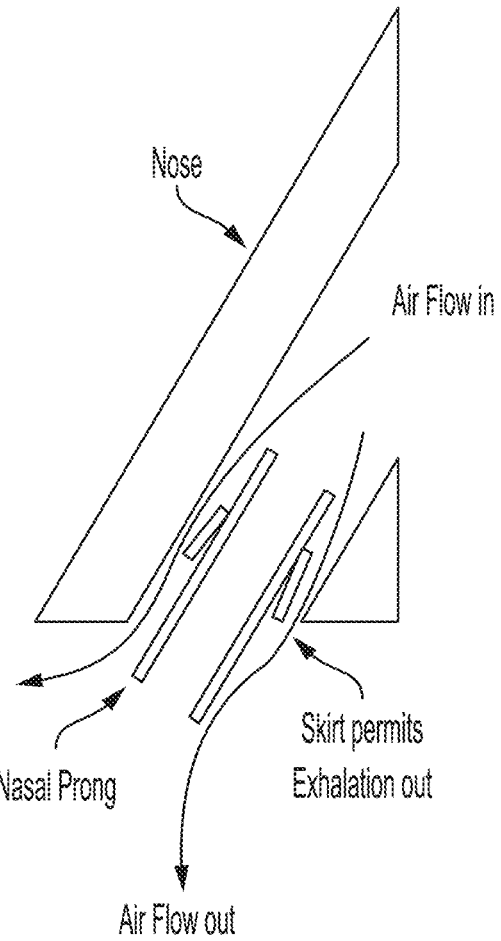

When a patient inspires gas from a nasal cannula, air from the environment entrains and is added to the flow, thereby diluting the gas delivered. In some embodiments, a nasal cannula with unique nose prongs that have a skirt around them can be used to decrease the dilution of the delivered gas. The skirt acts like a check valve, permitting exhalation flow around the prong, but sealing against the nostril wall to prevent entrainment of ambient air. An exemplary nasal cannula 1250 having features to prevent dilution of the delivered gas are shown in FIGS. 100A-100B.

A nasal cannula can also include features to allow for identification of the device. In some embodiments, a nasal cannula can include a unique identifier to allow the cannula to be identified. The unique identified can be positioned in various locations, including in a connector of the nasal cannula. The identifier can have various forms, including an RFID for wireless, a smart chip for direct electrical connection, a smart bar code to be read optically, or any other mechanism that would allow for identification. A controller can monitor how long the cannula is in use and can write to a memory device within the cannula to indicate it is used up and needs to be replaced or repaired. This can also prevent the use of a non-compatible cannula that could result in higher $NO_2$ levels. Other types of information that can be written to the cannula memory device are: part number, lot number, date of manufacture, date of expiration, date of first use, new/used status, patient treatment information, a device settings log, a device alarm log, patient log entries, patient parameter data (respiratory rate, heart rate, body temperature, $SpO_2$ level, $EtCO_2$, activity level).

In some embodiments, a sensor can be placed on the patient to monitor patient breathing. The sensor can be a microphone, pressure sensor, strain sensor, accelerometer or other type of sensor that detect patient breathing. In one embodiment, a microphone is placed on the patient neck. In another embodiment, a strain sensor is placed on the skin of the patients torso. By detecting patient respiratory activity, such as breathing rate, breathing depth, breath pulse shape, the NO generation system can optimize NO delivery. Patient-mounted sensors may be wired to the cannula or directly to the NO generator. In other embodiments, the sensors are wireless and communicate via Wifi, Bluetooth, infrared, RF or some other means to the controller.

Figure 101:
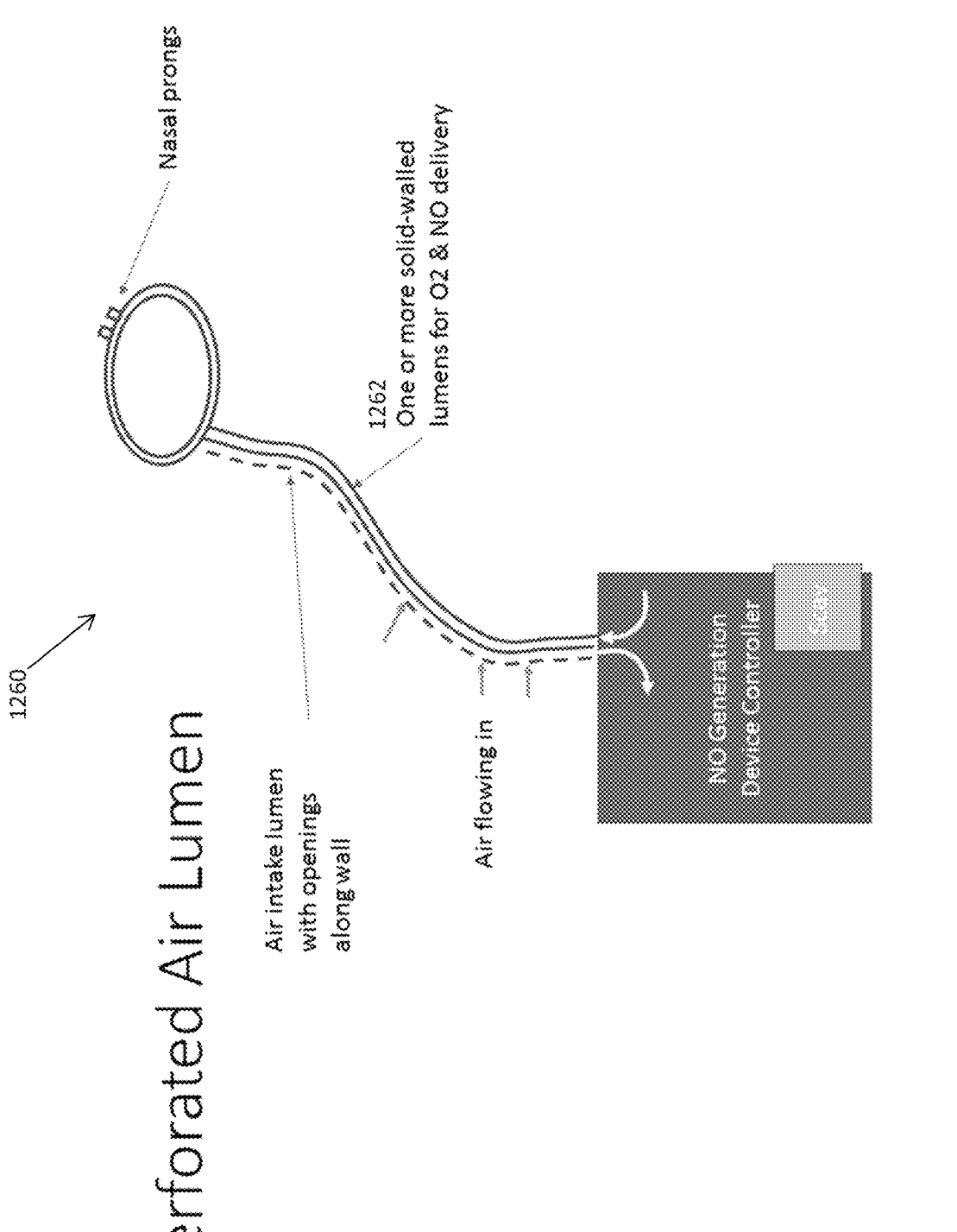
FIG. 101 is an embodiment of a cannula and tubing with a perforated air lumen.

It is important that an NO generation system have a sufficient amount of ambient air to function properly. As the ambulatory system can be located or worn by a user in various locations, including being placed in a bag or worn under an article of clothing, it can be possible that the device cannot source sufficient air to generate a therapeutic amount of NO. It is possible for the cannula to include features to allow for additional air to enter the device. In some embodiments, the cannula can include one or more extra lumens for sourcing air. The air lumen can have one or more openings (such as perforations) so that air can enter the lumen from anywhere along the length of the cannula. The perforations help ensure that the device can pull air from somewhere along the length of the cannula. An embodiment of a cannula 1260 with an additional lumen 1262 is shown in FIG. 101.

Figure 102:
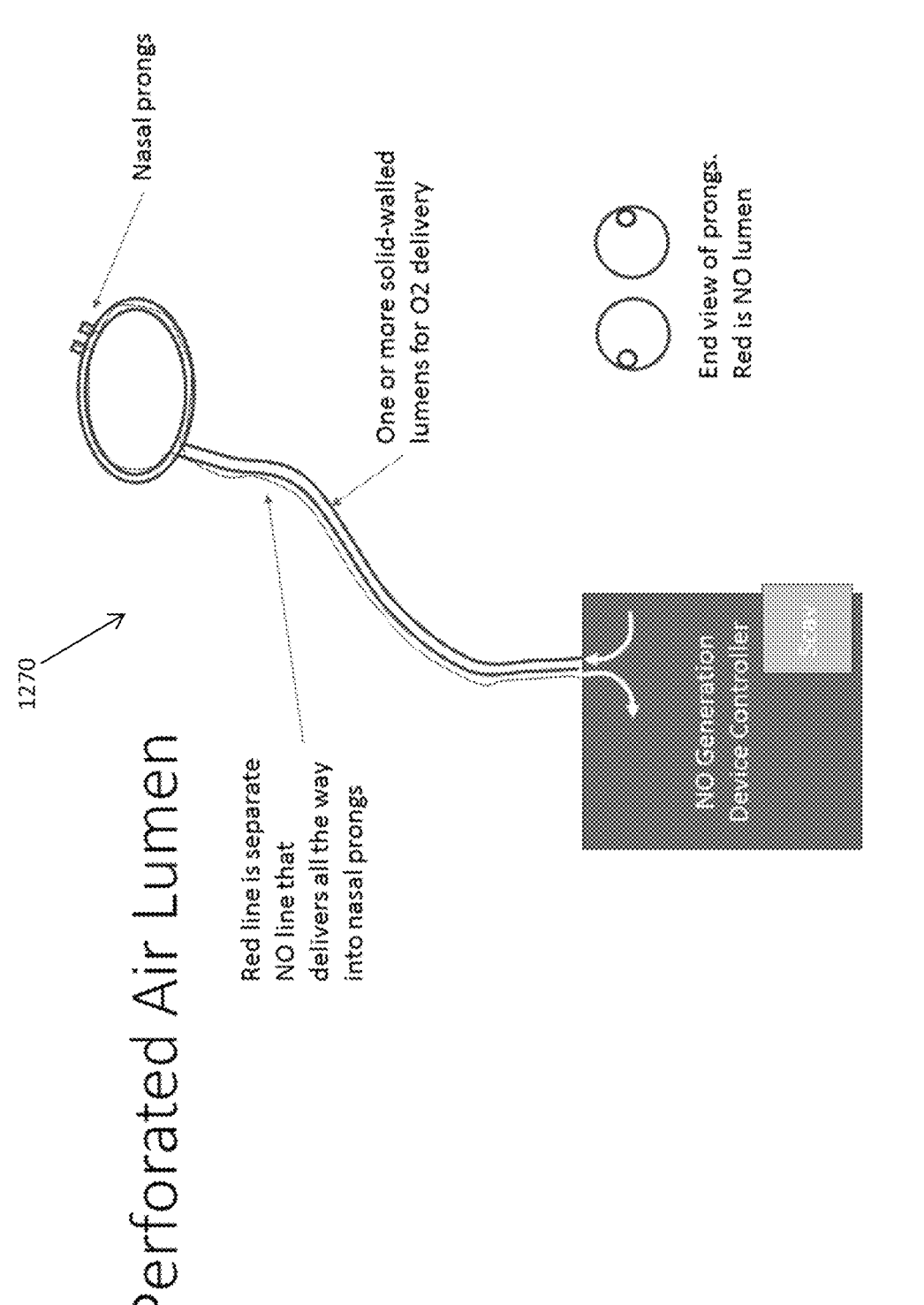
FIG. 102 is an embodiment of a cannula and tubing with a perforated air lumen.

In some embodiments, a nasal cannula can include one or more small NO tubes that go through each prong so that $O_2$ does not suppress NO flow due to its greater flow rate and pressure, as shown in the exemplary cannula 1270 shown in FIG. 102. In some embodiments, a nasal cannula can use a venturi or jet configuration to draw NO into the $O_2$ flow.

Figure 103:
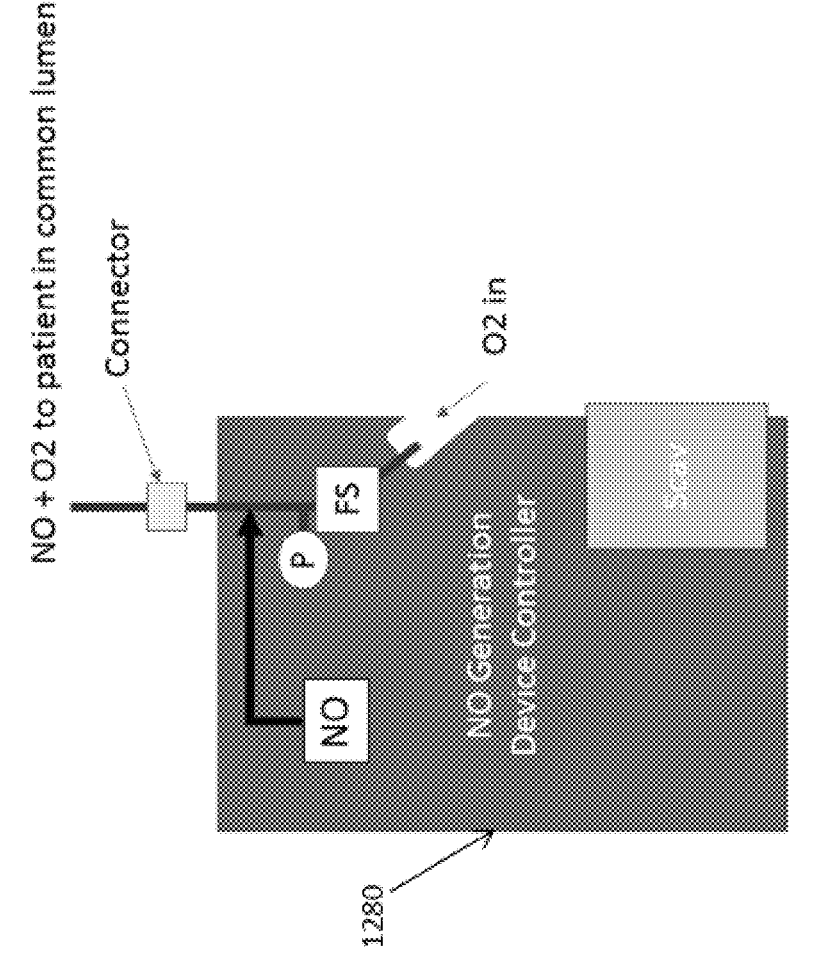
FIG. 103 is an embodiment of an ambulatory NO generation device.

There are different points along the cannula at which the $O_2$ and the NO can be mixed before the gases reach a patient. In some embodiments, it is possible to keep the NO and the $O_2$ separate as long as possible until it enters a patient's nose in order to reduce $NO_2$ formation. The $NO_2$ formation due to high NO concentration is the predominant effect. In some embodiments, it is possible to mix NO with the $O_2$ flow as soon as possible so that transit time to the patient is reduced. Thus, an ambulatory device that introduces high concentration NO to the $O_2$ flow within the ambulatory device can offer reduced $NO_2$ levels at the patient, as shown in an embodiment of an NO generation device 1280 shown in FIG. 103. In some embodiments, the device 1280 shown in FIG. 103 can measure the flow of 02 and scale NO delivery accordingly. As shown, the device 1280 can include a flow sensor (FS) and a pressure sensor for detecting inspirations (P). NO and $O_2$ can be mixed within the device controller such that the NO reaches a patient faster, reducing the amount of time that the NO can degrade.

Figure 104:
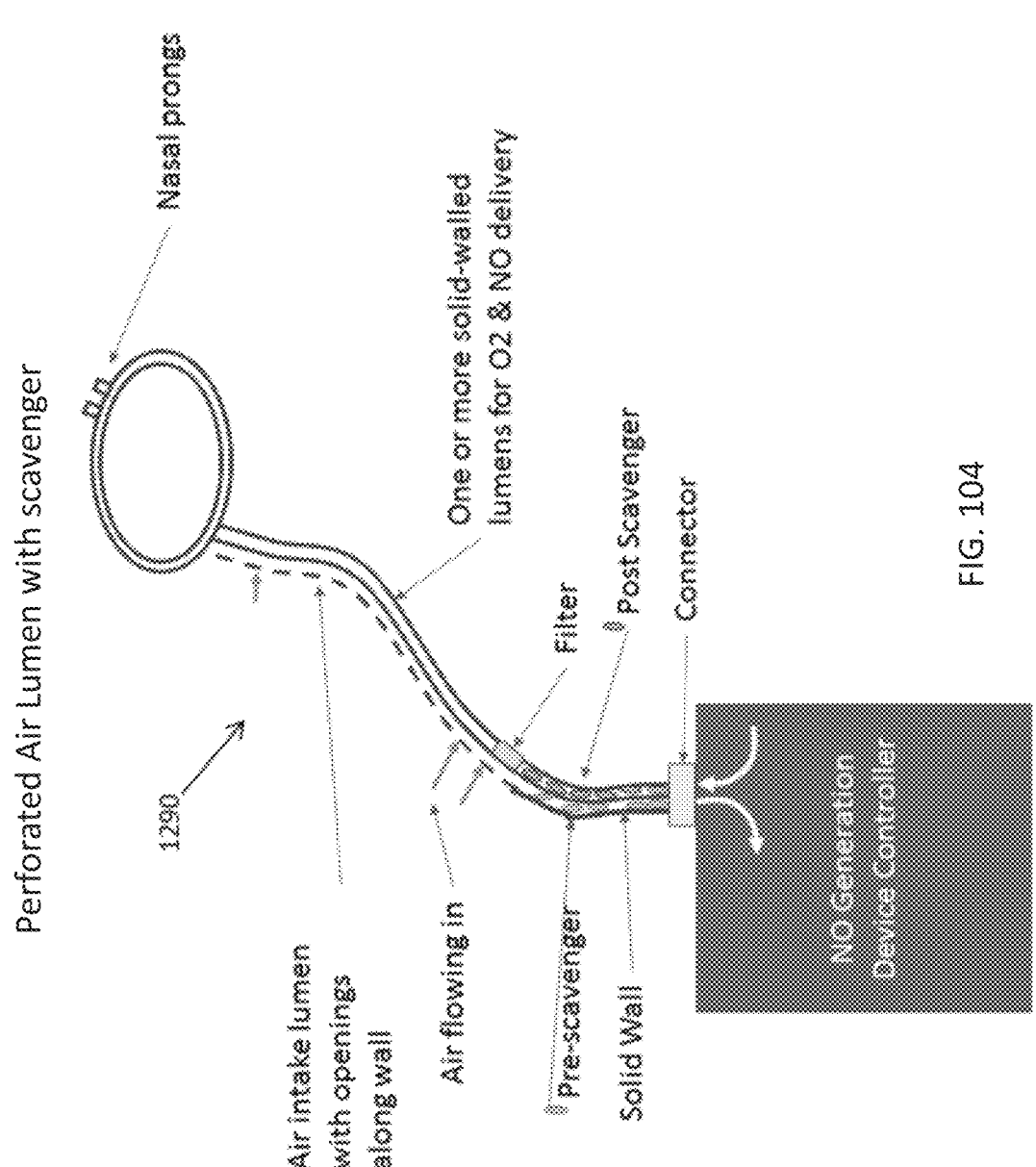
FIG. 104 is an embodiment of a cannula and tubing with a perforated air lumen and scavenger.
Figures 105A, 105B, 105C, 105D, 105E:
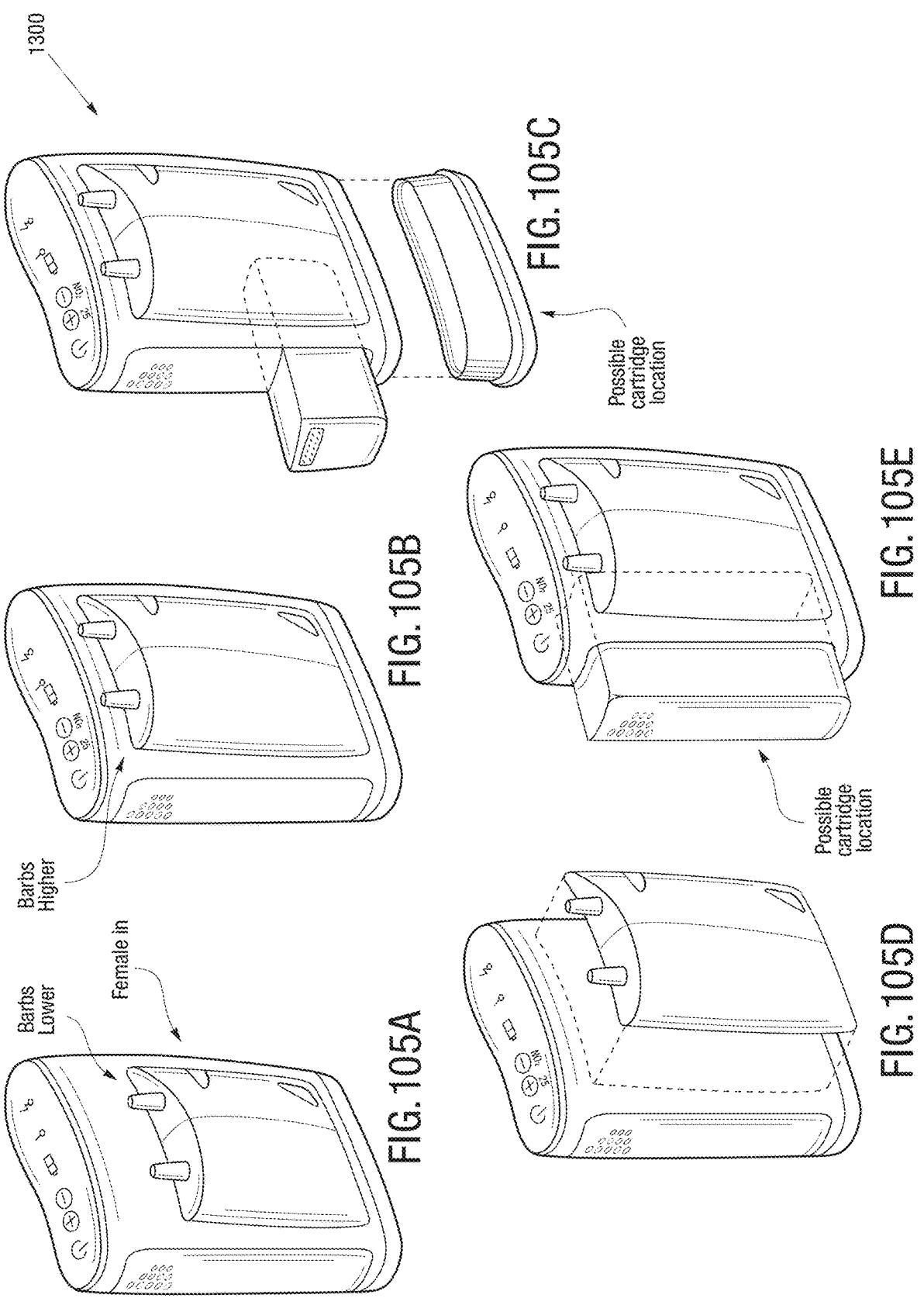
FIGS. 105A, 105B, 105C, 105D, and 105E are multiple view of embodiment of an ambulatory NO generation device.

There can be various ways to utilize scavenger material in an ambulatory NO generation system. In some embodiments, a cannula tube that is thin walled (as opposed to thick kink-proof versions) that is filled with scavenger material partially or completely along its length can be used. In some embodiments, a nasal cannula with pre-scavenger in addition to NO scavenger can be used. A controller does not have a cartridge at all, such that the system has one disposable component (a cannula 1290) instead of a cannula and a scavenger cartridge, as shown in FIG. 104. In some embodiments, a nasal cannula 1290 can include a scavenger near the point of inspiration (i.e. close to the nose). As shown in FIG. 104, air can flow into the cannula through perforations. Incoming air can be pre-scavenged within the nasal cannula. As shown, gas including NO and $NO_2$ can leave the device and can be scavenged in the delivery lumen. A filter, as shown in FIG. 104, can be used to prevent particulate from the scavenger from reaching the patient.

Figures 106A, 106B:
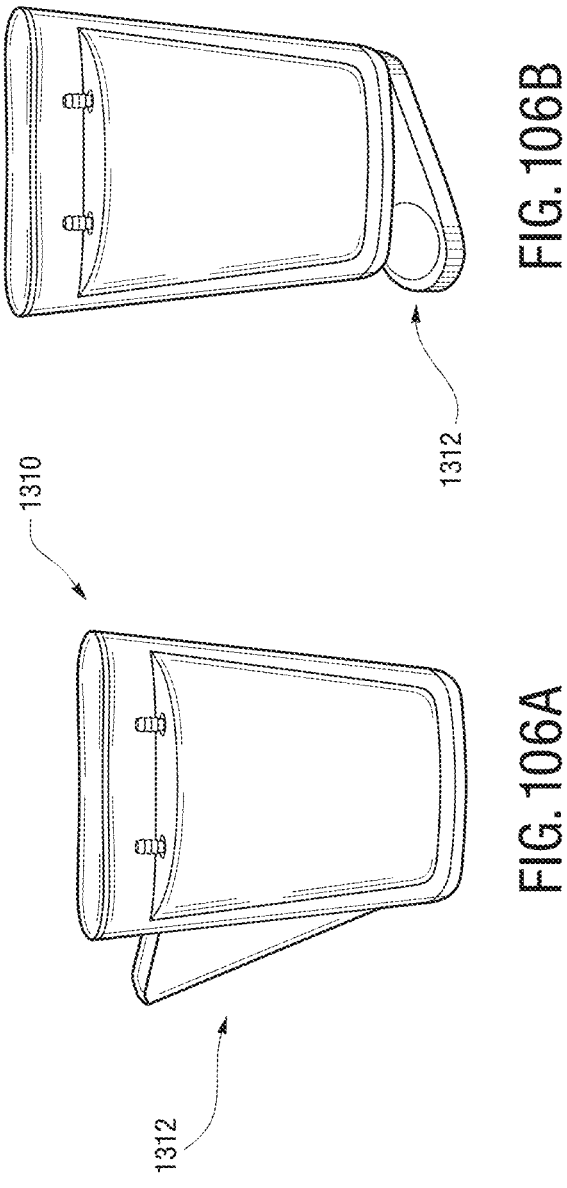
FIGS. 106A and 106B illustrate embodiments of an NO generation device with a scavenger cartridge located at side and bottom of the device, respectively.
Figure 107A:
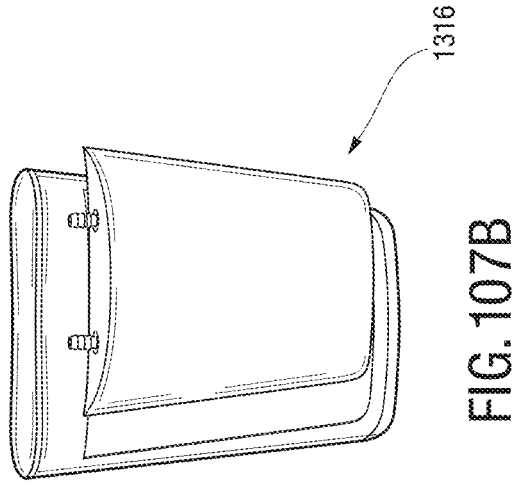
FIGS. 107A and 107B illustrate embodiments of an NO generation device with a user interface and a scavenger cartridge on side surfaces of the device.
Figure 107B:
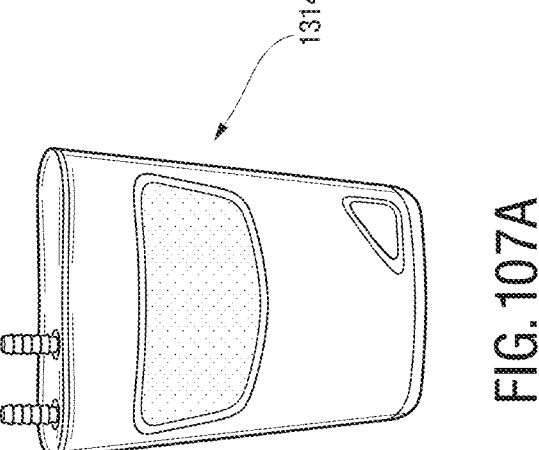

FIGS. 105A-105E are multiple views of an embodiment of an ambulatory NO generation device 1300. In some embodiments, a top of the device can be reserved for a user interface including but not limited to buttons and display information. Cannula and oxygen connections can be made on an upper edge of a bump on the side of the enclosure. The scavenger cartridge 1312 can be located in several locations, including the side (as shown in FIG. 106A) and the bottom (as shown in FIG. 106B) of the device 1310. In some embodiments, cannula and $O_2$ connections are on the top of the device. The user interface 1314 is on the side, as shown in FIG. 107A. The scavenger 1316 can be on the side, as shown in FIG. 107B, or bottom of the device.

Various methods can be used for respiration detection. In some embodiments, a wire runs up one tube and down the other tube of a nasal cannula. Between the nostrils, there is a piece of Mylar with sputtered aluminum (like a thermistor). Respirations are detected by looking at the changes in resistance of the thermistor, indicating the warmth of exhalation of cooling of inhalation. Two wires could run in one tube as well. In some embodiments, sensing can also be done by stretching the wire to be thinner in the area of temperature sensing. In some embodiments, a barb of a nasal cannula can be metallic and conductive so that it is part of the thermistor circuit. This works best when there is wire in two lumens and two barb connections to the controller. In some embodiments, a thermocouple under the nose can be provided. In some embodiments, an NO delivery device can include a cannula NO lumen that bifurcates as it reaches the controller. One lumen connects to the scavenger and the other lumen connects to a blind hole with a pressure sensor for detecting respirations. In some embodiments, an NO delivery device is provided where an NO line pressure is sensed within the controller near the cannula connection point so that patient respirations can be sensed via pressure.

Figure 108:
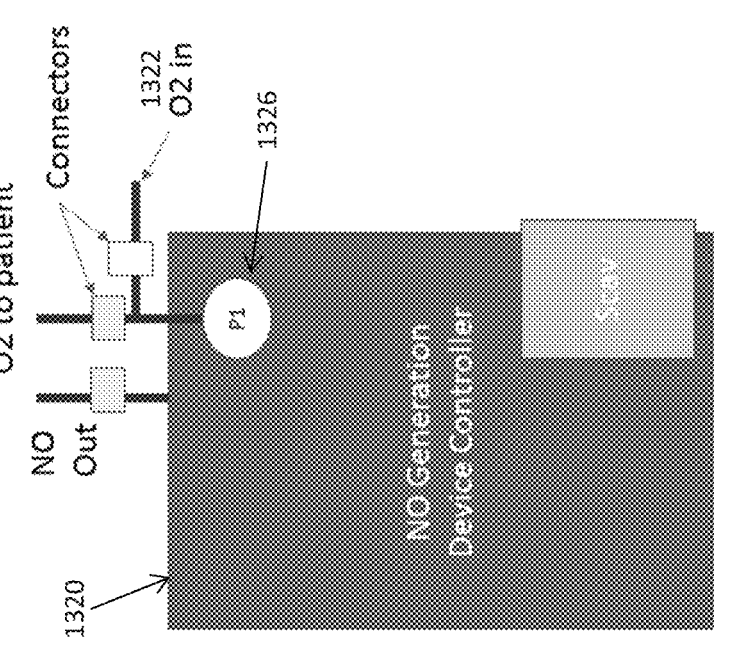
FIG. 108 is an embodiment of an ambulatory NO generation device.

Various mechanisms can be used for respiration detection relating to activity of an $O_2$ concentrator. In one embodiment, an NO delivery device 1320 is provided with a T-fitting that receives $O_2$ from an $O_2$ source 1322, sends $O_2$ to patient 1324 (via a cannula), and has a pressure sensor 1326 within the controller at the bottom of a blind hole, as shown in FIG. 108.

Figure 109:
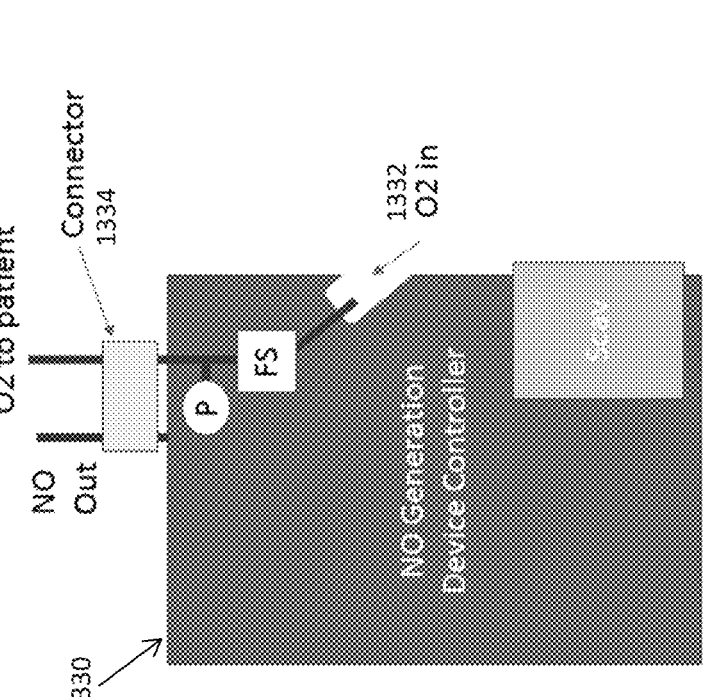
FIG. 109 is an embodiment of an ambulatory NO generation device.
Figure 110:
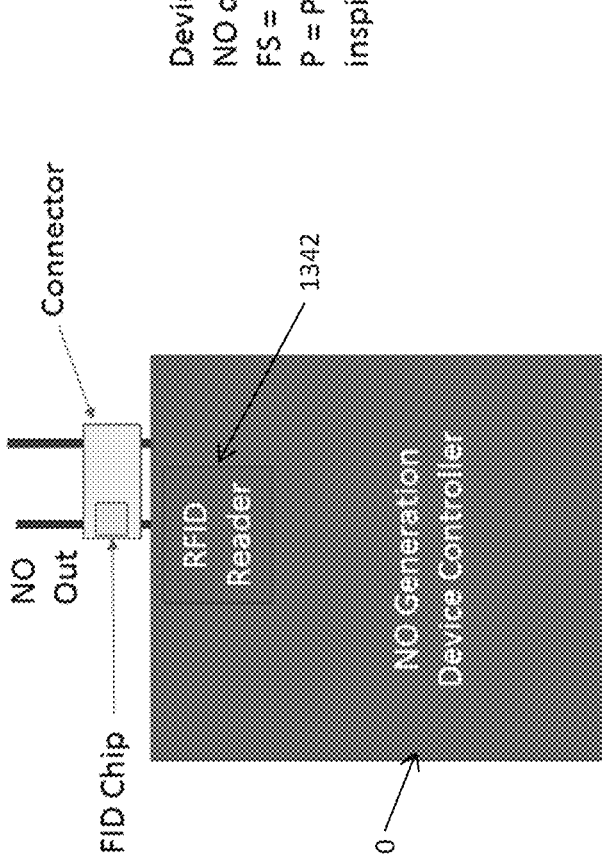
FIG. 110 is an embodiment of an ambulatory NO generation device.

In some embodiments, an NO delivery device 1330 is provided with an $O_2$ input connection 1332 and separate $O_2$ output connection 1334, as shown in FIG. 109. Between the two connections, the system senses pressure and/or flow to detect oxygen concentrator activity. NO and $O_2$ have separate output connections. There can be a single exit point with NO and $O_2$ combined. In some embodiments, an NO delivery device 1340 is provided that works in conjunction with an $O_2$ concentrator that includes a mechanism, such as an RFID reader 1342, to communicate with the NO delivery device, as shown in FIG. 110.

NO can be delivered to a patient using various techniques relative to the inspiration of the patient. In some embodiments, a molecular sieve can be used to decrease $O_2$ content in the gas after sparking. Removal of $O_2$ can decrease the rate of conversion to $NO_2$.

In some embodiments, an NO device that can operate in one or more modes, including a synchronized mode with pulsed NO delivery delivered in sync with $O_2$ delivery, an independent mode with pulsed NO delivery delivered in sync with patient respirations, and a constant mode with constant NO flow rate and concentration. In one embodiment, the NO delivery pulse begins 50 msec after inspiration detection and lasts 200 msec. In another embodiment, the NO delivery pulse lasts the duration of inspiration.

A patient's respiratory rate may vary with effort. Faster respiratory rates could lead to excessive NO delivery if the NO generation system delivers NO with every breath. It should also be noted that respiratory depth can vary as well and is generally independent of respiratory rate. For NO treatment to be effective, the concentration of NO in the patient lungs should be at therapeutic levels periodically, if not continuously. In one embodiment, the NO generation system uses respiratory rate, tidal volume and NO half-life to determine which inspirations to dose. In another embodiment, NO is delivered with each breath but pulse parameters are varied based on respiratory rate, tidal volume, entrainment fraction and NO half-life to achieve target NO concentration within the lung. In one embodiment, the NO generation system has a maximum number of breaths that it will dose per unit time. Based on a moving average, if the number of dosed breaths per unit time exceeds a threshold, the device stops NO delivery until the moving average falls below the threshold.

Respiratory events occur quickly, requiring a fast system response to deliver an NO pulse. In some cases, the pulse is delivered 50 msec after inspiration detection, which is faster than a pump could increase speed (i.e. spin up) and push a bolus of NO-containing gas into the nose. In one embodiment, an ambulatory device prepares a bolus of NO-containing air in a reservoir during patient expiration. When an inspiration is detected, air from a compressed source is released, pushing the NO bolus through the cannula to the patient. In one embodiment, the staging reservoir is a lumen within the cannula. In one embodiment, the lumen within the cannula is a dedicated NO-delivery lumen. The NO-containing gas can pass through a scrubber before staging in the reservoir, after the reservoir, at a location near the patient within the cannula, or not at all if $NO_2$ levels are sufficiently low.

As the ambulatory device can be placed in various locations, including on an $O_2$ generator trolley or a battery charger (for example, positioned at a 45 degree angle for stability and ease of reading a display), or be worn by a patient, for example on a belt, in a bag or worn under a coat, it is possible for the device to overheat. In some embodiments, the air that is used to generate NO could be run over heat exchangers to cool the electronics. In one embodiment, the NO generator is located at the air inlet for an $O_2$ concentrator.

Some users can prefer to connect to a stationary $O_2$ concentrator when at home and use a line, such as a 50 foot (15 m) line, to receive $O_2$. The transit time of NO in a 50' line could be long enough that unsafe levels of $NO_2$ can form. In some embodiments, a line, such as a 50' line, can be provided with proprietary connectors that have an $NO_2$ scavenger at the patient end to remove $NO_2$ close to the patient. For example, a connection could involve a custom thread, an RFID, a bar code, or other features.

Various safety features can be included with an ambulatory NO generation device. It is possible for users to forget to replace the $NO_2$ scavenger component at appropriate times. In some embodiments, a device can prompt a user to replace a scavenger when they remove the device from the charger in the morning. In some embodiments, an ambulatory device can include a built in accelerometer to detect patient activity. In some embodiments, an ambulatory device can include features to detect patient exertion and provide a warning. The warning can be based on various measurements and data, including accelerometer data and/or respiratory rate.

NO delivery tubing can be kinked during operation, potentially slowing or stopping NO delivery to the patient. In some embodiments, the system can use various indicators to detect a kinked line, including but not limited to NO line pressure, $O_2$ line pressure, NO pump current, NO line flow, $O_2$ line flow, respiration signal fidelity, spark activity (suppressed by high pressure).

It can be possible that patients that breathe through their mouth do not receive the same dose as when they breathe through their nose when wearing a nasal cannula. In some embodiments, the system can detect inadequate nasal respiration and/or mouth breathing and can respond by increasing the NO delivery to accommodate and/or warning a user. If the system is able to deliver NO to the patient (pump current is normal, NO flow is normal) but the system is not able to detect respirations at the nose, then the patient is probably breathing through their mouth.

Figure 111:
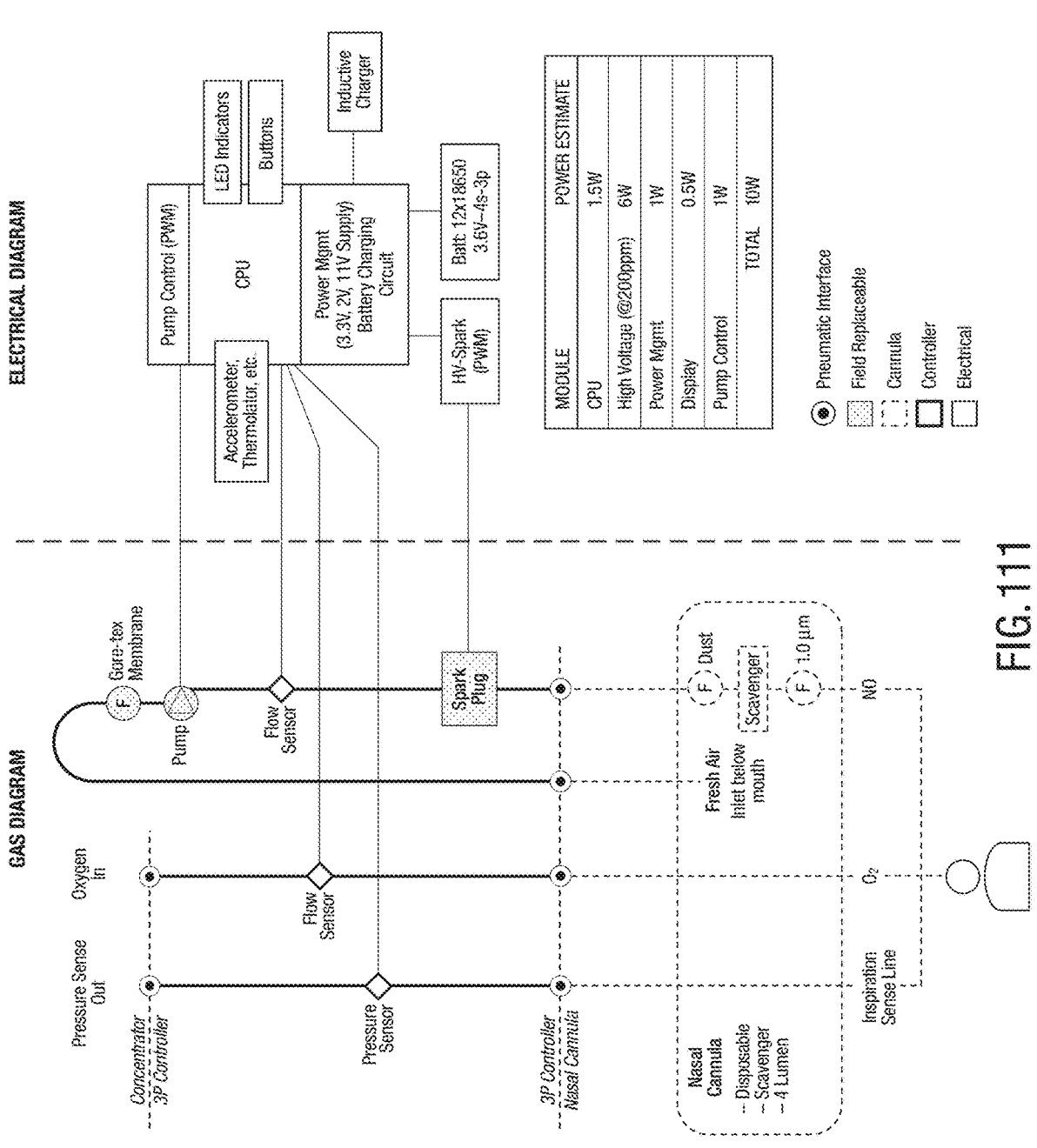
FIG. 111 is an embodiment of an ambulatory NO generation system.
Figure 112:
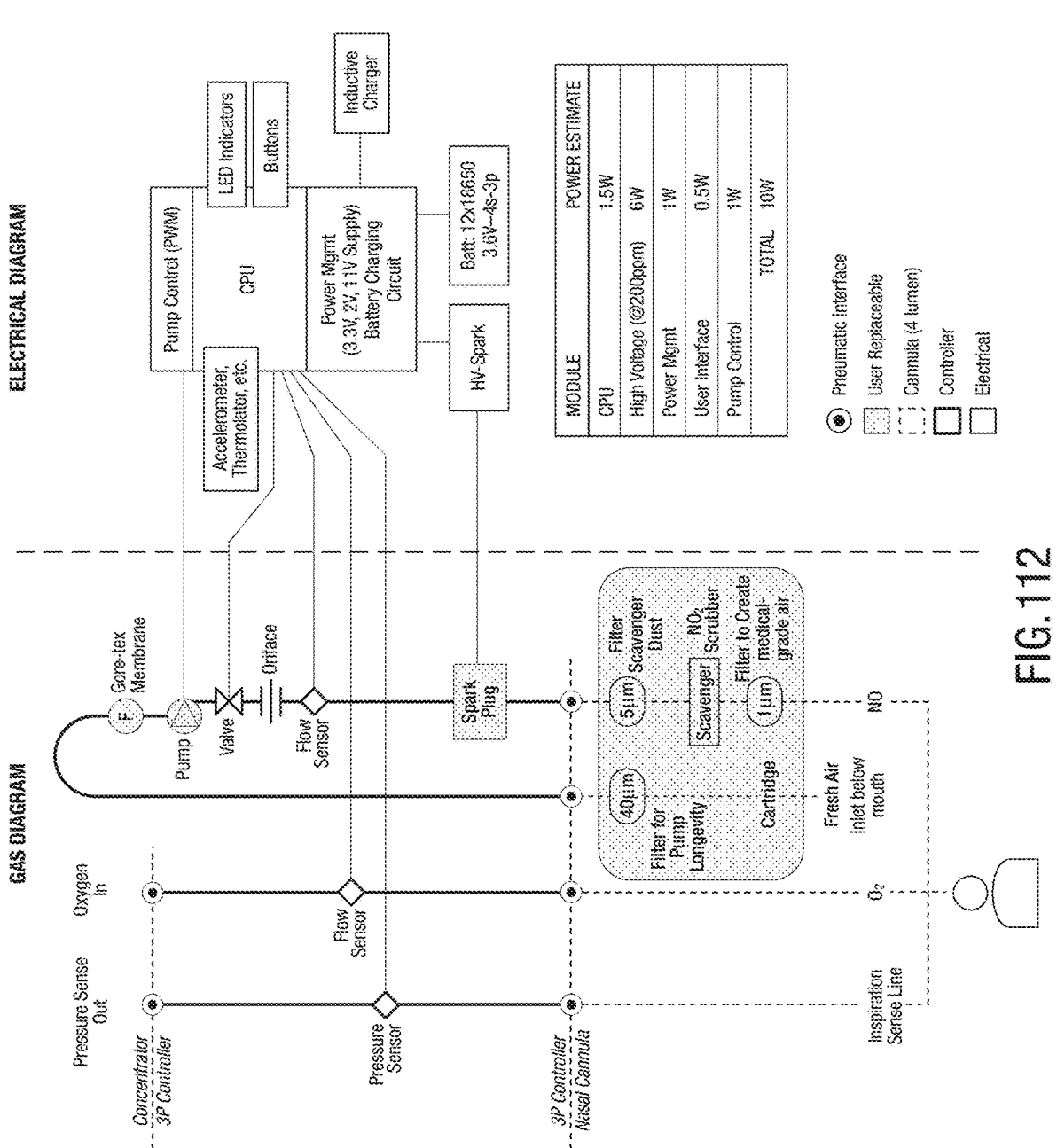
FIG. 112 is an embodiment of an ambulatory NO generation system.

FIGS. 111 and 112 illustrate embodiments of ambulatory NO generation systems. FIG. 1111 illustrates an embodiment of a portable ambulatory NO generation system that includes a delivery device, such as a cannula, for delivering a product gas containing NO to a patient, which includes a filter/scavenger. A controller is configured to control the production of NO by a plasma chamber using a variety of sensors. The controller includes a CPU with LEDs and buttons for communication therewith by a user, a high voltage circuit, a power source, an inductive charger, and a pump controller. FIG. 112 illustrates an embodiment of a portable ambulatory NO generation system that includes a delivery device, such as a cannula 32, and a disposable replaceable cartridge 34 that includes a scavenger therein.

Figure 113:
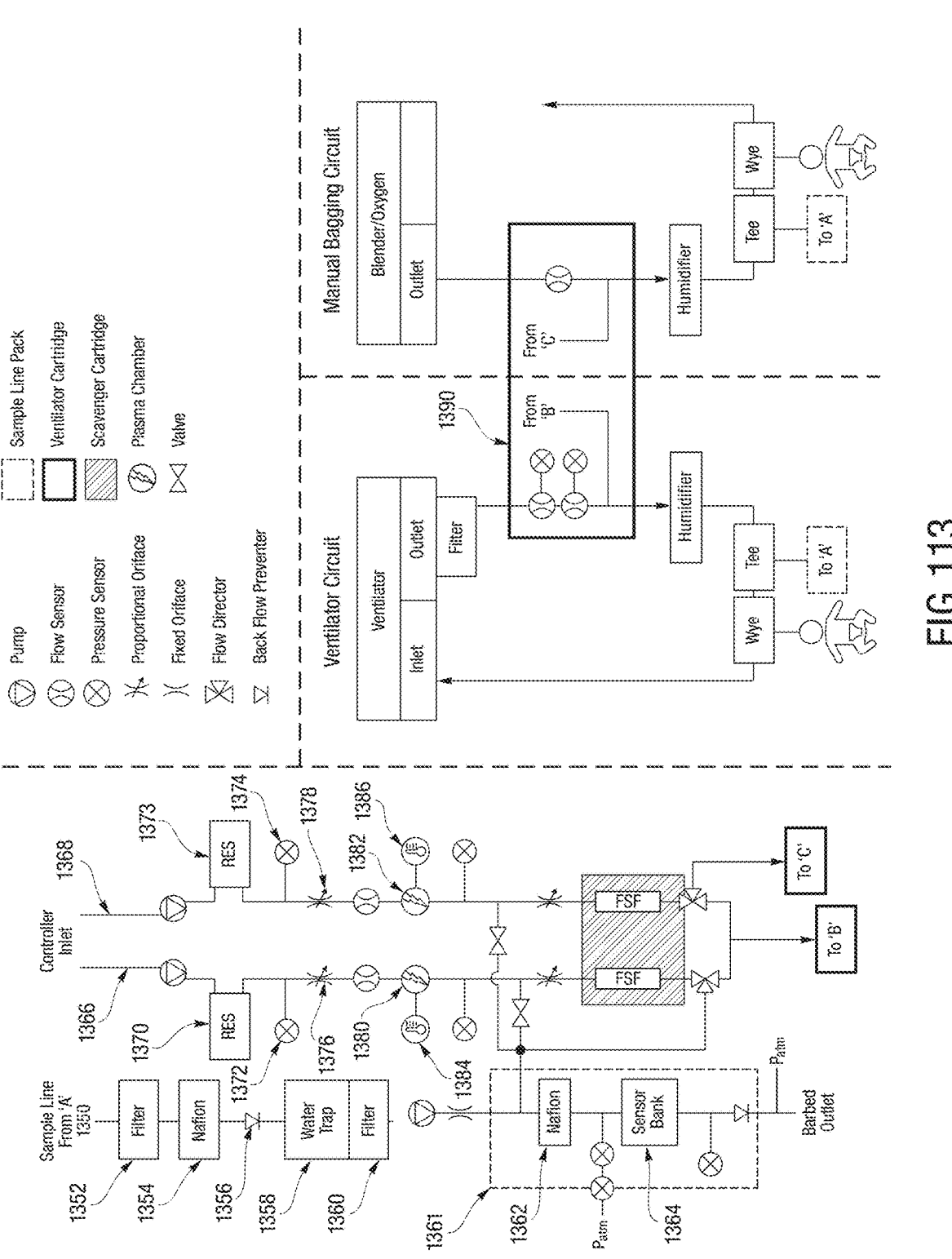
FIG. 113 is an embodiment of an NO generation system with redundancy.

FIG. 113 illustrates an embodiment of an NO generation system with redundancy. In the upper left of the figure, sample gases from an inspiratory flow enter a sample line 1350 and travel through a filter 1352 and Nafion tubing 1354 to remove humidity from humidified samples and add humidity to dry samples. The gas then flows through a 1-way valve 1356 that prevents contents from the gas sensor circuit from entering the patient airway. The gas flows through a water trap 1358 that removes humidity followed by a hydrophobic filter 1360 and into a sample gas pump. Beyond the pump is a critical orifice that governs the flow of gas through the sensors manifold 1361 and diminishes pulsatility in the flow from the pump. Gases pass through a second Nafion tube 1362 that protects the sensors in the case that dry gases as would be used during calibration are sent through the sensor pack. Pressure sensors monitor the flow and pressure through the sample pack. The gas then passes by gas analysis sensors and on past a pressure sensor and one-way check valve. Sample gases exit through a T-fitting that has one leg open to atmospheric pressure and provides a barb or small bore connector on the other leg for connection to hospital vacuum. The open leg to atmospheric prevents vacuum pressure from increasing the flow rate through the sensor pack and/or pulling more gases from the patient inspiratory flow than required.

In the middle-top of the figure, two independent flow paths 1366, 1368 provide reactant gases to two pumps. The pumps pressurize two independent reservoirs 1370, 1372 to a target pressure. In one embodiment, the target pressure is 2 atm. In each circuit, past the reservoir there is a pressure sensor 1372, 1374 for closed loop-feedback on reservoir pressure. This sensor could also be before the reservoir or within the reservoir so long as it is in fluid communication with the reservoir. A proportional valve 1376, 1378 regulates the exit flow from each reservoir. A flow sensor is used for closed-loop feedback to the proportional valve. Gases pass through a plasma chamber 1380, 1382. The plasma chambers shown include a temperature sensor 1384, 1386 on the chamber wall that can be used for NO algorithm tuning and closed-loop feedback to the device enclosure fan. Pressure sensors in fluid communication with the plasma chambers are used as input into the control algorithm to calculate NO production.

Beyond the plasma chamber and pressure sensors, the flow paths bifurcate. Shunt paths with a valve provide a means to drive product gases to the gas sensor pack for analysis. Proportional valves after the bifurcation can be used to provide a back pressure within the plasma chamber to compensate for elevation effects and low ambient pressure. The valves use a smaller orifice at higher elevations to increase back-pressure within the plasma chamber and increase NO production. After the proportional valves, product gas flows through a scavenger cartridge containing a filter, scavenger and filter (FSF) for each of the two paths. A first path is dedicated for ventilator applications while the second path may scrub gas for a ventilator or a manual bag circuit, depending on the position of a flow director in the second path. A proportional valve located after the FSF in the first (Figure left) flow path provides a means to sample gases post-FSF as well as evens the flow restriction between the sides.

Product gases flow to a ventilator cartridge 1390 through Channel B for ventilator applications of Channel C for manual bagging. Inspiratory gases from a ventilator enter the ventilator cartridge through a standard 22 mm connection prior to flowing through two flow sensors. Each flow sensor reports to a separate NO generator within the device for total redundancy. Pressure and/or humidity are also measured at the flow sensors. NO in injected into the patient airstream after the flow measurements and prior to gases exiting the vent cartridge through a second 22 mm fitting. The vent tube fittings can vary with application, from 10 mm for neonate circuits to 15 mm for pediatric applications. The flow sensors can detect reverse flow so the system can report an alarm if the ventilator circuit tubes have been connected in reverse.

Bag flow comes from an external source which could be an oxygen cylinder, blender, wall air, wall $O_2$, oxygen concentrator or another source. The flow connects to the ventilator cartridge with a pneumatic connection, such as small bore or barb fitting. The flow rate is measures by a flow sensor. In the embodiment depicted, flow is measured by a differential pressure sensor prior to the injection of NO-containing product gas. The flow then exits the vent cartridge through a similar small bore or barb connector and on to the manual respiration airway.

Current methods of NO therapy monetization on the market involve reading memory devices on gas cylinders or downloading use data from a controller to a portable memory device or writing down use data from an information screen. A wireless communication device can be incorporated in an NO generation device for the purposes of billing. This same capability can be used for remote support, monitoring and diagnostics too. The benefits of this concept are several-fold: reducing labor involved in obtaining billing information (it's automatically uploaded to the cloud), reducing labor involved in processing billing information (it's automatically calculated on one or more servers), improving tracking use of devices for service calls, and locating devices within a site.

Electromagnetic Interference (EMI)

Reactant and product gases are routed into and out of the plasma chamber, respectively. The plasma chamber is a source of electromagnetic emissions. Plastic tubing carrying the reactant gas present a portal of electromagnetic emissions where they connect to the plasma chamber.

In some embodiments, the plastic tubing is covered with an electrically-conductive mesh along its length from the plasma chamber to at least the first 90 degree bend. In some embodiments, metallic tubing is used to convey reactant and product gases to and from the plasma chamber to absorb EMI. In some embodiments, the manifold is made from metal or has a metallic coating. The manifold is designed so that there is no straight path from the exterior of the manifold to the plasma chamber that would provide a conduit for EMI to escape. In some embodiments, one or more grounded flame arrestors in the gas pathway upstream and/or downstream of the plasma chamber can be used to absorb EMI generated by the electrical discharge.

Modules

Systems and methods of nitric oxide generation and/or delivery for use in various applications can also be in the form of a module for use with various types of medical equipment and machines, such as various ventilation and respiratory devices.

In some embodiments, nitric oxide generation and/or gas sensing modules can integrate with a respiratory device by sharing resources and/or being fully embedded therein. The various NO generation modules or NO generation devices can control the generation of NO in a variety of ways. In some embodiments, an NO generation device or module can control NO generation by varying the air flow through a plasma, for example, to match a ventilator flow.

In some embodiments, an NO module can be configured to be removably inserted into module bay of a patient monitor. In some embodiments, an NO module can be physically integrated into a patient monitor. In some embodiment, an NO module can include a spirometry interface to an inline sensor and NO feeder assembly. The spirometry sensor can be thermistor based, ultrasound based, hot wire anemometer based, acoustic, microphone based, delta pressure based, single pressure based or other means. The NO module can include separate incoming air filter and NO scavenger components, or can include a combined air filter and NO scavenger.

A patient monitor can include a dock to receive an NO generation module. The patient monitor can have NO generation capabilities (embedded or removable) and replaceable air filter and $NO_2$ scavenger. In some embodiments, a patient monitor with NO generation capability can be coupled to a ventilator and can receive patient spirometry data from the ventilator, either using a wired or wireless connection. In some embodiments, a patient ventilator with NO generation capability can be coupled to a patient monitor, receiving patient $SpO_2$ data from the patient monitor, using a wired or wireless connection.

Numerous medical procedures involving a variety of equipment can be used to treat patient with the use of nitric oxide. Various types of equipment can be used to deliver air to a patient, including ventilators, anaesthesia machines, and C-PAP machines. There are also various types of equipment used to oxygenate patient blood, including ECMO systems that can add nitric oxide to the air/gas mixture. In some embodiments, a nitric oxide generation module can be integrated into various types of equipment such that machines/equipment from multiple suppliers of such equipment can have access to a source of nitric oxide. The NO generation module can leverage various resources within the primary equipment, including but not limited to electrical power, gas supply or oxygen and/or compressed air, treatment parameters (e.g., flow, volume, and/or pressure), a user interface, and/or alarm hardware.

An NO generation module coupled to or embedded within a medical machine/equipment can decrease user-established pneumatic connections. Pneumatic connections can take time to establish, can leak, and embedding an NO generator in an existing machine/controller can eliminate the need for a user to connect the air-delivery equipment to an external NO generator, thus reducing the number of connections to the machine. Shared hardware between the module and the equipment, such as a ventilator, can eliminate some redundancy and can help reduce power consumption and improve electrical power efficiency of a given treatment.

Improved accuracy of treatment parameters can be achieved when using a NO generation module. In some cases, an external NO generator senses ventilator activity with a sensor, such as a flow sensor and/or pressure sensor. An embedded NO generator, such as an NO generation module, can receive ventilator flow information directly, including flow rate, flow pressure, ventilator mode (pressure control, volume control, high frequency), and breath timing. This can improve accuracy of treatment by eliminating sensor and algorithm inaccuracies, and reducing lag time required to sense, process, and react to sensor readings.

User confusion about oxygen concentration being delivered to the patient can also be reduced. An external NO generation device can dilute the oxygen concentration in the gases exiting the ventilator, thus the NO generation device must have its own $O_2$ sensor which can have a different reading than the ventilator. This can introduce user uncertainty. In an integrated approach using an NO generator module, the ventilator can measure $O_2$ at the ventilator exit, thereby measuring $O_2$ in a single location that includes the effect of the NO generation module and its potential $O_2$ dilution.

The NO generation module can also make use of a display on an associated machine or medical device. For example, when coupled to a ventilator, NO generation-related information can be displayed on the ventilator display, including but not limited to target NO concentration and actual NO concentration, along with a plurality of ventilation parameters. This allows information to be displayed to the user on a single display rather than having two screens with redundant and/or conflicting information. The alarm information can also be consolidated into a single priority list such that multiple alarms from multiple sources (i.e. the respiratory machine and the NO generation device/module) are not alerting a user and creating confusion about alarm priorities and importance.

An NO generation module can be used with a ventilator. In some embodiments, an NO generation module can be removably inserted into a docking location in a ventilator enclosure and can be replaceable by a user when necessary. In some embodiments, an NO generation module can be fully or partially enveloped within a ventilator enclosure and can be a permanent feature, as long as there is the capability of user access to the module to allow for the replacement of certain portions of the module, such as scavenger material, electrodes, and/or other consumables. In both cases, the NO generation module can source power and input parameters such as target NO settings from the ventilator. In some embodiments, filtered air for NO generation can be sourced from the ventilator or the compressed gas supply of the treatment site. In some embodiments, the NO generation module can use an internal pump to source ambient air from the room. The NO generation module can send to the ventilator the status of NO production, any alarm conditions, and/or NO and $NO_2$ concentrations (if the module include gas sensors). In both cases, scavenger material for the removal of $NO_2$ can be consumed by the NO generation process. Scavenger material can be inserted into the module or the ventilator in the form of a cartridge that is removable and replaceable. In some embodiments, the ventilator can have a scavenger chamber within the flow path of ventilation gases. The loose scavenger material in the chamber can be replaced periodically, based on the amount of $NO_2$ absorbed, treatment time, single patient use, or other rationale. It will be understood that any of the NO generation modules described herein can include scavenger material that can be used for the removal of $NO_2$ from the gas. The synergy between the ventilator and the NO module can reduce the number of components required to generate NO for a ventilator circuit. This can save weight and volume of the combined devices, which can be important for in-hospital or between-hospital transport. In some embodiments, some ventilators can have a humidification feature. NO can be added to the ventilator flow before or after humidification.

Figure 114:
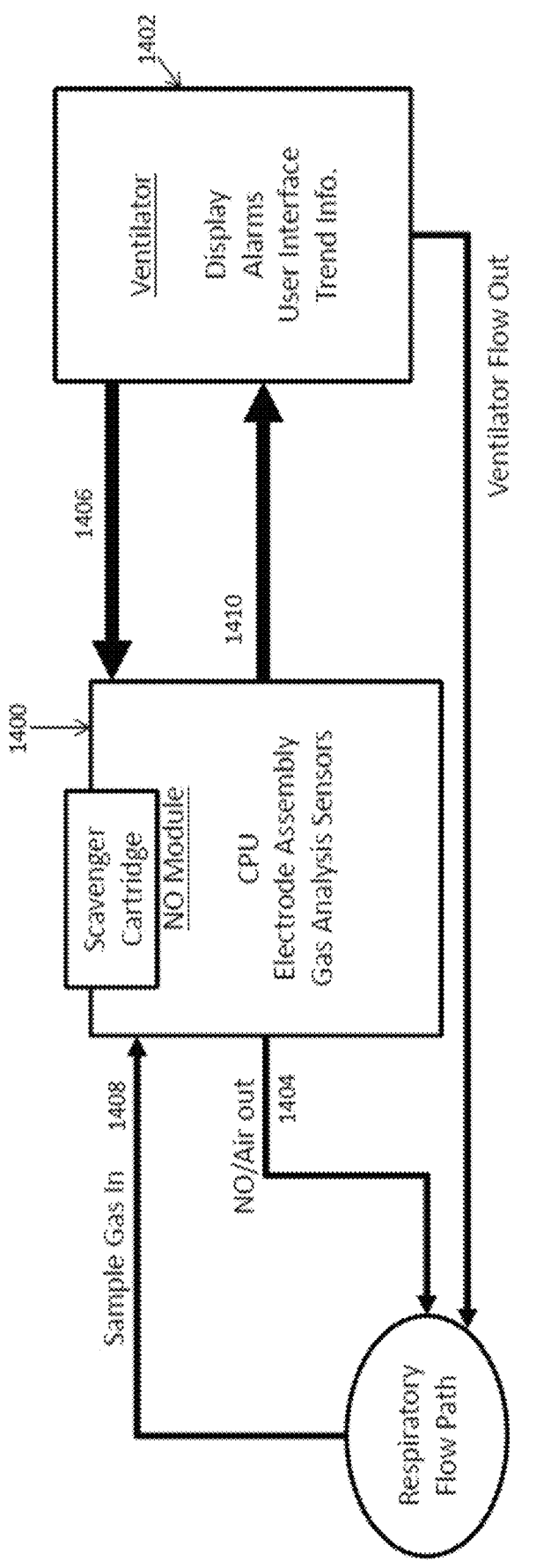
FIG. 114 is an exemplary embodiment of a nitric oxide generation module for use with a ventilator.

FIG. 114 illustrates an exemplary embodiment of an NO generation module 1400 for use with a ventilator 1402. The NO generation module includes various inputs and outputs for gas measurement, which can vary depending on how various gas levels are measured. As shown in FIG. 114, the NO generation module includes an output 1404 of NO/air, and inputs 1406 from the ventilator, such as power, a ventilator flow signal and/or setting, one or more treatment parameters such as a target NO concentration, a ventilator pressure signal and/or inspiration trigger, a ventilator mode such as VCV, PCV, or bag mode, and/or one or more ventilator parameters including tidal volume or minute volume. In some embodiments, the NO generation module can perform sample gas measurements, and can include an input 1408 for a sample gas, and an output 1410 to the ventilator in the form of one or more gas measurement readings, cartridge identification information, and/or alarms. The sample gas can be taken from either the ventilator or the ventilator circuit. It will be understood that the sample gas can be from anywhere in the system before patient inspiration. In some embodiments, the sample gas is taken from the ventilator circuit as close as possible to the patient before patient inspiration. In some embodiments, sample gas can be taken at a location a distance from the patient, and the system can calculate $NO_2$ levels based on factors including but not limited to circuit length, circuit cross section, circuit volume, transit time, NO concentration, $O_2$ concentration, and other parameters that compensate for the distance from the patient. In some embodiments, an $NO_2$ scavenger can be located close to the patient to help ensure that $NO_2$ remains at an acceptable level.

In some embodiments, sample gas measurement can be done within the ventilator. In some embodiments, the NO generation module can perform sample gas measurements to analyze breathing circuit gases. For example, either the NO generation module can include gas analysis sensors or there can be a separate gas analysis module that is used in conjunction with the NO generation module, such as the modules 1420, 1422 shown in FIG. 115.

In some embodiments, sample gases are drawn from the inspiratory limb, as close as possible before reaching a patient. For example, sample gases can be taken at roughly 6" upstream from the wye piece of a ventilator circuit to avoid interference from exhaled gases. In some embodiments, gases can go through the $NO_2$ sensor first since $NO_2$ levels increase over time as the NO oxidizes into $NO_2$ and surplus $NO_2$ generated in the sensor pack is not representative of the $NO_2$ concentration inspired by the patient. High levels of $NO_2$ can generate an alarm. Thus, sample gases can go through an NO generation module with gas analysis capabilities, and the module can pass the sample gases to the ventilator from there for further analysis, if needed. In some embodiments, the gases could be passed by an internal pneumatic connection where the module connects to the dock or an external connection (i.e. a tube running from an NO generation module to a sample gas inlet on the ventilator).

Various measurements can be taken by different parts of the system. In some embodiments, one or more gas sensors can be a separate module in the ventilator or other device, such as a sensor module, described in more detail below. NO and $NO_2$ sensors can be combined with an $etCO_2$ device or other patient monitor, gas monitor, or blood gas monitor. To prevent spontaneous cessation of NO delivery, the NO module can have redundant components, such as NO generators, scavengers, electrode assemblies, control circuits, flow sensors, etc. Flow measurement can be done by various components. In some embodiments, flow is measured by the ventilator, and the measured results can be delivered by a wired (analog, I2C or RS232) or a wireless connection. An NO generation module can also measure flow at the ventilator outlet and introduce NO to the ventilator flow in the same location. In some embodiments, the ventilator and NO generation module can communicate by any acceptable approach, including but not limited to RS232, I2C, analog signals, optical, wireless such as Bluetooth or other means.

If additional power is needed, an NO generation module can be double-width to draw from two power connections from the ventilator (i.e. two module bays). The double-width NO generation module could include the sensor pack, or the sensors can be in a separate module or in the ventilator. Redundant NO generation can draw from the two independent power connections for greater redundancy.

An NO generation module can access air and $O_2$ from a variety of sources. In some embodiments, the NO generation module uses ambient air. In some embodiments, the NO generation module can have its own air pump to move air through the electrodes and to the ventilator circuit. In some embodiments, the NO generation module can use air from the ventilator. For example, the NO generation module can send NO gas back into the ventilator to be added to the vent flow within the ventilator.

Figure 115:
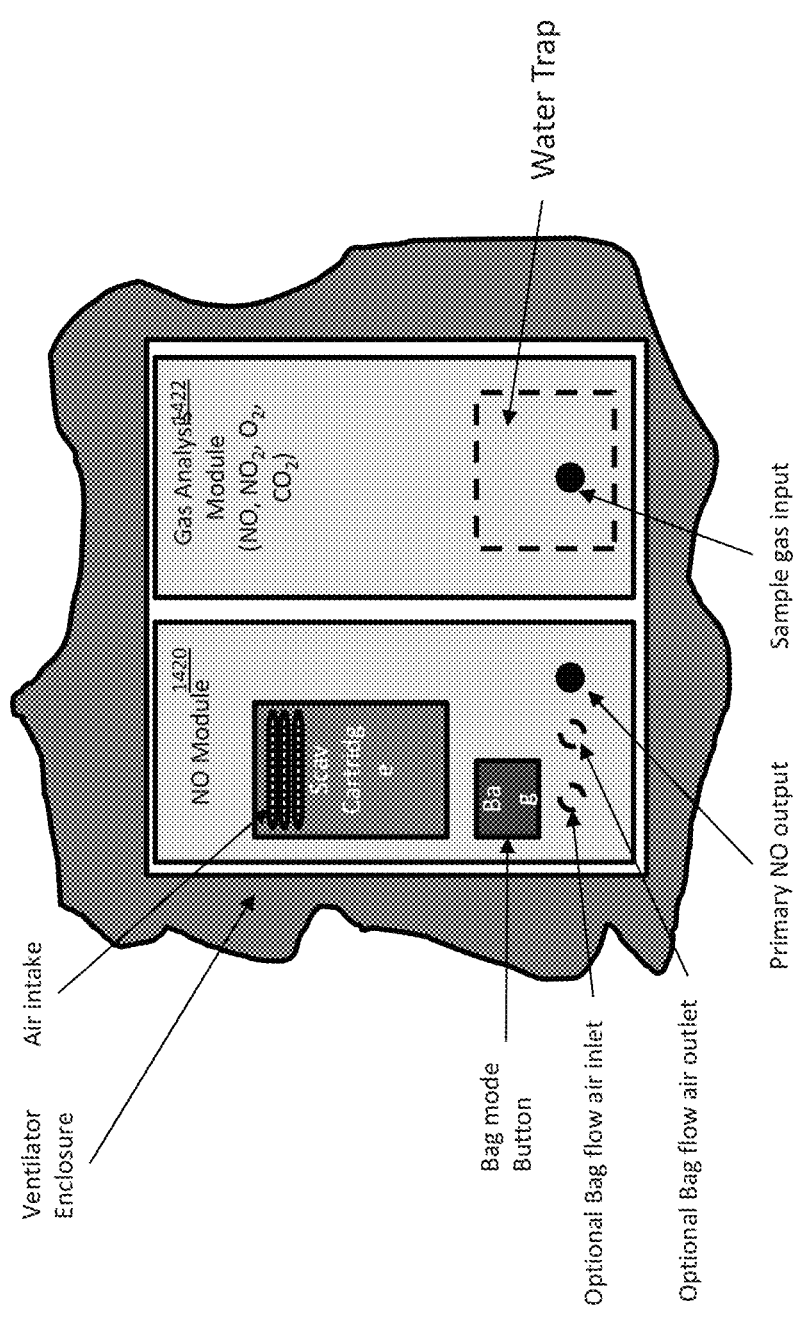
FIG. 115 is an exemplary embodiment of an NO generation module and a sensor module that are configured to be removably coupled to respiratory equipment.

FIG. 115 illustrates exemplary embodiment of an NO generation module for generating NO to be used by a respiratory device in conjunction with a sensor module for measuring information relating to gas concentrations in the system. In some embodiments, the NO generation module and the sensor module can be coupled to a device, such as a ventilator through various connections and/or ports. In some embodiments, the modules can be inserted into corresponding ports/bays in the ventilator that include the proper connections/ports for each module such that the modules are removably coupled to the ventilator. In some embodiments, the modules can be embedded into a respiratory device, and be either removable or permanently fixed therein. In some embodiments, inputs from the ventilator can include power, flow measurement, vent pressure, ambient pressure, and ventilator mode, and outputs to the ventilator can include alarms (electrical output), NO/air flow (for example, from the front nipple), and measurements to the ventilator. In some embodiment, inputs from the ventilator can also include power and sample gas In.

Figure 116:
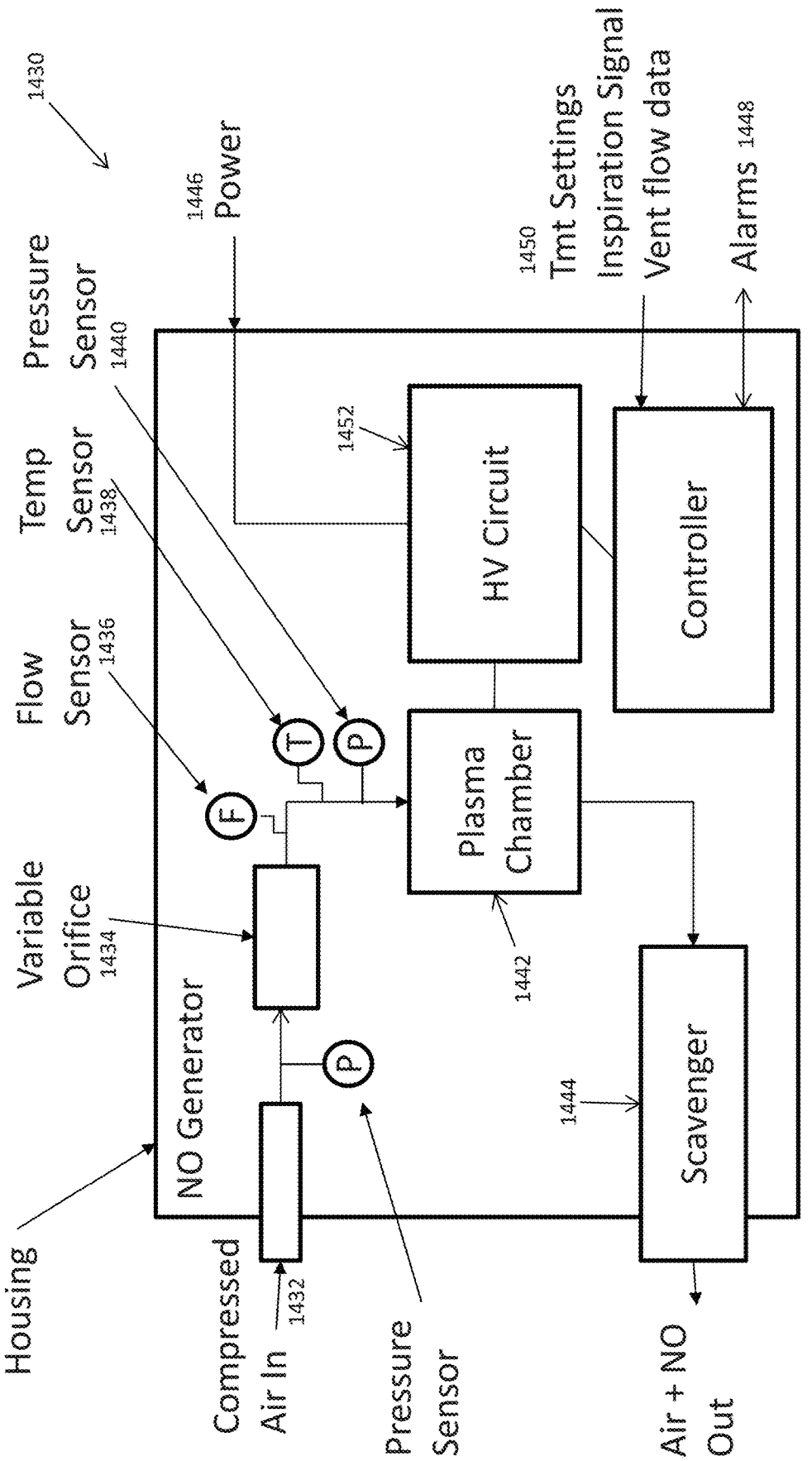
FIG. 116 is an exemplary embodiment of an NO generation module for generating NO.

FIG. 116 illustrates an exemplary embodiment of an NO generation module 1430. The NO generation module 1430 can include an air inlet 1432 that is coupled to a variable orifice 1434, or other flow control device, to control the flow of air into the NO generation module. The NO generation module can include various sensors, including a flow sensor 1436, a temperature sensor 1438, and a pressure sensor 1440 as shown in FIG. 116. The air flows into a plasma chamber 1442 that includes a plurality of electrodes therein for generating NO. The NO/air exiting the plasma chamber 1442 can pass through a scrubber or a scavenger 1444 to an outlet. The terms scavenger or scrubber may be used interchangeably. The NO generation module can include various other inputs and outputs, including but not limited to power 1446, alarms 1448, and treatment settings 1450. The NO generation module can also include a high voltage circuit 1452. The high voltage circuit can be formed from a variety of components, but in some embodiments the high voltage circuit includes a controller to receive commands, a resonant circuit and high voltage transformer. The HV circuit receives commands from the controller and interprets the commands as plasma parameters and creates pulses of current that are fed to a resonant circuit and generates AC voltage. The AC voltage has a frequency that is tuned to the natural resonance of the high voltage transformer to maximize electrical efficiency. The AC high voltage can be applied to the electrodes in the plasma chamber to make a discharge and is continuous until the pulse ends.

In some embodiments, the NO generation module can include a cartridge configured to produce nitric oxide to be delivered to a respiratory device or other medical device/equipment. The cartridge can include an inlet for receiving reactant gas, one or more plasma chambers configured to produce nitric oxide from the reactant gas using one or more electrodes, and an outlet for delivering the nitric oxide to the respiratory device. A controller is configured to receive feedback from the cartridge to allow the controller to regulate the production of nitric oxide by the cartridge by adjusting the flow rate of the plasma chamber gas and a duration of plasma activity in the plasma chamber. The cartridge in the NO generation module can also include one or more scavengers coupled between the one or more plasma chambers and the outlet, and the one or more scavengers can be configured to remove $NO_2$ and/or ozone from the generated nitric oxide. The cartridge can be removable and replaceable, or the entire module can be replaced when required.

There are a variety of ways to control NO generation in the NO generation module. In some embodiments, air flow rate and spark rate are controlled to control the generation of NO in the NO generation module. In some embodiments, air flow rate and spark duty cycle can be controlled. In some embodiments, air flow rate is varied in response to respiratory flow rate variation. The relationship between air flow rate and respiratory flow rate can be linear, non-linear, logarithmic, or some other repeatable relation. In some embodiments, plasma pulse rate can be varied as well to maintain constant NO concentration throughout the respiratory cycle. In some embodiments, air pump speed is held constant and only plasma control parameters (B=spark groups per second, P=time between discharges, N=number of discharges per group, and H=pulse time) are varied to produce required NO concentrations based on patient inspiratory flow. In some embodiments, air flow can be generated by an air pump that moves air through the plasma chamber. In some embodiments, a pump can fill a reservoir with pressurized air and a variable flow restriction can be used to control air flow rate from the reservoir through the plasma chamber. In some embodiments that source air from a pressurized air source, air flow through the plasma chamber can be controlled by a variable flow restriction. A flow sensor downstream from the variable flow restriction can be used for closed loop feedback to the variable flow restriction to ensure accurate air flow is achieved. In some embodiments, NO can be generated and accumulated in a pressurized reservoir, from which it is dispatched into the ventilator flow. In some embodiments, air can be sourced from a pressurized air source, and its pressure and flow are regulated to control flow through and pressure within the plasma chamber.

Other factors affecting NO generation include but are not limited to flow rate, ambient temperature, plasma chamber pressure (i.e. pressure inside the electrode chamber that sparks to produce the NO), ambient pressure, ambient humidity, and measured NO values in an inspiratory line. In some embodiments, it is possible that the pressure in the ventilator (or other device) circuit can increase when air is pushed to the patient by the ventilator (or other device). This increased pressure can stall flow within an NO delivery device. In some embodiments, a venturi can be inserted into a ventilator circuit. A high flow rate in the venturi can lead to low pressure in a venturi throat, which can draw NO into the vent flow like a carburetor draws liquid/gas into an intake air stream in a correct proportion. Thus, increased vent flow can increase NO flow proportionally. In some embodiments, a bluff body obstruction can be inserted into a ventilator circuit, and flow across the obstruction can create a low pressure wake which draws in NO. In some embodiments, a flow restriction can be included after the plasma to keep the pressure high in the spark chamber and increase NO output. This flow restriction can be useful for altitude compensation. In some embodiments, a flow restriction can be included at the end of the scavenger so that NO-containing gas is at higher pressure and can flow into the vent flow at all times, including when the vent flow is at high pressure. In some embodiments, a feedback control on the pump can be used to maintain constant pressure in a spark chamber. This can account for variance in ambient pressure and pre-scavenger resistance. Spark chamber pressure can also be used as an input into the NO generation control algorithm. In some embodiments, a variable orifice can be included after the plasma to increase pressure within a spark chamber, and the orifice can control NO flow during an inspiratory pulse.

Higher elevations have lower ambient pressure, and lower air density. Lower air density can decrease the electrical resistance between the electrodes and plasma breakdown across the electrode gap can occur at a lower voltage. With less air present and less voltage, there is a decrease in NO production at higher elevations measuring roughly 20% less at an elevation of 18,000 feet. In some embodiments, a variable flow restriction can be placed downstream of the plasma to create a back-pressure within the plasma chamber to increase absolute air pressure within the plasma chamber and NO production efficiency. The orifice can be controlled in a closed-loop fashion with plasma chamber pressure as the input and a target pressure of atmospheric pressure at sea level.

In some embodiments, an NO generation module can be provided that includes a manual ventilation mode (a bag mode) that allows the module to support the use of respiratory bag or other manual ventilation mechanism to ventilate a patient. Ventilators do not always support patient bagging. In some embodiments, a ventilator user interface can provide a user with a bag button that can toggle to bag mode operation, and the ventilator can communicate with the NO generation module and notify the NO generation module that a user has selected bag mode. In some embodiments, a bag button can be located on the NO generation module. Once the bag button is pressed, the system can automatically redirect product gases from the ventilator circuit to the manual bagging circuit. In some embodiments, the NO module can measure flow of bag gas as it flows from an inlet to an outlet through the NO module. In some embodiments, the ventilator can provide air for bag flow to the NO module and a combination of NO and air can travel through an outlet in the NO module and into the bag. In some embodiments, the NO generation module could have at least two outlets: 1 for a ventilator circuit and 1 for a bag output. In some embodiments, a source for air/gas for the bag can come from a cylinder or a wall outlet and can flow through an inlet in a module enclosure. Within the module, the flow of the source air can be measured and a proportional amount of NO can be added to the flow prior to exiting through a bag flow outlet. In some embodiments, source air/gas for a bag can be delivered to the module from the ventilator.

Figure 117:
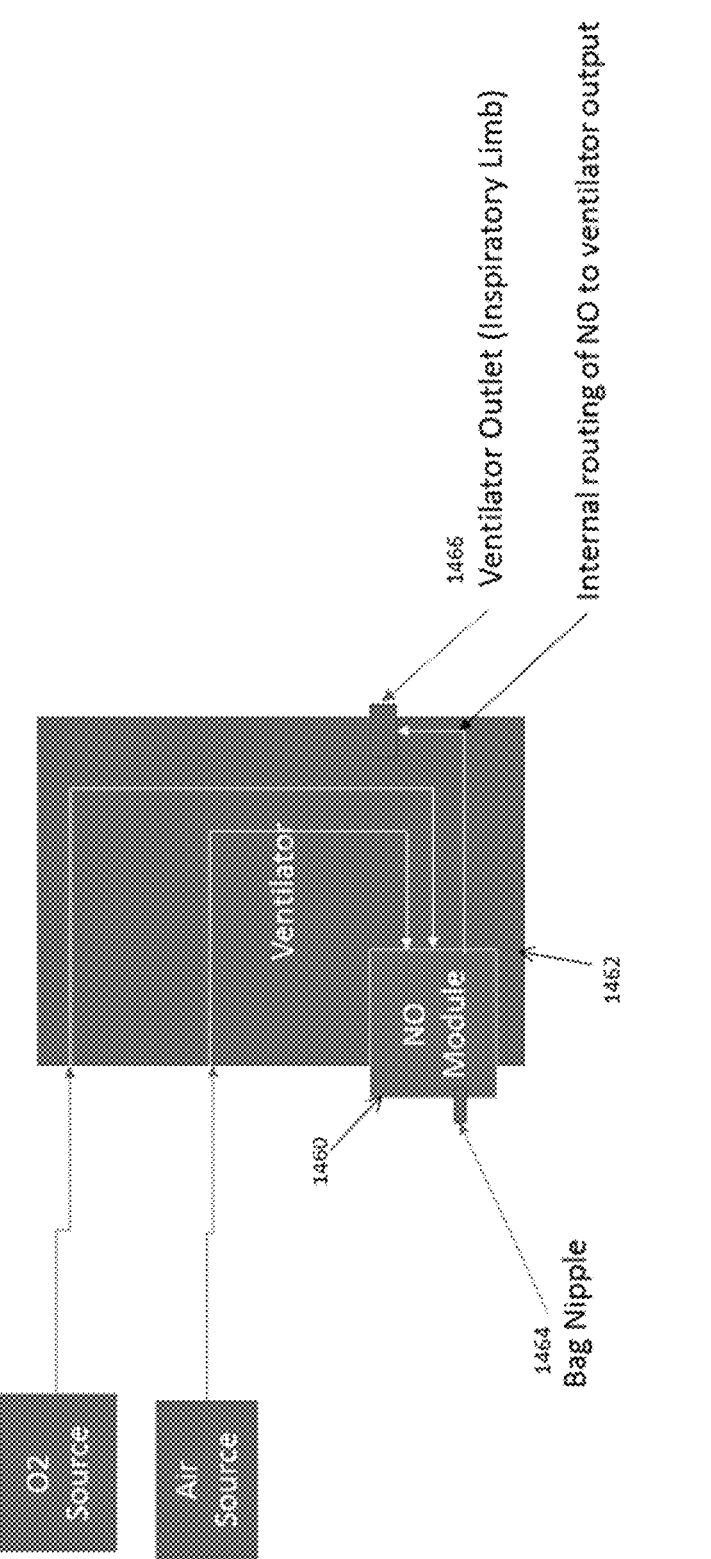
FIG. 117 is an exemplary embodiment of an NO generation module removably coupled to a ventilator.

FIG. 117 illustrates an exemplary NO delivery system including an NO generation module 1460 removably coupled and inserted into a ventilator 1462. The NO generation module, which adds NO to the air flow, includes a nipple 1464 to allow a bag to be attached thereto, and air/$O_2$ is sourced from the ventilator. The NO generation module is configured to generate NO and pumps the NO-infused air to either the bag nipple or to a ventilator output 1466. For example, the flow can merge within the NO module and exit out the nipple one the front of the NO module. In some embodiments, a ventilator can deliver independent supplies of air and oxygen to the module at desired flow rates.

The ventilator can have various additional features. NO weaning can be based on ventilator weaning or on $SpO_2$, which can be measured by the ventilator. By integrating the NO generation module, the ventilator can know how much the $O_2$ concentration is diluted by the addition of NO and can display the information accordingly. This can eliminate the need for a duplicate sensor that samples from the inspiratory limb. The ventilator can determine final concentration using a variety of techniques, including measuring $O_2$ levels of the inspiratory gas post-NO introduction, or using an algorithm or look-up table to determine $O_2$ level based on NO volume added and initial $O_2$ level. This can eliminate some user confusion by providing a single $O_2$ measurement, rather than upstream and downstream measurements.

A multiple gas monitor or module can also be used with the system that can measure various gas levels, including but not limited to $etCO_2$, $O_2$, NO and $NO_2$. In some embodiments, a single gas sample line can be used such that less volume is removed from the ventilator circuit. It can utilize the same sampling gas flow circuit (pump, filter, water trap) and a common processor, power supply, and/or user interface. The gas monitor can be a stand-alone monitor device (such as a sensor module as described in more detail below) or can be part of the ventilator. In some embodiments, this could be a module that is either built within the ventilator or can be installed and removed into a slot on the exterior of a ventilator. As a removable module, it can share power, alarms, user inputs, treatment settings, and other features with the primary piece of equipment, such as the ventilator.

Figure 118:
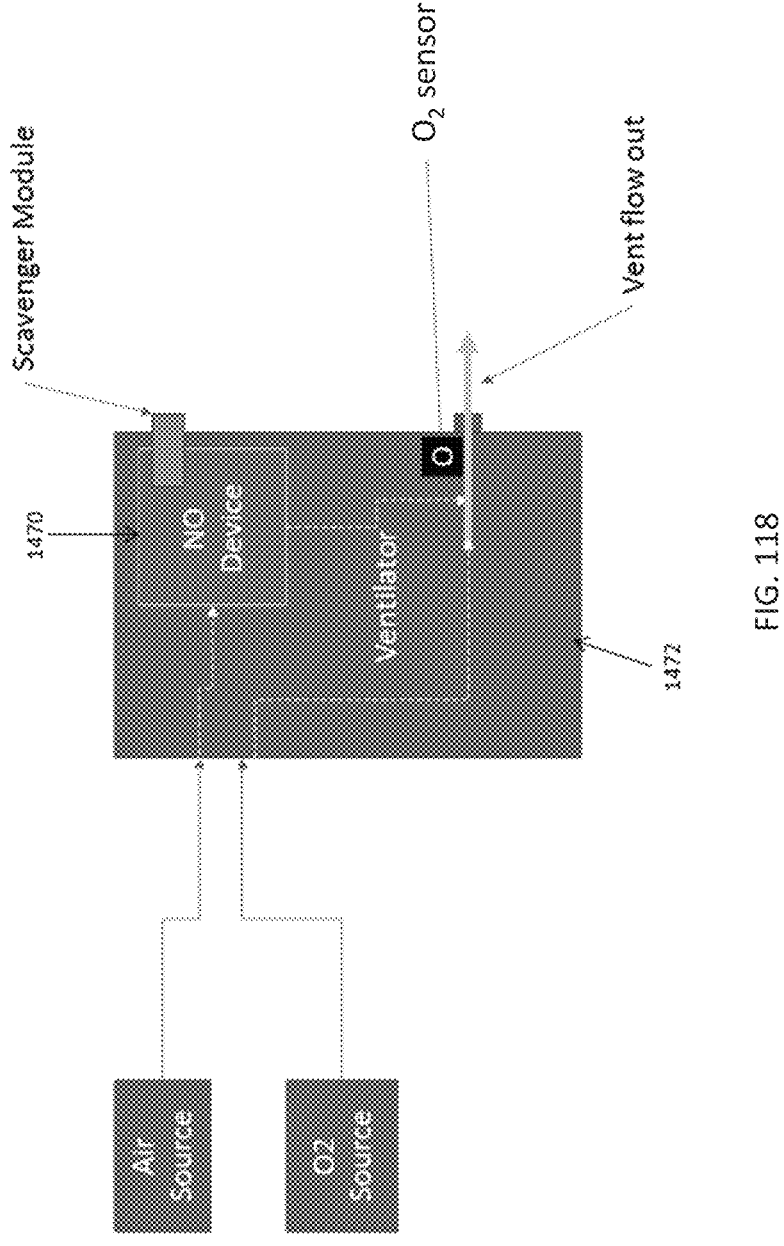
FIG. 118 is an exemplary embodiment of an NO generation module embedded in a ventilator.

FIG. 118 illustrates an exemplary embodiment of an NO generation module 1470 embedded inside a ventilator 1472. The module can be removable from the ventilator or can be permanently embedded therein. The NO generation module is configured to generate NO and deliver the NO-infused air to a ventilator output. In some embodiments, the O$_2$ level can be measured at the output of the ventilator to determine if the gas includes the proper gas levels required, such as O$_2$ gas. In some embodiments, the ventilator can decrease the 50 psi air input and pass it through to the NO device. Oxygen can be mixed with the low pressure air. In some embodiments, NO can be introduced at the outlet of the ventilator. Oxygen levels can be measured at the exit of the ventilator for accuracy.

Figure 119:
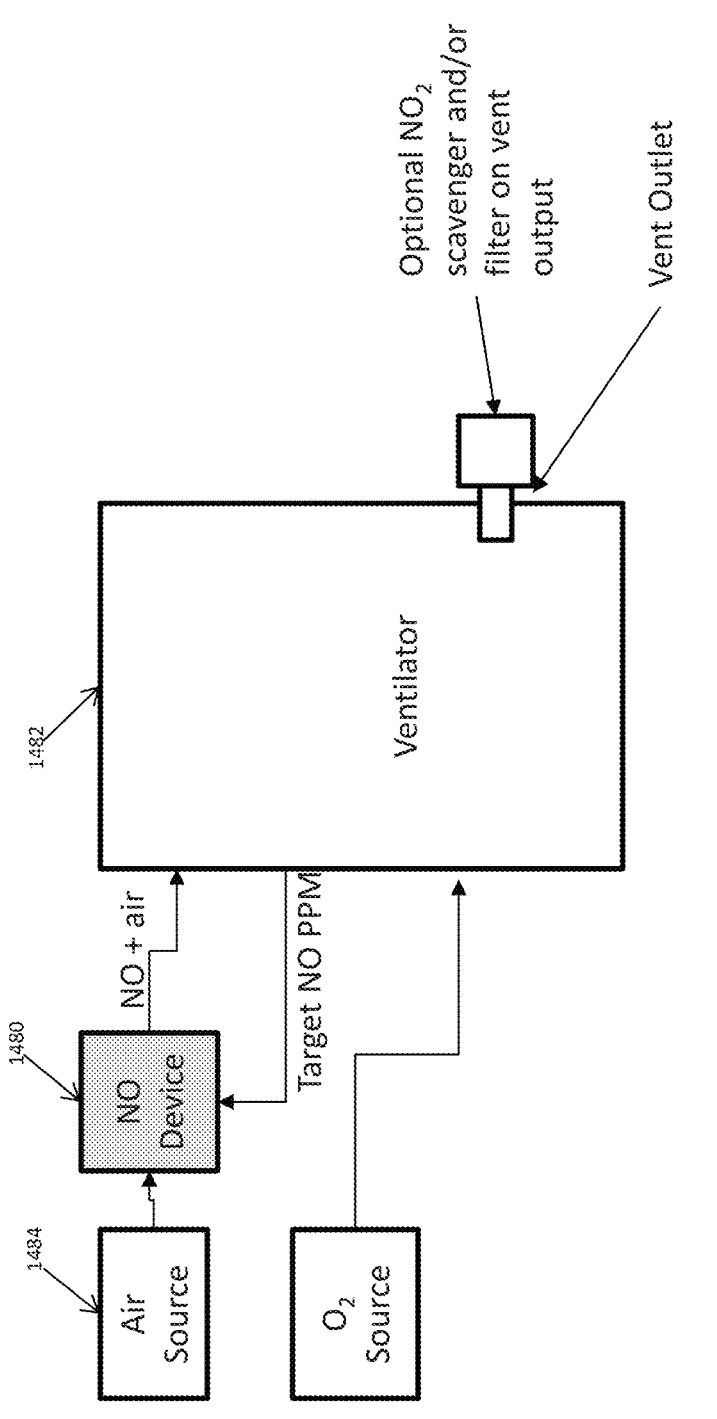
FIG. 119 is an exemplary embodiment of an NO generation module removably coupled to a ventilator.

FIG. 119 illustrates an exemplary embodiment of an NO generation module 1480 removably coupled to a ventilator 1482. The external NO generation module adds NO to air entering the ventilator. The ventilator provides the NO generation module with a target NO concentration. The NO generation module uses an air source 1484, such as ambient/atmospheric air, to generate NO in a product gas and pump the NO-infused product gas to the ventilator. In some embodiments, the NO device can be mounted one the wall and use house air. In some embodiments, the NO device can measure flow, add NO according to target NO concentration, and scavenge for NO$_2$.

Figure 120:
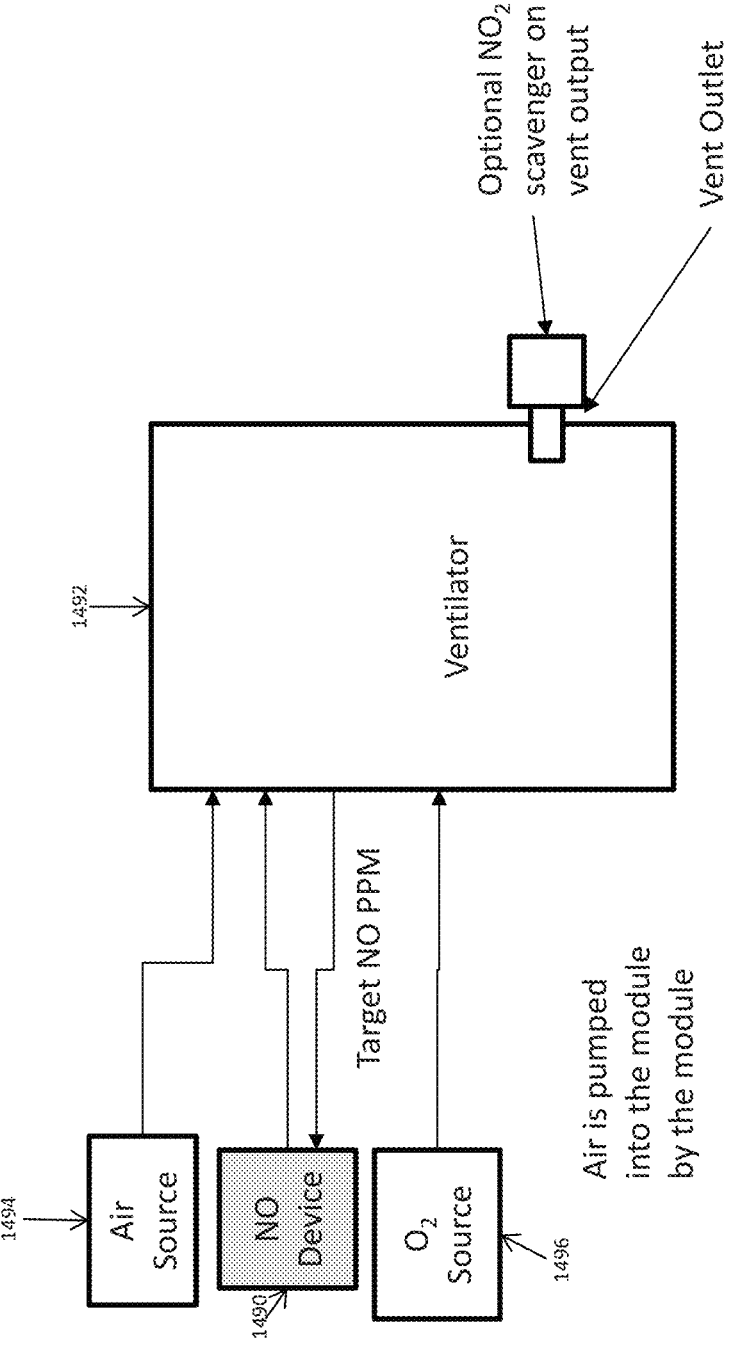
FIG. 120 is another exemplary embodiment of an NO generation module coupled to a ventilator pre-ventilation that utilizes ambient air for NO generation.

FIG. 120 illustrates an exemplary embodiment of an external NO generation module 1490 removably coupled to a ventilator 1492. The NO generation module may be removably attached to the wall of the clinic with a pneumatic connection to the ventilator for NO delivery. The ventilator provides the NO generation module with a target NO concentration. In some embodiments, the ventilator can provide target NO level information via wired and wireless connections. The NO generation module is configured to generate NO and to deliver NO to the ventilator, which also has its own air source 1494 and O$_2$ source 1496, as shown in FIG. 120.

Figure 121:
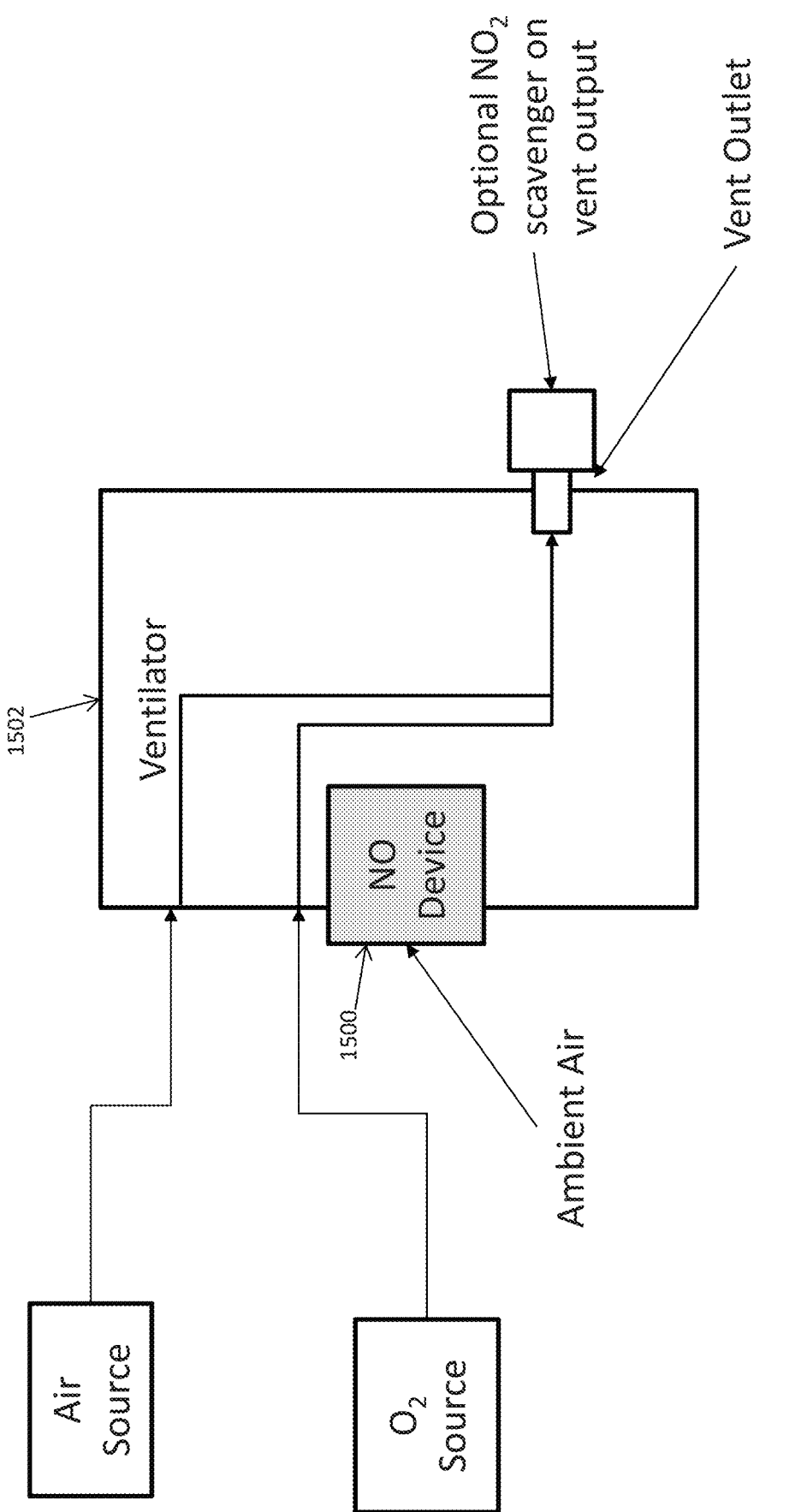
FIG. 121 is an exemplary embodiment of an NO generation module coupled to a ventilator with an air outlet from the module to the ventilator.

FIG. 121 illustrates an exemplary embodiment of an NO generation module 1500 removably inserted into a ventilator 1502, for example into a module dock or bay. The NO generation module uses ambient air as the reactant gas to generate NO and delivers the NO to the ventilator using an internal pneumatic fitting and tube or other mechanism internal to the ventilator.

Figure 122:
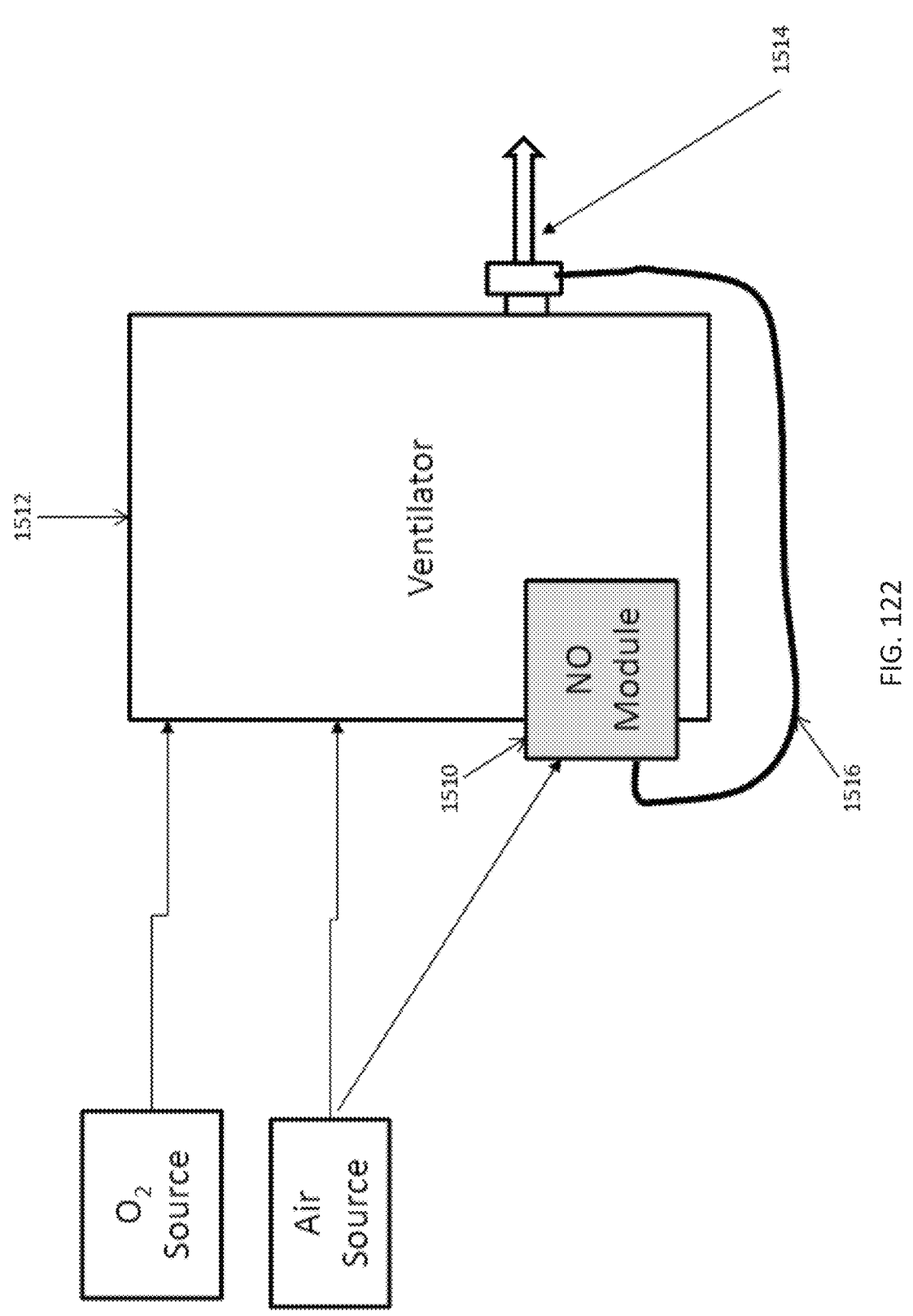
FIG. 122 is an exemplary embodiment of an NO generation module coupled to a ventilator.

FIG. 122 illustrates an exemplary embodiment of an NO generator 1510 removably inserted into a ventilator 1512, for example into a module dock or bay. The NO generation module uses ambient compressed air to generate NO and delivers the NO to an output 1514 of the ventilator 1512 using a tube 1516 or other mechanism external to the NO generation module and the ventilator. Thus, rather than an internal connection between the NO generation module and the ventilator, an external connection can be used to deliver NO from the module to the ventilator. In some embodiments, the NO generation module and the ventilator have separate air sources. In some embodiments, the NO generation module includes the NO$_2$ scavenger. In some embodiments, the NO module can communicate to the ventilator for power, alarms, and/or flow measurement.

An NO generation module can also be used with an anaesthesia machine. NO within an anaesthesia circuit can accumulate, and gas analysis sensor data can be used to control NO production. Gas analysis sensor measurements can be in the inspiratory limb and/or expiratory limb. If NO production is modified by feedback or monitoring of NO levels at one or more locations in a ventilation circuit, in some embodiments two or more NO sensors can be used to provide redundancy and/or fault tolerance for the control system. A pre-existing scavenger material in the anaesthesia circuit can be used to remove NO$_2$. NO production can be controlled based on exhaled NO levels as exhaled NO can be an indication of how much NO is within the patient. Thus, NO production could be modulated to control the level of exhaled NO.

Figure 123:
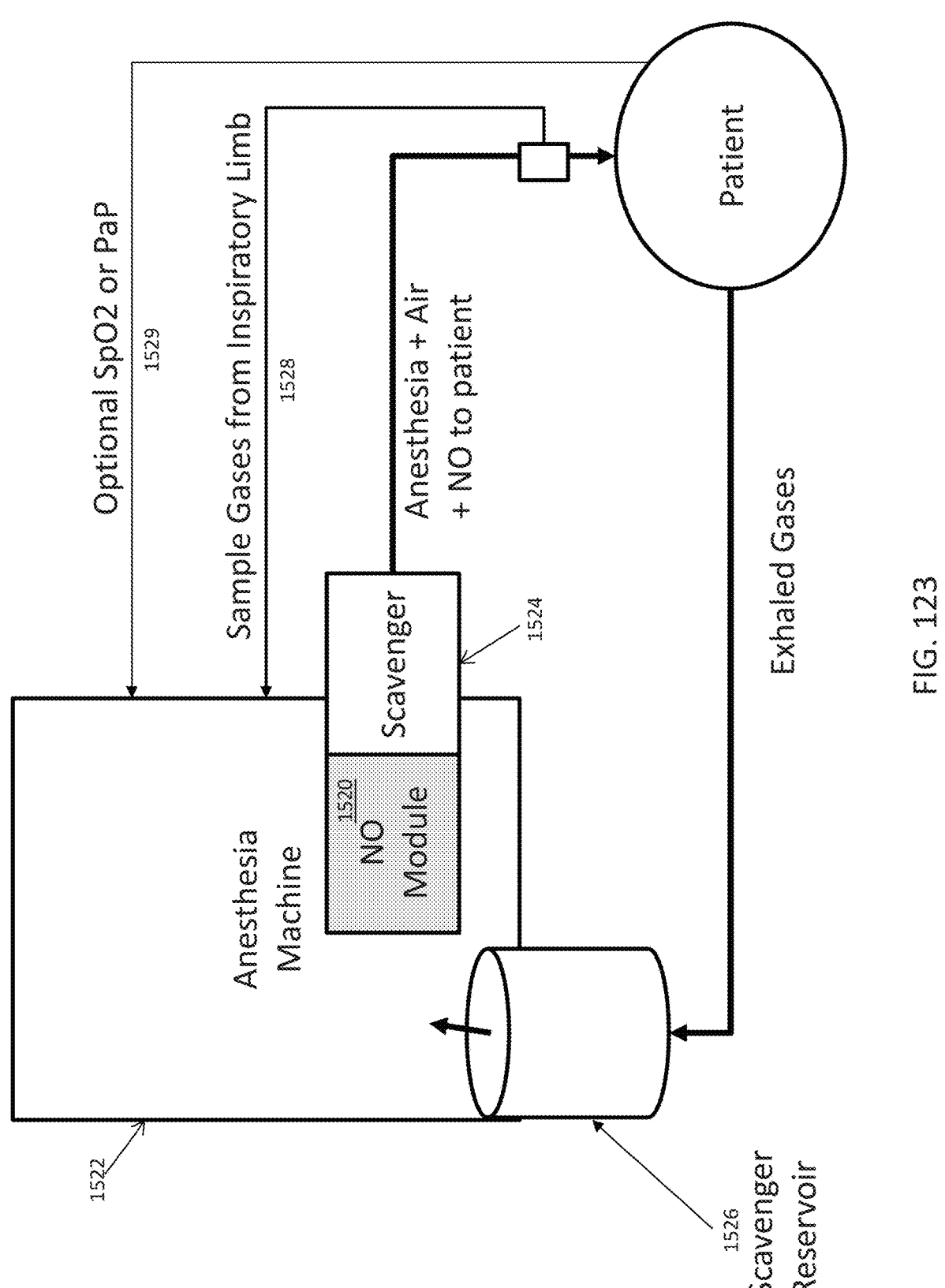
FIG. 123 is an exemplary embodiment of an NO generation module with an anaesthesia machine.

FIG. 123 illustrates an exemplary embodiment of an NO generation module 1520 with an anaesthesia machine 1522. The anaesthesia machine 1522 includes an NO generation module (either removably coupled thereto or embedded within the machine) and a scavenger 1524 that can be unitary with the NO generation module or separate therefrom as long as the scavenger can be removed and replaced when necessary. The anaesthesia machine 1522 and the NO generation module 1520 provide air that includes NO and anaesthesia to the patient. The exhaled gases from the patient can be passed to a scavenger reservoir 1526 and its output can go back into the anaesthesia machine. Sample gas 1528 can be sampled from the inspiratory limb before that gas reaches the patient. In some embodiments, the sample gas is used by the anaesthesia machine to measure concentration of various gases. In some embodiments, that sample gas can be tested by a sensor module or by sensors in the NO generation module. Also shown are optional blood oxygen saturation level (SpO$_2$) input and pulmonary artery pressure (PaP) input 1529 to the anesthesia machine as control inputs for setting NO levels.

Using an NO generation module with an anaesthesia machine is achieved with a similar approach as the ventilator with an NO generation module being able to share power, an air source, a user display, alarm hardware, treatment control software, and other features. Anaesthesia machines are typically operated in a closed loop so that anaesthesia gases are conserved and not dispersed into the room. The scavenger material of an anaesthesia machine can be used to absorb patient-exhaled CO$_2$ in the circuit. The same material, for example soda lime, can be used to scavenge NO$_2$ from the circuit, but NO levels would build up. In some embodiments, to prevent NO build-up, anaesthesia can be provided in an open-loop format where exhaust gases are vented to the outside, to a house vacuum, or deactivated with a charcoal filter or other means. In some embodiments, to prevent NO build-up, the module and/or anaesthesia machine can measure NO levels in the closed circuit and adjust NO production levels accordingly to achieve the target treatment level. The anesthesiologist can benefit from having NO and NO$_2$ levels present in their standard gas monitor equipment. In some embodiments, these monitors measure gases including CO$_2$, O$_2$, NO$_2$, Halothane, Isoflurane, Sevoflurane, Desflurane and Enflurane. The gas monitor would communicate with either the treatment control software in the anaesthesia machine or the NO generation module to control NO production levels.

NO generation modules can also be used in conjunction with C-PAP machines. C-PAP machines are used at night to prevent sleep apnea. In some embodiments, the addition of NO can improve blood oxygenation more than oxygen and C-PAP alone. An NO generation module can be integrated into the enclosure of a C-PAP machine, or can be a module that optionally removably inserts into the C-PAP machine or removably couples thereto. Similar synergies exist with a C-PAP machine, namely power, user interface, air source, alarm hardware.

Figure 124:
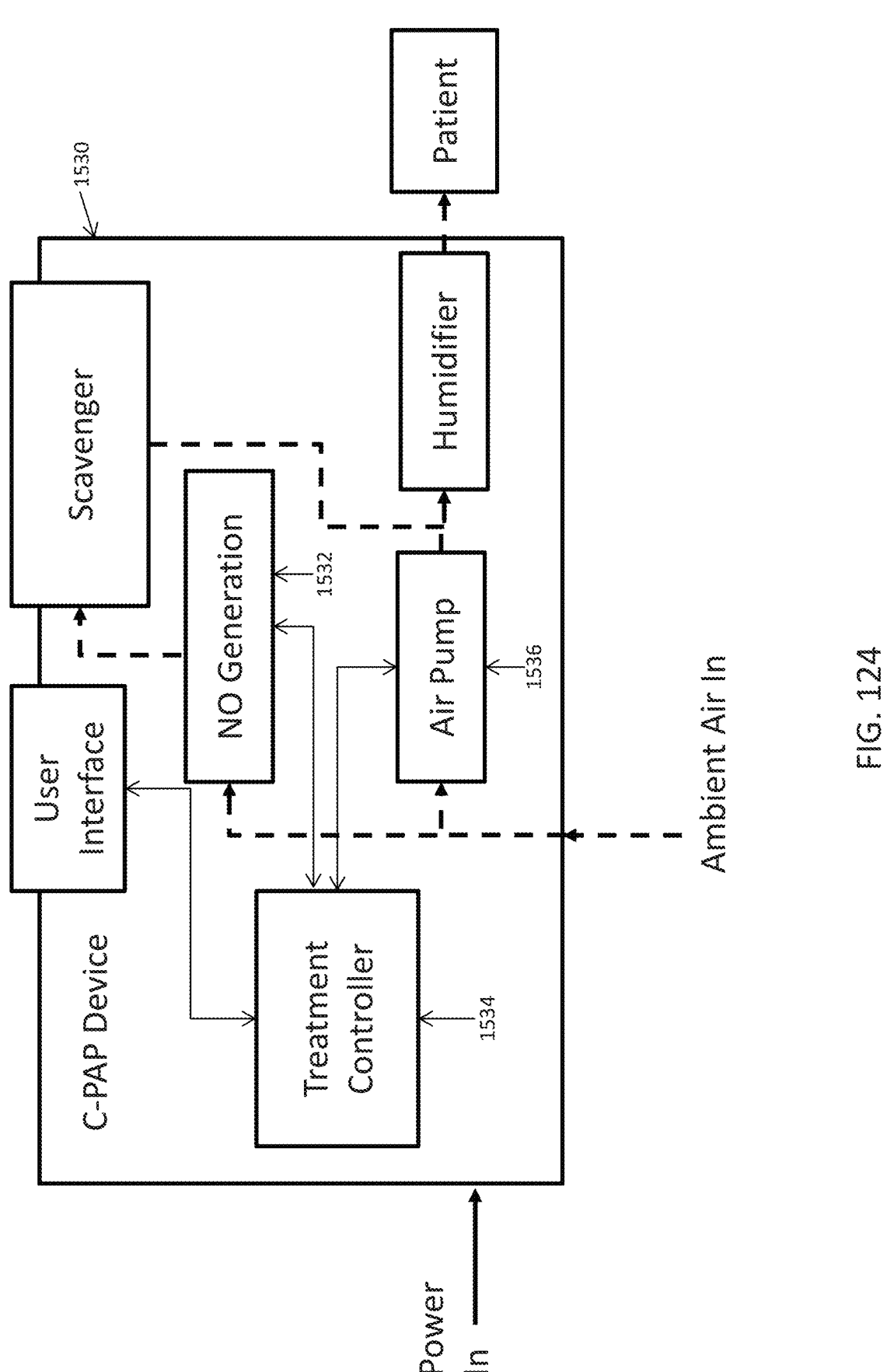
FIG. 124 is an exemplary embodiment of an NO generation module with a continuous positive airway pressure (C-PAP) machine.
Figure 125:
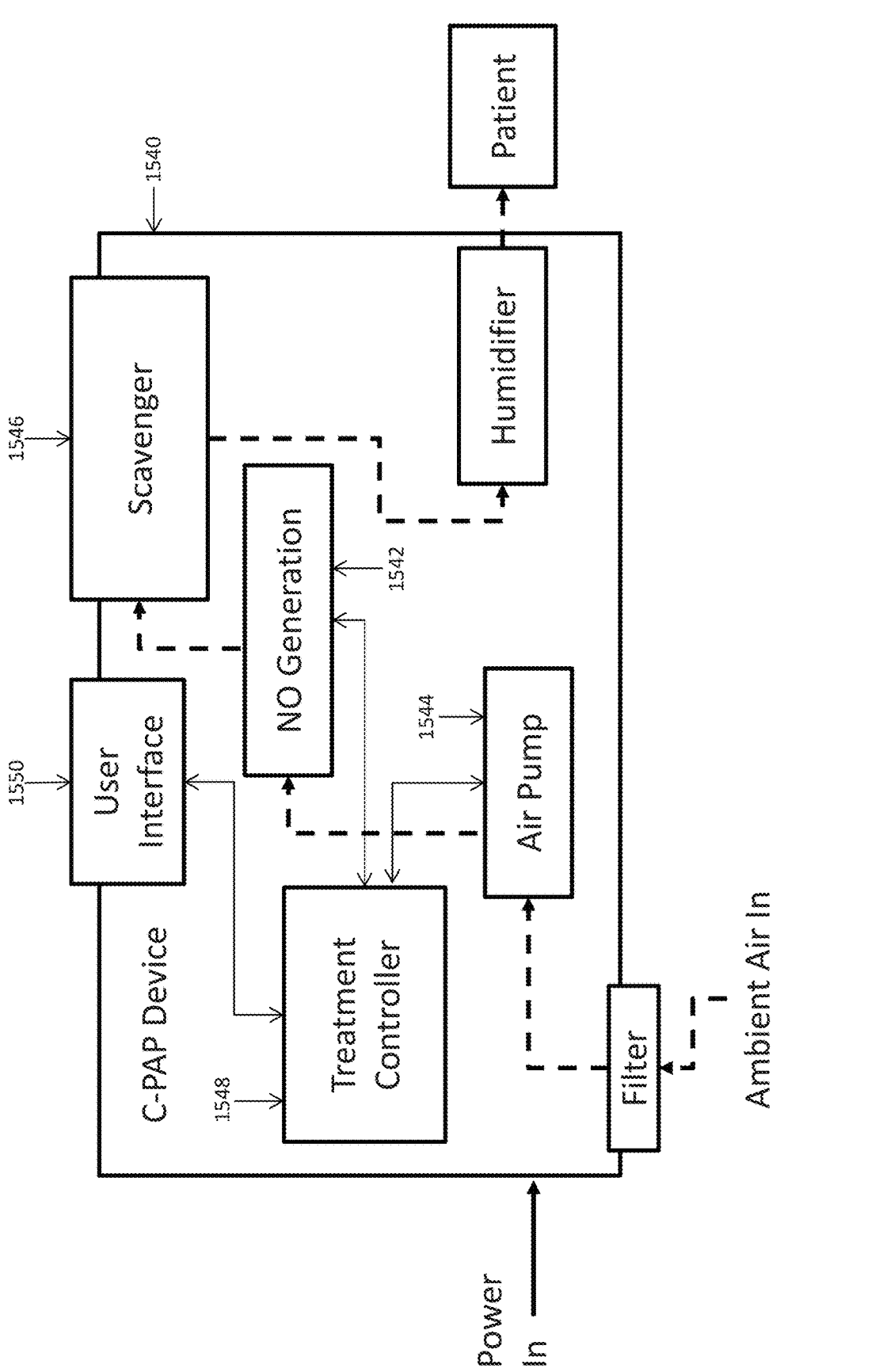
FIG. 125 is an exemplary embodiment of an NO generation module with a C-PAP machine.

FIG. 124 illustrates an exemplary embodiment of a C-PAP machine 1530 with an integrated NO generation module 1532. The NO generation module can share air supply, a controller 1534, power, and an enclosure with the C-PAP machine hardware. In some embodiments, the NO generation module 132 can include its own air pump 1536. In some embodiments, an air pump can be shared between the C-PAP machine and the NO generation module. FIG. 125 illustrates an exemplary embodiment of a C-PAP 1540 and an NO generation module 1542 in which all of the C-PAP flow travels through the NO generation module, which can allow for the dilution of the NO concentration to reduce $NO_2$ production. In some embodiments, the C-PAP device operates with a shared air pump 1544 for NO generation and the C-PAP. The $NO_2$ scavenger 1546 can be in the form of a removable scavenger cartridge or a reservoir that can support scavenger material replacement. The C-PAP machines can include a treatment controller 1548 that can be in communication with a user interface 1550 to allow a user to control the machine. In some embodiments, the treatment controller is configured to control the air pump and the generation of NO using the NO generation module.

Figures 126A, 126B, 126C:
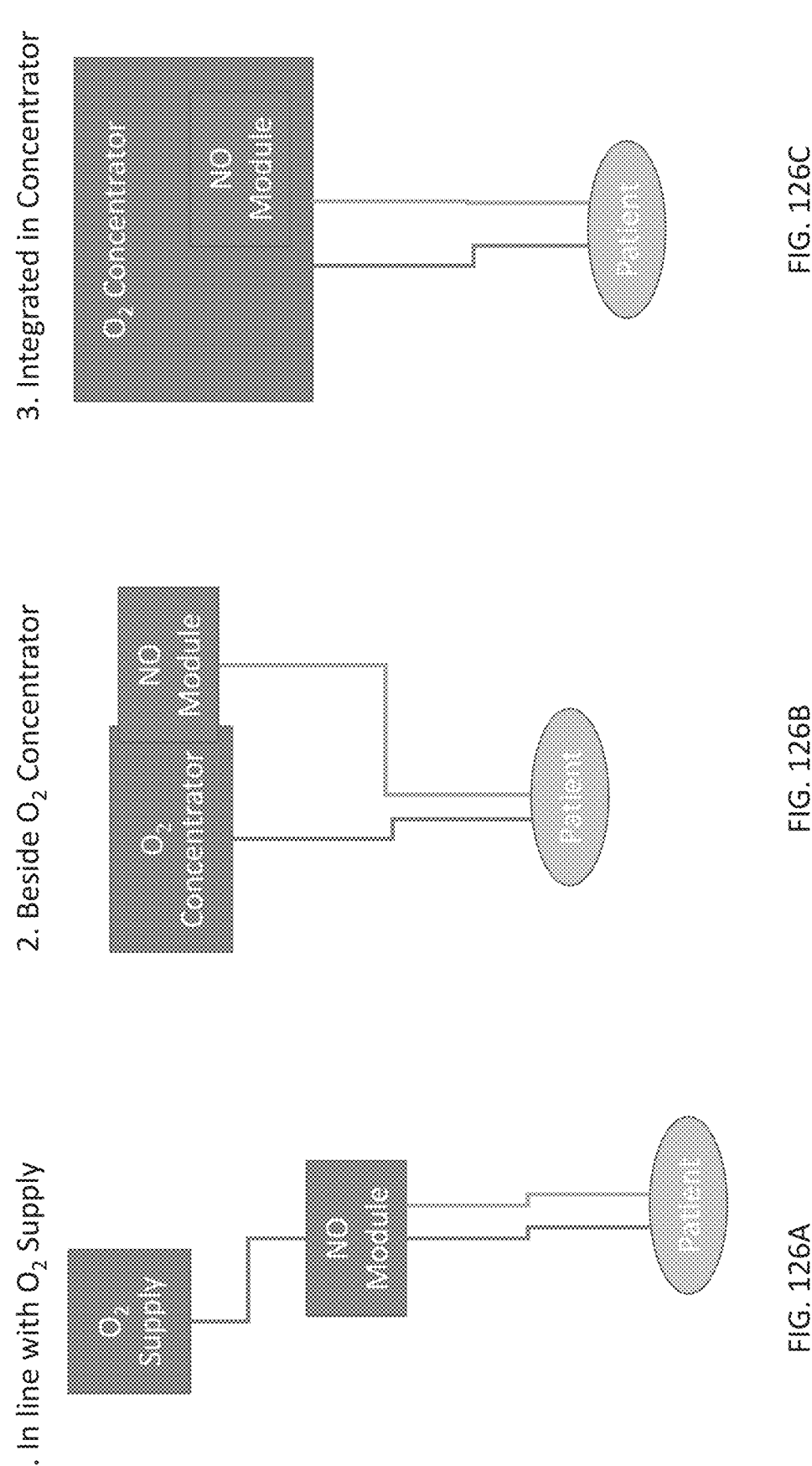
FIGS. 126A, 126B, and 126C depict various embodiments of NO generation modules in use with $O_2$ sources.

NO generation modules can be used with or combined with oxygen tanks or concentrators to improve blood oxygenation. FIGS. 126A-126C show how an NO module can be used in series with an $O_2$ source (FIG. 126A), in parallel with an $O_2$ source (FIG. 126B), or embedded in an $O_2$ source (FIG. 126C). FIGS. 126A-126C shows separate NO and $O_2$ lines going to the patient. Depending on the NO concentration, transit time, and oxygen levels, a single lumen can be used to deliver $O_2$ and NO as well.

$O_2$ delivery to a patient may be constant flow or pulsed. When $O_2$ flow is through the NO module, the flow rate of $O_2$ can be sensed by the NO module so that NO flow is scaled appropriately. During pulsed $O_2$ delivery, the NO module can sense pressure, flow, or sound variations in the $O_2$ flow in order to synchronize NO delivery with $O_2$ pulses. Alternatively, the NO concentration device can receive flow and timing data directly from an $O_2$ source via wired or wireless means.

One benefit of using an NO generation module in series with an $O_2$ source is that the NO generation module can detect a no-oxygen-flow condition and sound and alarm.

In another embodiment, an NO generation module shares resources with an $O_2$ Concentrator in a "piggy-back" configuration. In this embodiment, the NO device interfaces with the mobile concentrator or a stationary central oxygen delivery system to share battery power and AC power supply power from the oxygen system to avoid duplication and sentried charging and discharging behaviour. In this configuration, breath synchronization can be done with a wired or wireless signal from the $O_2$ source to the NO generation device. The signal can be related to breath detection, a flow rate, a pressure signal, a trigger signal, an acoustic signal, a temperature signal or other type of signal related to respiration.

The rate of NO conversion to $NO_2$ increases with increases in $O_2$ concentration, NO concentration, and time. In some embodiments, the $O_2$ source is up to 50 feet from the patient. If NO is added at the $O_2$ source, the transit time can be lengthy, thereby increasing the amount of NO to $NO_2$ conversion prior to patient inspiration. To address this potential for elevated $NO_2$ levels, a proximal scavenger unit near the patient can be used. The proximal scavenger consists of a chemical scavenger (typically soda lime) located near the patient. The scavenger may be in the form of a pendant at the base of the patient's neck, where the cannula bifurcates. In one embodiment, the scavenger material pellets and/or coatings are within the lumen of the cannula tubing.

Figure 127:
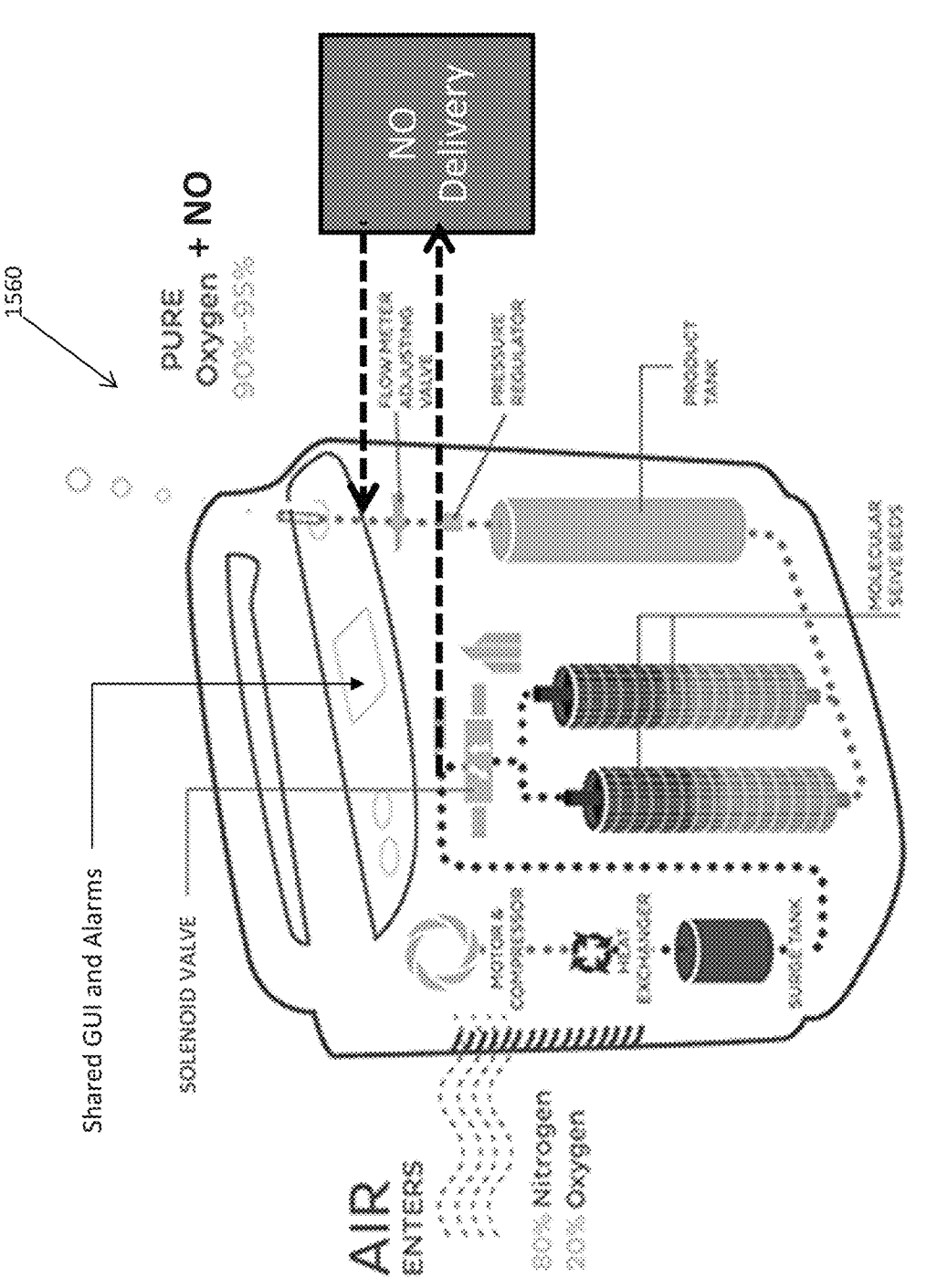
FIG. 127 is an exemplary Oxygen concentrator with embedded NO module.

FIG. 127 depicts an oxygen concentrator 1560 with integral NO module. Ambient air is compressed by the oxygen concentrator prior to being directed to both the NO generation device and molecular sieve beds. High concentration $O_2$ is stored within the product tank prior to delivery to the patient. The NO generation device receives treatment setting information and $O_2$ flow rate information from the $O_2$ concentrator. NO is generated in atmospheric air (20% $O_2$), however it is possible to send air with higher concentrations of $O_2$ to the NO module for improved NO production efficiency (50/50 ratio of $O_2$ to $N_2$ is optimal).

NO generation modules can also be used in conjunction with an extracorporeal membrane oxygenator (ECMO). An NO generation module can be added to an ECMO machine as a fully-embedded subcomponent or as an optional module that can be removably inserted or removably coupled thereto. In some embodiments, using NO with ECMO can improve long term survival rates by protecting the kidney. An NO module can receive power and/or treatment settings from the ECMO machine. In return, the NO generation module can provide NO and alarms. The two systems can share various features, including but not limited to alarm hardware, user display, a power supply, and an enclosure.

Figure 128:
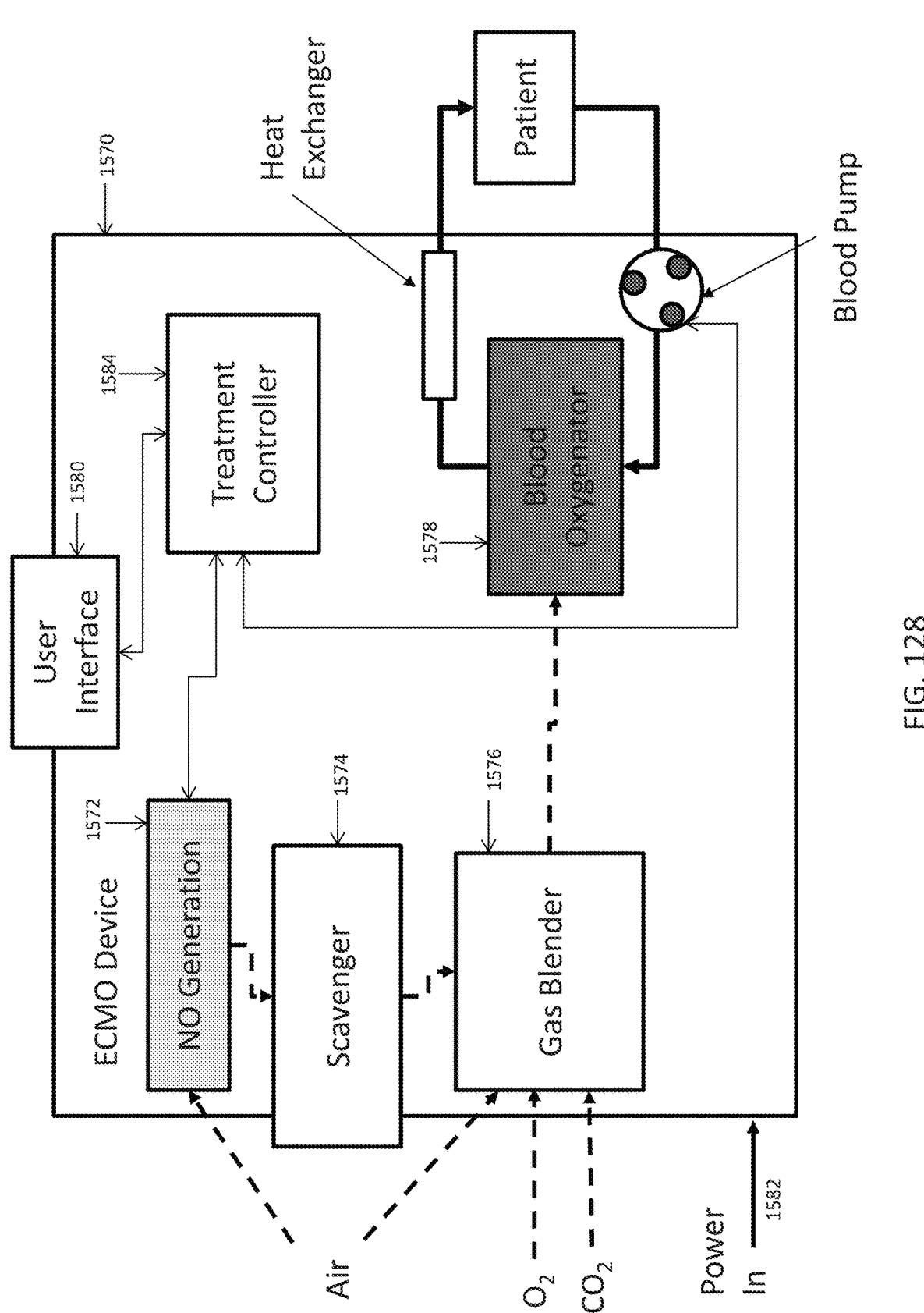
FIG. 128 is an exemplary embodiment of an NO generation module with an extracorporeal membrane oxygenator (ECMO) system.

FIG. 128 illustrates an exemplary embodiment of an ECMO system 1570 with an embedded NO generation module 1572. In some embodiments, air can be sourced from a house supply for NO generation and gas blending. In some embodiments, air for NO generation can be sourced from ambient, NO-containing air that passes from the NO generator through a scavenger 1574 to a gas blender 1576 and on to a blood oxygenator 1578. As shown in FIG. 128, the NO generation module can share various components with the ECMO system, including a user display 1580, a power supply 1582, a treatment controller 1584, an enclosure, an alarm system (not shown), and an air source. As shown in FIG. 128, an NO generation module can generate NO that can be passed through a scavenger to remove $NO_2$. The scavenger can be a separate component or can be housed within the NO generation module such that the scavenger can be replaced when necessary. The gas blender has a variety of inputs, including ambient air, $O_2$, $CO_2$, and the output from the NO generation module and scavenger. The output gas from the gas blender can be passed to a blood oxygenator that can send this gas to a patient. The ECMO system can also include a treatment controller to allow a user to control the gas passed to the patient.

In order to integrate an NO generation device into a piece of capital equipment, such as a ventilator, measurements of various gas levels, including NO and $NO_2$, can be needed. When using various respiratory or oxygen concentration-related devices, numerous sensors can be used for measuring concentrations of a variety of gases or other substances. A sensor module can be used alone or in combination with an NO generation module to measure various levels of substances related to the NO generation module, the medical machine, and/or the patient. For example, gas analysis sensors, such as electrochemical sensors, can be used and can have a finite service life and can be changed out periodically.

In some embodiments, the sensor module can include one or more standard inputs (for example, sample gas, power, sample gas pump commands, mode commands) and can return one or more outputs (for example, gas concentrations of one or more gases, water trap level, sample gas flow rate, and/or alarm conditions). Alarm conditions can include but are not limited to $NO_2$ high, water trap full, sample gas flow zero indicating a problem with a sample line, such as a kinked sample line. In some embodiments, the sensor module can receive a single power input, such as a 12 VDC, to power the pump, sensors, and/or microprocessor. In some embodiments, the sensors can be digitized and provided as an output via an I2C communication. In some embodiments, the sensor module can also monitor the water level in a water trap that is used to collect moisture from a gas sample. A water trap can be included as part of a sensor module. Drying of a sample gas can be accomplished using a coalescing filter, centripetal vortex, hydrophobic membrane, chemical desiccant, or other means. Depending on the sensor methodology, excessively dry sample gases can affect sensor performance. In some embodiments, to protect sample sensors from sample gas with inadequate humidity, a length of Nafion tubing can be included prior to the sensors to draw humidity from the ambient air into the sample.

One or more of the sensor outputs from the sensor module can be digitized and delivered over an I2C bus, or equivalent (USB, RS232, etc.). By standardizing the inputs and outputs to the sensor module, the internal components (for example, a pump, one or more gas sensors, one or more water level sensors, and one or more valves) can be upgraded without affecting the remainder of the capital equipment (i.e. a ventilator). By utilizing a sensor module, a user can also take advantage of improvements in sensing technology with the replacement of a sensor module with upgraded components.

NO generation devices typically measure various gases, including NO, $NO_2$ and $O_2$. By combining a plurality of sensors into a replaceable sensor module, it ensures that sensors are installed in the proper locations such that calibration and measurement accuracy are not compromised. The pneumatic connections from the sensor to a manifold can be made during manufacture of the module instead of by a user, thereby eliminating the potential for a partially-installed sensor introducing a leak to the system. Leaks can be a problem as they can affect sensor readings by decreasing the signal level and can introduce corrosive NO and $NO_2$ to the interior of the sensor module and/or NO generation equipment, which can lead to electrical failure. Replacement schedules can be easier to manage by a user because there is one replacement item (the entire sensor module) instead of individual sensors to be replaced.

By establishing a standard interface (for example, I2C communication) between the sensor module and capital equipment, internals to the sensor pack can be upgraded to take advantage of new sensor and/or pump technology without affecting the primary capital equipment.

In some embodiments, a pump that draws sample gas flow to the sensors can be located within the sensor module. This enables the use of a lower cost pump that can be replaced with the sensors, rather than requiring a long-term pump that is compatible for long term exposure to NO and $NO_2$. Including the sample pump within the sensor module allows the pump to be programmed to run at the correct speed for the sensors in the module. Furthermore, a sample gas pump within the sensor pack can be positioned before the sensors, thereby pushing air to the sensors with positive pressure, rather than subjecting the sensors to vacuum pressure. This can help to maintain a sample pressure closer to atmospheric levels at the location of the sensors, thereby preventing an excessive pressure differential between the sensor case and sensing element. It can also prevent introduction of ambient gases into the sample in the presence of a leak, thereby diluting the sample concentration.

In some embodiments, the sensor module can include a water trap sensor for determining water level within the sample gas water trap. In some embodiments, the water trap can use a capacitive means to measure fluid height. It will be understood that other approaches can be used to determine fluid height in the water trap, including but not limited to ultrasonic, optical, floating magnet, and conductive techniques.

Figure 129:
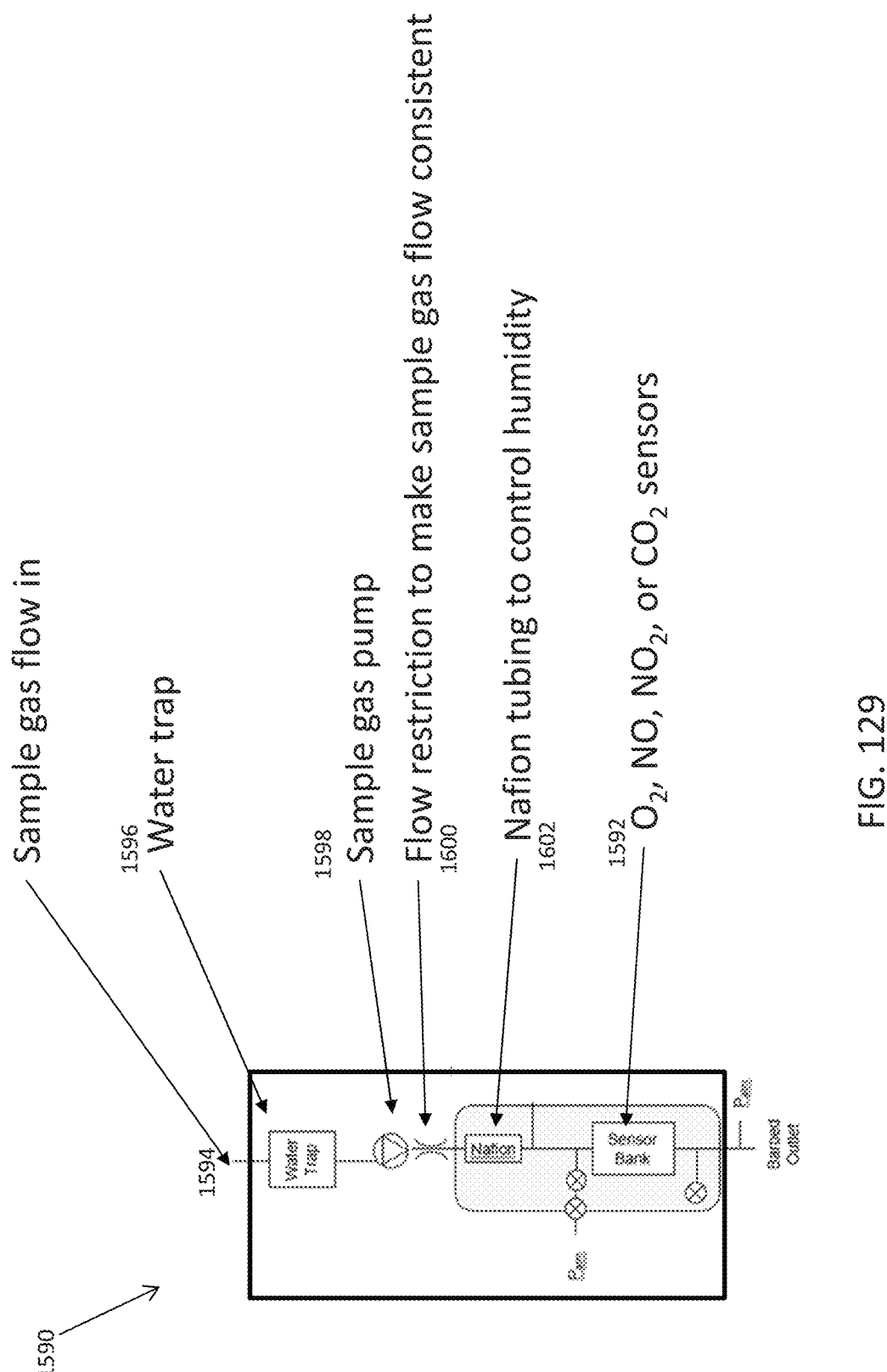
FIG. 129 is an exemplary embodiment of a sensor module.

An exemplary embodiment of a sensor module 1590 is shown in FIG. 129. In some embodiments, the sensor module 1590 includes one or more sensors 1592 for measuring NO, $NO_2$, $O_2$, and/or $CO_2$. Sample gas can flow into the sensor module 1590 through an inlet 1594 and can be directed through a water trap 1596 such water can collect in the trap and the sample gas can pass therethrough. The sample gas can be directed to a gas pump 1598 and a flow restriction device 1600 that can be configured to achieve consistent flow of the sample gas through the sensor module. In some embodiments, the sensor module can also include a water trap and a mechanism to control the humidity within the sensor module. For example, it can be a length of Nafion tubing 1602 to help convey humidity from the gas sample to the ambient surroundings or from the surroundings into the sample to help ensure that the humidity levels are acceptable for the gas sensors.

Additional sensors can also be included in the sensor module. For example, a sensor module can also include humidity, pressure and flow measurement sensors. One or more flow measurement sensors can be used to confirm that sample gases are flowing and that the pump is functional. In some embodiments, one or more flow measurement sensors, and/or one or more pressure sensors can be used to confirm that the sample line is properly connected to the inspiratory circuit, without kink or obstruction, by comparing the prevailing flow resistance to a known characteristic flow resistance. Other ways to ensure that the gases are flowing is to look at pump current, pump vibrations, sample line pressure/vacuum, and/or pump motor encoder. Sample gases can be pushed through the sensor module or pulled through the sensor module. In some embodiments, a low-cost pump can be included in the sensor module that can be replaced at the same frequency as the module. In some embodiments, the pump can be located before the sensors or after the sensors within the module. In some embodiments, the pump can be located in the capital equipment and not in the sensor module.

Figure 130:
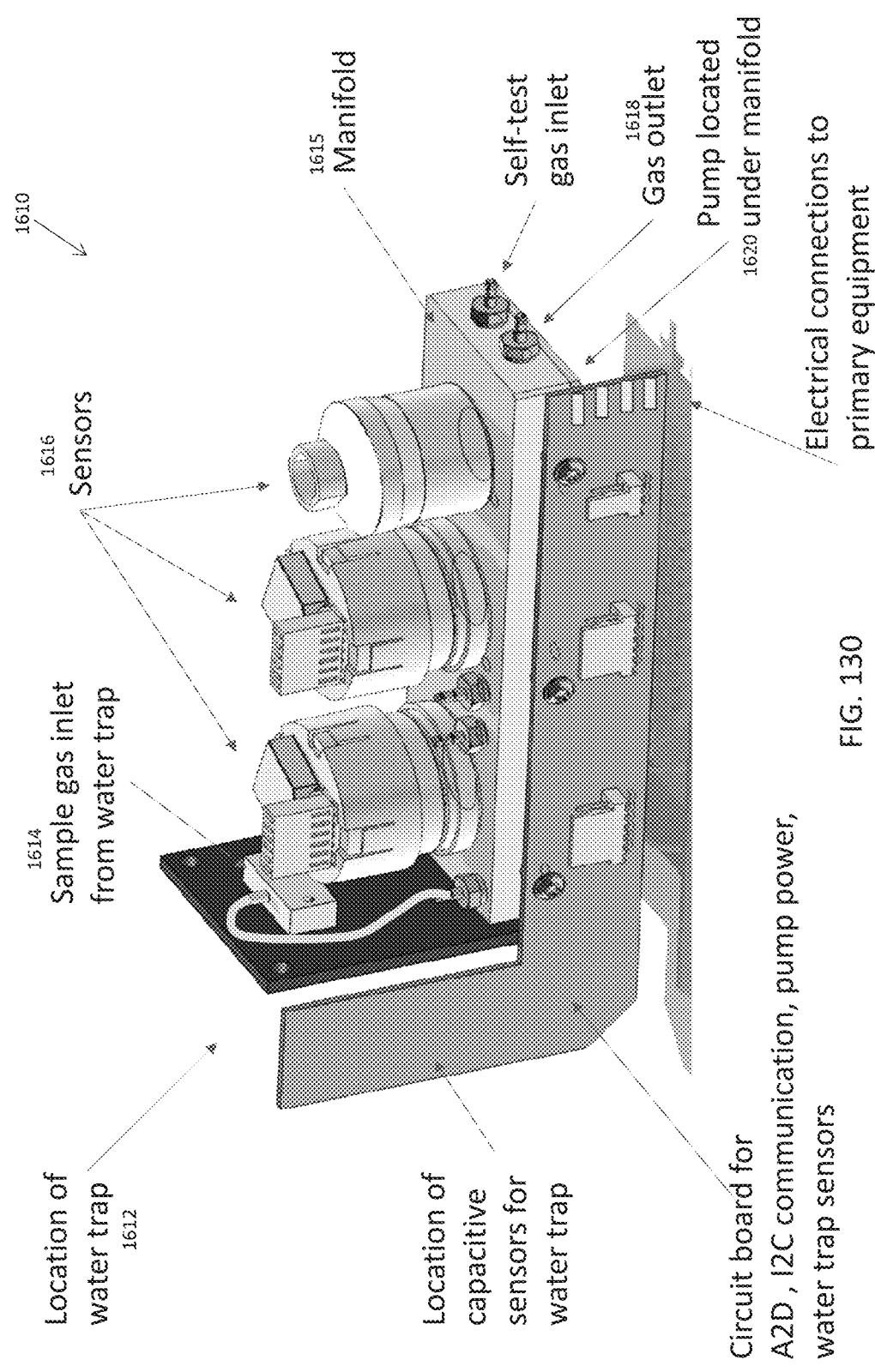
FIG. 130 is an exemplary embodiment of a perspective view of the components inside a sensor module.

FIG. 130 illustrates an exemplary embodiment of the internal components of a sensor module 1610 where sample gases are pulled through the sensor module. The sensor module can include an integrated water trap 1612 on the left side (as shown in FIG. 130 by a black dashed quadrilateral). Sample gases can flow into the water trap 1612 and can be dried before passing through the dry air inlet 1614 and into Nafion tubing. The Nafion tubing adds humidity from the ambient environment in the event that dry calibration gases have been introduced to the sensor pack. The Nafion tubing connects to the manifold. Sample gases flow through the sensor manifold 1615 by three sensors 1616 ($NO_2$, NO and $O_2$) and on to the gas outlet 1618. In some embodiments, the sample gas pump 1620 is located outside the module, downstream of the gas outlet, and pulls sample gases through the module.

Figure 131:
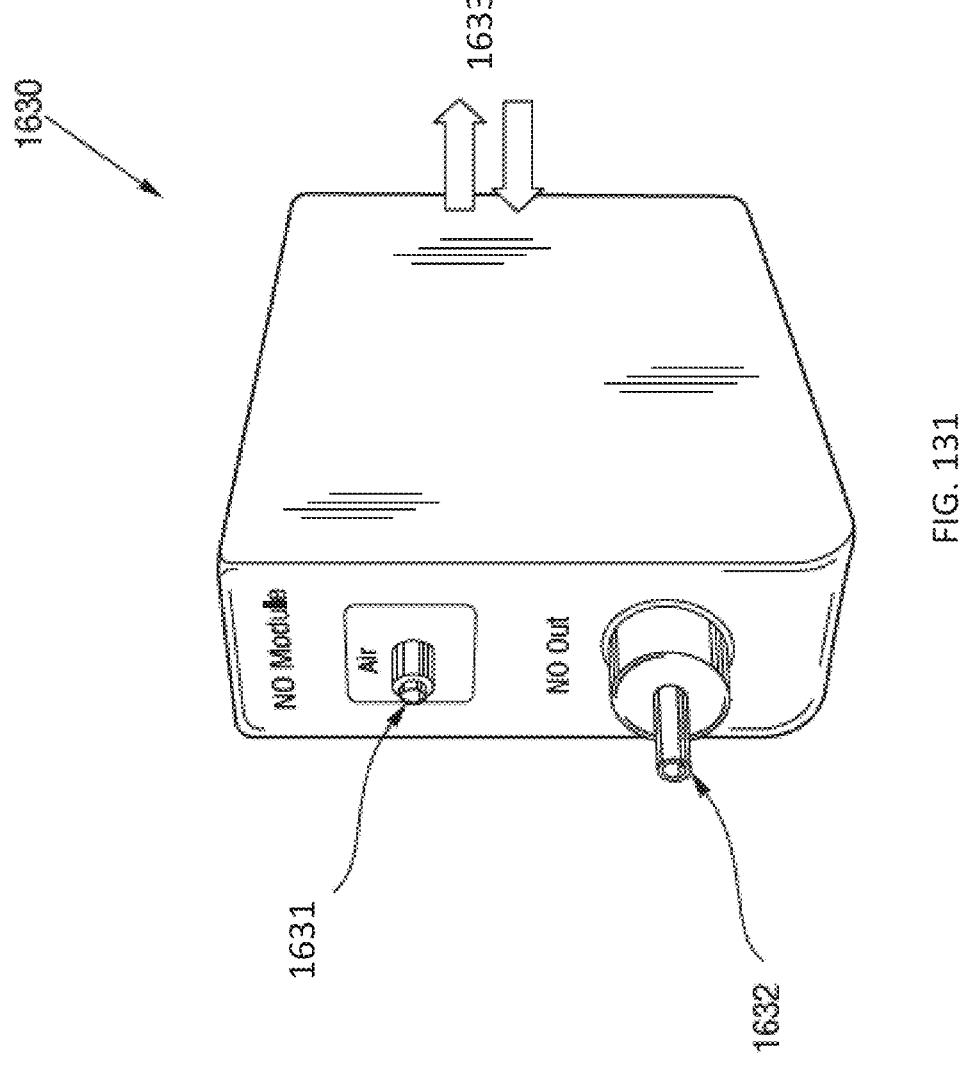
FIG. 131 is an exemplary removable NO generation module that accepts compressed air.

FIG. 131 depicts an exemplary removable NO generation module 1630. Compressed air enters the module from an upper fitting 1631. In some embodiments, the compressed air can be obtained from a wall outlet via a "T" connector, which can eliminate the need for a pump, pre-scavenger, and/or an air reservoir. A removable scavenger cartridge 1632 is inserted into the NO exit of the module on the bottom. The module receives power and treatment settings from the equipment the module is inserted into, such as a ventilator. In some embodiments, a bi-directional communication channel 1633 can be used to obtain ventilator data and/or control data and to send alarm and/or status messages back to the ventilator.

Figure 132:
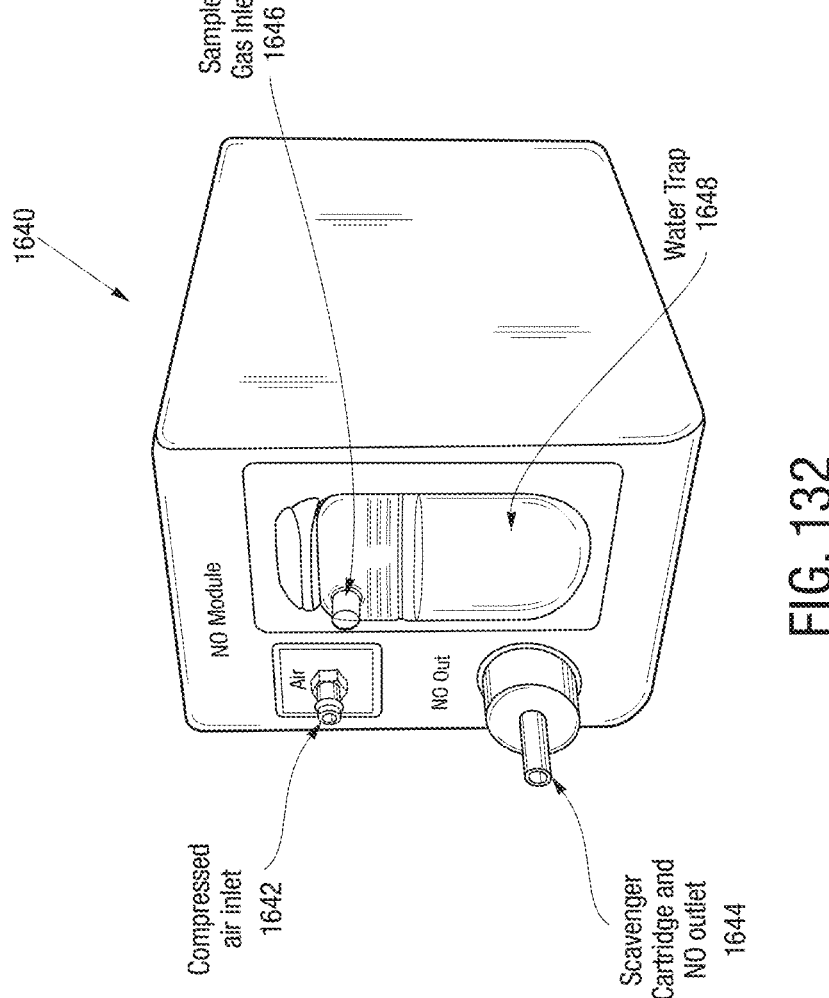

FIG. 132 depicts a combination NO generation and sensor gas analysis module 1640. The module uses compressed air sourced through an upper connection 1642. NO generation is powered by the equipment the module is inserted into. NO containing gas exits the bottom fitting through a replaceable $NO_2$ scavenger component 1644. Sample gases enter the upper right fitting 1646, where sample gases are dried in a water trap 1648. The reservoir of the water trap is removable for draining. This module contains NO and $NO_2$ sensors, however additional sensors could be included to analysis the same sample gas.

As explained above, NO generation can be associated with a patient monitor. The NO generation capabilities can be integrated into a patient monitor, or the patient monitor can be used with an NO generation module as described above.

The integration of an NO generation module or NO generation capabilities with any type of device, including but not limited to a patient monitor or a ventilator, can provide user benefits, including reduced cost due to shared hardware including, but not limited to user display, alarm lights, speaker, back-up battery, power supply, nurse call hardware, hardware watchdog, ambient temperature and pressure sensors, etc. A combined display enables a user to see the current patient vital signs, ventilation and hemodynamics in one location. This can save time and improves the user's ability to assess relationships between the data. Furthermore, there are consistent and identical user interfaces for alarm and alarms settings as well as trend analysis and the ability to plot relationships between patient data are only a few aspects of the benefits of an integrated solution. Since NO has a direct impact on the hemodynamic performance of the cardio pulmonary system, it can be beneficial for the clinician to control the NO dose and see the effects from one piece of equipment. Closed-loop control of NO delivery based on patient status can be facilitated. Patient monitor values, including but not limited to $SpO_2$, $ETCO_2$, respiratory rate, heart rate and other factors could serve as inputs into the NO generation algorithm.

In some embodiments, a patient monitor can be connected to a central station for remote viewing and alarming and to the hospital information system, providing seamless data integration in the patient legal record. In some embodiment, a patient monitor can also be connected to an export data stream of a ventilator to integrate the ventilator settings, flow and airway pressure curves into NO treatment algorithms and/or the patient treatment record.

Beside the benefit of data integration, an integrated device can reduce space and foot print which is highly desirable in a clinical setting. The space around a critically ill patient is occupied by monitoring and ventilation equipment, including up to 16 infusion pumps, so any reduction in foot print can make a clinical setting easier to work in and safer due a reduction in cables and tubes.

Figure 133:
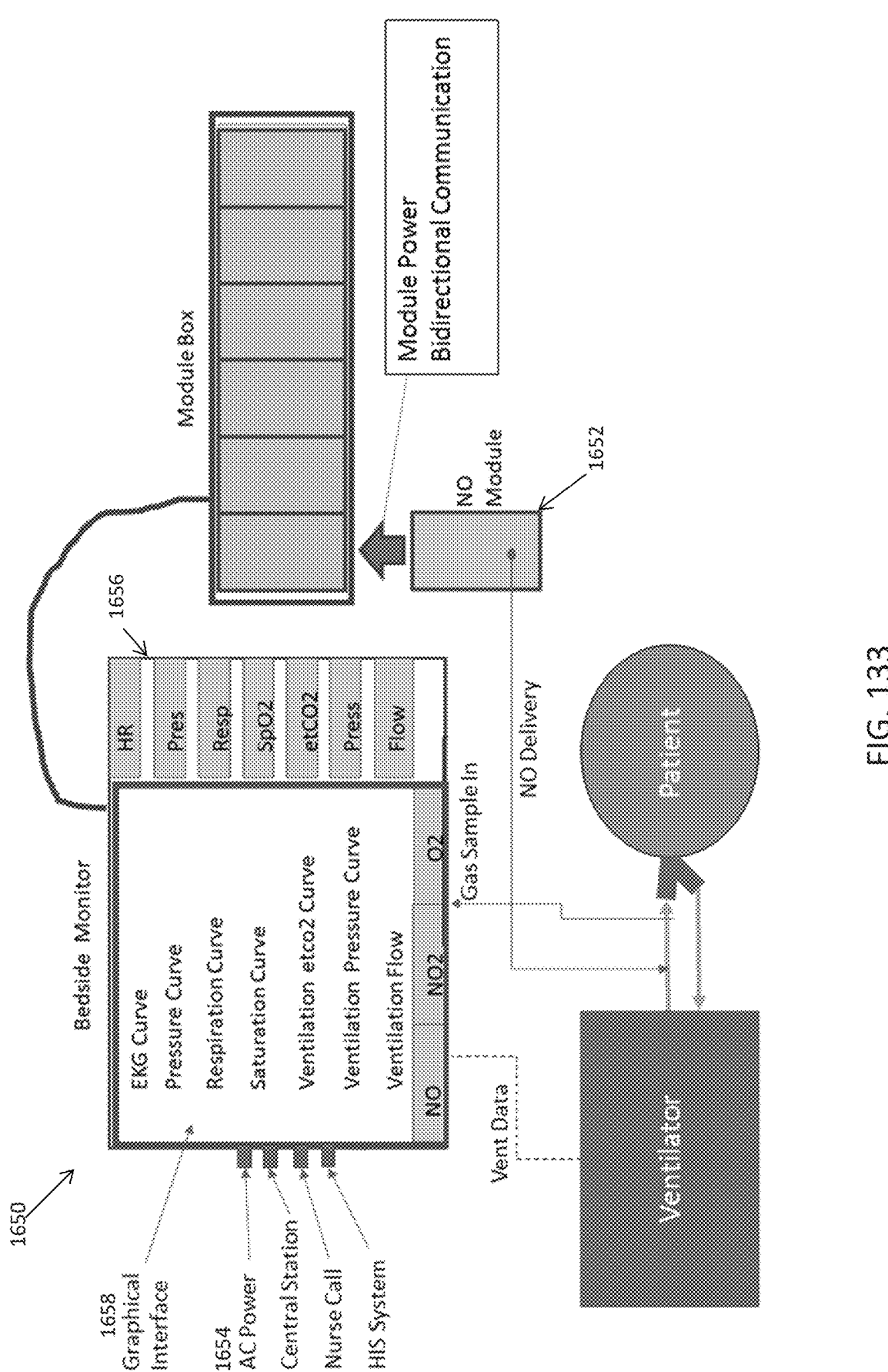
Figure 134:
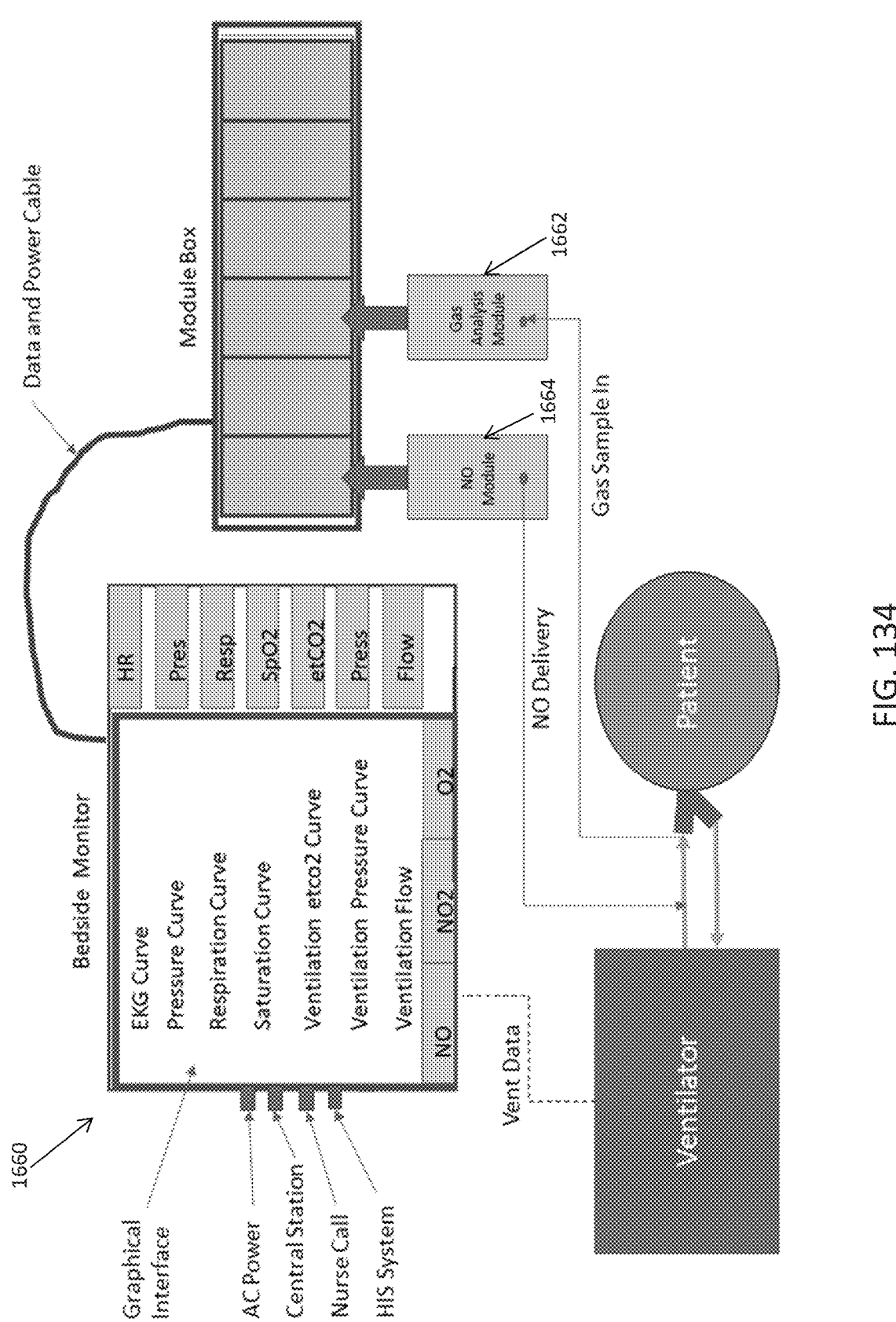

FIG. 133 illustrates an embodiment of a patient monitor 1650 with expansion slots for use with various modules, including an NO module 1652. The patient monitor is configured to receive AC power 1654 or DC power from a wall. The patient monitor can include built in monitoring capabilities 1656, including but not limited to heart rate, blood pressure, respiration rate, $SpO_2$, $etCO_2$, ventilation pressure, ventilation flow, NO gas concentration, $NO_2$ gas concentration, and $O_2$ gas concentration. Various connections to the patient for standard features such as EKG and $SpO_2$ can be included (these connections are not shown). The monitor 1650 can include a display 1658 for observing all data, trending and relationships between parameters. Time histories of patient parameters can also be shown on the display, while gauges for NO, $NO_2$ and $O_2$ can be shown (in some embodiments, at the bottom of the display). NO, $NO_2$ and $O_2$ gas analysis sensors can be embedded in the patient monitor, housed within a separate gas analysis device, or be within a module within the expansion dock (for example, as shown in FIG. 134). The monitor can also provide a consistent alarm and display format for one or more patient parameters, making alarm priority and legibility more consistent across potential issues. Gas samples can be drawn from the patient inspiratory limb, typically just before the patient wye connector. In some embodiments, the patient monitor can include a pump for drawing sample gases and a water trap and/or Nafion tubing to prepare the gas sample. Exhaust sample gases are either released to the room or connected to hospital vacuum.

FIG. 134 illustrates an embodiment of a patient monitor 1660 with an NO module 1664 and one or more gas analysis modules 1662. In some embodiments, inspiratory gas samples can be drawn into a gas analysis module. The gas analysis module can include a water trap, length of Nafion tubing, NO sensor, $O_2$ sensor, $NO_2$, sensor, pressure sensor and temperature sensor, and gas pump. The module box shown in FIG. 134 can be located in a separate housing, as shown, or could be integrated into the primary housing of the patient monitor.

In some embodiments, a patient monitor with an integrated NO module solution can be used in a catheterization laboratory where a patient is pretested for an upcoming open-heart surgery to determine if the patient is a responder to nitric oxide and can benefit from NO therapy during surgery and post-op in the ICU. In some embodiments of a catheterization laboratory implementation, there is no ventilator involved, only a hemodynamic monitor.

Figure 135:
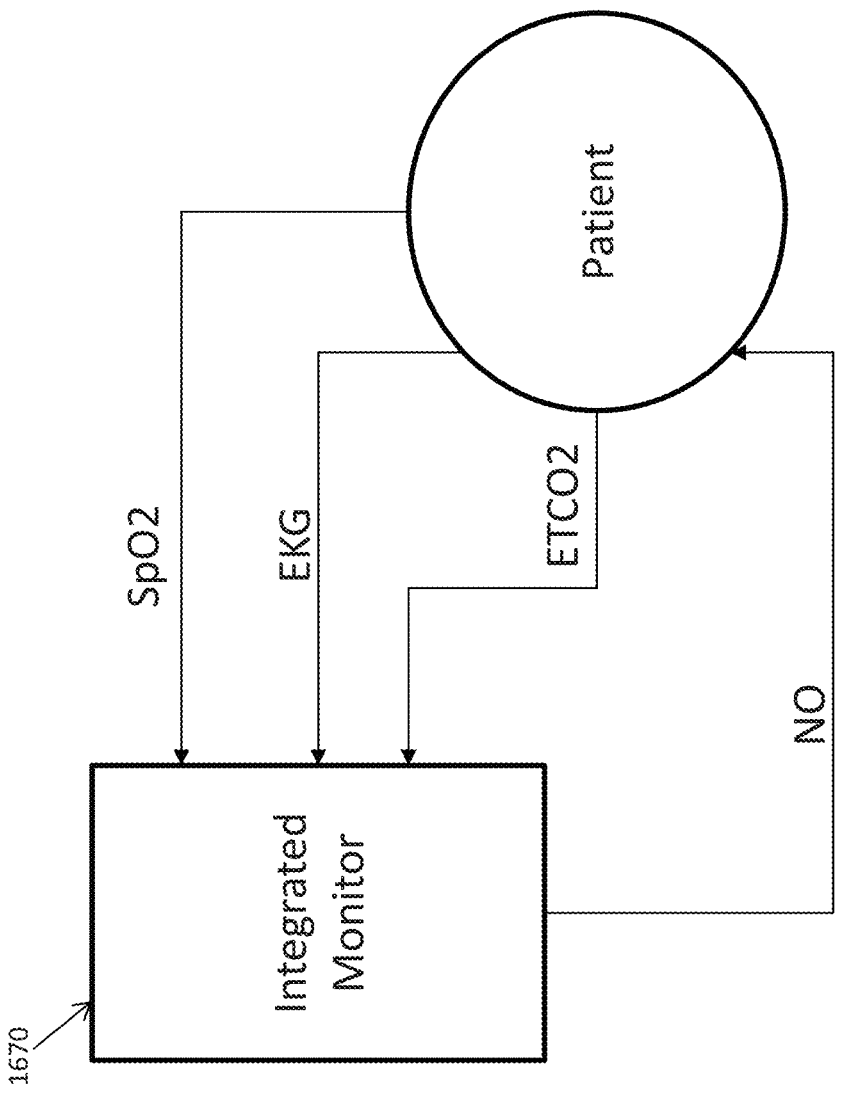

FIG. 135 illustrates an exemplary embodiment of a catheterization laboratory set-up utilizing a patient monitor 1670 with integrated NO generation. The patient monitor can receive patient parameters, such as $etCO_2$, respiration rate, EKG, and/or temperature. The patient monitor can have an output of NO that is delivered directly to the patient. Delivery can occur through various means, including through a nasal cannula, ET tube, face mask or other means. NO delivery and patient response data can be collected synchronously and can be viewed and stored within the patient monitor. This can facilitate the ability to assess the patient's response to NO.

Electronic No Tank

It is also possible for NO generation to be achieved using an electronic NO generation tank replacement device. This tank replacement device can used with any device that can utilize NO, including but not limited to a ventilator, a CPAP machine, an anaesthesia device, and a patient monitor. In some embodiments, the tank replacement device can be in the form of a standalone device that can generate NO to be added or blended into a medical gas stream or to be delivered directly to a patient in an undiluted form (for example, in the case of a test in a cath lab). In some embodiments, the tank replacement device can produce a constant amount of NO at a constant flow rate. While the tank replacement device can include various features, in some embodiments the device can be configured to automatically adjust air flow (pump speed, air pressure, flow controller orifice diameter, flow valve duty cycle) and/or plasma activity (including but not limited to pulse width, pulse frequency, electrical current frequency, current level, plasma energy, primary switching voltage, and/or power) in order to maintain a target NO concentration within the output of the device. The NO dose control can be achieved using a variety of mechanisms, including software controls, electrical hardware controls, or mechanical controls.

In some embodiments, an NO generation tank replacement device can include a means to know the amount of NO to be generated. The NO dose can be calculated based on data from a flow sensor in the medical gas air stream, or it can be from a user setting provided to the NO generator through various mechanisms, such as a touch screen interface, up-down buttons, a rotational knob, a linear potentiometer, or other means. The NO dose can also be calculated from flow data from a second device, such as a patient monitor, ventilator, CPAP machine, or other device that utilizes the NO.

The NO generation tank replacement device can include a means to generate an air flow. Air flow can be generated from a device, such as blower, fan, bellows, or diaphragm pump. Air flow can come from a compressed gas source, where the NO generation device varies air flow automatically with a flow controller, proportional valve, or the like. Air flow can come from a compressed gas source and be controlled mechanically with a valve that is adjusted by a user as part of setting the dose. The proportional valve can be part of the NO generation device or located in the air supply before the NO generation device.

Various other components of the NO generation tank replacement device can include one or more spark gaps to generate a plasma for the formation of NO. The spark gap can include either continuous or intermittent arcing. A high voltage circuit can be used to generate sufficient voltage to break down air at the spark gap. A scavenger with $NO_2$-absorbing material can be provided to remove $NO_2$ from the NO flow. The scavenger can be in the NO flow before introduction into the main flow, or the scavenger can be in the NO flow after introduction into the main flow.

In some embodiments, $O_2$ therapy can be administered to a patient at a constant flow rate. When NO is added to a constant flow of medical gas (air, $O_2$, other), the NO delivery can be constant as well. This treatment scenario can be addressed by a very simple NO generation device that is not burdened by fast responding flow sensors and high-performance pumps and flow controllers, such as the NO generation tank replacement device.

Figure 136:
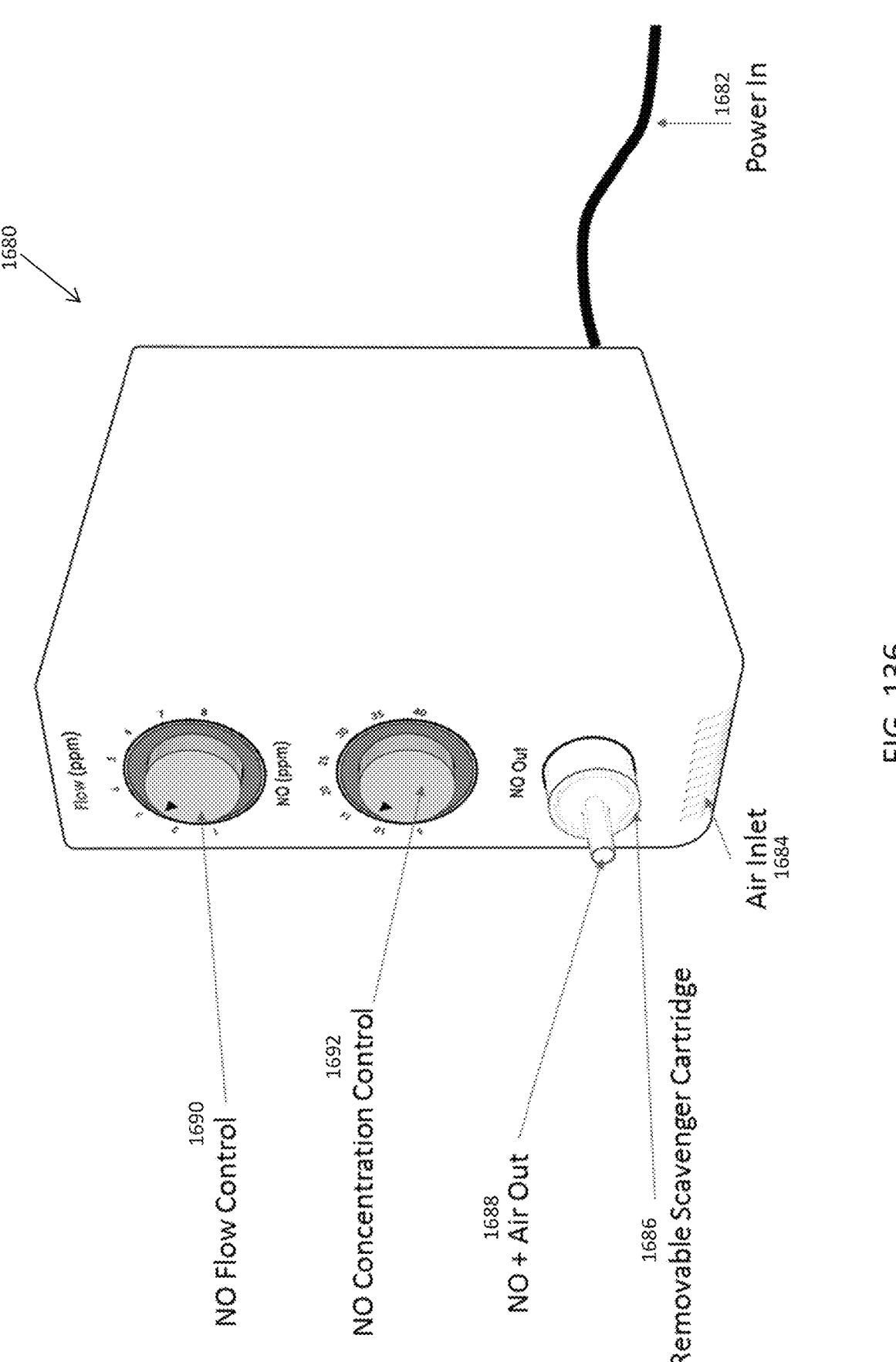

FIG. 136 illustrates an exemplary embodiment of an electric NO generation tank 1680. Electrical power 1682 can be supplied from either an AC or DC source. In some embodiments, air can be sourced from ambient air through air inlets 1684 in the housing. NO can be generated within the unit and can be passed through a removable $NO_2$ scavenger 1686 at the device outlet 1688. Various user adjustment devices can be provided. For example, air flow level 1690 and NO dose adjustments 1692 can be provided for a user to adjust settings of the NO generation tank.

Figure 137:
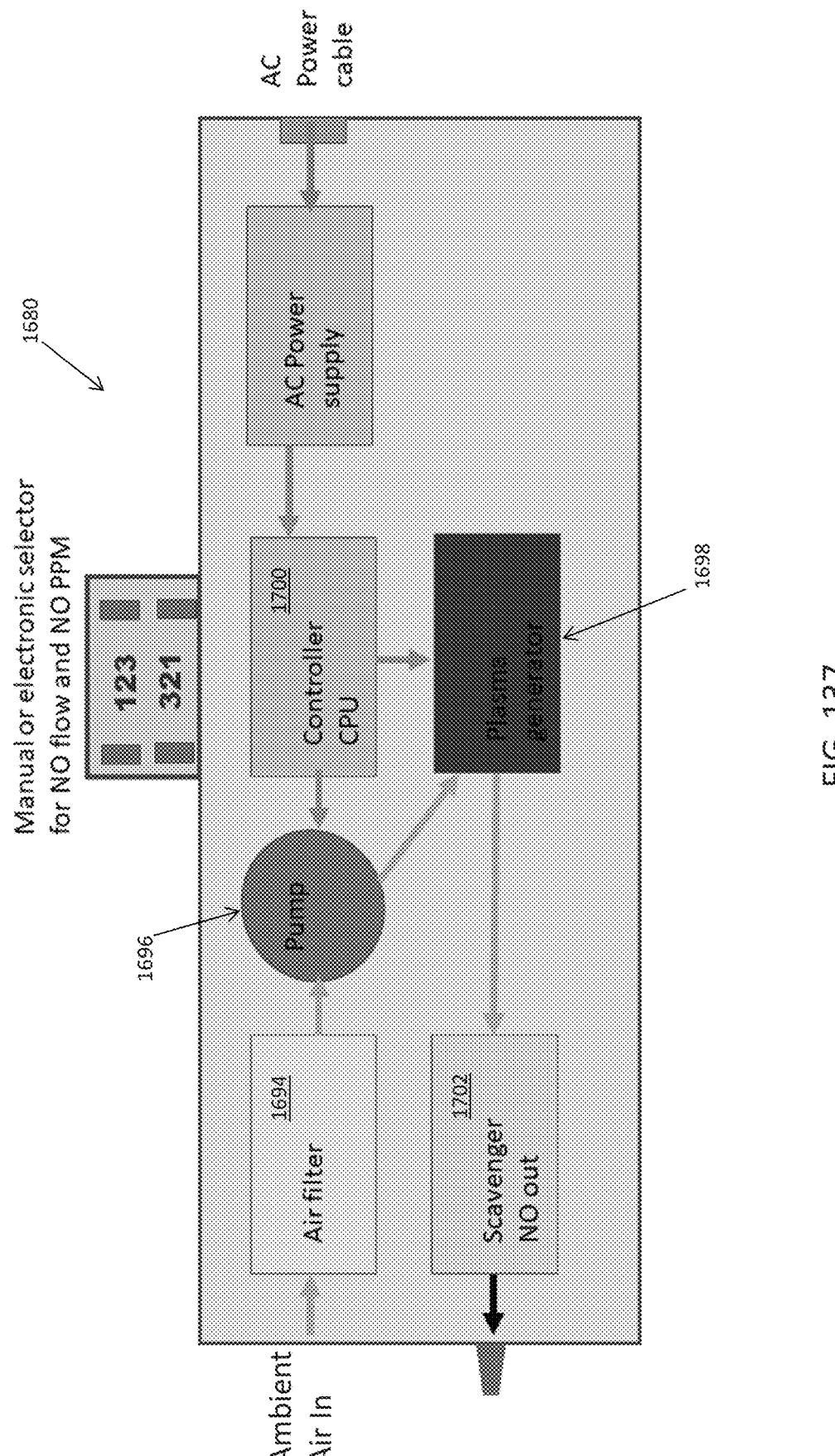

FIG. 137 illustrates an exemplary embodiment of an internal structure of the electric NO generation tank 1680 of FIG. 136. In some embodiments, air can be sourced from the environment and passes through a filter 1694 and pump 1696. Air leaves the pump and flows through a plasma chamber 1698. The plasma generator is controlled by a controller 1700, for example a CPU, which receives user dose and flow settings and transmits them to the plasma generator. The plasma generator can be comprised of a high voltage circuit with electrodes. Air passes through the plasma generator, where part of the $N_2$ and $O_2$ in the air is converted to NO and $NO_2$. The air then passes through a scavenger 1702 where $NO_2$ is absorbed but NO levels are left largely intact. A combination of NO and air exits the air tank.

Figure 138:
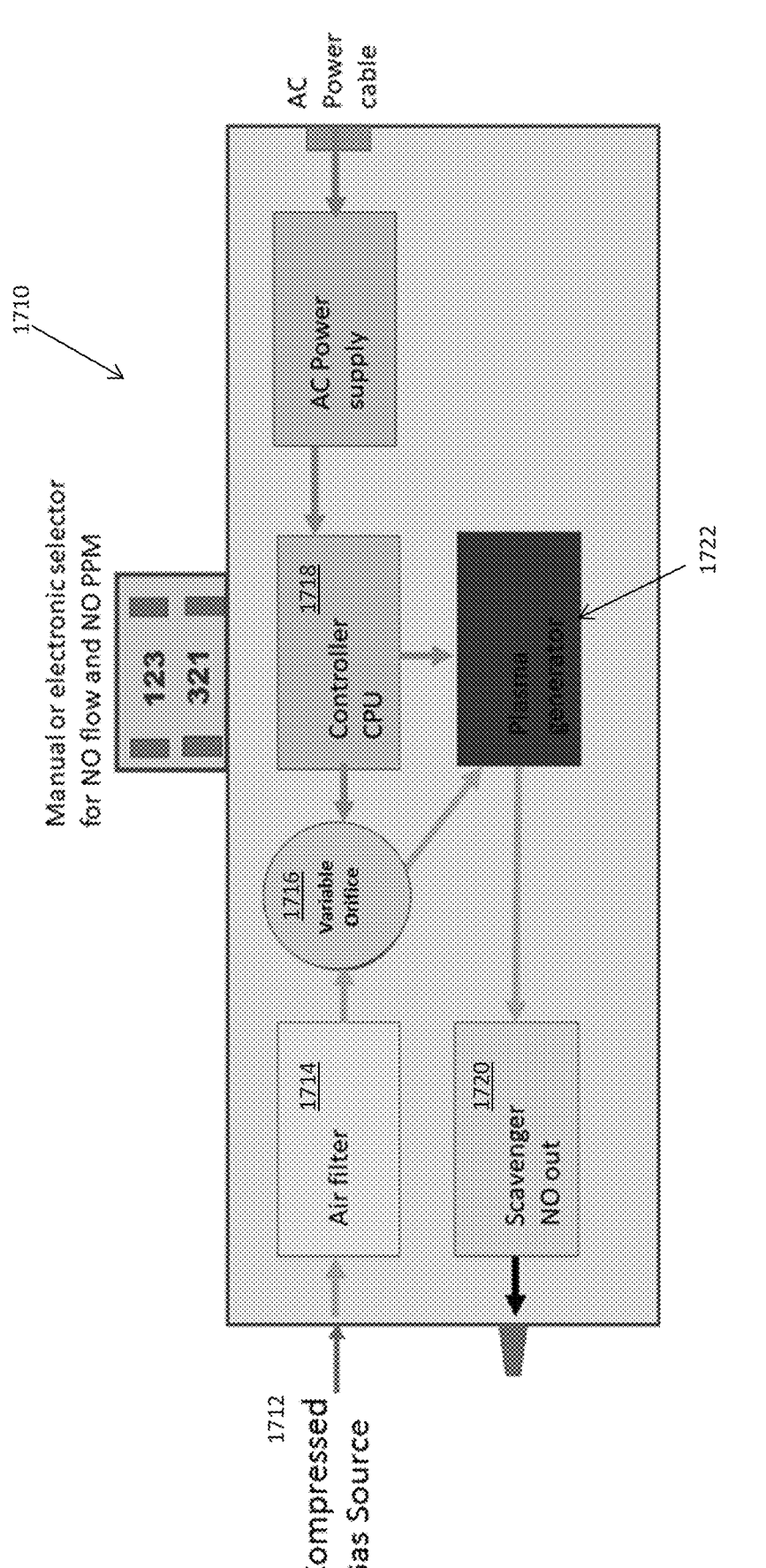

FIG. 138 illustrates an exemplary embodiment of an electric NO generation tank 1710 that can be connected to a pressurized gas source 1712. Typically, the incoming gas is air or another combination of $N_2$ and $O_2$. In some embodiments, the pressurized air can pass through a filter 1714 (although this can be optional, depending on the purity of the air source) and through a variable orifice 1716. The variable orifice can be controlled by a controller 1718, such as a controller CPU, however manual control of the orifice can also be achieved. The variable orifice can be used to control the amount of air that flows through the plasma generator 1722, thereby controlling the amount of NO generated. Additional NO generation controls can also be used, including by varying the plasma activity (energy, pulse width, electrical current frequency, current, primary switching voltage etc.). The output from the NO generator contains $NO_2$ (for example, 6% to 10% of the NO level when an iridium electrode is used). The $NO_2$ can be scrubbed using a scavenger (for example, soda lime) as it exits the tank. The scavenger 1720, such as soda lime, has a finite life so it is packed in a removable housing that can be replaced periodically.

In some embodiments, the system can periodically search for the resonant frequency within the high voltage circuit. This can be done when the system is powered on, at the beginning of a patient treatment, daily, or some other frequency. Determining the resonant frequency of the circuit accounts for variation in manufacturing, electrode gap (from wear and manufacturing), and transformer variance. By operating at the resonant frequency, the system can generate a spark with more energy, thereby increasing NO production.

Figure 139:
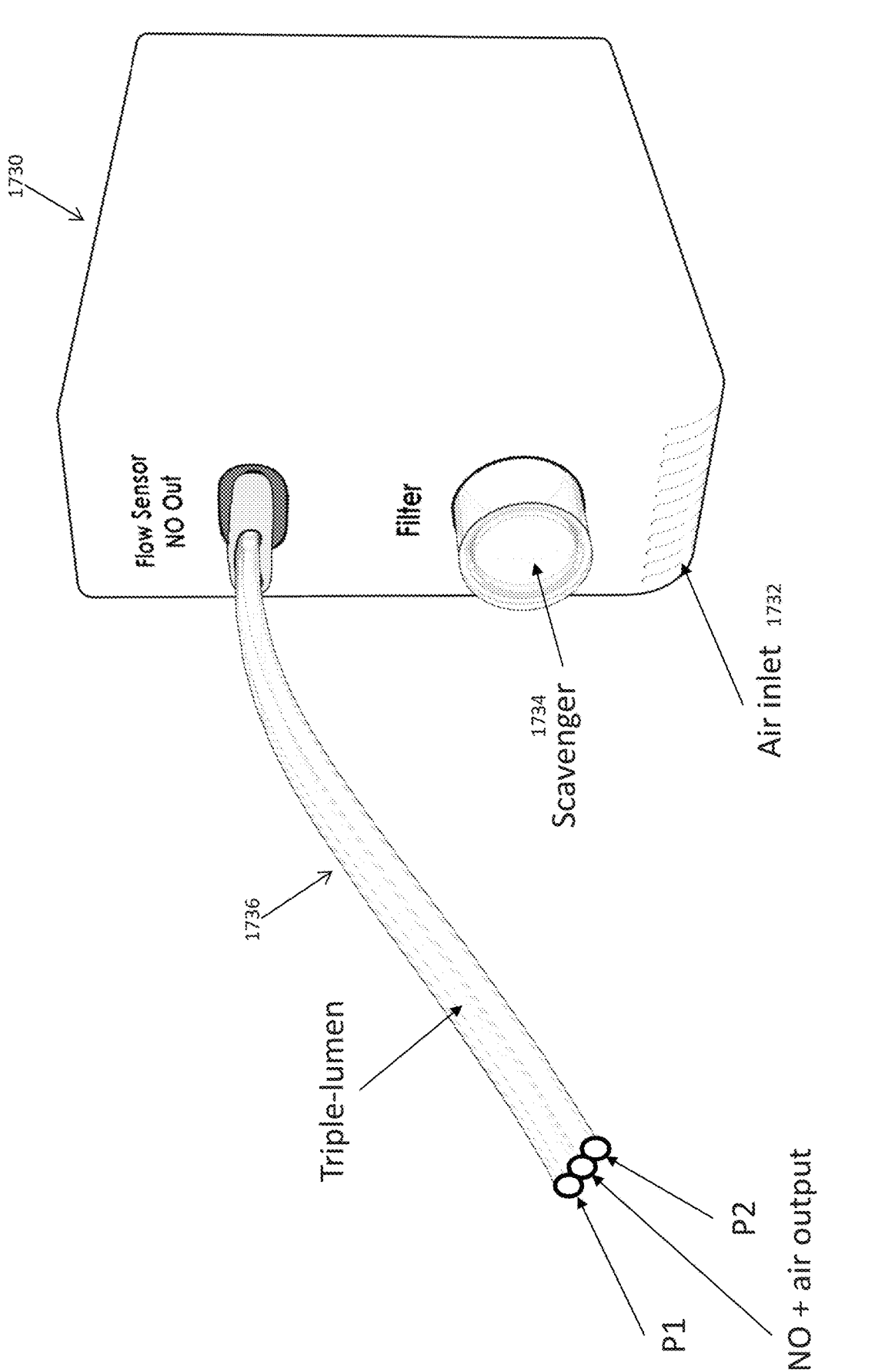

FIG. 139 illustrates an exemplary embodiment of an electric NO generation tank 1730 with a remote output. Air can be sourced from the environment through a grill 1732 or other opening in the enclosure of the tank. The air can be processed further by being passed through a HEPA filter. The HEPA filter can be included in the $NO_2$ scavenger cartridge 1734. In some embodiments, NO can be introduced to a flow of gases remote to the NO generation tank (for example, a ventilator circuit). A multiple lumen tube 1736, for example a three-lumen tube, can be used to deliver NO to the remote gas flow. The two remaining lumens are used to measure the flow in the remote gas flow using a differential pressure method, where the pressure sensor(s) are located within the NO generation tank device. Remote flow measurement can also be done with remote sensors at the end of the NO delivery tube, requiring both pneumatic and electrical connections to be made at the NO generation tank.

Figures 140A, 140B:
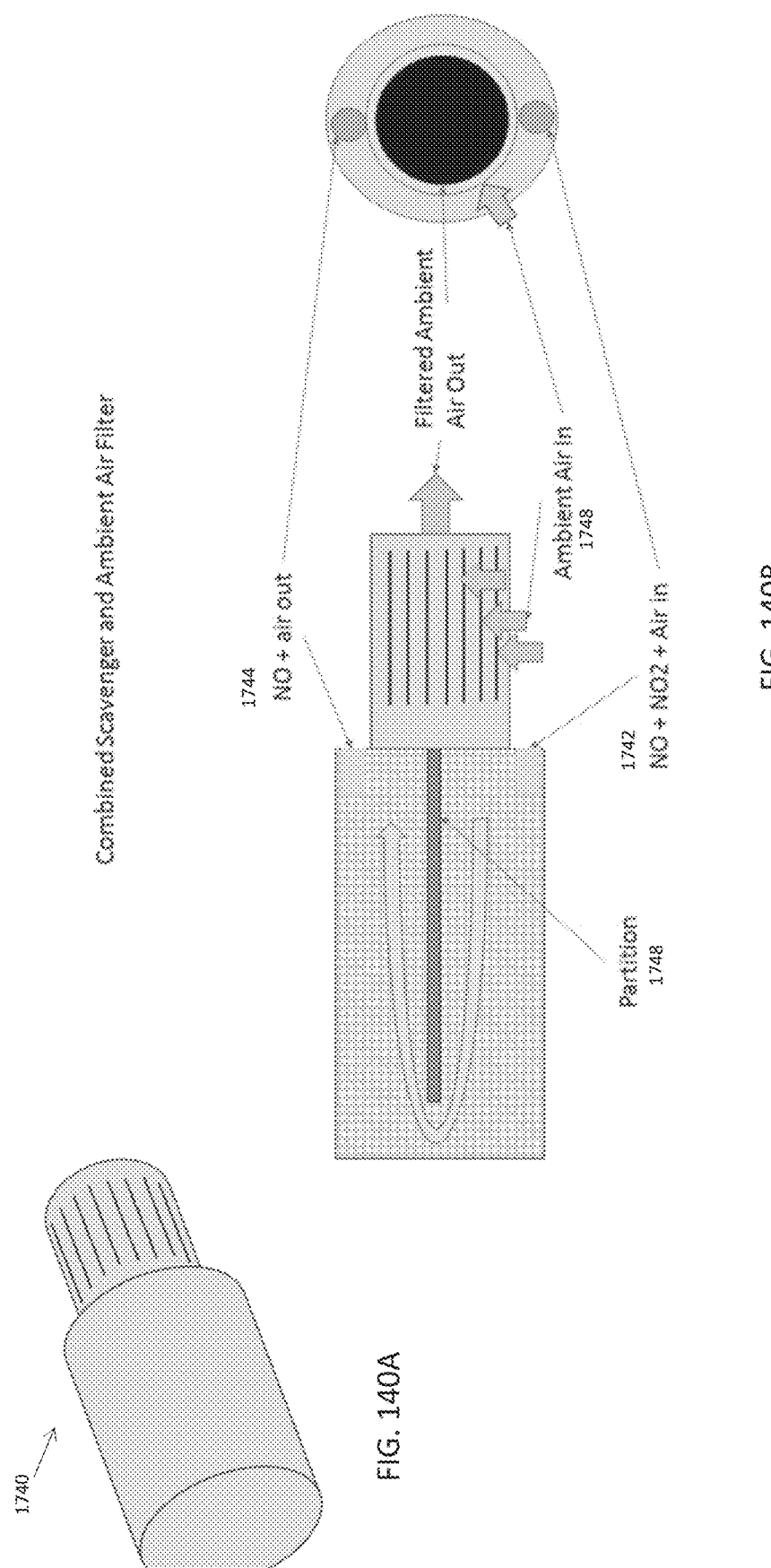

FIGS. 140A-140B illustrate an exemplary embodiment of a combined scavenger and ambient air filter 1740 (CSAAF), such as the one described in FIG. 139. The combined scavenger and ambient filter 1740 facilitates replacement for the user. The CSAAF can be connected to the NO generation device through three pneumatic connections: NO+$NO_2$+air in 1742, NO+air out 1744, and filtered ambient air in 1746. Ambient air can pass through a HEPA filter in the inserted end of the CSAFF and into an internal diameter, where it enters the internal pump. The external-facing end is filled with scavenger material. NO$_2$-containing air enters a pneumatic fitting on one side of the scavenger housing. A partition 1748 within the housing ensures that gases pass through a sufficient path length to absorb an acceptable amount of NO$_2$. A combination of NO and air exit the opposing pneumatic fitting and pass on to the NO outlet.

Figure 141:
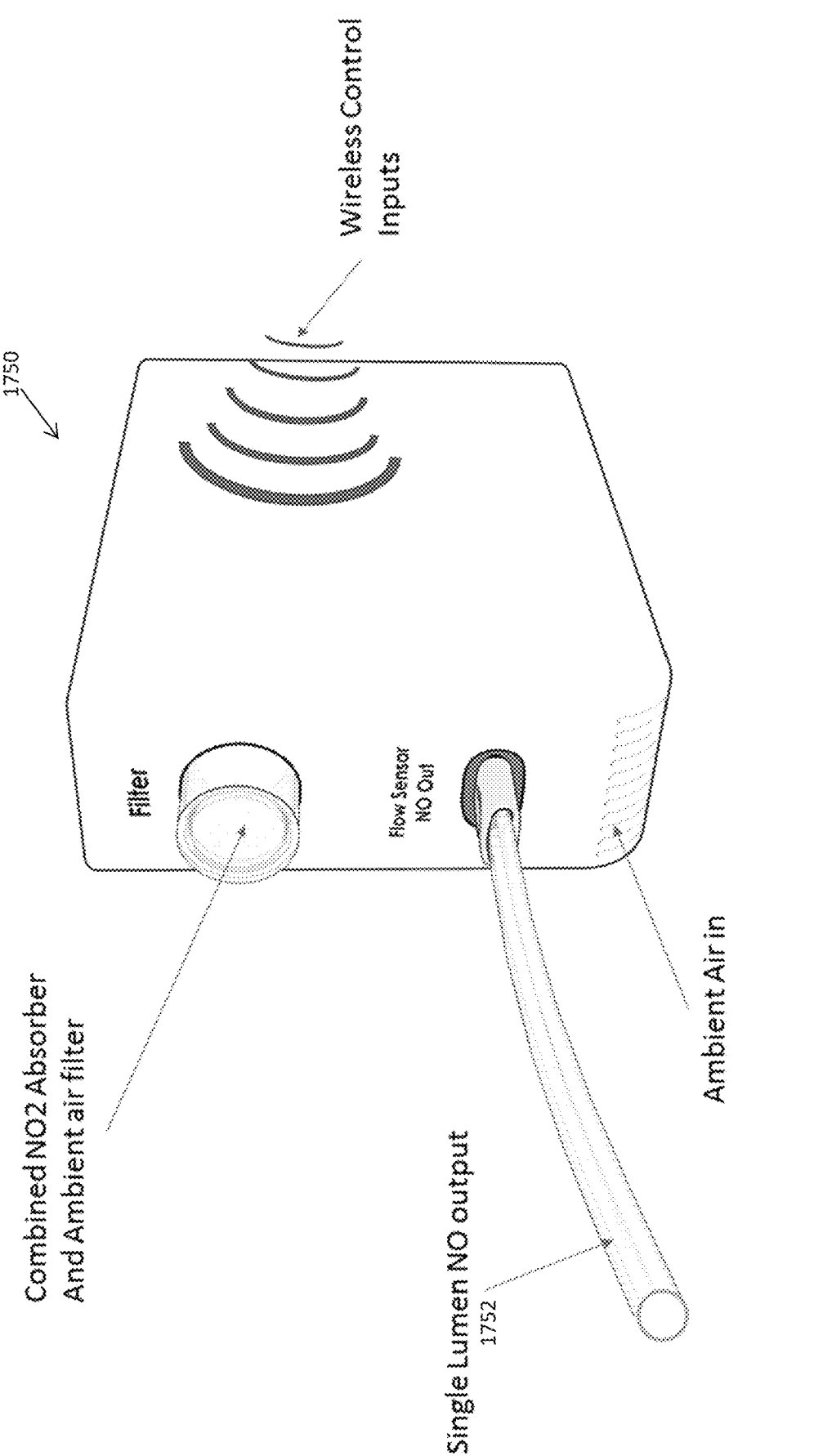

FIG. 141 illustrates an exemplary embodiment of an NO generation tank device 1750 having a single lumen output. The device shown can receive treatment parameters, wirelessly or by any other means, from other hospital equipment, such as a patient monitor or a ventilator. Example treatment parameters include but are not limited to patient respiratory rate, patient tidal volume, patient minute volume, patient air flow rate, ventilator settings, ventilator flow rate, ventilator flow trigger, SpO$_2$, pulmonary artery pressure, and target NO dose. The device uses this information to determine NO generation settings. The NO generation can be at a constant rate or vary with the patient treatment data (respiratory rate or ventilation rate for example). NO output is pumped down a tube 1752 to either the patient directly or indirectly via another medical gas stream.

Figure 142:
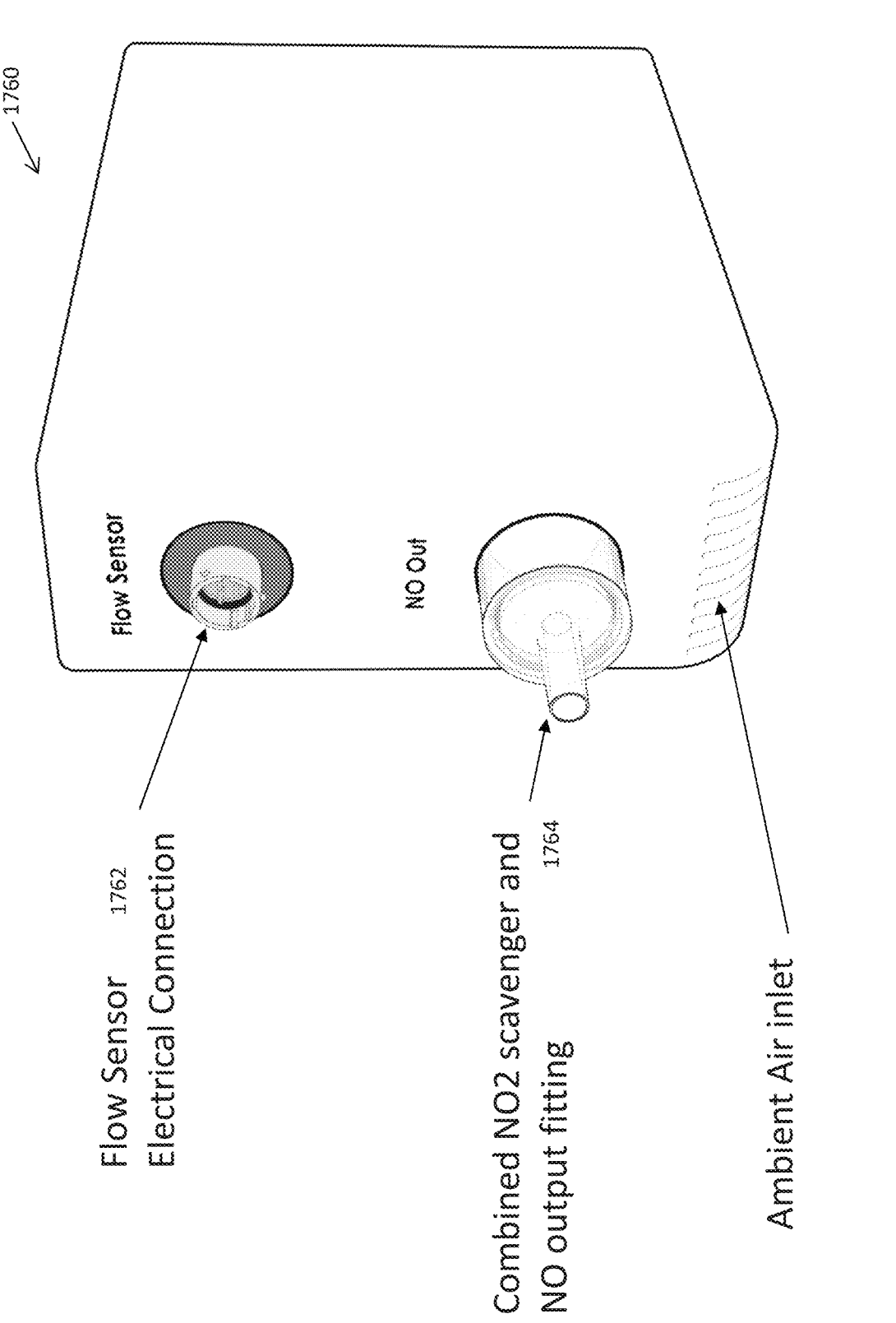

FIG. 142 illustrates an exemplary embodiment of an NO generator 1760 with a remote flow sensor. Flow can be measured by a flow sensor 1762 that is external to the NO generator. The flow sensor input can come from a dedicated flow sensor located within the patient inspiratory limb, or it can come from a ventilator, anaesthesia machine, CPAP machine or other medical device that measures air flow. The combination of NO and air exits the device through the scavenger component 1764. Air can be sourced from a variety of sources, such as air from the environment, a separate compressed air source, or other O$_2$ and N$_2$-containing gas mixtures.

During NO therapy, exhaled gases from a patient may contain NO and NO$_2$. These exhaled gases can be released into the surrounding environment, elevating NO$_2$ levels and potentially risking the health of the patient, care personnel and other nearby people. In one embodiment, the expiratory gases of a patient are scrubbed for NOx prior to release into the environment. Scrubbing for NOx can be done by carbon, soda lime and other materials. I one embodiment, a scrubber cartridge is attached to the exhaust port of a ventilator to remove NOx from patient expiratory gases. In one embodiment, a ventilator exhaust scrubber cartridge has an alarm feature that warns the user when the cartridge useable life has been exhausted. In one embodiment, an NO generation and delivery device tracks the use of a ventilator exhaust scrubber and alerts the user when replacement is warranted. In some embodiments, the replacement schedule is based on one or more of the following parameters: scrubber rated service life, elapsed time since the scrubber was installed, amount of NOx molecules delivered to the patient since the scrubber was installed, or other parameters that are related to the usable life of scrubber materials.

Ventilator treatment involves delivering to a patient the inspiratory pulses associated with breathing in addition to a bias flow which constantly flows. Some ventilators do not readily present the bias flow information, which could affect drug dosing of NO and other drugs delivered in the inspiratory airway. In one embodiment, an NO generation and delivery system presents to the user information on the ventilator flow, as detected by the NO generation and delivery device including one or more of: ventilator bias flow, peak airway pressure, minute volume, tidal volume, Inspiration to Expiration ratio, ventilator mode (volume control vs. pressure control) and other parameters pertinent to ventilation therapy. In one embodiment, an NO generation and delivery system provides alarms in the event that ventilator flows are outside of an acceptable range.

In one embodiment, an NO delivery system measures NO and/or NO$_2$ concentration in the product gas before it is injected into a patient airway.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A nitric oxide (NO) delivery system, comprising:
a NO source for providing a flow of NO-containing gas, the NO source comprising at least one plasma chamber configured to generate a plasma to ionize a reactant gas to generate the NO-containing gas;
at least one controller configured to communicate with a flow controller to control the flow of the NO-containing gas from the NO source using one or more parameters as an input to the at least one controller; and
a gas sensor pack comprising a manifold having a plurality of sensors attached thereto for measuring a plurality of characteristics of a flow of gas therethrough, the gas sensor pack configured to be removable from a housing of the NO delivery system such that all of the plurality of sensors are replaced simultaneously, the gas sensor pack in communication with the at least one controller to provide information regarding the plurality of measured characteristics.

2. The system of claim 1, wherein the plurality of sensors in the gas sensor pack comprises a NO sensor, and NO$_2$ sensor, and an oxygen sensor.

3. The system of claim 1, wherein the plurality of sensors in the gas sensor pack comprises at least one pressure sensor configured to monitor the flow and pressure of the gas through the gas sensor pack.

4. The system of claim 1, wherein the plurality of sensors in the gas sensor pack comprises at least one temperature sensor.

5. The system of claim 1, wherein the plurality of sensors in the gas sensor pack comprises a flow sensor for measuring flow through the gas sensor pack.

6. The system of claim 1, wherein a flow of sample gas into the gas sensor pack is selected between a gas flow from a sample line, a gas flow from a calibration gas source path, and a flow of the NO-containing gas.

7. The system of claim 6, further comprising a flow selector that is configured to control the flow of sample gas into the gas sensor pack.

8. The system of claim 7, wherein the flow selector is located inside the gas sensor pack.

9. The system of claim 1, wherein the gas sensor pack further comprises a pump such that the pump is replaced simultaneously with replacement of the plurality of sensors.

10. The system of claim 1, wherein the gas sensor pack further comprises a length of humidity exchange tubing.

11. The system of claim 10, wherein the humidity exchange tubing is configured to allow humidity in the atmosphere to enter a gas sample in the gas sensor pack.

12. The system of claim 10, wherein the humidity exchange tubing is configured to remove water from a gas sample before exposing the plurality of sensors to the gas sample.

13. The system of claim 1, wherein the plurality of sensors in the gas sensor pack are configured to measure a plurality of characteristics of the NO-containing gas, the plurality of sensors configured to communicate the plurality of measured characteristics to the at least one controller to determine if one of the plurality of measured characteristics are over a threshold.

14. The system of claim 13, wherein the at least one controller is configured to suspend the flow of the NO-containing gas from the NO source when one of the plurality of measured characteristics is over the threshold.

15. A nitric oxide (NO) delivery system, comprising:

a NO source for providing a flow of NO-containing gas, the NO source comprising at least one plasma chamber configured to generate a plasma to ionize a reactant gas to generate the NO-containing gas;

at least one controller configured to communicate with a flow controller to control the flow of the NO-containing gas from the NO source using one or more parameters as an input to the at least one controller; and a gas sensor pack comprising a manifold having a plurality of sensors attached thereto for measuring a plurality of characteristics of a flow of gas therethrough, the gas sensor pack configured to be removable from a housing of the NO delivery system such that all of the plurality of sensors are replaced simultaneously, the gas sensor pack in communication with the at least one controller to provide information regarding the plurality of measured characteristics, wherein the flow of gas through the gas sensor pack is one of a flow of the NO-containing gas and a flow of gas from a patient delivery device.

16. The system of claim 15, wherein the plurality of sensors in the gas sensor pack comprises a NO sensor, and $NO_2$ sensor, and an oxygen sensor.

17. The system of claim 15, wherein the plurality of sensors in the gas sensor pack comprises at least one pressure sensor configured to monitor the flow and pressure of the gas through the gas sensor pack.

18. The system of claim 15, wherein the plurality of sensors in the gas sensor pack comprises at least one temperature sensor.

19. The system of claim 15, wherein the plurality of sensors in the gas sensor pack comprises a flow sensor for measuring flow through the gas sensor pack.

20. The system of claim 15, wherein the flow of the NO-containing gas through the gas sensor pack is diluted prior to entering the gas sensor pack.

\*   \*   \*   \*   \*